United States Patent [19]

Ohno et al.

[11] Patent Number: 5,086,071
[45] Date of Patent: Feb. 4, 1992

[54] 2,5,6,7-TETRANOR-4,8-INTER-M-PHENYLENE PGI$_2$ DERIVATIVES

[75] Inventors: Kiyotaka Ohno, Fujisawa; Atsushi Ohtake, Kamakura; Takashi Endoh, Chigasaki; Shigeki Itou; Kazuhiro Hoshi, both of Kamakura, all of Japan

[73] Assignee: Toray Industries, Inc., Tokyo, Japan

[21] Appl. No.: 493,109

[22] Filed: Mar. 13, 1990

[30] Foreign Application Priority Data

Mar. 14, 1989 [JP] Japan ............................ 1-63241

[51] Int. Cl.$^5$ .................... A61K 31/34; C07D 307/93
[52] U.S. Cl. ......................................... 514/468; 549/458
[58] Field of Search ........................ 549/458; 514/468

[56] References Cited

U.S. PATENT DOCUMENTS

| | | | |
|---|---|---|---|
| 4,474,802 | 10/1984 | Ohno et al. | 549/458 |
| 4,564,620 | 1/1986 | Ohno et al. | 549/458 |
| 4,775,692 | 10/1988 | Ohno et al. | 549/458 |
| 4,822,804 | 4/1989 | Ohno et al. | 549/458 |

FOREIGN PATENT DOCUMENTS

WO89/03387  4/1989  PCT Int'l Appl. .

*Primary Examiner*—Bernard Dentz
*Attorney, Agent, or Firm*—Scully, Scott, Murphy & Presser

[57] ABSTRACT

Pharmaceutically useful compounds are 2,5,6,7-tetranor-4,8-inter-m-phenylene PGI$_2$ derivatives which are excellently stable and potent in vivo.

24 Claims, No Drawings

2,5,6,7-TETRANOR-4,8-INTER-M-PHENYLENE PGI₂ DERIVATIVES

FIELD OF THE INVENTION

The present invention relates to novel prostaglandin I₂ derivatives exhibiting in vivo excellent activities and duration.

BACKGROUND OF THE INVENTION

Prostaglandin I₂ (PGI₂, prostacyclin) is a compound discovered in 1976 by J. R. Vane et al., which has called attention as a substance exerting potent platelet aggregation—inhibiting and gastric acid secretion—inhibiting activities and potent peripheral vasodilative activities after having been biosynthesized from archidonic acid via an endo peroxide (PGH₂ or PGG₂) at the vascular wall [C & E N, Dec. 20, 1976, p17. and S. Moncada, R. Gryglewski, S. Bunting, J. R. Vane, Nature, 263, 633 (1976)].

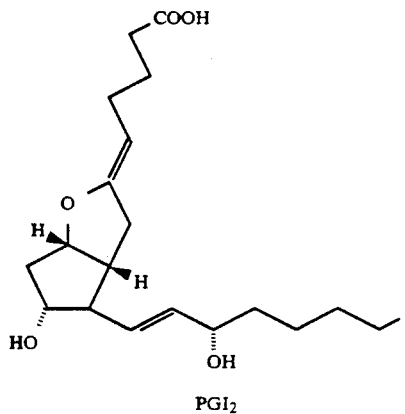

PGI₂

However, PGI₂ which has an exo-enol structure is extremely unstable even in neutral aqueous solution and is readily subjected to conversion to 6-oxo PGF₁ which has almost no physiological activities. Such instability of is a big obstacle to its use as a drug. PGI₂ is also metabolized quickly in vivo and disadvantageously shows only short duration of physiological activities in vivo.

A tremendous amount of research has been made on various derivatives for the purpose of improving the chemical stability and duration of activities in vivo of PGI₂.

The inventers resolved the problems of such chemical instabilities in PGI₂ by inventing novel derivatives which have a cyclopenta[b]benzofuran ring containing a phenol ring in place of unstable exo-enol structure therein and filed a series of patent applications (See, Japanese patent application Nos. 36477/81, 32277/82, 14427/82, 124778/83, 134787/84, and 265279/87).

As the result of further study, it has now been found that the novel PGI₂ derivatives having the general formula [I] have strong pharmacological activities and in vivo excellent stability.

An object of the present invention is to provide novel PGI₂ derivatives which are excellently stable and potent in vivo.

SUMMARY OF THE INVENTION

The present invention relates to 2,5,6,7-tetranor-4,8-inter-m-phenylene PGI₂ derivatives having the following formula:

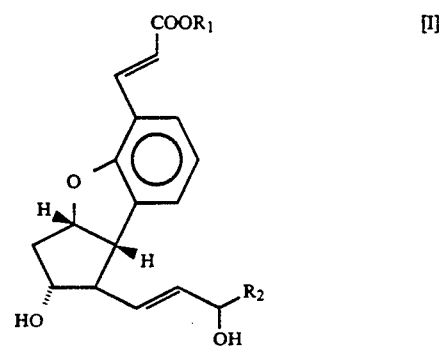

wherein R is hydrogen, a pharmacologically acceptable cation, or an ester residue;

R₂ is
(i) normal alkyl group having 1 to 12 carbon atoms or branched alkyl group having 3 to 14 carbon atoms;
(ii) —Z—Ar wherein Z is a valence bond or normal or branched alkylene group having the formula: $C_tH_{2t}$, t is an integer of 1 to 6, and Ar is phenyl unsubstituted or substituted by 1 to 4 substituents selected from alkyl, methoxy, chloro, bromo, fluoro, iodo, trifluoromethyl, nitro, cyano, phenyl and phenoxy;
(iii) —Z—R₃ wherein Z is as defined above, R₃ is cycloalkyl group having 3 to 12 carbon atoms or cycloalkyl group having 3 to 12 carbon atoms substituted by 1 to 4 normal alkyl substituents containing 1 to 4 carbon atoms;
(iv) —$C_tH_{2t}$—C≡C—R₄ wherein $C_tH_{2t}$ is as defined above, R₄ is normal alkyl group having 1 to 6 carbon atoms;
(v) —$C_tH_{2t}$—O—R₅ wherein $C_tH_{2t}$ is as defined above, R₅ is (1) normal alkyl group having 1 to 6 carbon atoms or branched alkyl group having 3 to 6 carbon atoms, (2) cyclopentyl or cyclohexyl group unsubstituted or substituted by 1 to 4 normal alkyl substituents containing 1 to 4 carbon atoms, or (3) Ar wherein Ar is as defined above.

DETAILED DESCRIPTION OF THE INVENTION

When R₁ in the above-given general formula (I) is an ester residue, R₁ is preferably
(i) normal alkyl group having 1 to 12 carbon atoms or branched alkyl group having 3 to 14 carbon atoms;
(ii) —Z—R₃ wherein Z and R₃ are as defined above, and R₁ and R₂ are independent each other in the same formula;
(iii) —Z—Ar wherein Z and Ar are as defined above, and R₁ and R₂ are independent each other in the same formula;
(iv) —(CH₂CH₂O)ₙ—CH₃ wherein n is an integer of 1 to 5;
(v) —Z—R₆ wherein Z is as defined above, when R₂ is represented by the formula containing Z, R₂ and Z are independent each other, and R₆ is α-naphthyl, β-naphthyl, 2-pyridyl, 3-pyridyl, 4-pyridyl, α-furyl, β-furyl, α-thienyl, or β-thienyl;

(vi) $-C_tH_{2t}-COOR_7$ wherein $C_tH_{2t}$ is as defined above, when $R_2$ is represented by the formula containing $C_tH_{2t}$, each $C_tH_{2t}$ in $R_1 R_2$ is independent each other, and $R_7$ is methyl, ethyl or propyl; or (vii)

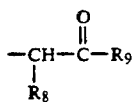

wherein $R_8$ is hydrogen or benzoyl group and $R_9$ is phenyl, p-bromophenyl, p-chlorophenyl, p-biphenyl, p-nitrophenyl, p-benzamidephenyl or 2-naphthyl.

Examples of the pharmacologically acceptable cation in $R_1$ include metal cations, ammonium cations, amine cations, and quaternary ammonium cations. Particularly preferred metal cations are those derived from alkali metals, for example, lithium, sodium, potassium and alkaline earth metals, for example, magnesium and calcium. In addition, those cations from other metals such as, for example, aluminum, zinc and iron are within the scope of the present invention.

Pharmacologically acceptable amine cations are those derived from primary, secondary or tertiary amines. Examples of the suitable amines are methylamine, dimethylamine, triethylamine, ethylamine, dibutylamine, triisopropylamine, N-methylhexylamine, decylamine, dodecylamine, allylamine, crotylamine, cyclopentylamine, dicyclohexylamine, benzylamine, dibenzylamine, α-phenylethylamine, β-phenylethylamine, ethylenediamine, diethylenetriamine, and similar aliphatic, alicyclic and heterocyclic amines containing up to about 18 carbon atoms, for example, 1-methylpiperidine, 4-ethyl morpholine, 1-isopropylpyrolidine, 2-methylpyrolidine, 4-dimethylpiperadine, 2-methylpiperadine and the like. Further examples are those amines containing water-soluble or hydrophilic groups such as, for example, mono-, di- and triethanolamines, ethyldiethylamine, N-butylethanolamine, 2-amino-1-butanol, 2-amino-2-ethyl-1,3-propanediol, tris(hydroxymethyl)aminomethane, N-phenylethanolamine, N-(p-tert-aminophenyl)diethanolamine, galactamine, N-methylglutamine, N-methyl glucosamine, ephedrine, phenylephrine, epinephrine, procaine and the like. Basic amino acids, specifically lysine, arginine, and the like may also be mentioned.

Examples of $R_1$ and $R_2$ either or both of which are normal alkyl groups containing 1-12 carbon atoms include methyl, ethyl, propyl, butyl, pentyl, hexyl, heptyl, octyl, dodecyl and the like. Further examples of $R_1$ and $R_2$ either or both of which are branched alkyl groups containing 3-14 carbon atoms include isopropyl, sec-butyl, t-butyl, iso-butyl, 1-methylpentyl, 2-methylpentyl, 3-methylpentyl, 4-methylpentyl, 1-methylhexyl, 2-methylhexyl, 3-methylhexyl, 4-methylhexyl, 5-methylhexyl, 1-methylheptyl, 2-methylheptyl, 3-methylheptyl, 4-methylheptyl, 5-methylheptyl, 6-methylheptyl, 1-methyloctyl, 2-methyloctyl, 3-methyloctyl, 4-methyloctyl, 5-methyloctyl, 6-methyloctyl, 7-methyloctyl, 1-methylnonyl, 1-methyldecanyl, 2-methylnonyl, 2-methyldecanyl, 1,1-dimethylbutyl, 2,2-dimethylbutyl, 1,1-dimethylpentyl, 2,2-dimethylpentyl, 3,3-dimethylpentyl, 4,4-dimethylpentyl, 1,1-dimethylhexyl, 2,2-dimethylhexyl, 3,3-dimethylhexyl, 4,4-dimethylhexyl, 5,5-dimethylhexyl, 1,1-dimethylheptyl, 2,2-dimethylheptyl, 3,3-dimethylheptyl, 4,4-dimethylheptyl, 5,5-dimethylheptyl, 6,6-dimethylheptyl, 1,1-dimethyloctyl, 2,2-dimethyloctyl, 3,3-dimethyloctyl, 1,1-dimethylnonyl, 2,2-dimethylnonyl, 3,3-dimethylnonyl, 1,1-dimethyldecanyl, 2,2-dimethyldecanyl, 3,3-dimethyldecanyl, 1,1,2,2-tetramethylpentyl, 1,1,3,3-tetramethylpentyl, 1,1,2,2-tetramethylhexyl, 1,1,3,3-tetramethylhexyl, 2,2,3,3-tetramethylhexyl and the like.

Examples of $R_1$ and $R_2$ either or both of which are $-Z-Ar$ include phenyl, p-chlorophenyl, p-bromophenyl, p-fluorophenyl, 3,4-dichlorophenyl, m-fluorophenyl, m-trifluoromethylphenyl, p-trifluoromethylphenyl, p-nitrophenyl, p-anisyl, 3,4-dimethoxyphenyl, p-tolyl, m-tolyl, o-tolyl, p-ethylphenyl, p-propylphenyl, p-butylphenyl, 3,4-dimethylphenyl, 2,4-dimethylphenyl, 3-chloro-4-methylphenyl, 3-fluoro-4-methylphenyl, 4-biphenyl, p-phenoxyphenyl, 3-chloro-4-phenoxyphenyl, benzyl, p-chlorobenzyl, m-chlorobenzyl, p-methoxybenzyl, o-methoxybenzyl, p-methylbenzyl, p-ethylbenzyl, p-propylbenzyl, p-nitrobenzyl, 3,4-dichlorobenzyl, α-methylbenzyl, α,α'-dimethylbenzyl, phenetyl, p-chlorophenetyl, p-bromophenetyl, p-fluorophenetyl, m-chlorophenetyl, m-fluorophenetyl, o-chlorophenetyl, p-methylphenetyl, p-methoxyphenetyl, 3,4-dimethoxyphenetyl p-ethylphenetyl, α-methylphenetyl, β-methylphenetyl, α,α'-dimethylphenetyl, β,β'-dimethylphenetyl, 3-phenylpropyl, 3-(p-chlorophenyl)propyl, 3-(p-fluorophenyl)propyl, 3-(p-bromophenyl)propyl, 3-(m-chlorophenyl)propyl, 3-(3,4-dichlorophenyl)propyl, 3-(p-tolyl)propyl, 3-(p-ethylphenyl)propyl, 4-phenylbutyl, 4-(p-chlorophenyl)butyl, 4-(3,4-dichlorophenyl)butyl, 4-(p-tolyl)butyl, 5-phenylpentyl, α,α'-dimethyl-p-chlorophenetyl, α,α'-dimethyl-p-bromophenetyl, α,α'-dimethyl-p-fluorophenetyl, α,α'-dimethyl-m-chlorophenetyl, α,α'-dimethyl-m-bromophenetyl, α,α'-dimethyl-m-fluoro phenetyl, α,α'-dimethyl-p-trifluoromethylphenetyl, α,α'-dimethyl-m-trifluoromethylphenetyl, α,α'-dimethyl-p-methylphenetyl, α,α'-dimethyl-p-methoxyphenetyl, α,α'-dimethyl-p-cyanophenetyl, 1,1-dimethyl-3-phenyl propyl, 1,1-dimethyl-4-phenylbutyl and the like.

Examples of $R_1$ and $R_2$ either or both of which are $-Z-R_3$ include cyclopentyl, cyclohexyl, cycloheptyl, cyclooctyl, cyclododecyl, cyclopentylmethyl, cyclohexylmethyl, cycloheptylmethyl, cyclododecylmethyl, cyclopentylethyl, cyclohexylethyl, cycloheptylethyl, cyclopentylpropyl, cyclohexylpropyl, cyclopentylbutyl, cyclohexylbutyl, cyclohexylpentyl, 2-methylcyclopentyl, 3-methylcyclopentyl, 2-methylcyclohexyl, 3-methylcyclohexyl, 4-methylcyclohexyl, 2-methylcycloheptyl, 3-methylcycloheptyl, 4-methylcyclooctyl, 2-ethylcyclopentyl, 4-methylcycloheptyl, 4-ethylcyclopentyl, 2-ethylcyclohexyl, 3-ethylcyclohexyl, 4-ethylcyclohexyl, 2-ethylcycloheptyl, 2-ethylcyclooctyl, 3-ethylcyclooctyl, 2-methylcyclopentylmethyl, 3-methylcyclopentylmethyl, 2-methylcyclohexylmethyl, 3-methylcyclohexylmethyl, 4-methylcyclohexylmethyl, 2-methylcycloheptylmethyl, 3-methylcycloheptylmethyl, 2-methylcyclooctylmethyl, 2-(2-methylcyclopentyl)ethyl, 2-(3-methylcyclopentyl)ethyl, 2-(2-methylcyclohexyl)ethyl, 2-(3-methylcyclohexyl)ethyl, 2-(4-methylcyclohexyl)ethyl, 2-(2-methylcycloheptyl)ethyl, 2-(2-methylcyclooctyl)ethyl, 3-(2-methylcyclopentyl)propyl, 3-(3-methylcyclopentyl)propyl, 3-(2-methylcyclohexyl)propyl, 3-(3-methylcyclohexyl)propyl, 3-(4-methylcyclohexyl)propyl, 5-(2- methylcyclopentyl)pentyl, 2-ethylcyclopentylmethyl, 3-ethylcyclopentylmethyl, 2-ethylcyclohexylmethyl, 3-ethylcyclohexylmethyl, 4-ethylcyclohexylmethyl, 2-ethylcycloheptylmethyl, 3-ethylcycloheptylmethyl, 2-ethylcyclooctylmethyl, 2-(2-ethylcyclopentyl)ethyl, 2-(3-ethylcyclopentyl)ethyl, 2-(4-ethylcyclohexyl)ethyl, 2-(2-ethylcycloheptyl)ethyl, 2-(2-ethylcyclooctyl)ethyl, 3-(2-ethylcyclopentyl)propyl, 3-(3-ethylcyclopentyl)propyl, 3-(2-ethylcyclohexyl)propyl, 3-(3-ethylcyclohexyl)propyl, 3-(4-ethylcyclohexyl)propyl, 5-(2-ethylcyclopentyl)pentyl, cyclopropyl, cyclobutyl, 2,3-dimethylcyclopropyl, 2,4-dimethylcyclobutyl, 3,3-dimethylcyclobutyl, 1-cyclopentyl-1-methylethyl, 1-cyclohexyl-1-methylethyl, 1-cyclooctyl-1-methylethyl, 2-cyclopentyl-1,1-dimethylethyl, 2-cyclohexyl-1,1-dimethylethyl, 2-cyclooctyl-1,1-dimethylethyl, 2-cyclododecyl-1,1-dimethylethyl, 3-cyclopentyl-1,1-dimethylpropyl, 3-cyclohexyl-1,1-dimethylpropyl, 3-cyclooctyl-1,1-dimethylpropyl, 4-cyclopentyl-1,1-dimethylbutyl, 4-cyclohexyl-1,1-dimethylbutyl, 4-cyclooctyl-1,1-dimethylbutyl, 2-cyclopentyl-2,2-dimethylethyl, 2-cyclohexyl-2,2-dimethylethyl, 2-cyclooctyl-2,2-dimethylethyl, and the like.

Examples of $R_2$ which is $-C_tH_{2t}-C\equiv C-R_4$ include 2-pentynyl, 3-pentynyl, 2-hexynyl, 3-hexynyl, 4-hexynyl, 2-heptynyl, 3-heptynyl, 4-heptynyl, 5-heptynyl, 2-octynyl, 3-octynyl, 4-octynyl, 5-octynyl, 6-octynyl, 2-nonynyl, 3-nonynyl, 4-nonynyl, 5-nonynyl, 6-nonynyl, 7-nonynyl, 1-methyl-2-pentynyl, 1-methyl-3-pentynyl, 1-methyl-2-hexynyl, 1-methyl-3-hexynyl, 1-methyl-4-hexynyl, 1-methyl-2-heptynyl, 1-methyl-3-heptynyl, 1-methyl-4-heptynyl, 1-methyl-5-heptynyl, 1-methyl-2-octynyl, 1-methyl-3-octynyl, 1-methyl-4-octynyl, 1-methyl-5-octynyl, 1-methyl-6-octynyl, 1-methyl-2-nonynyl, 1-methyl-3-nonynyl, 1-methyl-4-nonynyl, 1-methyl-5-nonynyl, 1-methyl-6-nonynyl, 1,1-dimethyl-2-pentynyl, 1,1-dimethyl-3-pentynyl, 1,1-dimethyl-2-hexynyl, 1,1-dimethyl-3-hexynyl, 1,1-dimethyl-4-hexynyl, 1,1-dimethyl-2-heptynyl, 1,1-dimethyl-3-heptynyl, 1,1-dimethyl-4-heptynyl, 1,1-dimethyl-5-heptynyl, 1,1-dimethyl-2-octynyl, 1,1-dimethyl-3-octynyl, 1,1-dimethyl-4-octynyl, 1,1-dimethyl-5-octynyl, 1,1-dimethyl-2-nonynyl, 1,1-dimethyl-3-nonynyl, 1,1-dimethyl-4-nonynyl, 1,1-dimethyl-5-nonynyl, 2,2-dimethyl-3-pentynyl, 2,2-dimethyl-3-hexynyl, 2,2-dimethyl-4-hexynyl, 2,2-dimethyl-3-heptynyl, 2,2-dimethyl-4-heptynyl, and the like.

Examples of $R_2$ which is $-C_tH_{2t}-O-R_5$ include methoxymethyl, ethoxymethyl, propoxymethyl, butoxymethyl, n-pentyloxymethyl, n-hexyloxymethyl, 1-methoxy-1-methylethyl, 1-ethoxy-1-methylethyl, 1-methyl-1-propoxyethyl, 1-butoxy-1-methylethyl, 1-methyl-1-n-pentyloxyethyl, 1-n-hexyl-1-methylethyl, isopropoxymethyl, sec-butoxymethyl, iso-butoxymethyl, t-butoxymethyl, (1,1-dimethylbutoxy)methyl, (1,1-dimethyl-n-pentyloxy)methyl, (1,1-dimethyl-n-hexyloxy)methyl, 2-methoxyethyl, 2-ethoxyethyl, 2-propoxyethyl, 2-butoxyethyl, 2-n-pentyloxyethyl, 2-n-hexyloxyethyl, 2-methoxy-1,1-dimethylethyl, 2-ethoxy-1,1-dimethylethyl, 1,1-dimethyl-2-propoxyethyl, 2-butoxy-1,1-dimethylethyl, 1,1-dimethyl-2-n-pentyloxyethyl, 2-n-hexyloxy-1,1-dimethylethyl, 3-methoxypropyl, 3-ethoxypropyl, 3-propoxypropyl, 3-butoxypropyl, 3-n-pentyloxypropyl, 3-n-hexyloxy-propyl, 3-methoxy-1,1-dimethylpropyl, 3-ethoxy-1,1-dimethylpropyl, 1,1-dimethyl-3-propoxypropyl, 3-butoxy-1,1-dimethylpropyl, 1,1-dimethyl-3-n-pentyloxypropyl, 2-isopropoxyethyl, 2-sec-butoxyethyl, 2-t-butoxy-ethyl, 2-methoxy-1-methylethyl, 2-ethoxy-1-methylethyl, 1-methyl-2-propoxyethyl, 2-butoxy-1-methylethyl, cyclopentyloxymethyl, cyclohexyloxymethyl, 1-cyclopentyloxy-1-methylethyl, 1-cyclohexyloxy-1-methylethyl, (2,5-dimethylcyclopentyloxy)methyl, (3,4-dimethylcyclopentyloxy)methyl, (4-methyl-cyclohexyloxy)methyl, (2,6-dimethylcyclohexyloxy)methyl, (2,2,6,6-tetramethylcyclohexyloxy)methyl, 1-methyl-1-(3,4-dimethylcyclopentyloxy)ethyl, 1-methyl-1-(4-methylcyclohexyloxy)ethyl, 2-(cyclopentyloxy)ethyl, 2-(cyclohexyloxy)ethyl, 2-(cyclopentyloxy)-1,1-dimethylethyl, 2-(cyclohexyloxy)-1,1-dimethylethyl, 3-cyclopentyloxypropyl, 3-cyclohexyloxypropyl, 3-(cyclopentyloxy)-1,1-dimethylpropyl, 3-(cyclohexyloxy)-1,1-dimethylpropyl, phenoxymethyl, p-chlorophenoxymethyl, m-chlorophenoxymethyl, 2,4-dichlorophenoxymethyl, 3,4-dichlorophenoxymethyl, p-bromophenoxymethyl, m-bromophenoxymethyl, 2,4-dibromophenoxymethyl, 3,4-dibromophenoxymethyl, p-fluorophenoxymethyl, m-fluorophenoxymethyl, o-fluorophenoxymethyl, p-trifluoromethylphenoxymethyl, m-trifluoromethylphenoxymethyl, o-trifluoromethylphenoxymethyl, p-nitrophenoxymethyl, p-cyanophenoxymethyl, p-phenylphenoxy-methyl, p-methylphenoxymethyl, m-methylphenoxymethyl, o-methylphenoxymethyl, p-methoxyphenoxymethyl, m-methoxyphenoxymethyl, o-methoxyphenoxymethyl, 1-methyl-1-phenoxyethyl, 1-(p-chlorophenoxy)-1-methylethyl, 1-(m-chlorophenoxy)-1-methylethyl, 1-(2,4-dichlorophenoxy)-1-methylethyl, 1-(3,4-dichlorophenoxy)-1-methylethyl, 1-(p-bromophenoxy)-1-methylethyl, 1-(m-bromophenoxy)-1-methylethyl, 1-(2,4-dibromophenoxy)-1-methylethyl, 1-(3,4-dibromophenoxy)-1-methylethyl, 1-(p-fluorophenoxy)-1-methylethyl, 1-(m-fluorophenoxy)-1-methylethyl, 1-(o-fluorophenoxy)-1-methylethyl, 1-(p-trifluoromethylphenoxy)-1-methylethyl, 1-(m-trifluoromethylphenoxy)-1-methylethyl, 1-(o-trifluoromethylphenoxy)-1-methylethyl, 1-methyl-1-(p-nitrophenoxy)ethyl, 1-(p-cyanophenoxy)-1-methylethyl, 1-methyl-1-(p-phenylphenoxy)ethyl, 1-methyl-1-(p-methylphenoxy)ethyl, 1-methyl-1-(m-methylphenoxy)ethyl, 1-methyl-1-(o-methylphenoxy)ethyl, 1-(p-methoxyphenoxy)-1-methylethyl, 1-(m-methoxyphenoxy)-1-methylethyl, 1-(o-methoxyphenoxy)-1-methylethyl, 2-phenoxyethyl, 2-(p-chlorophenoxy)ethyl, 2-(m-chlorophenoxy)ethyl, 2-(2,4-dichlorophenoxy)ethyl, 2-(3,4-dichlorophenoxy)ethyl, 2-(p-bromophenoxy)ethyl, 2-(m-bromophenoxy)ethyl, 2-(2,4-dibromophenoxy)ethyl, 2-(3,4-dibromophenoxy)ethyl, 2-(p-fluorophenoxy)ethyl, 2-(m-fluorophenoxy)ethyl, 2-(o-fluorophenoxy)ethyl, 2-(p-trifluoromethylphenoxy)ethyl, 2-(m-trifluoromethylphenoxy)ethyl, 2-(o-trifluoromethylphenoxy)ethyl, 2-(p-nitrophenoxy)ethyl, 2-(p-cyanophenoxy)ethyl, 2-(p-phenylphenoxy)ethyl, 2-(p-methylphenoxy)ethyl, 2-(m-methylphenoxy)ethyl, 2-(o-methylphenoxy)ethyl, 2-(p-methoxyphenoxy)ethyl, 2-(m-methoxyphenoxy)ethyl, 2-(o-methoxyphenoxy)ethyl, 3-phenoxypropyl, 1,1-dimethyl-3-phenoxypropyl, 1-phenoxyethyl, 1-methyl-2-phenoxyethyl, 1-methyl-3-phenoxyethyl, and the like.

Examples of $R_1$ which is $-(CH_2CH_2O)_n-CH_3$ include $-CH_2CH_2OCH_3$, $-CH_2CH_2OCH_2CH_2OCH_3$, $-(CH_2CH_2O)_3-CH_3$, $-(CH_2CH_2O)_4-CH_3$, $-(CH_2CH_2O)_5-CH_3$, and the like.

Examples of $R_1$ which is $-Z-R_6$ include α-naphthyl, β-naphthyl, 2-pyridyl, 3-pyridyl, 4-pyridyl, α-furyl, β-furyl, α-thienyl, β-thienyl, α-naphthylmethyl, β- naphthylmethyl, 2-pyridylmethyl, 3-pyridylmethyl, 4-pyridylmethyl, α-furylmethyl, β-furylmethyl, α-thienylmethyl, β-thienylmethyl, 2-(α-naphthyl)ethyl, 2-(β-naphthyl)ethyl, 2-(2-pyridyl)ethyl, 2-(3-pyridyl)ethyl, 2-(4-pyridyl)ethyl, 2-(α-furyl)ethyl, 2-(β-furyl)ethyl, 2-(α-thienyl)ethyl, 2-(β-thienyl)ethyl, 3-(α-naphthyl)propyl, 3-(β-naphthyl)propyl, 3-(2-pyridyl)propyl, 3-(3-pyridyl)propyl, 3-(4-pyridyl)propyl, 3-(α-furyl)propyl, 3-(β-furyl)propyl, 3-(α-thienyl)propyl, 3-(β-thienyl)propyl, and the like.

Examples of $R_1$ which is $-C_tH_{2t}COOR_7$ include methoxycarbonylmethyl, ethoxycarbonylmethyl, propoxycarbonylmethyl, 1-methoxycarbonylethyl, 1-ethoxycarbonylethyl, 1-propoxycarbonylethyl, 2-methoxycarbonylethyl, 2-ethoxycarbonylethyl, 2-propoxycarbonylethyl, 3-methoxycarbonylpropyl, 3-ethoxycarbonylpropyl, and the like.

Examples of $R_1$ which is

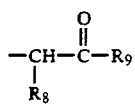

include phenacyl, p-bromophenacyl, p-nitrophenacyl, p-phenylphenacyl, p-benzamidephenacyl, 2-naphthoylmethyl, α-benzoylphenacyl, and the like.

The compounds having the above-mentioned general formula (I) produced by the present invention are named according to the nomenclature for prostaglandins and prostaglandin analogs proposed by N. A. Nelson et al. [N. A. Nelson, J. Med. Chem. 17, 911, (1974) and R. A. Johnson, D. R. Morton, N. A. Nelson, Prostaglandins, 15, 737 (1978)].

The most fundamental compounds among a series of compounds (not including the compounds of the present invention) are represented by the following formula which is numbered as shown in the figure below and named 5,6,7-trinor-4,8-inter-m-phenylene $PGI_2$.

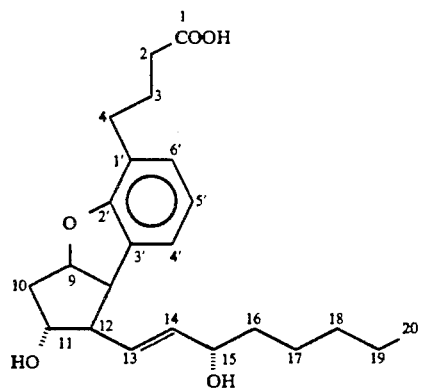

This name is not reasonably derived from the nomenclature according to the above-mentioned references; however, to avoid confusion the above nomenclature on the basis of 5,6,7-trinor-4,8-inter-m-phenylene $PGI_2$ is used only in naming the compounds of the present invention which are unique $PGI_2$ derivatives having a cyclopenta[b]benzofuran skeleton. The above-mentioned fundamental compound is named 9-deoxy-2',9α-epoxy-5,6,7-trinor-4,8-inter-m-phenylene $PGF_{1α}$ according to the nomenclature cited in the above-mentioned references. In the specification, the compounds are named, for example, 5,6,7-trinor-4,8-inter-m-phenylene $PGI_2$ according to the simplified nomenclature as mentioned previously, but otherwise according to the nomenclature cited in the above-mentioned references. By the way, the nomenclature according to the above-mentioned references is also simplified.

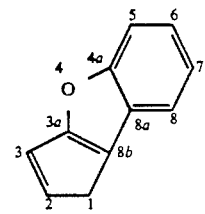

1H-cyclopenta [b] benzofuran

The above fundamental compound is named as a derivative substituted on a cyclopenta[b]benzofuran ring according to the I U P A C nomenclature system, namely, formally 4-[1β-(3-hydroxy-octenyl)-2-αβH, 8b βH-2,3,3a,8b-tetrahydro-5-1H-cyclopenta[b]benzofuranyl) butanoic acid. However, the compounds of the present invention are named according to the simplified nomenclature as mentioned above.

The naming of the compounds according to the present invention will be illustrated together with structure thereof as follows;

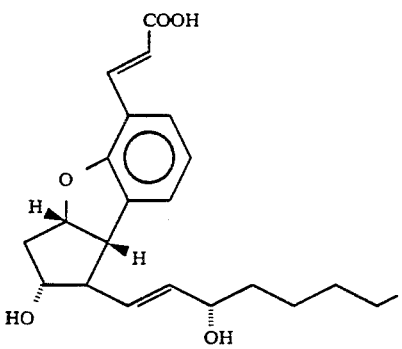

(3E)-2,5,6,7-tetranor-3,4-didehydro-4,8-inter-m-phenylenePGI₂

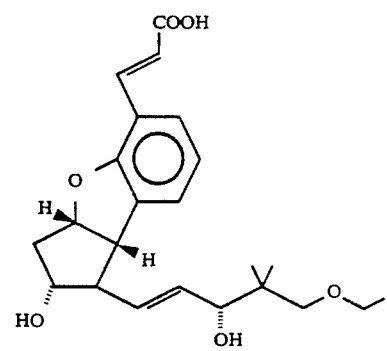

(3E)-16,16-dimethyl-18-oxa-2,5,6,7-tetranor-3,4-didehydro-4,8-inter-m-phenylenePGI₂

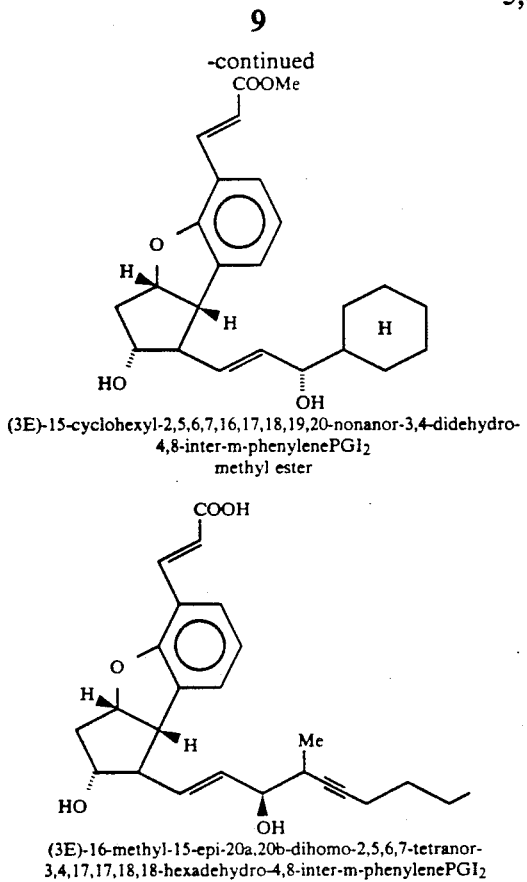

(3E)-15-cyclohexyl-2,5,6,7,16,17,18,19,20-nonanor-3,4-didehydro-4,8-inter-m-phenylenePGI₂ methyl ester (3E)-16-methyl-15-epi-20a,20b-dihomo-2,5,6,7-tetranor-3,4,17,17,18,18-hexadehydro-4,8-inter-m-phenylenePGI₂

Illustrative compounds of the present invention according to the above-cited nomenclature are listed below.

The compounds wherein R₂ is normal or branched alkyl group are illustrated by but not limited to:

(3E)-2,5,6,7,17,18,19,20-octanor-3,4-didehydro-4,8-inter-m-phenylene-PGI₂
(3E)-2,5,6,7,18,19,20-heptanor-3,4-didehydro-4,8-inter-m-phenylene-PGI₂
(3E)-2,5,6,7,19,20-hexanor-3,4-didehydro-4,8-inter-m-phenylene-PGI₂
(3E)-2,5,6,7,20-pentanor-3,4-didehydro-4,8-inter-m-phenylene-PGI₂
(3E)-2,5,6,7-tetranor-3,4-didehydro-4,8-inter-m-phenylene-PGI₂
(3E)-20a-homo-2,5,6,7-tetranor-3,4-didehydro-4,8-inter-m-phenylene-PGI₂
(3E)-20a,20b-dihomo-2,5,6,7-tetranor-3,4-didehydro-4,8-inter-m-phenylene-PGI₂
(3E)-20a,20b,20c-trihomo-2,5,6,7-tetranor-3,4-didehydro-4,8-inter-m-phenylene-PGI₂
(3E)-20a,20b,20c,20d-tetrahomo-2,5,6,7-tetranor-3,4-didehydro-4,8-inter-m-phenylene-PGI₂
(3E)-20a,20b,20c,20d,20e-pentahomo-2,5,6,7-tetranor-3,4-didehydro-4,8-inter-m-phenylene-PGI₂
(3E)-20a,20b,20c,20d,20e,20f-hexahomo-2,5,6,7-tetranor-3,4-didehydro-4,8-inter-m-phenylene-PGI₂
(3E)-20a,20b,20c,20d,20e,20f,20g-heptahomo-2,5,6,7-tetranor-3,4-didehydro-4,8-inter-m-phenylene-PGI₂
(3E)-16-methyl-2,5,6,7,18,19,20-heptanor-3,4-didehydro-4,8-inter-m-phenylene-PGI₂
(3E)-16-methyl-2,5,6,7,19,20-hexanor-3,4-didehydro-4,8-inter-m-phenylene-PGI₂
(3E)-16-methyl-2,5,6,7,20-pentanor-3,4-didehydro-4,8-inter-m-phenylene-PGI₂
(3E)-16-methyl-2,5,6,7-tetranor-3,4-didehydro-4,8-inter-m-phenylene-PGI₂
(3E)-16-methyl-20a-homo-2,5,6,7-tetranor-3,4-didehydro-4,8-inter-m-phenylene-PGI₂
(3E)-16-methyl-20a,20b-dihomo-2,5,6,7-tetranor-3,4-didehydro-4,8-inter-m-phenylene-PGI₂
(3E)-16-methyl-20a,20b,20c-trihomo-2,5,6,7-tetranor-3,4-didehydro-4,8-inter-m-phenylene-PGI₂
(3E)-16-methyl-20a,20b,20c,20d-tetrahomo-2,5,6,7-tetranor-3,4-didehydro-4,8-inter-m-phenylene-PGI₂
(3E)-16-methyl-20a,20b,20c,20d,20e-pentahomo-2,5,6,7-tetranor-3,4-didehydro-4,8-inter-m-phenylene-PGI₂
(3E)-16-methyl-20a,20b,20c,20d,20e,20f-hexahomo-2,5,6,7-tetranor-3,4-didehydro-4,8-inter-m-phenylene-PGI₂
(3E)-16-methyl-20a,20b,20c,20d,20e,20f,20g-heptahomo-2,5,6,7-tetranor-3,4-didehydro-4,8-inter-m-phenylene-PGI₂
(3E)-17-methyl-2,5,6,7,19,20-hexanor-3,4-didehydro-4,8-inter-m-phenylene-PGI₂
(3E)-17-methyl-2,5,6,7,20-pentanor-3,4-didehydro-4,8-inter-m-phenylene-PGI₂
(3E)-17-methyl-2,5,6,7-tetranor-3,4-didehydro-4,8-inter-m-phenylene-PGI₂
(3E)-17-methyl-20a-homo-2,5,6,7-tetranor-3,4-didehydro-4,8-inter-m-phenylene-PGI₂
(3E)-17-methyl-20a,20b-dihomo-2,5,6,7-tetranor-3,4-didehydro-4,8-inter-m-phenylene-PGI₂
(3E)-17-methyl-20a,20b,20c-trihomo-2,5,6,7-tetranor-3,4-didehydro-4,8-inter-m-phenylene-PGI₂
(3E)-17-methyl-20a,20b,20c,20d-tetrahomo-2,5,6,7-tetranor-3,4-didehydro-4,8-inter-m-phenylene-PGI₂
(3E)-17-methyl-20a,20b,20c,20d,20e-pentahomo-2,5,6,7-tetranor-3,4-didehydro-4,8-inter-m-phenylene-PGI₂
(3E)-17-methyl-20a,20b,20c,20d,20e,20f-hexahomo-2,5,6,7-tetranor-3,4-didehydro-4,8-inter-m-phenylene-PGI₂
(3E)-17-methyl-20a,20b,20c,20d,20e,20f,20g-heptahomo-2,5,6,7-tetranor-3,4-didehydro-4,8-inter-m-phenylene-PGI₂
(3E)-18-methyl-2,5,6,7,20-pentanor-3,4-didehydro-4,8-inter-m-phenylene-PGI₂
(3E)-18-methyl-2,5,6,7-tetranor-3,4-didehydro-4,8-inter-m-phenylene-PGI₂
(3E)-18-methyl-20a-homo-2,5,6,7-tetranor-3,4-didehydro-4,8-inter-m-phenylene-PGI₂
(3E)-18-methyl-20a,20b-dihomo-2,5,6,7-tetranor-3,4-didehydro-4,8-inter-m-phenylene-PGI₂
(3E)-18-methyl-20a,20b,20c-trihomo-2,5,6,7-tetranor-3,4-didehydro-4,8-inter-m-phenylene-PGI₂
(3E)-18-methyl-20a,20b,20c,20d-tetrahomo-2,5,6,7-tetranor-3,4-didehydro-4,8-inter-m-phenylene-PGI₂
(3E)-18-methyl-20a,20b,20c,20d,20e-pentahomo-2,5,6,7-tetranor-3,4-didehydro-4,8-inter-m-phenylene-PGI₂
(3E)-18-methyl-20a,20b,20c,20d,20e,20f-hexahomo-2,5,6,7-tetranor-3,4-didehydro-4,8-inter-m-phenylene-PGI₂

(3E)-18-methyl-20a,20b,20c,20d,20e,20f,20g-heptahomo-2,5,6,7-tetranor-3,4-didehydro-4,8-inter-m-phenylene-PGI$_2$
(3E)-19-methyl-2,5,6,7-tetranor-3,4-didehydro-4,8-inter-m-phenylene-PGI$_2$
(3E)-19-methyl-20a-homo-2,5,6,7-tetranor-3,4-didehydro-4,8-inter-m-phenylene-PGI$_2$
(3E)-19-methyl-20a,20b-dihomo-2,5,6,7-tetranor-3,4-didehydro-4,8-inter-m-phenylene-PGI$_2$
(3E)-19-methyl-20a,20b,20c-trihomo-2,5,6,7-tetranor-3,4-didehydro-4,8-inter-m-phenylene-PGI$_2$
(3E)-19-methyl-20a,20b,20c,20d-tetrahomo-2,5,6,7-tetranor-3,4-didehydro-4,8-inter-m-phenylene-PGI$_2$
(3E)-19-methyl-20a,20b,20c,20d,20e-pentahomo-2,5,6,7-tetranor-3,4-didehydro-4,8-inter-m-phenylene-PGI$_2$
(3E)-19-methyl-20a,20b,20c,20d,20e,20f-hexahomo-2,5,6,7-tetranor-3,4-didehydro-4,8-inter-m-phenylene-PGI$_2$
(3E)-19-methyl-20a,20b,20c,20d,20e,20f,20g-heptahomo-2,5,6,7-tetranor-3,4-didehydro-4,8-inter-m-phenylene-PGI$_2$
(3E)-20-methyl-20a-homo-2,5,6,7-tetranor-3,4-didehydro-4,8-inter-m-phenylene-PGI$_2$
(3E)-20-methyl-20a,20b-dihomo-2,5,6,7-tetranor-3,4-didehydro-4,8-inter-m-phenylene-PGI$_2$
(3E)-20-methyl-20a,20b,20c-trihomo-2,5,6,7-tetranor-3,4-didehydro-4,8-inter-m-phenylene-PGI$_2$
(3E)-20-methyl-20a,20b,20c,20d-tetrahomo-2,5,6,7-tetranor-3,4-didehydro-4,8-inter-m-phenylene-PGI$_2$
(3E)-20-methyl-20a,20b,20c,20d,20e-pentahomo-2,5,6,7-tetranor-3,4-didehydro-4,8-inter-m-phenylene-PGI$_2$
(3E)-20-methyl-20a,20b,20c,20d,20e,20f-hexahomo-2,5,6,7-tetranor-3,4-didehydro-4,8-inter-m-phenylene-PGI$_2$
(3E)-20-methyl-20a,20b,20c,20d,20e,20f,20g-heptahomo-2,5,6,7-tetranor-3,4-didehydro-4,8-inter-m-phenylene-PGI$_2$
(3E)-20a-methyl-20a,20b-dihomo-2,5,6,7-tetranor-3,4-didehydro-4,8-inter-m-phenylene-PGI$_2$
(3E)-20a-methyl-20a,20b,20c-trihomo-2,5,6,7-tetranor-3,4-didehydro-4,8-inter-m-phenylene-PGI$_2$
(3E)-20a-methyl-20a,20b,20c,20d-tetrahomo-2,5,6,7-tetranor-3,4-didehydro-4,8-inter-m-phenylene-PGI$_2$
(3E)-20a-methyl-20a,20b,20c,20d,20e-pentahomo-2,5,6,7-tetranor-3,4-didehydro-4,8inter-m-phenylene-PGI$_2$
(3E)-20a-methyl-20a,20b,20c,20d,20e,20f-hexahomo-2,5,6,7-tetranor-3,4-didehydro-4,8-inter-m-phenylene-PGI$_2$
(3E)-20a-methyl-20a,20b,20c,20d,20e,20f,20g-heptahomo-2,5,6,7-tetranor-3,4-didehydro-4,8-inter-m-phenylene-PGI$_2$
(3E)-20b-methyl-20a,20b,20c-trihomo-2,5,6,7-tetranor-3,4-didehydro-4,8-inter-m-phenylene-PGI$_2$
(3E)-20b-methyl-20a,20b,20c,20d-tetrahomo-2,5,6,7-tetranor-3,4-didehydro-4,8-inter-m-phenylene-PGI$_2$
(3E)-20b-methyl-20a,20b,20c,20d,20e-pentahomo-2,5,6,7-tetranor-3,4-didehydro-4,8-inter-m-phenylene-PGI$_2$
(3E)-20b-methyl-20a,20b,20c,20d,20e,20f-hexahomo-2,5,6,7-tetranor-3,4-didehydro-4,8-inter-m-phenylene-PGI$_2$
(3E)-20b-methyl-20a,20b,20c,20d,20e,20f,20g-heptahomo-2,5,6,7-tetranor-3,4-didehydro-4,8-inter-m-phenylene-PGI$_2$
(3E)-20c-methyl-20a,20b,20c,20d-tetrahomo-2,5,6,7-tetranor-3,4-didehydro-4,8-inter-m-phenylene-PGI$_2$
(3E)-20c-methyl-20a,20b,20c,20d,20e-pentahomo-2,5,6,7-tetranor-3,4-didehydro-4,8-inter-m-phenylene-PGI$_2$
(3E)-20c-methyl-20a,20b,20c,20d,20e,20f-hexahomo-2,5,6,7-tetranor-3,4-didehydro-4,8-inter-m-phenylene-PGI$_2$
(3E)-20c-methyl-20a,20b,20c,20d,20e,20f,20g-heptahomo-2,5,6,7-tetranor-3,4-didehydro-4,8-inter-m-phenylene-PGI$_2$
(3E)-20d-methyl-20a,20b,20c,20d,20e-pentahomo-2,5,6,7-tetranor-3,4-didehydro-4,8-inter-m-phenylene-PGI$_2$
(3E)-20d-methyl-20a,20b,20c,20d,20e,20f-hexahomo-2,5,6,7-tetranor-3,4-didehydro-4,8-inter-m-phenylene-PGI$_2$
(3E)-20d-methyl-20a,20b,20c,20d,20e,20f,20g-heptahomo-2,5,6,7-tetranor-3,4-didehydro-4,8-inter-m-phenylene-PGI$_2$
(3E)-20e-methyl-20a,20b,20c,20d,20e,20f-hexahomo-2,5,6,7-tetranor-3,4-didehydro-4,8-inter-m-phenylene-PGI$_2$
(3E)-20e-methyl-20a,20b,20c,20d,20e,20f,20g-heptahomo-2,5,6,7-tetranor-3,4-didehydro-4,8-inter-m-phenylene-PGI$_2$
(3E)-20f-methyl-20a,20b,20c,20d,20e,20f,20g-heptahomo-2,5,6,7-tetranor-3,4-didehydro-4,8-inter-m-phenylene-PGI$_2$
(3E)-16,16-dimethyl-2,5,6,7,18,19,20-heptanor-3,4-didehydro-4,8-inter-m-phenylene-PGI$_2$
(3E)-16,16-dimethyl-2,5,6,7,19,20-hexanor-3,4-didehydro-4,8-inter-m-phenylene-PGI$_2$
(3E)-16,16-dimethyl-2,5,6,7,20-pentanor-3,4-didehydro-4,8-inter-m-phenylene-PGI$_2$
(3E)-16,16-dimethyl-2,5,6,7-tetranor-3,4-didehydro-4,8-inter-m-phenylene-PGI$_2$
(3E)-16,16-dimethyl-20a-homo-2,5,6,7-tetranor-3,4-didehydro-4,8-inter-m-phenylene-PGI$_2$
(3E)-16,16-dimethyl-20a,20b-dihomo-2,5,6,7-tetranor-3,4-didehydro-4,8-inter-m-phenylene-PGI$_2$
(3E)-16,16-dimethyl-20a,20b,20c-trihomo-2,5,6,7-tetranor-3,4-didehydro-4,8-inter-m-phenylene-PGI$_2$
(3E)-16,16-dimethyl-20a,20b,20c,20d-tetrahomo-2,5,6,7-tetranor-3,4-didehydro-4,8-inter-m-phenylene-PGI$_2$
(3E)-16,16-dimethyl-20a,20b,20c,20d,20e-pentahomo-2,5,6,7-tetranor-3,4-didehydro-4,8-inter-m-phenylene-PGI$_2$
(3E)-16,16-dimethyl-20a,20b,20c,20d,20e,20f-hexahomo-2,5,6,7-tetranor-3,4-didehydro-4,8-inter-m-phenylene-PGI$_2$
(3E)-16,16-dimethyl-20a,20b,20c,20d,20e,20f,20g-heptahomo-2,5,6,7-tetranor-3,4-didehydro-4,8-inter-m-phenylene-PGI$_2$
(3E)-17,17-dimethyl-2,5,6,7,19,20-hexanor-3,4-didehydro-4,8-inter-m-phenylene-PGI$_2$
(3E)-17,17-dimethyl-2,5,6,7,20-pentanor-3,4-didehydro-4,8-inter-m-phenylene-PGI$_2$
(3E)-17,17-dimethyl-2,5,6,7-tetranor-3,4-didehydro-4,8-inter-m-phenylene-PGI$_2$ (3E)-17,17-dimethyl-20a-homo-2,5,6,7-tetranor-3,4-didehydro-4,8-inter-m-phenylene-PGI$_2$
(3E)-17,17-dimethyl-20a,20b-dihomo-2,5,6,7-tetranor-3,4-didehydro-4,8-inter-m-phenylene-PGI$_2$
(3E)-17,17-dimethyl-20a,20b,20c-trihomo-2,5,6,7-tetranor-3,4-didehydro-4,8-inter-m-phenylene-PGI$_2$
(3E)-17,17-dimethyl-20a,20b,20c,20d-tetrahomo-2,5,6,7-tetranor-3,4-didehydro-4,8-inter-m-phenylene-PGI$_2$
(3E)-17,17-dimethyl-20a,20b,20c,20d,20e-pentahomo-2,5,6,7-tetranor-3,4-didehydro-4,8-inter-m-phenylene-PGI$_2$
(3E)-17,17-dimethyl-20a,20b,20c,20d,20e,20f-hexahomo-2,5,6,7-tetranor-3,4-didehydro-4,8-inter-m-phenylene-PGI$_2$
(3E)-17,17-dimethyl-20a,20b,20c,20d,20e,20f,20g-heptahomo-2,5,6,7-tetranor-3,4-didehydro-4,8-inter-m-phenylene-PGI$_2$
(3E)-18,18-dimethyl-2,5,6,7,20-pentanor-3,4-didehydro-4,8-inter-m-phenylene-PGI$_2$
(3E)-18,18-dimethyl-2,5,6,7-tetranor-3,4-didehydro-4,8-inter-m-phenylene-PGI$_2$
(3E)-18,18-dimethyl-20a-homo-2,5,6,7-tetranor-3,4-didehydro-4,8-inter-m-phenylene-PGI$_2$
(3E)-18,18-dimethyl-20a,20b-dihomo-2,5,6,7-tetranor-3,4-didehydro-4,8-inter-m-phenylene-PGI$_2$
(3E)-18,18-dimethyl-20a,20b,20c-trihomo-2,5,6,7-tetranor-3,4-didehydro-4,8-inter-m-phenylene-PGI$_2$
(3E)-18,18-dimethyl-20a,20b,20c,20d-tetrahomo-2,5,6,7-tetranor-3,4-didehydro-4,8-inter-m-phenylene-PGI$_2$
(3E)-18,18-dimethyl-20a,20b,20c,20d,20e-pentahomo-2,5,6,7-tetranor-3,4-didehydro-4,8-inter-m-phenylene-PGI$_2$
(3E)-18,18-dimethyl-20a,20b,20c,20d,20e,20f-hexahomo-2,5,6,7-tetranor-3,4-didehydro-4,8-inter-m-phenylene-PGI$_2$
(3E)-18,18-dimethyl-20a,20b,20c,20d,20e,20f,20g-heptahomo-2,5,6,7-tetranor-3,4-didehydro-4,8-inter-m-phenylene-PGI$_2$
(3E)-19,19-dimethyl-2,5,6,7-tetranor-3,4-didehydro-4,8-inter-m-phenylene-PGI$_2$
(3E)-19,19-dimethyl-20a-homo-2,5,6,7-tetranor-3,4-didehydro-4,8-inter-m-phenylene-PGI$_2$
(3E)-19,19-dimethyl-20a,20b-dihomo-2,5,6,7-tetranor-3,4-didehydro-4,8-inter-m-phenylene-PGI$_2$
(3E)-19,19-dimethyl-20a,20b,20c-trihomo-2,5,6,7-tetranor-3,4-didehydro-4,8-inter-m-phenylene-PGI$_2$
(3E)-19,19-dimethyl-20a,20b,20c,20d-tetrahomo-2,5,6,7-tetranor-3,4-didehydro-4,8-inter-m-phenylene-PGI$_2$
(3E)-19,19-dimethyl-20a,20b,20c,20d,20e-pentahomo-2,5,6,7-tetranor-3,4-didehydro-4,8-inter-m-phenylene-PGI$_2$
(3E)-19,19-dimethyl-20a,20b,20c,20d,20e,20f-hexahomo-2,5,6,7-tetranor-3,4-didehydro-4,8-inter-m-phenylene-PGI$_2$
(3E)-19,19-dimethyl-20a,20b,20c,20d,20e,20f,20g-heptahomo-2,5,6,7-tetranor-3,4-didehydro-4,8-inter-m-phenylene-PGI$_2$
(3E)-20,20-dimethyl-20a-homo-2,5,6,7-tetranor-3,4-didehydro-4,8-inter-m-phenylene-PGI$_2$
(3E)-20,20-dimethyl-20a,20b-dihomo-2,5,6,7-tetranor-3,4-didehydro-4,8-inter-m-phenylene-PGI$_2$
(3E)-20,20-dimethyl-20a,20b,20c-trihomo-2,5,6,7-tetranor-3,4-didehydro-4,8-inter-m-phenylene-PGI$_2$
(3E)-20,20-dimethyl-20a,20b,20c,20d-tetrahomo-2,5,6,7-tetranor-3,4-didehydro-4,8-inter-m-phenylene-PGI$_2$
(3E)-20,20-dimethyl-20a,20b,20c,20d,20e-pentahomo-2,5,6,7-tetranor-3,4-didehydro-4,8-inter-m-phenylene-PGI$_2$
(3E)-20,20-dimethyl-20a,20b,20c,20d,20e,20f-hexahomo-2,5,6,7-tetranor-3,4-didehydro-4,8-inter-m-phenylene-PGI$_2$
(3E)-20,20-dimethyl-20a,20b,20c,20d,20e,20f,20g-heptahomo-2,5,6,7-tetranor-3,4-didehydro-4,8-inter-m-phenylene-PGI$_2$
(3E)-20a,20a-dimethyl-20a,20b-dihomo-2,5,6,7-tetranor-3,4-didehydro-4,8-inter-m-phenylene-PGI$_2$
(3E)-20a,20a-dimethyl-20a,20b,20c-trihomo-2,5,6,7-tetranor-3,4-didehydro-4,8-inter-m-phenylene-PGI$_2$
(3E)-20a,20a-dimethyl-20a,20b,20c,20d-tetrahomo-2,5,6,7-tetranor-3,4-didehydro-4,8-inter-m-phenylene-PGI$_2$
(3E)-20a,20a-dimethyl-20a,20b,20c,20d,20e-pentahomo-2,5,6,7-tetranor-3,4-didehydro-4,8-inter-m-phenylene-PGI$_2$
(3E)-20a,20a-dimethyl-20a,20b,20c,20d,20e,20f-hexahomo-2,5,6,7-tetranor-3,4-didehydro-4,8-inter-m-phenylene-PGI$_2$
(3E)-20a,20a-dimethyl-20a,20b,20c,20d,20e,20f,20g-heptahomo-2,5,6,7-tetranor-3,4-didehydro-4,8-inter-m-phenylene-PGI$_2$
(3E)-20b,20b-dimethyl-20a,20b,20c-trihomo-2,5,6,7-tetranor-3,4-didehydro-4,8-inter-m-phenylene-PGI$_2$
(3E)-20b,20b-dimethyl-20a,20b,20c,20d-tetrahomo-2,5,6,7-tetranor-3,4-didehydro-4,8-inter-m-phenylene-PGI$_2$
(3E)-20b,20b-dimethyl-20a,20b,20c,20d,20e-pentahomo-2,5,6,7-tetranor-3,4-didehydro-4,8-inter-m-phenylene-PGI$_2$
(3E)-20b,20b-dimethyl-20a,20b,20c,20d,20e,20f-hexahomo-2,5,6,7-tetranor-3,4-didehydro-4,8-inter-m-phenylene-PGI$_2$
(3E)-20b,20b-dimethyl-20a,20b,20c,20d,20e,20f,20g-heptahomo-2,5,6,7-tetranor-3,4-didehydro-4,8-inter-m-phenylene-PGI$_2$
(3E)-20c,20c-dimethyl-20a,20b,20c,20d-tetrahomo-2,5,6,7-tetranor-3,4-didehydro-4,8-inter-m-phenylene-PGI$_2$
(3E)-20c,20c-dimethyl-20a,20b,20c,20d,20e-pentahomo-2,5,6,7-tetranor-3,4-didehydro-4,8-inter-m-phenylene-PGI$_2$
(3E)-20c,20c-dimethyl-20a,20b,20c,20d,20e,20f-hexahomo-2,5,6,7-tetranor-3,4-didehydro-4,8-inter-m-phenylene-PGI$_2$
(3E)-20c,20c-dimethyl-20a,20b,20c,20d,20e,20f,20g-heptahomo-2,5,6,7-tetranor-3,4-didehydro-4,8-inter-m-phenylene-PGI$_2$
(3E)-20d,20d-dimethyl-20a,20b,20c,20d,20e-pentahomo-2,5,6,7-tetranor-3,4-didehydro-4,8-inter-m-phenylene-PGI$_2$
(3E)-20d,20d-dimethyl-20a,20b,20c,20d,20e,20f-hexahomo-2,5,6,7-tetranor-3,4-didehydro-4,8-inter-m-phenylene-PGI$_2$
(3E)-20d,20d-dimethyl-20a,20b,20c,20d,20e,20f,20g-heptahomo-2,5,6,7-tetranor-3,4-didehydro-4,8-inter-m-phenylene-PGI$_2$ (3E)-20e,20e-dimethyl-20a,20b,20c,20d,20e,20f-hexahomo-2,5,6,7-tetranor-3,4-didehydro-4,8-inter-m-phenylene-PGI$_2$ (3E)-20e,20e-dimethyl-20a,20b,20c,20d,20e,20f,20g-heptahomo-2,5,6,7-tetranor-3,4-didehydro-4,8-inter-m-phenylene-PGI$_2$ (3E)-20f,20f-dimethyl-20a,20b,20c,20d,20e,20f,20g-heptahomo-2,5,6,7-tetranor-3,4-didehydro-4,8-inter-m-phenylene-PGI$_2$ (3E)-16,16,17-trimethyl-2,5,6,7,19,20-hexanor-3,4-didehydro-4,8-inter-m-phenylene-PGI$_2$ (3E)-16,16,17-trimethyl-2,5,6,7,20-pentanor-3,4-didehydro-4,8-inter-m-phenylene-PGI$_2$ (3E)-16,16,17-trimethyl-2,5,6,7-tetranor-3,4-didehydro-4,8-inter-m-phenylene-PGI$_2$ (3E)-16,16,17-trimethyl-20a-homo-2,5,6,7-tetranor-3,4-didehydro-4,8-inter-m-phenylene-PGI$_2$ (3E)-16,16,17-trimethyl-20a,20b-dihomo-2,5,6,7-tetranor-3,4-didehydro-4,8-inter-m-phenylene-PGI$_2$ (3E)-16,16,17-trimethyl-20a,20b,20c-trihomo-2,5,6,7-tetranor-3,4-didehydro-4,8-inter-m-phenylene-PGI$_2$ (3E)-16,16,17-trimethyl-20a,20b,20c,20d-tetrahomo-2,5,6,7-tetranor-3,4-didehydro-4,8-inter-m-phenylene-PGI$_2$ (3E)-16,16,17-trimethyl-20a,20b,20c,20d,20e-pentahomo-2,5,6,7-tetranor-3,4-didehydro-4,8-inter-m-phenylene-PGI$_2$ (3E)-16,16,17-trimethyl-20a,20b,20c,20d,20e,20f-hexahomo-2,5,6,7-tetranor-3,4-didehydro-4,8-inter-m-phenylene-PGI$_2$.

The compounds wherein R$_2$ is —Z—Ar are illustrated by but not limited to:

(3E)-15-phenyl-2,5,6,7,16,17,18,19,20-nonanor-3,4-didehydro-4,8-inter-m-phenylene-PGI$_2$ (3E)-15-(o-chlorophenyl)-2,5,6,7,16,17,18,19,20-nonanor-3,4-didehydro-4,8-inter-m-phenylene-PGI$_2$ (3E)-15-(m-chlorophenyl)-2,5,6,7,16,17,18,19,20-nonanor-3,4-didehydro-4,8-inter-m-phenylene-PGI$_2$ (3E)-15-(p-chlorophenyl)-2,5,6,7,16,17,18,19,20-nonanor-3,4-didehydro-4,8-inter-m-phenylene-PGI$_2$ (3E)-15-(o-bromophenyl)-2,5,6,7,16,17,18,19,20-nonanor-3,4-didehydro-4,8-inter-m-phenylene-PGI$_2$ (3E)-15-(m-bromophenyl)-2,5,6,7,16,17,18,19,20-nonanor-3,4-didehydro-4,8-inter-m-phenylene-PGI$_2$ (3E)-15-(p-bromophenyl)-2,5,6,7,16,17,18,19,20-nonanor-3,4-didehydro-4,8-inter-m-phenylene-PGI$_2$ (3E)-15-(o-fluorophenyl)-2,5,6,7,16,17,18,19,20-nonanor-3,4-didehydro-4,8-inter-m-phenylene-PGI$_2$ (3E)-15-(m-fluorophenyl)-2,5,6,7,16,17,18,19,20-nonanor-3,4-didehydro-4,8-inter-m-phenylene-PGI$_2$ (3E)-15-(p-fluorophenyl)-2,5,6,7,16,17,18,19,20-nonanor-3,4-didehydro-4,8-inter-m-phenylene-PGI$_2$ (3E)-15-(o-methylphenyl)-2,5,6,7,16,17,18,19,20-nonanor-3,4-didehydro-4,8-inter-m-phenylene-PGI$_2$ (3E)-15-(m-methylphenyl)-2,5,6,7,16,17,18,19,20-nonanor-3,4-didehydro-4,8-inter-m-phenylene-PGI$_2$ (3E)-15-(p-methylphenyl)-2,5,6,7,16,17,18,19,20-nonanor-3,4-didehydro-4,8-inter-m-phenylene-PGI$_2$ (3E)-15-(p-trifluoromethylphenyl)-2,5,6,7,16,17,18,19,20-nonanor-3,4-didehydro-4,8-inter-m-phenylene-PGI$_2$ (3E)-15-(p-nitrophenyl)-2,5,6,7,16,17,18,19,20-nonanor-3,4-didehydro-4,8-inter-m-phenylene-PGI$_2$ (3E)-15-(p-cyanophenyl)-2,5,6,7,16,17,18,19,20-nonanor-3,4-didehydro-4,8-inter-m-phenylene-PGI$_2$ (3E)-15-(2,4-dichlorophenyl)-2,5,6,7,16,17,18,19,20-nonanor-3,4-didehydro-4,8-inter-m-phenylene-PGI$_2$ (3E)-15-(3,4-dimethylphenyl)-2,5,6,7,16,17,18,19,20-nonanor-3,4-didehydro-4,8-inter-m-phenylene-PGI$_2$ (3E)-16-phenyl-2,5,6,7,17,18,19,20-octanor-3,4-didehydro-4,8-inter-m-phenylene-PGI$_2$ (3E)-16-(o-chlorophenyl)-2,5,6,7,17,18,19,20-octanor-3,4-didehydro-4,8-inter-m-phenylene-PGI$_2$ (3E)-16-(m-chlorophenyl)-2,5,6,7,17,18,19,20-octanor-3,4-didehydro-4,8-inter-m-phenylene-PGI$_2$ (3E)-16-(p-chlorophenyl)-2,5,6,7,17,18,19,20-octanor-3,4-didehydro-4,8-inter-m-phenylene-PGI$_2$ (3E)-16-(o-bromophenyl)-2,5,6,7,17,18,19,20-octanor-3,4-didehydro-4,8-inter-m-phenylene-PGI$_2$ (3E)-16-(m-bromophenyl)-2,5,6,7,17,18,19,20-octanor-3,4-didehydro-4,8-inter-m-phenylene-PGI$_2$ (3E)-16-(p-bromophenyl)-2,5,6,7,17,18,19,20-octanor-3,4-didehydro-4,8-inter-m-phenylene-PGI$_2$ (3E)-16-(o-fluorophenyl)-2,5,6,7,17,18,19,20-octanor-3,4-didehydro-4,8-inter-m-phenylene-PGI$_2$ (3E)-16-(m-fluorophenyl)-2,5,6,7,17,18,19,20-octanor-3,4-didehydro-4,8-inter-m-phenylene-PGI$_2$ (3E)-16-(p-fluorophenyl)-2,5,6,7,17,18,19,20-octanor-3,4-didehydro-4,8-inter-m-phenylene-PGI$_2$ (3E)-16-(o-methylphenyl)-2,5,6,7,17,18,19,20-octanor-3,4-didehydro-4,8-inter-m-phenylene-PGI$_2$ (3E)-16-(m-methylphenyl)-2,5,6,7,17,18,19,20-octanor-3,4-didehydro-4,8-inter-m-phenylene-PGI$_2$ (3E)-16-(p-methylphenyl)-2,5,6,7,17,18,19,20-octanor-3,4-didehydro-4,8-inter-m-phenylene-PGI$_2$ (3E)-16-(p-trifluoromethylphenyl)-2,5,6,7,17,18,19,20-octanor-3,4-didehydro-4,8-inter-m-phenylene-PGI$_2$ (3E)-16-(p-nitrophenyl)-2,5,6,7,17,18,19,20-octanor-3,4-didehydro-4,8-inter-m-phenylene-PGI$_2$ (3E)-16-(p-cyanophenyl)-2,5,6,7,17,18,19,20-octanor-3,4-didehydro-4,8-inter-m-phenylene-PGI$_2$ (3E)-16-(2,4-dichlorophenyl)-2,5,6,7,17,18,19,20-octanor-3,4-didehydro-4,8-inter-m-phenylene-PGI$_2$ (3E)-16-(3,4-dimethylphenyl)-2,5,6,7,17,18,19,20-octanor-3,4-didehydro-4,8-inter-m-phenylene-PGI$_2$ (3E)-16-phenyl-2,5,6,7,18,19,20-heptanor-3,4-didehydro-4,8-inter-m-phenylene-PGI$_2$ (3E)-16-(o-chlorophenyl)-2,5,6,7,18,19,20-heptanor-3,4-didehydro-4,8-inter-m-phenylene-PGI$_2$ (3E)-16-(m-chlorophenyl)-2,5,6,7,18,19,20-heptanor-3,4-didehydro-4,8-inter-m-phenylene-PGI$_2$ (3E)-16-(p-chlorophenyl)-2,5,6,7,18,19,20-heptanor-3,4-didehydro-4,8-inter-m-phenylene-PGI$_2$ (3E)-16-(o-bromophenyl)-2,5,6,7,18,19,20-heptanor-3,4-didehydro-4,8-inter-m-phenylene-PGI$_2$ (3E)-16-(m-bromophenyl)-2,5,6,7,18,19,20-heptanor-3,4-didehydro-4,8-inter-m-phenylene-PGI$_2$ (3E)-16-(p-bromophenyl)-2,5,6,7,18,19,20-heptanor-3,4-didehydro-4,8-inter-m-phenylene-PGI$_2$ (3E)-16-(o-fluorophenyl)-2,5,6,7,18,19,20-heptanor-3,4-didehydro-4,8-inter-m-phenylene-PGI$_2$ (3E)-16-(m-fluorophenyl)-2,5,6,7,18,19,20-heptanor-3,4-didehydro-4,8-inter-m-phenylene-PGI$_2$ (3E)-16-(p-fluorophenyl)-2,5,6,7,18,19,20-heptanor-3,4-didehydro-4,8-inter-m-phenylene-PGI$_2$ (3E)-16-(o-methylphenyl)-2,5,6,7,18,19,20-heptanor-3,4-didehydro-4,8-inter-m-phenylene-PGI$_2$ (3E)-16-(m-methylphenyl)-2,5,6,7,18,19,20-heptanor-3,4-didehydro-4,8-inter-m-phenylene-PGI₂
(3E)-16-(p-methylphenyl)-2,5,6,7,18,19,20-heptanor-3,4-didehydro-4,8-inter-m-phenylene-PGI₂
(3E)-16-(p-trifluoromethylphenyl)-2,5,6,7,18,19,20-heptanor-3,4-didehydro-4,8-inter-m-phenylene-PGI₂
(3E)-16-(p-nitrophenyl)-2,5,6,7,18,19,20-heptanor-3,4-didehydro-4,8-inter-m-phenylene-PGI₂
(3E)-16-(p-cyanophenyl)-2,5,6,7,18,19,20-heptanor-3,4-didehydro-4,8-inter-m-phenylene-PGI₂
(3E)-16-(2,4-dichlorophenyl)-2,5,6,7,18,19,20-heptanor-3,4-didehydro-4,8-inter-m-phenylene-PGI₂
(3E)-16-(3,4-dimethylphenyl)-2,5,6,7,18,19,20-heptanor-3,4-didehydro-4,8-inter-m-phenylene-PGI₂
(3E)-16-methyl-16-phenyl-2,5,6,7,18,19,20-heptanor-3,4-didehydro-4,8-inter-m-phenylene-PGI₂
(3E)-16-(o-chlorophenyl)-16-methyl-2,5,6,7,18,19,20-heptanor-3,4-didehydro-4,8-inter-m-phenylene-PGI₂
(3E)-16-(m-chlorophenyl)-16-methyl-2,5,6,7,18,19,20-heptanor-3,4-didehydro-4,8-inter-m-phenylene-PGI₂
(3E)-16-(p-chlorophenyl)-16-methyl-2,5,6,7,18,19,20-heptanor-3,4-didehydro-4,8-inter-m-phenylene-PGI₂
(3E)-16-(o-bromophenyl)-16-methyl-2,5,6,7,18,19,20-heptanor-3,4-didehydro-4,8-inter-m-phenylene-PGI₂
(3E)-16-(m-bromophenyl)-16-methyl-2,5,6,7,18,19,20-heptanor-3,4-didehydro-4,8-inter-m-phenylene-PGI₂
(3E)-16-(p-bromophenyl)-16-methyl-2,5,6,7,18,19,20-heptanor-3,4-didehydro-4,8-inter-m-phenylene-PGI₂
(3E)-16-(o-fluorophenyl)-16-methyl-2,5,6,7,18,19,20-heptanor-3,4-didehydro-4,8-inter-m-phenylene-PGI₂
(3E)-16-(m-fluorophenyl)-16-methyl-2,5,6,7,18,19,20-heptanor-3,4-didehydro-4,8-inter-m-phenylene-PGI₂
(3E)-16-(p-fluorophenyl)-16-methyl-2,5,6,7,18,19,20-heptanor-3,4-didehydro-4,8-inter-m-phenylene-PGI₂
(3E)-16-methyl-16-(o-methylphenyl)-2,5,6,7,18,19,20-heptanor-3,4-didehydro-4,8-inter-m-phenylene-PGI₂
(3E)-16-methyl-16-(m-methylphenyl)-2,5,6,7,18,19,20-heptanor-3,4-didehydro-4,8-inter-m-phenylene-PGI₂
(3E)-16-methyl-16-(p-methylphenyl)-2,5,6,7,18,19,20-heptanor-3,4-didehydro-4,8-inter-m-phenylene-PGI₂
(3E)-16-methyl-16-(p-trifluoromethylphenyl)-2,5,6,7,18,19,20-heptanor-3,4-didehydro-4,8-inter-m-phenylene-PGI₂
(3E)-16-methyl-16-(p-nitrophenyl)-2,5,6,7,18,19,20-heptanor-3,4-didehydro-4,8-inter-m-phenylene-PGI₂
(3E)-16-(p-cyanophenyl)-16-methyl-2,5,6,7,18,19,20-heptanor-3,4-didehydro-4,8-inter-m-phenylene-PGI₂
(3E)-16-(2,4-dichlorophenyl)-16-methyl-2,5,6,7,18,19,20-heptanor-3,4-didehydro-4,8-inter-m-phenylene-PGI₂
(3E)-16-(3,4-dimethylphenyl)-16-methyl-2,5,6,7,18,19,20-heptanor-3,4-didehydro-4,8-inter-m-phenylene-PGI₂
(3E)-17-phenyl-2,5,6,7,18,19,20-heptanor-3,4-didehydro-4,8-inter-m-phenylene-PGI₂
(3E)-17-(o-chlorophenyl)-2,5,6,7,18,19,20-heptanor-3,4-didehydro-4,8-inter-m-phenylene-PGI₂
(3E)-17-(m-chlorophenyl)-2,5,6,7,18,19,20-heptanor-3,4-didehydro-4,8-inter-m-phenylene-PGI₂
(3E)-17-(p-chlorophenyl)-2,5,6,7,18,19,20-heptanor-3,4-didehydro-4,8-inter-m-phenylene-PGI₂
(3E)-17-(o-bromophenyl)-2,5,6,7,18,19,20-heptanor-3,4-didehydro-4,8-inter-m-phenylene-PGI₂
(3E)-17-(m-bromophenyl)-2,5,6,7,18,19,20-heptanor-3,4-didehydro-4,8-inter-m-phenylene-PGI₂
(3E)-17-(p-bromophenyl)-2,5,6,7,18,19,20-heptanor-3,4-didehydro-4,8-inter-m-phenylene-PGI₂
(3E)-17-(o-fluorophenyl)-2,5,6,7,18,19,20-heptanor-3,4-didehydro-4,8-inter-m-phenylene-PGI₂
(3E)-17-(m-fluorophenyl)-2,5,6,7,18,19,20-heptanor-3,4-didehydro-4,8-inter-m-phenylene-PGI₂
(3E)-17-(p-fluorophenyl)-2,5,6,7,18,19,20-heptanor-3,4-didehydro-4,8-inter-m-phenylene-PGI₂
(3E)-17-(o-methylphenyl)-2,5,6,7,18,19,20-heptanor-3,4-didehydro-4,8-inter-m-phenylene-PGI₂
(3E)-17-(m-methylphenyl)-2,5,6,7,18,19,20-heptanor-3,4-didehydro-4,8-inter-m-phenylene-PGI₂
(3E)-17-(p-methylphenyl)-2,5,6,7,18,19,20-heptanor-3,4-didehydro-4,8-inter-m-phenylene-PGI₂
(3E)-17-(p-trifluoromethylphenyl)-2,5,6,7,18,19,20-heptanor-3,4-didehydro-4,8-inter-m-phenylene-PGI₂
(3E)-17-(p-nitrophenyl)-2,5,6,7,18,19,20-heptanor-3,4-didehydro-4,8-inter-m-phenylene-PGI₂
(3E)-17-(p-cyanophenyl)-2,5,6,7,18,19,20-heptanor-3,4-didehydro-4,8-inter-m-phenylene-PGI₂
(3E)-17-(2,4-dichlorophenyl)-2,5,6,7,18,19,20-heptanor-3,4-didehydro-4,8-inter-m-phenylene-PGI₂
(3E)-17-(3,4-dimethylphenyl)-2,5,6,7,18,19,20-heptanor-3,4-didehydro-4,8-inter-m-phenylene-PGI₂
(3E)-16-methyl-17-phenyl-2,5,6,7,18,19,20-heptanor-3,4-didehydro-4,8-inter-m-phenylene-PGI₂
(3E)-17-(o-chlorophenyl)-16-methyl-2,5,6,7,18,19,20-heptanor-3,4-didehydro-4,8-inter-m-phenylene-PGI₂
(3E)-17-(m-chlorophenyl)-16-methyl-2,5,6,7,18,19,20-heptanor-3,4-didehydro-4,8-inter-m-phenylene-PGI₂
(3E)-17-(p-chlorophenyl)-16-methyl-2,5,6,7,18,19,20-heptanor-3,4-didehydro-4,8-inter-m-phenylene-PGI₂
(3E)-17-(o-bromophenyl)-16-methyl-2,5,6,7,18,19,20-heptanor-3,4-didehydro-4,8-inter-m-phenylene-PGI₂
(3E)-17-(m-bromophenyl)-16-methyl-2,5,6,7,18,19,20-heptanor-3,4-didehydro-4,8-inter-m-phenylene-PGI₂
(3E)-17-(p-bromophenyl)-16-methyl-2,5,6,7,18,19,20-heptanor-3,4-didehydro-4,8-inter-m-phenylene-PGI₂
(3E)-17-(o-fluorophenyl)-16-methyl-2,5,6,7,18,19,20-heptanor-3,4-didehydro-4,8-inter-m-phenylene-PGI₂
(3E)-17-(m-fluorophenyl)-16-methyl-2,5,6,7,18,19,20-heptanor-3,4-didehydro-4,8-inter-m-phenylene-PGI₂
(3E)-17-(p-fluorophenyl)-16-methyl-2,5,6,7,18,19,20-heptanor-3,4-didehydro-4,8-inter-m-phenylene-PGI₂
(3E)-16-methyl-17-(o-methylphenyl)-2,5,6,7,18,19,20-heptanor-3,4-didehydro-4,8-inter-m-phenylene-PGI₂
(3E)-16-methyl-17-(m-methylphenyl)-2,5,6,7,18,19,20-heptanor-3,4-didehydro-4,8-inter-m-phenylene-PGI₂
(3E)-16-methyl-17-(p-methylphenyl)-2,5,6,7,18,19,20-heptanor-3,4-didehydro-4,8-inter-m-phenylene-PGI₂
(3E)-16-methyl-17-(p-trifluoromethylphenyl)-2,5,6,7,18,19,20-heptanor-3,4-didehydro-4,8-inter-m-phenylene-PGI₂
(3E)-16-methyl-17-(p-nitrophenyl)-2,5,6,7,18,19,20-heptanor-3,4-didehydro-4,8-inter-m-phenylene-PGI₂
(3E)-17-(p-cyanophenyl)-16-methyl-2,5,6,7,18,19,20-heptanor-3,4-didehydro-4,8-inter-m-phenylene-PGI₂
(3E)-17-(2,4-dichlorophenyl)-16-methyl-2,5,6,7,18,19,20-heptanor-3,4-didehydro-4,8-inter-m-phenylene-PGI₂

(3E)-17-(3,4-dimethylphenyl)-16-methyl-2,5,6,7,18,19,20-heptanor-3,4-didehydro-4,8-inter-m-phenylene-PGI$_2$
(3E)-16,16-dimethyl-17-phenyl-2,5,6,7,18,19,20-heptanor-3,4-didehydro-4,8-inter-m-phenylene-PGI$_2$
(3E)-17-(o-chlorophenyl)-16,16-dimethyl-2,5,6,7,18,19,20-heptanor-3,4-didehydro-4,8-inter-m-phenylene-PGI$_2$
(3E)-17-(m-chlorophenyl)-16,16-dimethyl-2,5,6,7,18,19,20-heptanor-3,4-didehydro-4,8-inter-m-phenylene-PGI$_2$
(3E)-17-(p-chlorophenyl)-16,16-dimethyl-2,5,6,7,18,19,20-heptanor-3,4-didehydro-4,8-inter-m-phenylene-PGI$_2$
(3E)-17-(o-bromophenyl)-16,16-dimethyl-2,5,6,7,18,19,20-heptanor-3,4-didehydro-4,8-inter-m-phenylene-PGI$_2$
(3E)-17-(m-bromophenyl)-16,16-dimethyl-2,5,6,7,18,19,20-heptanor-3,4-didehydro-4,8-inter-m-phenylene-PGI$_2$
(3E)-17-(p-bromophenyl)-16,16-dimethyl-2,5,6,7,18,19,20-heptanor-3,4-didehydro-4,8-inter-m-phenylene-PGI$_2$
(3E)-17-(o-fluorophenyl)-16,16-dimethyl-2,5,6,7,18,19,20-heptanor-3,4-didehydro-4,8-inter-m-phenylene-PGI$_2$
(3E)-17-(m-fluorophenyl)-16,16-dimethyl-2,5,6,7,18,19,20-heptanor-3,4-didehydro-4,8-inter-m-phenylene-PGI$_2$
(3E)-17-(p-fluorophenyl)-16,16-dimethyl-2,5,6,7,18,19,20-heptanor-3,4-didehydro-4,8-inter-m-phenylene-PGI$_2$
(3E)-16,16-dimethyl-17-(o-methylphenyl)-2,5,6,7,18,19,20-heptanor-3,4-didehydro-4,8-inter-m-phenylene-PGI$_2$
(3E)-16,16-dimethyl-17-(m-methylphenyl)-2,5,6,7,18,19,20-heptanor-3,4-didehydro-4,8-inter-m-phenylene-PGI$_2$
(3E)-16,16-dimethyl-17-(p-methylphenyl)-2,5,6,7,18,19,20-heptanor-3,4-didehydro-4,8-inter-m-phenylene-PGI$_2$
(3E)-16,16-dimethyl-17-(p-trifluoromethylphenyl)-2,5,6,7,18,19,20-heptanor-3,4-didehydro-4,8-inter-m-phenylene-PGI$_2$
(3E)-16,16-dimethyl-17-(p-nitrophenyl)-2,5,6,7,18,19,20-heptanor-3,4-didehydro-4,8-inter-m-phenylene-PGI$_2$
(3E)-17-(p-cyanophenyl)-16,16-dimethyl-2,5,6,7,18,19,20-heptanor-3,4-didehydro-4,8-inter-m-phenylene-PGI$_2$
(3E)-17-(2,4-dichlorophenyl)-16,16-dimethyl-2,5,6,7,18,19,20-heptanor-3,4-didehydro-4,8-inter-m-phenylene-PGI$_2$
(3E)-17-(3,4-dimethylphenyl)-16,16-dimethyl-2,5,6,7,18,19,20-heptanor-3,4-didehydro-4,8-inter-m-phenylene-PGI$_2$
(3E)-18-phenyl-2,5,6,7,19,20-hexanor-3,4-didehydro-4,8-inter-m-phenylene-PGI$_2$
(3E)-16-methyl-18-phenyl-2,5,6,7,19,20-hexanor-3,4-didehydro-4,8-inter-m-phenylene-PGI$_2$
(3E)-16,16-dimethyl-18-phenyl-2,5,6,7,19,20-hexanor-3,4-didehydro-4,8-inter-m-phenylene-PGI$_2$
(3E)-19-phenyl-2,5,6,7,20-pentanor-3,4-didehydro-4,8-inter-m-phenylene-PGI$_2$
(3E)-16-methyl-19-phenyl-2,5,6,7,20-pentanor-3,4-didehydro-4,8-inter-m-phenylene-PGI$_2$
(3E)-16,16-dimethyl-19-phenyl-2,5,6,7,20-pentanor-3,4-didehydro-4,8-inter-m-phenylene-PGI$_2$
(3E)-20-phenyl-2,5,6,7-tetranor-3,4-didehydro-4,8-inter-m-phenylene-PGI$_2$.

The compounds wherein $R_2$ is —Z—$R_3$ are illustrated by but not limited to:
(3E)-15-cyclopropyl-2,5,6,7,16,17,18,19,20-nonanor-3,4-didehydro-4,8-inter-m-phenylene-PGI$_2$
(3E)-15-cyclobutyl-2,5,6,7,16,17,18,19,20-nonanor-3,4-didehydro-4,8-inter-m-phenylene-PGI$_2$
(3E)-15-cyclopentyl-2,5,6,7,16,17,18,19,20-nonanor-3,4-didehydro-4,8-inter-m-phenylene-PGI$_2$
(3E)-15-(2-methylcyclopentyl)-2,5,6,7,16,17,18,19,20-nonanor-3,4-didehydro-4,8-inter-m-phenylene-PGI$_2$
(3E)-15-(3-methylcyclopentyl)-2,5,6,7,16,17,18,19,20-nonanor-3,4-didehydro-4,8-inter-m-phenylene-PGI$_2$
(3E)-15-(2,5-dimethylcyclopentyl)-2,5,6,7,16,17,18,19,20-nonanor-3,4-didehydro-4,8-inter-m-phenylene-PGI$_2$
(3E)-15-(3,4-dimethylcyclopentyl)-2,5,6,7,16,17,18,19,20-nonanor-3,4-didehydro-4,8-inter-m-phenylene-PGI$_2$
(3E)-15-cyclohexyl-2,5,6,7,16,17,18,19,20-nonanor-3,4-didehydro-4,8-inter-m-phenylene-PGI$_2$
(3E)-15-(4-methylcyclohexyl)-2,5,6,7,16,17,18,19,20-nonanor-3,4-didehydro-4,8-inter-m-phenylene-PGI$_2$
(3E)-15-(4-ethylcyclohexyl)-2,5,6,7,16,17,18,19,20-nonanor-3,4-didehydro-4,8-inter-m-phenylene-PGI$_2$
(3E)-15-(4,4-dimethylcyclohexyl)-2,5,6,7,16,17,18,19,20-nonanor-3,4-didehydro-4,8-inter-m-phenylene-PGI$_2$
(3E)-15-(2,6-dimethylcyclohexyl)-2,5,6,7,16,17,18,19,20-nonanor-3,4-didehydro-4,8-inter-m-phenylene-PGI$_2$
(3E)-15-(2,4,6-trimethylcyclohexyl)-2,5,6,7,16,17,18,19,20-nonanor-3,4-didehydro-4,8-inter-m-phenylene-PGI$_2$
(3E)-15-cyclooctyl-2,5,6,7,16,17,18,19,20-nonanor-3,4-didehydro-4,8-inter-m-phenylene-PGI$_2$
(3E)-15-cyclododecyl-2,5,6,7,16,17,18,19,20-nonanor-3,4-didehydro-4,8-inter-m-phenylene-PGI$_2$
(3E)-16-cyclopropyl-2,5,6,7,17,18,19,20-octanor-3,4-didehydro-4,8-inter-m-phenylene-PGI$_2$
(3E)-16-cyclobutyl-2,5,6,7,17,18,19,20-octanor-3,4-didehydro-4,8-inter-m-phenylene-PGI$_2$
(3E)-16-cyclopentyl-2,5,6,7,17,18,19,20-octanor-3,4-didehydro-4,8-inter-m-phenylene-PGI$_2$
(3E)-16-(2-methylcyclopentyl)-2,5,6,7,17,18,19,20-octanor-3,4-didehydro-4,8-inter-m-phenylene-PGI$_2$
(3E)-16-(3-methylcyclopentyl)-2,5,6,7,17,18,19,20-octanor-3,4-didehydro-4,8-inter-m-phenylene-PGI$_2$
(3E)-16-(2,5-dimethylcyclopentyl)-2,5,6,7,17,18,19,20-octanor-3,4-didehydro-4,8-inter-m-phenylene-PGI$_2$
(3E)-16-(3,4-dimethylcyclopentyl)-2,5,6,7,17,18,19,20-octanor-3,4-didehydro-4,8-inter-m-phenylene-PGI$_2$
(3E)-16-cyclohexyl-2,5,6,7,17,18,19,20-octanor-3,4-didehydro-4,8-inter-m-phenylene-PGI$_2$
(3E)-16-(4-methylcyclohexyl)-2,5,6,7,17,18,19,20-octanor-3,4-didehydro-4,8-inter-m-phenylene-PGI$_2$
(3E)-16-(4-ethylcyclohexyl)-2,5,6,7,17,18,19,20-octanor-3,4-didehydro-4,8-inter-m-phenylene-PGI$_2$ (3E)-16-(4,4-dimethylcyclohexyl)-2,5,6,7,17,18,19,20-octanor-3,4-didehydro-4,8-inter-m-phenylene-PGI$_2$ (3E)-16-(2,6-dimethylcyclohexyl)-2,5,6,7,17,18,19,20-octanor-3,4-didehydro-4,8inter-m-phenylene-PGI$_2$ (3E)-16-(2,4,6-trimethylcyclohexyl)-2,5,6,7,17,18,19,20-octanor-3,4-didehydro-4,8-inter-m-phenylene-PGI$_2$ (3E)-16-cyclooctyl-2,5,6,7,17,18,19,20-octanor-3,4-didehydro-4,8-inter-m-phenylene-PGI$_2$ (3E)-16-cyclododecyl-2,5,6,7,17,18,19,20-octanor-3,4-didehydro-4,8-inter-m-phenylene-PGI$_2$ (3E)-16-cyclopropyl-2,5,6,7,18,19,20-heptanor-3,4-didehydro-4,8-inter-m-phenylene-PGI$_2$ (3E)-16-cyclobutyl-2,5,6,7,18,19,20-heptanor-3,4-didehydro-4,8-inter-m-phenylene-PGI$_2$ (3E)-16-cyclopentyl-2,5,6,7,18,19,20-heptanor-3,4-didehydro-4,8-inter-m-phenylene-PGI$_2$ (3E)-16-(2-methylcyclopentyl)-2,5,6,7,18,19,20-heptanor-3,4-didehydro-4,8-inter-m-phenylene-PGI$_2$ (3E)-16-(3-methylcyclopentyl)-2,5,6,7,18,19,20-heptanor-3,4-didehydro-4,8-inter-m-phenylene-PGI$_2$ (3E)-16-(2,5-dimethylcyclopentyl)-2,5,6,7,18,19,20-heptanor-3,4-didehydro-4,8-inter-m-phenylene-PGI$_2$ (3E)-16-(3,4-dimethylcyclopentyl)-2,5,6,7,18,19,20-heptanor-3,4-didehydro-4,8-inter-m-phenylene-PGI$_2$ (3E)-16-cyclohexyl-2,5,6,7,18,19,20-heptanor-3,4-didehydro-4,8-inter-m-phenylene-PGI$_2$ (3E)-16-(4-methylcyclohexyl)-2,5,6,7,18,19,20-heptanor-3,4-didehydro-4,8-inter-m-phenylene-PGI$_2$ (3E)-16-(4-ethylcyclohexyl)-2,5,6,7,18,19,20-heptanor-3,4-didehydro-4,8-inter-m-phenylene-PGI$_2$ (3E)-16-(4,4-dimethylcyclohexyl)-2,5,6,7,18,19,20-heptanor-3,4-didehydro-4,8-inter-m-phenylene-PGI$_2$ (3E)-16-(2,6-dimethylcyclohexyl)-2,5,6,7,18,19,20-heptanor-3,4-didehydro-4,8-inter-m-phenylene-PGI$_2$ (3E)-16-(2,4,6-trimethylcyclohexyl)-2,5,6,7,18,19,20-heptanor-3,4-didehydro-4,8-inter-m-phenylene-PGI$_2$ (3E)-16-cyclooctyl-2,5,6,7,18,19,20-heptanor-3,4-didehydro-4,8-inter-m-phenylene-PGI$_2$ (3E)-16-cyclododecyl-2,5,6,7,18,19,20-heptanor-3,4-didehydro-4,8-inter-m-phenylene-PGI$_2$ (3E)-16-cyclopropyl-16-methyl-2,5,6,7,18,19,20-heptanor-3,4-didehydro-4,8-inter-m-phenylene-PGI$_2$ (3E)-16-cyclobutyl-16-methyl-2,5,6,7,18,19,20-heptanor-3,4-didehydro-4,8-inter-m-phenylene-PGI$_2$ (3E)-16-cyclopentyl-16-methyl-2,5,6,7,18,19,20-heptanor-3,4-didehydro-4,8-inter-m-phenylene-PGI$_2$ (3E)-16-methyl-16-(2-methylcyclopentyl)-2,5,6,7,18,19,20-heptanor-3,4-didehydro-4,8-inter-m-phenylene-PGI$_2$ (3E)-16-methyl-16-(3-methylcyclopentyl)-2,5,6,7,18,19,20-heptanor-3,4-didehydro-4,8-inter-m-phenylene-PGI$_2$ (3E)-16-(2,5-dimethylcyclopentyl)-16-methyl-2,5,6,7,18,19,20-heptanor-3,4-didehydro-4,8-inter-m-phenylene-PGI$_2$ (3E)-16-(3,4-dimethylcyclopentyl)-16-methyl-2,5,6,7,18,19,20-heptanor-3,4-didehydro-4,8-inter-m-phenylene-PGI$_2$ (3E)-16-cyclohexyl-16-methyl-2,5,6,7,18,19,20-heptanor-3,4-didehydro-4,8-inter-m-phenylene-PGI$_2$ (3E)-16-methyl-16-(4-methylcyclohexyl)-2,5,6,7,18,19,20-heptanor-3,4-didehydro-4,8-inter-m-phenylene-PGI$_2$ (3E)-16-(4-ethylcyclohexyl)-16-methyl-2,5,6,7,18,19,20-heptanor-3,4-didehydro-4,8-inter-m-phenylene-PGI$_2$ (3E)-16-(4,4-dimethylcyclohexyl)-16-methyl-2,5,6,7,18,19,20-heptanor-3,4-didehydro-4,8-inter-m-phenylene-PGI$_2$ (3E)-16-(2,6-dimethylcyclohexyl)-16-methyl-2,5,6,7,18,19,20-heptanor-3,4-didehydro-4,8-inter-m-phenylene-PGI$_2$ (3E)-16-methyl-16-(2,4,6-trimethylcyclohexyl)-2,5,6,7,18,19,20-heptanor-3,4-didehydro-4,8-inter-m-phenylene-PGI$_2$ (3E)-16-cyclooctyl-16-methyl-2,5,6,7,18,19,20-heptanor-3,4-didehydro-4,8-inter-m-phenylene-PGI$_2$ (3E)-16-cyclododecyl-16-methyl-2,5,6,7,18,19,20-heptanor-3,4-didehydro-4,8-inter-m-phenylene-PGI$_2$ (3E)-17-cyclopropyl-2,5,6,7,18,19,20-heptanor-3,4-didehydro-4,8-inter-m-phenylene-PGI$_2$ (3E)-17-cyclobutyl-2,5,6,7,18,19,20-heptanor-3,4-didehydro-4,8-inter-m-phenylene-PGI$_2$ (3E)-17-cyclopentyl-2,5,6,7,18,19,20-heptanor-3,4-didehydro-4,8-inter-m-phenylene-PGI$_2$ (3E)-17-(2-methylcyclopentyl)-2,5,6,7,18,19,20-heptanor-3,4-didehydro-4,8-inter-m-phenylene-PGI$_2$ (3E)-17-(3-methylcyclopentyl)-2,5,6,7,18,19,20-heptanor-3,4-didehydro-4,8-inter-m-phenylene-PGI$_2$ (3E)-17-(2,5-dimethylcyclopentyl)-2,5,6,7,18,19,20-heptanor-3,4-didehydro-4,8-inter-m-phenylene-PGI$_2$ (3E)-17-(3,4-dimethylcyclopentyl)-2,5,6,7,18,19,20-heptanor-3,4-didehydro-4,8-inter-m-phenylene-PGI$_2$ (3E)-17-cyclohexyl-2,5,6,7,18,19,20-heptanor-3,4-didehydro-4,8-inter-m-phenylene-PGI$_2$ (3E)-17-(4-methylcyclohexyl)-2,5,6,7,18,19,20-heptanor-3,4-didehydro-4,8-inter-m-phenylene-PGI$_2$ (3E)-17-(4-ethylcyclohexyl)-2,5,6,7,18,19,20-heptanor-3,4-didehydro-4,8-inter-m-phenylene-PGI$_2$ (3E)-17-(4,4-dimethylcyclohexyl)-2,5,6,7,18,19,20-heptanor-3,4-didehydro-4,8-inter-m-phenylene-PGI$_2$ (3E)-17-(2,6-dimethylcyclohexyl)-2,5,6,7,18,19,20-heptanor-3,4-didehydro-4,8-inter-m-phenylene-PGI$_2$ (3E)-17-(2,4,6-trimethylcyclohexyl)-2,5,6,7,18,19,20-heptanor-3,4-didehydro-4,8-inter-m-phenylene-PGI$_2$ (3E)-17-cyclooctyl-2,5,6,7,18,19,20-heptanor-3,4-didehydro-4,8-inter-m-phenylene-PGI$_2$ (3E)-17-cyclododecyl-2,5,6,7,18,19,20-heptanor-3,4-didehydro-4,8-inter-m-phenylene-PGI$_2$ (3E)-17-cyclopropyl-16-methyl-2,5,6,7,18,19,20-heptanor-3,4-didehydro-4,8-inter-m-phenylene-PGI$_2$ (3E)-17-cyclobutyl-16-methyl-2,5,6,7,18,19,20-heptanor-3,4-didehydro-4,8-inter-m-phenylene-PGI$_2$ (3E)-17-cyclopentyl-16-methyl-2,5,6,7,18,19,20-heptanor-3,4-didehydro-4,8-inter-m-phenylene-PGI$_2$ (3E)-16-methyl-17-(2-methylcyclopentyl)-2,5,6,7,18,19,20-heptanor-3,4-didehydro-4,8-inter-m-phenylene-PGI$_2$ (3E)-16-methyl-17-(3-methylcyclopentyl)-2,5,6,7,18,19,20-heptanor-3,4-didehydro-4,8-inter-m-phenylene-PGI$_2$ (3E)-17-(2,5-dimethylcyclopentyl)-16-methyl-2,5,6,7,18,19,20-heptanor-3,4-didehydro-4,8-inter-m-phenylene-PGI$_2$ (3E)-17-(3,4-dimethylcyclopentyl)-16-methyl-2,5,6,7,18,19,20-heptanor-3,4-didehydro-4,8-inter-m-phenylene-PGI$_2$ (3E)-17-cyclohexyl-16-methyl-2,5,6,7,18,19,20-heptanor-3,4-didehydro-4,8-inter-m-phenylene-PGI$_2$
(3E)-16-methyl-17-(4-methylcyclohexyl)-2,5,6,7,18,19,20-heptanor-3,4-didehydro-4,8-inter-m-phenylene-PGI$_2$
(3E)-17-(4-ethylcyclohexyl)-16-methyl-2,5,6,7,18,19,20-heptanor-3,4-didehydro-4,8-inter-m-phenylene-PGI$_2$
(3E)-17-(4,4-dimethylcyclohexyl)-16-methyl-2,5,6,7,18,19,20-heptanor-3,4-didehydro-4,8-inter-m-phenylene-PGI$_2$
(3E)-17-(2,6-dimethylcyclohexyl)-16-methyl-2,5,6,7,18,19,20-heptanor-3,4-didehydro-4,8-inter-m-phenylene-PGI$_2$
(3E)-16-methyl-17-(2,4,6-trimethylcyclohexyl)-2,5,6,7,18,19,20-heptanor-3,4-didehydro-4,8-inter-m-phenylene-PGI$_2$
(3E)-17-cyclooctyl-16-methyl-2,5,6,7,18,19,20-heptanor-3,4-didehydro-4,8-inter-m-phenylene-PGI$_2$
(3E)-17-cyclododecyl-16-methyl-2,5,6,7,18,19,20-heptanor-3,4-didehydro-4,8-inter-m-phenylene-PGI$_2$
(3E)-17-cyclopropyl-16,16-dimethyl-2,5,6,7,18,19,20-heptanor-3,4-didehydro-4,8-inter-m-phenylene-PGI$_2$
(3E)-17-cyclobutyl-16,16-dimethyl-2,5,6,7,18,19,20-heptanor-3,4-didehydro-4,8-inter-m-phenylene-PGI$_2$
(3E)-17-cyclopentyl-16,16-dimethyl-2,5,6,7,18,19,20-heptanor-3,4-didehydro-4,8-inter-m-phenylene-PGI$_2$
(3E)-16,16-dimethyl-17-(2-methylcyclopentyl)-2,5,6,7,18,19,20-heptanor-3,4-didehydro-4,8-inter-m-phenylene-PGI$_2$
(3E)-16,16-dimethyl-17-(3-methylcyclopentyl)-2,5,6,7,18,19,20-heptanor-3,4-didehydro-4,8-inter-m-phenylene-PGI$_2$
(3E)-17-(2,5-dimethylcyclopentyl)-16,16-dimethyl-2,5,6,7,18,19,20-heptanor-3,4-didehydro-4,8-inter-m-phenylene-PGI$_2$
(3E)-17-(3,4-dimethylcyclopentyl)-16,16-dimethyl-2,5,6,7,18,19,20-heptanor-3,4-didehydro-4,8-inter-m-phenylene-PGI$_2$
(3E)-17-cyclohexyl-16,16-dimethyl-2,5,6,7,18,19,20-heptanor-3,4-didehydro-4,8-inter-m-phenylene-PGI$_2$
(3E)-16,16-dimethyl-17-(4-methylcyclohexyl)-2,5,6,7,18,19,20-heptanor-3,4-didehydro-4,8-inter-m-phenylene-PGI$_2$
(3E)-17-(4-ethylcyclohexyl)-16,16-dimethyl-2,5,6,7,18,19,20-heptanor-3,4-didehydro-4,8-inter-m-phenylene-PGI$_2$
(3E)-17-(4,4-dimethylcyclohexyl)-16,16-dimethyl-2,5,6,7,18,19,20-heptanor-3,4-didehydro-4,8-inter-m-phenylene-PGI$_2$
(3E)-17-(2,6-dimethylcyclohexyl)-16,16-dimethyl-2,5,6,7,18,19,20-heptanor-3,4-didehydro-4,8-inter-m-phenylene-PGI$_2$
(3E)-16,16-dimethyl-17-(2,4,6-trimethylcyclohexyl)-2,5,6,7,18,19,20-heptanor-3,4-didehydro-4,8-inter-m-phenylene-PGI$_2$
(3E)-17-cyclooctyl-16,16-dimethyl-2,5,6,7,18,19,20-heptanor-3,4-didehydro-4,8-inter-m-phenylene-PGI$_2$
(3E)-17-cyclododecyl-16,16-dimethyl-2,5,6,7,18,19,20-heptanor-3,4-didehydro-4,8-inter-m-phenylene-PGI$_2$
(3E)-17-cyclopentyl-2,5,6,7,19,20-hexanor-3,4-didehydro-4,8-inter-m-phenylene-PGI$_2$
(3E)-17-cyclohexyl-2,5,6,7,19,20-hexanor-3,4-didehydro-4,8-inter-m-phenylene-PGI$_2$
(3E)-17-cyclopentyl-17-methyl-2,5,6,7,19,20-hexanor-3,4-didehydro-4,8-inter-m-phenylene-PGI$_2$
(3E)-17-cyclohexyl-17-methyl-2,5,6,7,18,19,20-hexanor-3,4-didehydro-4,8-inter-m-phenylene-PGI$_2$
(3E)-18-cyclopentyl-2,5,6,7,19,20-hexanor-3,4-didehydro-4,8-inter-m-phenylene-PGI$_2$
(3E)-18-cyclohexyl-2,5,6,7,19,20-hexanor-3,4-didehydro-4,8-inter-m-phenylene-PGI$_2$
(3E)-18-cyclopentyl-16-methyl-2,5,6,7,19,20-hexanor-3,4-didehydro-4,8-inter-m-phenylene-PGI$_2$
(3E)-18-cyclohexyl-16-methyl-2,5,6,7,18,19,20-hexanor-3,4-didehydro-4,8-inter-m-phenylene-PGI$_2$
(3E)-18-cyclopentyl-16,16-dimethyl-2,5,6,7,19,20-hexanor-3,4-didehydro-4,8-inter-m-phenylene-PGI$_2$
(3E)-18-cyclohexyl-16,16-dimethyl-2,5,6,7,19,20-hexanor-3,4-didehydro-4,8-inter-m-phenylene-PGI$_2$
(3E)-19-cyclopentyl-2,5,6,7,20-pentanor-3,4-didehydro-4,8-inter-m-phenylene-PGI$_2$
(3E)-19-cyclohexyl-2,5,6,7,20-pentanor-3,4-didehydro-4,8-inter-m-phenylene-PGI$_2$
(3E)-19-cyclopentyl-16-methyl-2,5,6,7,20-pentanor-3,4-didehydro-4,8-inter-m-phenylene-PGI$_2$
(3E)-19-cyclohexyl-16-methyl-2,5,6,7,20-pentanor-3,4-didehydro-4,8-inter-m-phenylene-PGI$_2$
(3E)-19-cyclopentyl-16,16-dimethyl-2,5,6,7,20-pentanor-3,4-didehydro-4,8-inter-m-phenylene-PGI$_2$
(3E)-19-cyclohexyl-16,16-dimethyl-2,5,6,7,20-pentanor-3,4-didehydro-4,8-inter-m-phenylene-PGI$_2$.

The compounds wherein R$_2$ is —C$_t$H$_{2t}$—C≡C—R$_4$ are illustrated by but not limited to:
(3E)-2,5,6,7-tetranor-3,4,18,18,19,19-hexadehydro-4,8-inter-m-phenylene-PGI$_2$
(3E)-20a-homo-2,5,6,7-tetranor-3,4,18,18,19,19-hexadehydro-4,8-inter-m-phenylene-PGI$_2$
(3E)-20a,20b-dihomo-2,5,6,7-tetranor-3,4,18,18,19,19-hexadehydro-4,8-inter-m-phenylene-PGI$_2$
(3E)-20a,20b,20c-trihomo-2,5,6,7-tetranor-3,4,18,18,19,19-hexadehydro-4,8-inter-m-phenylene-PGI$_2$
(3E)-20a,20b,20c,20d-tetrahomo-2,5,6,7-tetranor-3,4,18,18,19,19-hexadehydro-4,8-inter-m-phenylene-PGI$_2$
(3E)-20a,20b,20c,20d,20e-pentahomo-2,5,6,7-tetranor-3,4,18,18,19,19-hexadehydro-4,8-inter-m-phenylene-PGI$_2$
(3E)-16-methyl-2,5,6,7-tetranor-3,4,18,18,19,19-hexadehydro-4,8-inter-m-phenylene-PGI$_2$
(3E)-16-methyl-20a-homo-2,5,6,7-tetranor-3,4,18,18,19,19-hexadehydro-4,8-inter-m-phenylene-PGI$_2$
(3E)-16-methyl-20a,20b-dihomo-2,5,6,7-tetranor-3,4,18,18,19,19-hexadehydro-4,8-inter-m-phenylene-PGI$_2$
(3E)-16-methyl-20a,20b,20c-trihomo-2,5,6,7-tetranor-3,4,18,18,19,19-hexadehydro-4,8-inter-m-phenylene-PGI$_2$
(3E)-16-methyl-20a,20b,20c,20d-tetrahomo-2,5,6,7-tetranor-3,4,18,18,19,19-hexadehydro-4,8-inter-m-phenylene-PGI$_2$
(3E)-16-methyl-20a,20b,20c,20d,20e-pentahomo-2,5,6,7-tetranor-3,4,18,18,19,19-hexadehydro-4,8-inter-m-phenylene-PGI$_2$
(3E)-16,16-dimethyl-2,5,6,7-tetranor-3,4,18,18,19,19-hexadehydro-4,8-inter-m-phenylene-PGI$_2$ (3E)-16,16-dimethyl-20a-homo-2,5,6,7-tetranor-3,4,18,18,19,19-hexadehydro-4,8-inter-m-phenylene-PGI$_2$ (3E)-16,16-dimethyl-20a,20b-dihomo-2,5,6,7-tetranor-3,4,18,18,19,19-hexadehydro-4,8-inter-m-phenylene-PGI$_2$ (3E)-16,16-dimethyl-20a,20b,20c-trihomo-2,5,6,7-tetranor-3,4,18,18,19,19-hexadehydro-4,8-inter-m-phenylene-PGI$_2$ (3E)-16,16-dimethyl-20a,20b,20c,20d-tetrahomo-2,5,6,7-tetranor-3,4,18,18,19,19-hexadehydro-4,8-inter-m-phenylene-PGI$_2$ (3E)-16,16-dimethyl-20a,20b,20c,20d,20e-pentahomo-2,5,6,7-tetranor-3,4,18,18,19,19-hexadehydro-4,8-inter-m-phenylene-PGI$_2$ (3E)-20a-homo-2,5,6,7-tetranor-3,4,19,19,20,20-hexadehydro-4,8-inter-m-phenylene-PGI$_2$ (3E)-20a,20b-dihomo-2,5,6,7-tetranor-3,4,19,19,20,20-hexadehydro-4,8-inter-m-phenylene-PGI$_2$ (3E)-20a,20b,20c-trihomo-2,5,6,7-tetranor-3,4,19,19,20,20-hexadehydro-4,8-inter-m-phenylene-PGI$_2$ (3E)-20a,20b,20c,20d-tetrahomo-2,5,6,7-tetranor-3,4,19,19,20,20-hexadehydro-4,8-inter-m-phenylene-PGI$_2$ (3E)-20a,20b,20c,20d,20e-pentahomo-2,5,6,7-tetranor-3,4,19,19,20,20-hexadehydro-4,8-inter-m-phenylene-PGI$_2$ (3E)-16-methyl-20a-homo-2,5,6,7-tetranor-3,4,19,19,20,20-hexadehydro-4,8-inter-m-phenylene-PGI$_2$ (3E)-16-methyl-20a,20b-dihomo-2,5,6,7-tetranor-3,4,19,19,20,20-hexadehydro-4,8-inter-m-phenylene-PGI$_2$ (3E)-16-methyl-20a,20b,20c-trihomo-2,5,6,7-tetranor-3,4,19,19,20,20-hexadehydro-4,8-inter-m-phenylene-PGI$_2$ (3E)-16-methyl-20a,20b,20c,20d-tetrahomo-2,5,6,7-tetranor-3,4,19,19,20,20-hexadehydro-4,8-inter-m-phenylene-PGI$_2$ (3E)-16-methyl-20a,20b,20c,20d,20e-pentahomo-2,5,6,7-tetranor-3,4,19,19,20,20-hexadehydro-4,8-inter-m-phenylene-PGI$_2$ (3E)-16,16-dimethyl-20a-homo-2,5,6,7-tetranor-3,4,19,19,20,20-hexadehydro-4,8-inter-m-phenylene-PGI$_2$ (3E)-16,16-dimethyl-20a,20b-dihomo-2,5,6,7-tetranor-3,4,19,19,20,20-hexadehydro-4,8-inter-m-phenylene-PGI$_2$ (3E)-16,16-dimethyl-20a,20b,20c-trihomo-2,5,6,7-tetranor-3,4,19,19,20,20-hexadehydro-4,8-inter-m-phenylene-PGI$_2$ (3E)-16,16-dimethyl-20a,20b,20c,20d-tetrahomo-2,5,6,7-tetranor-3,4,19,19,20,20-hexadehydro-4,8-inter-m-phenylene-PGI$_2$ (3E)-16,16-dimethyl-20a,20b,20c,20d,20e-pentahomo-2,5,6,7-tetranor-3,4,19,19,20,20-hexadehydro-4,8-inter-m-phenylene-PGI$_2$.

The compounds wherein R$_2$ is —C$_t$H$_{2t}$—O—R$_5$ are illustrated by but not limited to:

(3E)-2,5,6,7,19,20-hexanor-17-oxa-3,4-didehydro-4,8-inter-m-phenylene-PGI$_2$ (3E)-2,5,6,7,20-pentanor-17-oxa-3,4-didehydro-4,8-inter-m-phenylene-PGI$_2$ (3E)-2,5,6,7-tetranor-17-oxa-3,4-didehydro-4,8-inter-m-phenylene-PGI$_2$ (3E)-20a-homo-2,5,6,7-tetranor-17-oxa-3,4-didehydro-4,8-inter-m-phenylene-PGI$_2$ (3E)-20a,20b-dihomo-2,5,6,7-tetranor-17-oxa-3,4-didehydro-4,8-inter-m-phenylene-PGI$_2$ (3E)-20a,20b,20c-trihomo-2,5,6,7-tetranor-17-oxa-3,4-didehydro-4,8-inter-m-phenylene-PGI$_2$ (3E)-16-methyl-2,5,6,7,19,20-hexanor-17-oxa-3,4-didehydro-4,8-inter-m-phenylene-PGI$_2$ (3E)-16-methyl-2,5,6,7,20-pentanor-17-oxa-3,4-didehydro-4,8-inter-m-phenylene-PGI$_2$ (3E)-16-methyl-2,5,6,7-tetranor-17-oxa-3,4-didehydro-4,8-inter-m-phenylene-PGI$_2$ (3E)-16-methyl-20a-homo-2,5,6,7-tetranor-17-oxa-3,4-didehydro-4,8-inter-m-phenylene-PGI$_2$ (3E)-16-methyl-20a,20b-dihomo-2,5,6,7-tetranor-17-oxa-3,4-didehydro-4,8-inter-m-phenylene-PGI$_2$ (3E)-16-methyl-20a,20b,20c-trihomo-2,5,6,7-tetranor-17-oxa-3,4-didehydro-4,8-inter-m-phenylene-PGI$_2$ (3E)-16,16-dimethyl-2,5,6,7,19,20-hexanor-17-oxa-3,4-didehydro-4,8-inter-m-phenylene-PGI$_2$ (3E)-16,16-dimethyl-2,5,6,7,20-pentanor-17-oxa-3,4-didehydro-4,8-inter-m-phenylene-PGI$_2$ (3E)-16,16-dimethyl-2,5,6,7-tetranor-17-oxa-3,4-didehydro-4,8-inter-m-phenylene-PGI$_2$ (3E)-16,16-dimethyl-20a-homo-2,5,6,7-tetranor-17-oxa-3,4-didehydro-4,8-inter-m-phenylene-PGI$_2$ (3E)-16,16-dimethyl-20a,20b-dihomo-2,5,6,7-tetranor-17-oxa-3,4-didehydro-4,8-inter-m-phenylene-PGI$_2$ (3E)-16,16-dimethyl-20a,20b,20c-trihomo-2,5,6,7-tetranor-17-oxa-3,4-didehydro-4,8-inter-m-phenylene-PGI$_2$ (3E)-18-methyl-2,5,6,7,20-pentanor-17-oxa-3,4-didehydro-4,8-inter-m-phenylene-PGI$_2$ (3E)-18-methyl-2,5,6,7-tetranor-17-oxa-3,4-didehydro-4,8-inter-m-phenylene-PGI$_2$ (3E)-18,18-dimethyl-2,5,6,7,20-pentanor-17-oxa-3,4-didehydro-4,8-inter-m-phenylene-PGI$_2$ (3E)-16,18-dimethyl-2,5,6,7,20-pentanor-17-oxa-3,4-didehydro-4,8-inter-m-phenylene-PGI$_2$ (3E)-16,18-dimethyl-2,5,6,7-tetranor-17-oxa-3,4-didehydro-4,8-inter-m-phenylene-PGI$_2$ (3E)-16,18,18-trimethyl-2,5,6,7,20-pentanor-17-oxa-3,4-didehydro-4,8-inter-m-phenylene-PGI$_2$ (3E)-16,16,18-trimethyl-2,5,6,7,20-pentanor-17-oxa-3,4-didehydro-4,8-inter-m-phenylene-PGI$_2$ (3E)-16,16,18-trimethyl-2,5,6,7-tetranor-17-oxa-3,4-didehydro-4,8-inter-m-phenylene-PGI$_2$ (3E)-16,16,18,18-tetramethyl-2,5,6,7,20-pentanor-17-oxa-3,4-didehydro-4,8-inter-m-phenylene-PGI$_2$ (3E)-2,5,6,7,20-pentanor-18-oxa-3,4-didehydro-4,8-inter-m-phenylene-PGI$_2$ (3E)-2,5,6,7-tetranor-18-oxa-3,4-didehydro-4,8-inter-m-phenylene-PGI$_2$ (3E)-20a-homo-2,5,6,7-tetranor-18-oxa-3,4-didehydro-4,8-inter-m-phenylene-PGI$_2$ (3E)-20a,20b-dihomo-2,5,6,7-tetranor-18-oxa-3,4-didehydro-4,8-inter-m-phenylene-PGI$_2$ (3E)-20a,20b,20c-trihomo-2,5,6,7-tetranor-18-oxa-3,4-didehydro-4,8-inter-m-phenylene-PGI$_2$ (3E)-20a,20b,20c,20d-tetrahomo-2,5,6,7-tetranor-18-oxa-3,4-didehydro-4,8-inter-m-phenylene-PGI$_2$ (3E)-16-methyl-2,5,6,7,20-pentanor-18-oxa-3,4-didehydro-4,8-inter-m-phenylene-PGI$_2$
(3E)-16-methyl-2,5,6,7-tetranor-18-oxa-3,4-didehydro-4,8-inter-m-phenylene-PGI$_2$
(3E)-16-methyl-20a-homo-2,5,6,7-tetranor-18-oxa-3,4-didehydro-4,8-inter-m-phenylene-PGI$_2$
(3E)-16-methyl-20a,20b-dihomo-2,5,6,7-tetranor-18-oxa-3,4-didehydro-4,8-inter-m-phenylene-PGI$_2$
(3E)-16-methyl-20a,20b,20c-trihomo-2,5,6,7-tetranor-18-oxa-3,4-didehydro-4,8-inter-m-phenylene-PGI$_2$
(3E)-16-methyl-20a,20b,20c,20d-tetrahomo-2,5,6,7-tetranor-18-oxa-3,4-didehydro-4,8-inter-m-phenylene-PGI$_2$
(3E)-16,16-dimethyl-2,5,6,7,20-pentanor-18-oxa-3,4-didehydro-4,8-inter-m-phenylene-PGI$_2$
(3E)-16,16-dimethyl-2,5,6,7-tetranor-18-oxa-3,4-didehydro-4,8-inter-m-phenylene-PGI$_2$
(3E)-16,16-dimethyl-20a-homo-2,5,6,7-tetranor-18-oxa-3,4-didehydro-4,8-inter-m-phenylene-PGI$_2$
(3E)-16,16-dimethyl-20a,20b-dihomo-2,5,6,7-tetranor-18-oxa-3,4-didehydro-4,8-inter-m-phenylene-PGI$_2$
(3E)-16,16-dimethyl-20a,20b,20c-trihomo-2,5,6,7-tetranor-18-oxa-3,4-didehydro-4,8-inter-m-phenylene-PGI$_2$
(3E)-16,16-dimethyl-20a,20b,20c,20d-tetrahomo-2,5,6,7-tetranor-18-oxa-3,4-didehydro-4,8-inter-m-phenylene-PGI$_2$
(3E)-2,5,6,7-tetranor-19-oxa-3,4-didehydro-4,8-inter-m-phenylene-PGI$_2$
(3E)-20a-homo-2,5,6,7-tetranor-19-oxa-3,4-didehydro-4,8-inter-m-phenylene-PGI$_2$
(3E)-20a,20b-dihomo-2,5,6,7-tetranor-19-oxa-3,4-didehydro-4,8-inter-m-phenylene-PGI$_2$
(3E)-16-methyl-2,5,6,7-tetranor-19-oxa-3,4-didehydro-4,8-inter-m-phenylene-PGI$_2$
(3E)-16-methyl-20a-homo-2,5,6,7-tetranor-19-oxa-3,4-didehydro-4,8-inter-m-phenylene-PGI$_2$
(3E)-16-methyl-20a,20b-dihomo-2,5,6,7-tetranor-19-oxa-3,4-didehydro-4,8-inter-m-phenylene-PGI$_2$
(3E)-16,16-dimethyl-2,5,6,7-tetranor-19-oxa-3,4-didehydro-4,8-inter-m-phenylene-PGI$_2$
(3E)-16,16-dimethyl-20a-homo-2,5,6,7-tetranor-19-oxa-3,4-didehydro-4,8-inter-m-phenylene-PGI$_2$
(3E)-16,16-dimethyl-20a,20b-dihomo-2,5,6,7-tetranor-19-oxa-3,4-didehydro-4,8-inter-m-phenylene-PGI$_2$
(3E)-20a-homo-2,5,6,7-tetranor-20-oxa-3,4-didehydro-4,8-inter-m-phenylene-PGI$_2$
(3E)-20a,20b-dihomo-2,5,6,7-tetranor-20-oxa-3,4-didehydro-4,8-inter-m-phenylene-PGI$_2$
(3E)-16-methyl-20a-homo-2,5,6,7-tetranor-20-oxa-3,4-didehydro-4,8-inter-m-phenylene-PGI$_2$
(3E)-16-methyl-20a,20b-dihomo-2,5,6,7-tetranor-20-oxa-3,4-didehydro-4,8-inter-m-phenylene-PGI$_2$
(3E)-16,16-dimethyl-20a-homo-2,5,6,7-tetranor-20-oxa-3,4-didehydro-4,8-inter-m-phenylene-PGI$_2$
(3E)-16,16-dimethyl-20a,20b-dihomo-2,5,6,7-tetranor-20-oxa-3,4-didehydro-4,8-inter-m-phenylene-PGI$_2$
(3E)-16-cyclopentyloxy-2,5,6,7,17,18,19,20-octanor-3,4-didehydro-4,8-inter-m-phenylene-PGI$_2$
(3E)-16-(2-methylcyclopentyloxy)-2,5,6,7,17,18,19,20-octanor-3,4-didehydro-4,8-inter-m-phenylene-PGI$_2$
(3E)-16-(3-methylcyclopentyloxy)-2,5,6,7,17,18,19,20-octanor-3,4-didehydro-4,8-inter-m-phenylene-PGI$_2$
(3E)-16-(2,5-dimethylcyclopentyloxy)-2,5,6,7,17,18,19,20-octanor-3,4-didehydro-4,8-inter-m-phenylene-PGI$_2$
(3E)-16-(3,4-dimethylcyclopentyloxy)-2,5,6,7,17,18,19,20-octanor-3,4-didehydro-4,8-inter-m-phenylene-PGI$_2$
(3E)-16-cyclohexyloxy-2,5,6,7,17,18,19,20-octanor-3,4-didehydro-4,8-inter-m-phenylene-PGI$_2$
(3E)-16-(4-methylcyclohexyloxy)-2,5,6,7,17,18,19,20-octanor-3,4-didehydro-4,8-inter-m-phenylene-PGI$_2$
(3E)-16-(4-ethylcyclohexyloxy)-2,5,6,7,17,18,19,20-octanor-3,4-didehydro-4,8-inter-m-phenylene-PGI$_2$
(3E)-16-(4-propylcyclohexyloxy)-2,5,6,7,17,18,19,20-octanor-3,4-didehydro-4,8-inter-m-phenylene-PGI$_2$
(3E)-16-(4-butylcyclohexyloxy)-2,5,6,7,17,18,19,20-octanor-3,4-didehydro-4,8-inter-m-phenylene-PGI$_2$
(3E)-16-(4,4-dimethylcyclohexyloxy)-2,5,6,7,17,18,19,20-octanor-3,4-didehydro-4,8-inter-m-phenylene-PGI$_2$
(3E)-16-(2,6-dimethycyclohexyloxy)-2,5,6,7,17,18,19,20-octanor-3,4-didehydro-4,8-inter-m-phenylene-PGI$_2$
(3E)-16-(2,4,6-trimethylcyclohexyloxy)-2,5,6,7,17,18,19,20-octanor-3,4-didehydro-4,8-inter-m-phenylene-PGI$_2$
(3E)-16-cyclopentyloxy-2,5,6,7,18,19,20-heptanor-3,4-didehydro-4,8-inter-m-phenylene-PGI$_2$
(3E)-16-(2-methylcyclopentyloxy)-2,5,6,7,18,19,20-heptanor-3,4-didehydro-4,8-inter-m-phenylene-PGI$_2$
(3E)-16-(3-methylcyclopentyloxy)-2,5,6,7,18,19,20-heptanor-3,4-didehydro-4,8-inter-m-phenylene-PGI$_2$
(3E)-16-(2,5-dimethylcyclopentyloxy)-2,5,6,7,18,19,20-heptanor-3,4-didehydro-4,8-inter-m-phenylene-PGI$_2$
(3E)-16-(3,4-dimethylcyclopentyloxy)-2,5,6,7,18,19,20-heptanor-3,4-didehydro-4,8-inter-m-phenylene-PGI$_2$
(3E)-16-cyclohexyloxy-2,5,6,7,18,19,20-heptanor-3,4-didehydro-4,8-inter-m-phenylene-PGI$_2$
(3E)-16-(4-methylcyclohexyloxy)-2,5,6,7,18,19,20-heptanor-3,4-didehydro-4,8-inter-m-phenylene-PGI$_2$
(3E)-16-(4-ethylcyclohexyloxy)-2,5,6,7,18,19,20-heptanor-3,4-didehydro-4,8-inter-m-phenylene-PGI$_2$
(3E)-16-(4-propylcyclohexyloxy)-2,5,6,7,18,19,20-heptanor-3,4-didehydro-4,8-inter-m-phenylene-PGI$_2$
(3E)-16-(4-butylcyclohexyloxy)-2,5,6,7,18,19,20-heptanor-3,4-didehydro-4,8-inter-m-phenylene-PGI$_2$
(3E)-16-(4,4-dimethylcyclohexyloxy)-2,5,6,7,18,19,20-heptanor-3,4-didehydro-4,8-inter-m-phenylene-PGI$_2$
(3E)-16-(2,6-dimethylcyclohexyloxy)-2,5,6,7,18,19,20-heptanor-3,4-didehydro-4,8-inter-m-phenylene-PGI$_2$
(3E)-16-(2,4,6-trimethylcyclohexyloxy)-2,5,6,7,18,19,20-heptanor-3,4-didehydro-4,8-inter-m-phenylene-PGI$_2$
(3E)-16-cyclopentyloxy-16-methyl-2,5,6,7,18,19,20-heptanor-3,4-didehydro-4,8-inter-m-phenylene-PGI$_2$
(3E)-16-methyl-16-(2-methylcyclopentyloxy)-2,5,6,7,18,19,20-heptanor-3,4-didehydro-4,8-inter-m-phenylene-PGI$_2$
(3E)-16-methyl-16-(3-methylcyclopentyloxy)-2,5,6,7,18,19,20-heptanor-3,4-didehydro-4,8-inter-m-phenylene-PGI$_2$
(3E)-16-(2,5-dimethylcyclopentyloxy)-16-methyl-2,5,6,7,18,19,20-heptanor-3,4-didehydro-4,8-inter-m-phenylene-PGI$_2$ (3E)-16-(3,4-dimethylcyclopentyloxy)-16-methyl-2,5,6,7,18,19,20-heptanor-3,4-didehydro-4,8-inter-m-phenylene-PGI$_2$ (3E)-16-cyclohexyloxy-16-methyl-2,5,6,7,18,19,20-heptanor-3,4-didehydro-4,8-inter-m-phenylene-PGI$_2$ (3E)-16-methyl-16-(4-methylcyclohexyloxy)-2,5,6,7,18,19,20-heptanor-3,4-didehydro-4,8-inter-m-phenylene-PGI$_2$ (3E)-16-(4-ethylcyclohexyloxy)-16-methyl-2,5,6,7,18,19,20-heptanor-3,4-didehydro-4,8-inter-m-phenylene-PGI$_2$ (3E)-16-methyl-16-(4-propylcyclohexyloxy)-2,5,6,7,18,19,20-heptanor-3,4-didehydro-4,8-inter-m-phenylene-PGI$_2$ (3E)-16-(4-butylcyclohexyloxy)-16-methyl-2,5,6,7,18,19,20-heptanor-3,4-didehydro-4,8-inter-m-phenylene-PGI$_2$ (3E)-16-(4,4-dimethylcyclohexyloxy)-16-methyl-2,5,6,7,18,19,20-heptanor-3,4-didehydro-4,8-inter-m-phenylene-PGI$_2$ (3E)-16-(2,6-dimethylcyclohexyloxy)-16-methyl-2,5,6,7,18,19,20-heptanor-3,4-didehydro-4,8-inter-m-phenylene-PGI$_2$ (3E)-16-methyl-16-(2,4,6-trimethylcyclohexyloxy)-2,5,6,7,18,19,20-heptanor-3,4-didehydro-4,8-inter-m-phenylene-PGI$_2$ (3E)-17-cyclopentyloxy-2,5,6,7,18,19,20-heptanor-3,4-didehydro-4,8-inter-m-phenylene-PGI$_2$ (3E)-17-(2-methylcyclopentyloxy)-2,5,6,7,18,19,20-heptanor-3,4-didehydro-4,8-inter-m-phenylene-PGI$_2$ (3E)-17-(3-methylcyclopentyloxy)-2,5,6,7,18,19,20-heptanor-3,4-didehydro-4,8-inter-m-phenylene-PGI$_2$ (3E)-17-(2,5-dimethylcyclopentyloxy)-2,5,6,7,18,19,20-heptanor-3,4-didehydro-4,8-inter-m-phenylene-PGI$_2$ (3E)-17-(3,4-dimethylcyclopentyloxy)-2,5,6,7,18,19,20-heptanor-3,4-didehydro-4,8-inter-m-phenylene-PGI$_2$ (3E)-17-cyclohexyloxy-2,5,6,7,18,19,20-heptanor-3,4-didehydro-4,8-inter-m-phenylene-PGI$_2$ (3E)-17-(4-methylcyclohexyloxy)-2,5,6,7,18,19,20-heptanor-3,4-didehydro-4,8-inter-m-phenylene-PGI$_2$ (3E)-17-(4-ethylcyclohexyloxy)-2,5,6,7,18,19,20-heptanor-3,4-didehydro-4,8-inter-m-phenylene-PGI$_2$ (3E)-17-(4-propylcyclohexyloxy)-2,5,6,7,18,19,20-heptanor-3,4-didehydro-4,8-inter-m-phenylene-PGI$_2$ (3E)-17-(4-butylcyclohexyloxy)-2,5,6,7,18,19,20-heptanor-3,4-didehydro-4,8-inter-m-phenylene-PGI$_2$ (3E)-17-(4,4-dimethylcyclohexyloxy)-2,5,6,7,18,19,20-heptanor-3,4-didehydro-4,8-inter-m-phenylene-PGI$_2$ (3E)-17-(2,6-dimethylcyclohexyloxy)-2,5,6,7,18,19,20-heptanor-3,4-didehydro-4,8-inter-m-phenylene-PGI$_2$ (3E)-17-(2,4,6-trimethylcyclohexyloxy)-2,5,6,7,18,19,20-heptanor-3,4-didehydro-4,8-inter-m-phenylene-PGI$_2$ (3E)-17-cyclopentyloxy-16-methyl-2,5,6,7,18,19,20-heptanor-3,4-didehydro-4,8-inter-m-phenylene-PGI$_2$ (3E)-16-methyl-17-(2-methylcyclopentyloxy)-2,5,6,7,18,19,20-heptanor-3,4-didehydro-4,8-inter-m-phenylene-PGI$_2$ (3E)-16-methyl-17-(3-methylcyclopentyloxy)-2,5,6,7,18,19,20-heptanor-3,4-didehydro-4,8-inter-m-phenylene-PGI$_2$ (3E)-17-(2,5-dimethylcyclopentyloxy)-16-methyl-2,5,6,7,18,19,20-heptanor-3,4-didehydro-4,8-inter-m-phenylene-PGI$_2$ (3E)-17-(3,4-dimethylcyclopentyloxy)-16-methyl-2,5,6,7,18,19,20-heptanor-3,4-didehydro-4,8-inter-m-phenylene-PGI$_2$ (3E)-17-cyclohexyloxy-16-methyl-2,5,6,7,18,19,20-heptanor-3,4-didehydro-4,8-inter-m-phenylene-PGI$_2$ (3E)-16-methyl-17-(4-methylcyclohexyloxy)-2,5,6,7,18,19,20-heptanor-3,4-didehydro-4,8-inter-m-phenylene-PGI$_2$ (3E)-17-(4-ethylcyclohexyloxy)-16-methyl-2,5,6,7,18,19,20-heptanor-3,4-didehydro-4,8-inter-m-phenylene-PGI$_2$ (3E)-16-methyl-17-(4-propylcyclohexyloxy)-2,5,6,7,18,19,20-heptanor-3,4-didehydro-4,8-inter-m-phenylene-PGI$_2$ (3E)-17-(4-butylcyclohexyloxy)-16-methyl-2,5,6,7,18,19,20-heptanor-3,4-didehydro-4,8-inter-m-phenylene-PGI$_2$ (3E)-17-(4,4-dimethylcyclohexyloxy)-16-methyl-2,5,6,7,18,19,20-heptanor-3,4-didehydro-4,8-inter-m-phenylene-PGI$_2$ (3E)-17-(2,6-dimethylcyclohexyloxy)-16-methyl-2,5,6,7,18,19,20-heptanor-3,4-didehydro-4,8-inter-m-phenylene-PGI$_2$ (3E)-16-methyl-17-(2,4,6-trimethylcyclohexyloxy)-2,5,6,7,18,19,20-heptanor-3,4-didehydro-4,8-inter-m-phenylene-PGI$_2$ (3E)-17-cyclopentyloxy-16,16-dimethyl-2,5,6,7,18,19,20-heptanor-3,4-didehydro-4,8-inter-m-phenylene-PGI$_2$ (3E)-16,16-dimethyl-17-(2-methylcyclopentyloxy)-2,5,6,7,18,19,20-heptanor-3,4-didehydro-4,8-inter-m-phenylene-PGI$_2$ (3E)-16,16-dimethyl-17-(3-methylcyclopentyloxy)-2,5,6,7,18,19,20-heptanor-3,4-didehydro-4,8-inter-m-phenylene-PGI$_2$ (3E)-17-(2,5-dimethylcyclopentyloxy)-16,16-dimethyl-2,5,6,7,18,19,20-heptanor-3,4-didehydro-4,8-inter-m-phenylene-PGI$_2$ (3E)-17-(3,4-dimethylcyclopentyloxy)-16,16-dimethyl-2,5,6,7,18,19,20-heptanor-3,4-didehydro-4,8-inter-m-phenylene-PGI$_2$ (3E)-17-cyclohexyloxy-16,16-dimethyl-2,5,6,7,18,19,20-heptanor-3,4-didehydro-4,8-inter-m-phenylene-PGI$_2$ (3E)-16,16-dimethyl-17-(4-methylcyclohexyloxy)-2,5,6,7,18,19,20-heptanor-3,4-didehydro-4,8-inter-m-phenylene-PGI$_2$ (3E)-17-(4-ethylcyclohexyloxy)-16,16-dimethyl-2,5,6,7,18,19,20-heptanor-3,4-didehydro-4,8-inter-m-phenylene-PGI$_2$ (3E)-16,16-dimethyl-17-(4-propylcyclohexyloxy)-2,5,6,7,18,19,20-heptanor-3,4-didehydro-4,8-inter-m-phenylene-PGI$_2$ (3E)-17-(4-butylcyclohexyloxy)-16,16-dimethyl-2,5,6,7,18,19,20-heptanor-3,4-didehydro-4,8-inter-m-phenylene-PGI$_2$ (3E)-17-(4,4-dimethylcyclohexyloxy)-16,16-dimethyl-2,5,6,7,18,19,20-heptanor-3,4-didehydro-4,8-inter-m-phenylene-PGI$_2$ (3E)-17-(2,6-dimethylcyclohexyloxy)-16,16-dimethyl-2,5,6,7,18,19,20-heptanor-3,4-didehydro-4,8-inter-m-phenylene-PGI$_2$ (3E)-16,16-dimethyl-17-(2,4,6-trimethylcyclohexyloxy)-2,5,6,7,18,19,20-heptanor-3,4-didehydro-4,8-inter-m-phenylene-PGI$_2$ (3E)-16-phenoxy-2,5,6,7,17,18,19,20-octanor-3,4-didehydro-4,8-inter-m-phenylene-PGI₂

(3E)-16-(o-chlorophenoxy)-2,5,6,7,17,18,19,20-octanor-3,4-didehydro-4,8-inter-m-phenylene-PGI₂

(3E)-16-(m-chlorophenoxy)-2,5,6,7,17,18,19,20-octanor-3,4-didehydro-4,8-inter-m-phenylene-PGI₂

(3E)-16-(p-chlorophenoxy)-2,5,6,7,17,18,19,20-octanor-3,4-didehydro-4,8-inter-m-phenylene-PGI₂

(3E)-16-(o-bromophenoxy)-2,5,6,7,17,18,19,20-octanor-3,4-didehydro-4,8-inter-m-phenylene-PGI₂

(3E)-16-(m-bromophenoxy)-2,5,6,7,17,18,19,20-octanor-3,4-didehydro-4,8-inter-m-phenylene-PGI₂

(3E)-16-(p-bromophenoxy)-2,5,6,7,17,18,19,20-octanor-3,4-didehydro-4,8-inter-m-phenylene-PGI₂

(3E)-16-(o-fluorophenoxy)-2,5,6,7,17,18,19,20-octanor-3,4-didehydro-4,8-inter-m-phenylene-PGI₂

(3E)-16-(m-fluorophenoxy)-2,5,6,7,17,18,19,20-octanor-3,4-didehydro-4,8-inter-m-phenylene-PGI₂

(3E)-16-(p-fluorophenoxy)-2,5,6,7,17,18,19,20-octanor-3,4-didehydro-4,8-inter-m-phenylene-PGI₂

(3E)-16-(o-methylphenoxy)-2,5,6,7,17,18,19,20-octanor-3,4-didehydro-4,8-inter-m-phenylene-PGI₂

(3E)-16-(m-methylphenoxy)-2,5,6,7,17,18,19,20-octanor-3,4-didehydro-4,8-inter-m-phenylene-PGI₂

(3E)-16-(p-methylphenoxy)-2,5,6,7,17,18,19,20-octanor-3,4-didehydro-4,8-inter-m-phenylene-PGI₂

(3E)-16-(o-methoxyphenoxy)-2,5,6,7,17,18,19,20-octanor-3,4-didehydro-4,8-inter-m-phenylene-PGI₂

(3E)-16-(m-methoxyphenoxy)-2,5,6,7,17,18,19,20-octanor-3,4-didehydro-4,8-inter-m-phenylene-PGI₂

(3E)-16-(m-trifluoromethylphenoxy)-2,5,6,7,17,18,19,20-octanor-3,4-didehydro-4,8-inter-m-phenylene-PGI₂

(3E)-16-(p-trifluoromethylphenoxy)-2,5,6,7,17,18,19,20-octanor-3,4-didehydro-4,8-inter-m-phenylene-PGI₂

(3E)-16-phenoxy-2,5,6,7,18,19,20-heptanor-3,4-didehydro-4,8-inter-m-phenylene-PGI₂

(3E)-16-(o-chlorophenoxy)-2,5,6,7,18,19,20-heptanor-3,4-didehydro-4,8-inter-m-phenylene-PGI₂

(3E)-16-(m-chlorophenoxy)-2,5,6,7,18,19,20-heptanor-3,4-didehydro-4,8-inter-m-phenylene-PGI₂

(3E)-16-(p-chlorophenoxy)-2,5,6,7,18,19,20-heptanor-3,4-didehydro-4,8-inter-m-phenylene-PGI₂

(3E)-16-(o-bromophenoxy)-2,5,6,7,18,19,20-heptanor-3,4-didehydro-4,8-inter-m-phenylene-PGI₂

(3E)-16-(m-bromophenoxy)-2,5,6,7,18,19,20-heptanor-3,4-didehydro-4,8-inter-m-phenylene-PGI₂

(3E)-16-(p-bromophenoxy)-2,5,6,7,18,19,20-heptanor-3,4-didehydro-4,8-inter-m-phenylene-PGI₂

(3E)-16-(o-fluorophenoxy)-2,5,6,7,18,19,20-heptanor-3,4-didehydro-4,8-inter-m-phenylene-PGI₂

(3E)-16-(m-fluorophenoxy)-2,5,6,7,18,19,20-heptanor-3,4-didehydro-4,8-inter-m-phenylene-PGI₂

(3E)-16-(p-fluorophenoxy)-2,5,6,7,18,19,20-heptanor-3,4-didehydro-4,8-inter-m-phenylene-PGI₂

(3E)-16-(o-methylphenoxy)-2,5,6,7,18,19,20-heptanor-3,4-didehydro-4,8-inter-m-phenylene-PGI₂

(3E)-16-(m-methylphenoxy)-2,5,6,7,18,19,20-heptanor-3,4-didehydro-4,8-inter-m-phenylene-PGI₂

(3E)-16-(p-methylphenoxy)-2,5,6,7,18,19,20-heptanor-3,4-didehydro-4,8-inter-m-phenylene-PGI₂

(3E)-16-(o-methoxyphenoxy)-2,5,6,7,18,19,20-heptanor-3,4-didehydro-4,8-inter-m-phenylene-PGI₂

(3E)-16-(p-methoxyphenoxy)-2,5,6,7,18,19,20-heptanor-3,4-didehydro-4,8-inter-m-phenylene-PGI₂

(3E)-16-(m-trifluoromethylphenoxy)-2,5,6,7,18,19,20-heptanor-3,4-didehydro-4,8-inter-m-phenylene-PGI₂

(3E)-16-(p-trifluoromethylphenoxy)-2,5,6,7,18,19,20-heptanor-3,4-didehydro-4,8-inter-m-phenylene-PGI₂

(3E)-16-methyl-16-phenoxy-2,5,6,7,18,19,20-heptanor-3,4-didehydro-4,8-inter-m-phenylene-PGI₂

(3E)-16-(o-chlorophenoxy)-16-methyl-2,5,6,7,18,19,20-heptanor-3,4-didehydro-4,8-inter-m-phenylene-PGI₂

(3E)-16-(m-chlorophenoxy)-16-methyl-2,5,6,7,18,19,20-heptanor-3,4-didehydro-4,8-inter-m-phenylene-PGI₂

(3E)-16-(p-chlorophenoxy)-16-methyl-2,5,6,7,18,19,20-heptanor-3,4-didehydro-4,8-inter-m-phenylene-PGI₂

(3E)-16-(o-bromophenoxy)-16-methyl-2,5,6,7,18,19,20-heptanor-3,4-didehydro-4,8-inter-m-phenylene-PGI₂

(3E)-16-(m-bromophenoxy)-16-methyl-2,5,6,7,18,19,20-heptanor-3,4-didehydro-4,8-inter-m-phenylene-PGI₂

(3E)-16-(p-bromophenoxy)-16-methyl-2,5,6,7,18,19,20-heptanor-3,4-didehydro-4,8-inter-m-phenylene-PGI₂

(3E)-16-(o-fluorophenoxy)-16-methyl-2,5,6,7,18,19,20-heptanor-3,4-didehydro-4,8-inter-m-phenylene-PGI₂

(3E)-16-(m-fluorophenoxy)-16-methyl-2,5,6,7,18,19,20-heptanor-3,4-didehydro-4,8-inter-m-phenylene-PGI₂

(3E)-16-(p-fluorophenoxy)-16-methyl-2,5,6,7,18,19,20-heptanor-3,4-didehydro-4,8-inter-m-phenylene-PGI₂

(3E)-16-methyl-16-(o-methylphenoxy)-2,5,6,7,18,19,20-heptanor-3,4-didehydro-4,8-inter-m-phenylene-PGI₂

(3E)-16-methyl-16-(m-methylphenoxy)-2,5,6,7,18,19,20-heptanor-3,4-didehydro-4,8-inter-m-phenylene-PGI₂

(3E)-16-methyl-16-(p-methylphenoxy)-2,5,6,7,18,19,20-heptanor-3,4-didehydro-4,8-inter-m-phenylene-PGI₂

(3E)-16-(o-methoxyphenoxy)-16-methyl-2,5,6,7,18,19,20-heptanor-3,4-didehydro-4,8-inter-m-phenylene-PGI₂

(3E)-16-(p-methoxyphenoxy)-16-methyl-2,5,6,7,18,19,20-heptanor-3,4-didehydro-4,8-inter-m-phenylene-PGI₂

(3E)-16-methyl-16-(m-trifluoromethylphenoxy)-2,5,6,7,18,19,20-heptanor-3,4-didehydro-4,8-inter-m-phenylene-PGI₂

(3E)-16-methyl-16-(p-trifluoromethylphenoxy)-2,5,6,7,18,19,20-heptanor-3,4-didehydro-4,8-inter-m-phenylene-PGI₂

(3E)-17-phenoxy-2,5,6,7,18,19,20-heptanor-3,4-didehydro-4,8-inter-m-phenylene-PGI₂

(3E)-17-(o-chlorophenoxy)-2,5,6,7,18,19,20-heptanor-3,4-didehydro-4,8-inter-m-phenylene-PGI₂

(3E)-17-(m-chlorophenoxy)-2,5,6,7,18,19,20-heptanor-3,4-didehydro-4,8-inter-m-phenylene-PGI₂

(3E)-17-(p-chlorophenoxy)-2,5,6,7,18,19,20-heptanor-3,4-didehydro-4,8-inter-m-phenylene-PGI₂

(3E)-17-(o-bromophenoxy)-2,5,6,7,18,19,20-heptanor-3,4-didehydro-4,8-inter-m-phenylene-PGI₂

(3E)-17-(m-bromophenoxy)-2,5,6,7,18,19,20-heptanor-3,4-didehydro-4,8-inter-m-phenylene-PGI₂

(3E)-17-(p-bromophenoxy)-2,5,6,7,18,19,20-heptanor-3,4-didehydro-4,8-inter-m-phenylene-PGI₂

(3E)-17-(o-fluorophenoxy)-2,5,6,7,18,19,20-heptanor-3,4-didehydro-4,8-inter-m-phenylene-PGI₂

(3E)-17-(m-fluorophenoxy)-2,5,6,7,18,19,20-heptanor-3,4-didehydro-4,8-inter-m-phenylene-PGI₂

(3E)-17-(p-fluorophenoxy)-2,5,6,7,18,19,20-heptanor-3,4-didehydro-4,8-inter-m-phenylene-PGI₂

(3E)-17-(o-methylphenoxy)-2,5,6,7,18,19,20-heptanor-3,4-didehydro-4,8-inter-m-phenylene-PGI$_2$
(3E)-17-(m-methylphenoxy)-2,5,6,7,18,19,20-heptanor-3,4-didehydro-4,8-inter-m-phenylene-PGI$_2$
(3E)-17-(p-methylphenoxy)-2,5,6,7,18,19,20-heptanor-3,4-didehydro-4,8-inter-m-phenylene-PGI$_2$
(3E)-17-(o-methoxyphenoxy)-2,5,6,7,18,19,20-heptanor-3,4-didehydro-4,8-inter-m-phenylene-PGI$_2$
(3E)-17-(p-methoxyphenoxy)-2,5,6,7,18,19,20-heptanor-3,4-didehydro-4,8-inter-m-phenylene-PGI$_2$
(3E)-17-(m-trifluoromethylphenoxy)-2,5,6,7,18,19,20-heptanor-3,4-didehydro-4,8-inter-m-phenylene-PGI$_2$
(3E)-17-(p-trifluoromethylphenoxy)-2,5,6,7,18,19,20-heptanor-3,4-didehydro-4,8-inter-m-phenylene-PGI$_2$
(3E)-16-methyl-17-phenoxy-2,5,6,7,18,19,20-heptanor-3,4-didehydro-4,8-inter-m-phenylene-PGI$_2$
(3E)-17-(o-chlorophenoxy)-16-methyl-2,5,6,7,18,19,20-heptanor-3,4-didehydro-4,8-inter-m-phenylene-PGI$_2$
(3E)-17-(m-chlorophenoxy)-16-methyl-2,5,6,7,18,19,20-heptanor-3,4-didehydro-4,8-inter-m-phenylene-PGI$_2$
(3E)-17-(p-chlorophenoxy)-16-methyl-2,5,6,7,18,19,20-heptanor-3,4-didehydro-4,8-inter-m-phenylene-PGI$_2$
(3E)-17-(o-bromophenoxy)-16-methyl-2,5,6,7,18,19,20-heptanor-3,4-didehydro-4,8-inter-m-phenylene-PGI$_2$
(3E)-17-(m-bromophenoxy)-16-methyl-2,5,6,7,18,19,20-heptanor-3,4-didehydro-4,8-inter-m-phenylene-PGI$_2$
(3E)-17-(p-bromophenoxy)-16-methyl-2,5,6,7,18,19,20-heptanor-3,4-didehydro-4,8-inter-m-phenylene-PGI$_2$
(3E)-17-(o-fluorophenoxy)-16-methyl-2,5,6,7,18,19,20-heptanor-3,4-didehydro-4,8-inter-m-phenylene-PGI$_2$
(3E)-17-(m-fluorophenoxy)-16-methyl-2,5,6,7,18,19,20-heptanor-3,4-didehydro-4,8-inter-m-phenylene-PGI$_2$
(3E)-17-(p-fluorophenoxy)-16-methyl-2,5,6,7,18,19,20-heptanor-3,4-didehydro-4,8-inter-m-phenylene-PGI$_2$
(3E)-16-methyl-17-(o-methylphenoxy)-2,5,6,7,18,19,20-heptanor-3,4-didehydro-4,8-inter-m-phenylene-PGI$_2$
(3E)-16-methyl-17-(m-methylphenoxy)-2,5,6,7,18,19,20-heptanor-3,4-didehydro-4,8-inter-m-phenylene-PGI$_2$
(3E)-16-methyl-17-(p-methylphenoxy)-2,5,6,7,18,19,20-heptanor-3,4-didehydro-4,8-inter-m-phenylene-PGI$_2$
(3E)-17-(o-methoxyphenoxy)-16-methyl-2,5,6,7,18,19,20-heptanor-3,4-didehydro-4,8-inter-m-phenylene-PGI$_2$
(3E)-17-(p-methoxyphenoxy)-16-methyl-2,5,6,7,18,19,20-heptanor-3,4-didehydro-4,8-inter-m-phenylene-PGI$_2$
(3E)-16-methyl-17-(m-trifluoromethylphenoxy)-2,5,6,7,18,19,20-heptanor-3,4-didehydro-4,8-inter-m-phenylene-PGI$_2$
(3E)-16-methyl-17-(p-trifluoromethylphenoxy)-2,5,6,7,18,19,20-heptanor-3,4-didehydro-4,8-inter-m-phenylene-PGI$_2$
(3E)-16,16-dimethyl-17-phenoxy-2,5,6,7,18,19,20-heptanor-3,4-didehydro-4,8-inter-m-phenylene-PGI$_2$
(3E)-17-(o-chlorophenoxy)-16,16-dimethy-2,5,6,7,18,19,20-heptanor-3,4-didehydro-4,8-inter-m-phenylene-PGI$_2$
(3E)-17-(m-chlorophenoxy)-16,16-dimethyl-2,5,6,7,18,19,20-heptanor-3,4-didehydro-4,8-inter-m-phenylene-PGI$_2$
(3E)-17-(p-chlorophenoxy)-16,16-dimethyl-2,5,6,7,18,19,20-heptanor-3,4-didehydro-4,8-inter-m-phenylene-PGI$_2$
(3E)-17-(o-bromophenoxy)-16,16-dimethyl-2,5,6,7,18,19,20-heptanor-3,4-didehydro-4,8-inter-m-phenylene-PGI$_2$
(3E)-17-(m-bromophenoxy)-16,16-dimethyl-2,5,6,7,18,19,20-heptanor-3,4-didehydro-4,8-inter-m-phenylene-PGI$_2$
(3E)-17-(p-bromophenoxy)-16,16-dimethyl-2,5,6,7,18,19,20-heptanor-3,4-didehydro-4,8-inter-m-phenylene-PGI$_2$
(3E)-17-(o-fluorophenoxy)-16,16-dimethyl-2,5,6,7,18,19,20-heptanor-3,4-didehydro-4,8-inter-m-phenylene-PGI$_2$
(3E)-17-(m-fluorophenoxy)-16,16-dimethyl-2,5,6,7,18,19,20-heptanor-3,4-didehydro-4,8-inter-m-phenylene-PGI$_2$
(3E)-17-(p-fluorophenoxy)-16,16-dimethyl-2,5,6,7,18,19,20-heptanor-3,4-didehydro-4,8-inter-m-phenylene-PGI$_2$
(3E)-16,16-dimethyl-17-(o-methylphenoxy)-2,5,6,7,18,19,20-heptanor-3,4-didehydro-4,8-inter-m-phenylene-PGI$_2$
(3E)-16,16-dimethyl-17-(m-methylphenoxy)-2,5,6,7,18,19,20-heptanor-3,4-didehydro-4,8-inter-m-phenylene-PGI$_2$
(3E)-16,16-dimethyl-17-(p-methylphenoxy)-2,5,6,7,18,19,20-heptanor-3,4-didehydro-4,8-inter-m-phenylene-PGI$_2$
(3E)-17-(o-methoxyphenoxy)-16,16-dimethyl-2,5,6,7,18,19,20-heptanor-3,4-didehydro-4,8-inter-m-phenylene-PGI$_2$
(3E)-17-(p-methoxyphenoxy)-16,16-dimethyl-2,5,6,7,18,19,20-heptanor-3,4-didehydro-4,8-inter-m-phenylene-PGI$_2$
(3E)-16,16-dimethyl-17-(m-trifluoromethylphenoxy)-2,5,6,7,18,19,20-heptanor-3,4-didehydro-4,8-inter-m-phenylene-PGI$_2$
(3E)-16,16-dimethyl-17-(p-trifluoromethylphenoxy)-2,5,6,7,18,19,20-heptanor-3,4-didehydro-4,8-inter-m-phenylene-PGI$_2$
(3E)-18-phenoxy-2,5,6,7,19,20-hexanor-3,4-didehydro-4,8-inter-m-phenylene-PGI$_2$
(3E)-16-methyl-18-phenoxy-2,5,6,7,19,20-hexanor-3,4-didehydro-4,8-inter-m-phenylene-PGI$_2$
(3E)-16,16-dimethyl-18-phenoxy-2,5,6,7,19,20-hexanor-3,4-didehydro-4,8-inter-m-phenylene-PGI$_2$
(3E)-19-phenoxy-2,5,6,7,20-pentanor-3,4-didehydro-4,8-inter-m-phenylene-PGI$_2$
(3E)-16-methyl-19-phenoxy-2,5,6,7,20-pentanor-3,4-didehydro-4,8-inter-m-phenylene-PGI$_2$
(3E)-16,16-dimethyl-19-phenoxy-2,5,6,7,20-pentanor-3,4-didehydro-4,8-inter-m-phenylene-PGI$_2$
and their methyl ester, ethyl ester, butyl ester, isobutyl ester, phenyl ester, benzyl ester, phenetyl ester, cyclopentyl ester, cyclohexyl ester, cyclohexylmethyl ester, furylmethyl ester, 1-carbomethoxy ester, phenacyl ester, p-bromophenacyl ester, and the like.

The compounds wherein $R_1$ is methyl may be prepared according to processes as shown in the scheme A.

Scheme A:

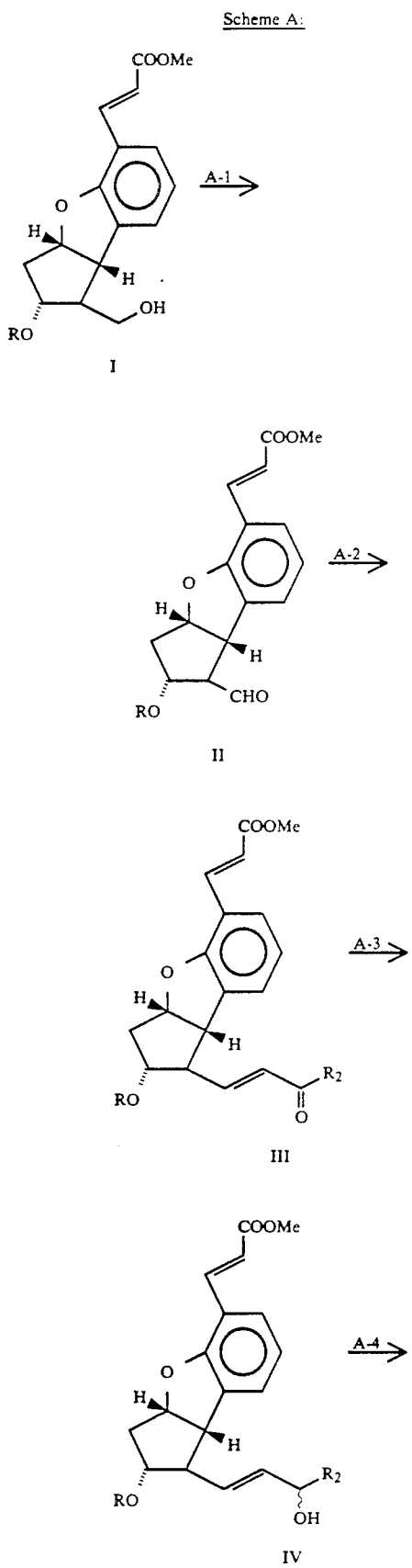

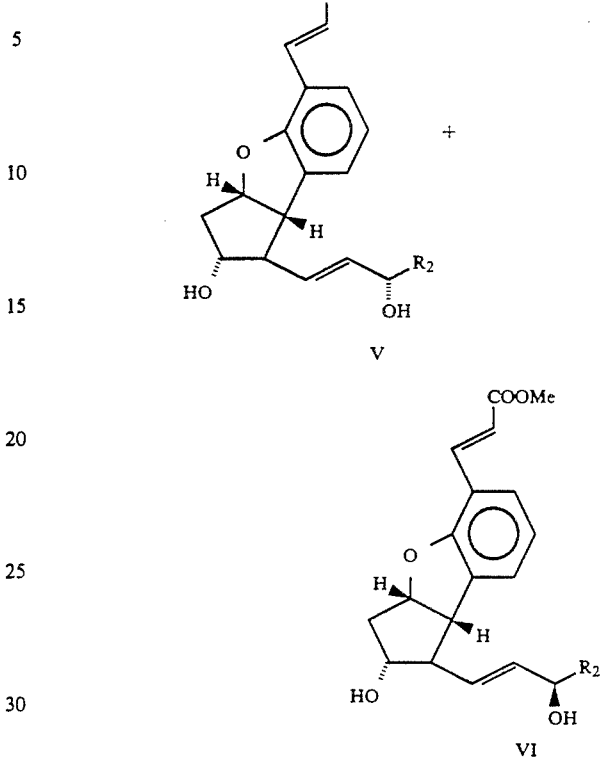

The step A-1 is so-called oxidation of alcohol to aldehyde. In this step, various oxidizing agents may be used. For oxidation of the compounds having Formula I wherein R is an ester residue, the oxidizing agents such as a complex of anhydrous chromic acid and pyridine (Collins reagent), dimethylsulfoxide-dicyclohexylcarbodiimide, dimethylsulfide-chlorine, N-bromosuccinimide-chlorine and the like are preferably used.

The step A-2 is carried out by condensing the aldehyde II with dimethyl phosphonate having the following formula:

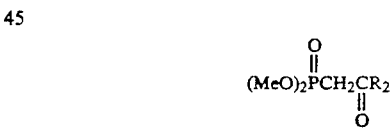

wherein $R_2$ is as defined above. The dimethyl phosphonate is usually reacted with a metal hydride such as sodium hydride, potassium hydride and the like in an ether solvent such as tetrahydrofuran, dimethoxyethane and the like to produce the corresponding salt, followed by the addition of the aldehyde II. The reaction temperature is selected from the range between $-30°$ C. to $100°$ C. and preferably from $0°$ C. to room temperature to give a prefered reaction. The dimethyl phosphonate used in this reaction may be prepared according to the following procedure [E. J. Cory et al., J. Am. Chem. Soc., 88, 5654 (1966)].

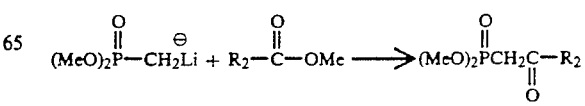

The step A-3 represents the preparation of the allylalcohols IV by reducing the α, β-unsaturated ketones III. For this reduction, the reducing agents which can reduce selectively only a ketone radical without reduction of an ester radical or a double bond of α, β-unsaturated ketone are employed. For this purpose, metal hydrides, trialkoxy aluminium compounds, or dialkyl aluminium compounds are preferably used. Preferable examples of the reducing agent include zinc boron compounds (for example, Zn (BH$_4$)$_2$), combined reagents of sodium borohydride and cerium trichloride, diisobutyl (2,6-dimethlphenoxy) aluminium, triisopropoxyaluminium and the like but is not limited to. Sodium borohydride/cerium trichloride is usually used to give a preferable result. As a solvent for this reaction, methanol is most preferably used. When the zinc borohydride compounds and the organic aluminium reducing agents are used, etheric solvents such as ether, tetrahydrofuran and dimethoxyethane are preferably used. The reaction temperature is selected from the range between −110° C. to 80° C. and preferably from −78° C. to room temperature. The compound IV obtained according to the step A-3 is usually a mixture of 15-α isomer and 15-β isomer and used as a starting material in the step A-4 without further isolation.

The step A-4 is transesterification of R radical by methanol. For this purpose, the compounds IV is dissolved in methanol, followed by the addition of appropriate base and allowed to stand at temperature of from −30° C. to 100° C. Anhydrous sodium carbonate, anhydrous potassium carbonate, sodium methoxide, and potassium methoxide are preferably employed as the base. The compounds obtained according to the step A-4 is usually a mixture of the 15-α isomer (V) and the 15-β isomer (VI). The 15-α isomer and the 15-β isomer are isolated by column chromatography technique (ordinary phase silica gel; when ethyl acetate/cyclohexane mixture is used as an developing eluent, preferable isolation is usually achieved).

The compounds wherein R$_1$ is methyl may be prepared according to processes as shown in the scheme B.

Scheme B:

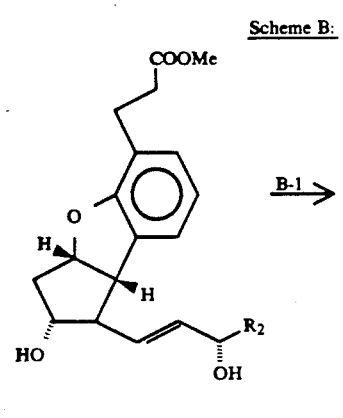

VII

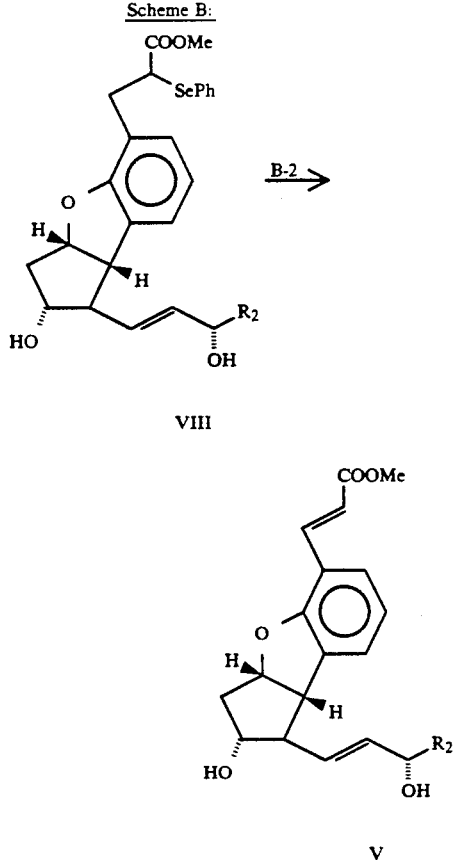

Illustrative preparation of the starting compound VII in the scheme B wherein R$_2$ is as defined above is disclosed in Japanese Patent Application No. 262021/1987.

The step B-1 represents phenylselenization of α-carbon in a carboxylic acid methyl ester. This step is carried out by reacting the carboxylic acid methyl ester VII with from 3 to 4 equivalents of lithium diisopropylamide, followed by reaction with diphenyl diselenide. As a solvent for this step, tetrahydrofuran is most preferably used but not limited to. The reaction temperature after diphenyl diselenide is added to the compound VII is usually in the range between −80° C. to 40° C. After the addition of diphenyl diselenide, hexamethyl phosphoric triamide (HMPA) is preferably added to the mixture. The step B-2 represents dephenylselenization. Usually, for this purpose, elimination during oxidation by hydrogen peroxide is usually used. In this case, hydrogen peroxide is usually employed in an excess amount of 35% aqueous solution. After completion of the reaction, the hydrogen peroxide is reduced with reducing agent such as dimethylsulfide, sodium thiosulfate, sodium hydrogen bisulfate and the like.

The compounds wherein R$_1$ is hydrogen may be prepared according to processes as shown in the scheme C and the scheme D.

Scheme C:

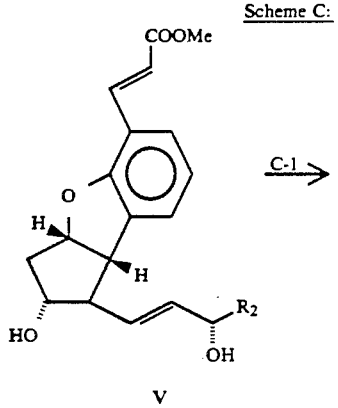

V

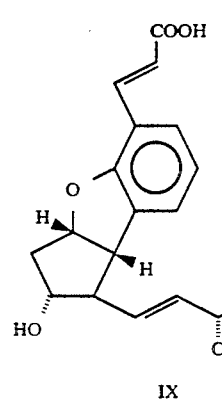

IX

Scheme D:

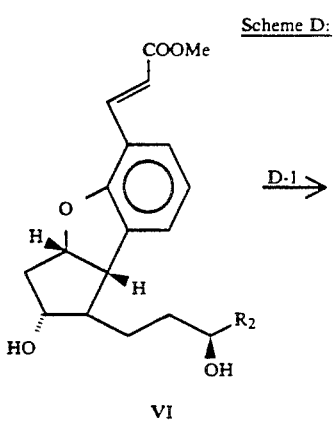

VI

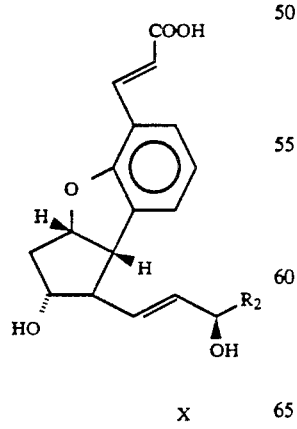

X

The step C-1 and the step D-1 represent hydrolysis of the methyl ester. Usually, the compound V or VI is reacted with base in aqueous alcohol solvent such as aqueous methanol and aqueous ethanol, or aqueous ether solvent such as aqueous dioxane and aqueous tetrahydrofuran. The base includes preferably inorganic bases such as sodium hydroxide, potassium hydroxide, sodium carbonate, and potassium carbonate. The reaction temperature is selected from the range between $-20°$ C. to $150°$ C. and preferably room temperature to give a preferable reaction rate.

The compounds having Formula I used in the scheme A wherein R is an ester residue, may be prepared according to processes as shown in the scheme E. Further detailed description for carrying out the processes is illustrated in Examples 1 and 2. Illustrative preparation of the starting compound XI in the scheme E is disclosed in Japanese Patent Application No. 262021/1987.

Scheme E:

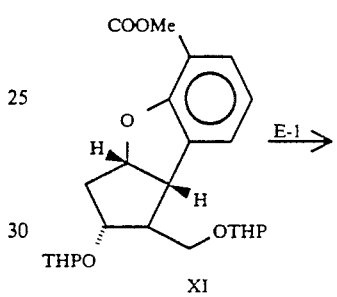

XI

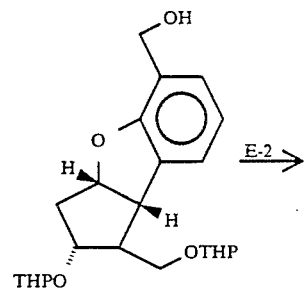

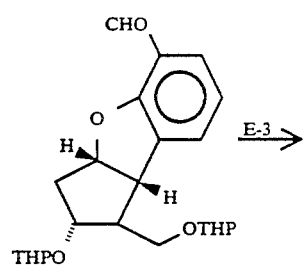

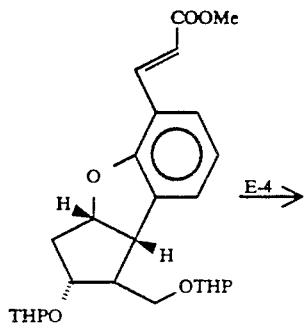

-continued
Scheme E:

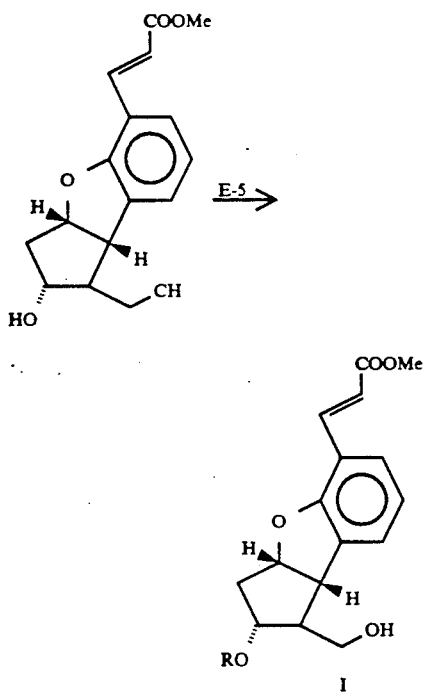

The compounds wherein $R_1$ is not hydrogen and cation but an ester residue, may be prepared by esterification of the corresponding carboxylic acid wherein $R_1$ is hydrogen.

Many methods of esterification are known. Methods which may especially be preferred to practice the present invention include the diazoalkane method, the method by utilizing the action of active halides on silver or tertiary amine salts of carboxylic acids, and the mixed acid anhydride method.

In producing the ester by the diazoalkane, the carboxylic acid may be reacted with the diazoalkane in a solvent to give a product. As the diazoalkane may be mentioned diazomethane, diazoethane, diazopropane, diazodecane and the like.

The diazoalkanes, however, are not limited to those mentioned above.

The second method may usually be performed by reacting a silver or tertiary amine salt of a carboxylic acid with an active halide in an aprotic polar solvent such as dimethylformamide, acetonitrile, etc. Examples of the active halides may include, but are not limited to, benzyl chloride, benzyl bromide, p-bromobenzyl bromide, p-methoxybenzyl bromide, p-phenyl benzyl bromide, phenacyl bromide, p-bromophenacyl bromide, p-nitrophenacyl bromide, α-benzoyl phenacyl bromide, etc.

The third mixed acid anhydride method is most applicable. Most of the esters according to the present invention can be prepared by the mixed acid anhydride method.

In this method, a salt of the carboxylic acid is reacted with ethyl chlorocarbonate, pivaloyl chloride, p-toluenesulfonic chloride to form a mixed acid anhydride.

An excess amount of an alcohol represented by the formula $R_1OH$ wherein $R_1$ is as defined above but does not represent hydrogen nor cation is then added to the mixed anhydride followed by heating.

Specific examples of the alcohol include but are not limited to methanol, ethanol, propanol, butanol, octanol, decanol, isopropanol, 2-ethylhexanol, benzylalcohol, p-bromobenzylalcohol, phenetylalcohol, cyclopentylalcohol, cyclopentylmethylalcohol, cyclohexanol, cyclohexylmethylalcohol, 2-methoxyethanol, 2-(2-methoxyethoxy)ethanol, hydroxyacetic acid methyl ester, lactic acid methyl ester, γ-hydroxybutylic acid methyl ester, phenol, p-bromophenol, p-fluorophenol, m-chlorophenol, m-fluorophenol, 3,4-dichlorophenol, p-(trifluoromethyl)phenol, p-methylphenol, 3,4-dimethylphenol, p-methoxyphenol, 4-phenoxyphenol and the like.

The compounds according to the present invention are illustrated by the structural formula of an optical active isomer; however, this general formula is also to represent d, l and dl isomers.

The schemes A-E are also illustrated by use of the structural formula with regard to one of the optical active isomers; however, they are applicable to any of d, l and dl isomers in the same manner.

The compounds according to the present invention have potent pharmacological activities such as platelet-aggregation inhibiting, platelet-adhesion inhibiting, vasodilative, gastric acid secretion inhibiting, gastric mucosa cell protecting, bronchodilative, luteo-regressive and uterotonic activities and the like.

The potent platelet-aggregation inhibiting, platelet-adhesion inhibiting, vasodilative, hypolipidemic, and cholesterol and neutral lipid lowering activities can be applied prophylactically and therapeutically to hypertention, myocardial infarction, angina pectoris, ischemic cerebral disease such as cerebral infarction and the like, TIA, peripheral circulatory disturbance (Berger's disease, Behcet's syndrome, Raynaud's disease, thrombotic thrombocytopenic purpura, arterio-venous fistula, liver diseases, and renal diseases and the like), atherosclerosis, arteriosclerosis, diabetic platelet dysfunction and neuropathy, retinal vascular obstruction hyperlipidemia, vibration diseases and the like.

For the purpose, the compounds of the present invention may be administered intravenously, intra-arterially, intramuscularly, percutaneously, subcutaneously or orally. Oral or intrarectal administration needs a usual daily dose in the range of from 0.01 μg/Kg to 10 mg/Kg. The drugs are administered at one to four times a day. In the case of intravenous infution or intra-arterial injection the range of from 0.1 ng/Kg/min. to 1 μg/Kg/min. may cause good therapeutical results. In the case of usual intravenous, intramuscular or subcutaneous injection, a daily dose in the range of from 0.01 μg/Kg to 10 mg/Kg may be used at one to four times a day.

Upon these administration, the dose will be determined through taking many factors including, for example, age and sex of patients; time of administration; conditions of the patients into account. For percutaneous administration, the dosage will vary widely depending on the dosage forms and be controlled to give a absorption of 0.001 μg/Kg-10 mg/Kg a day per Kg body weight.

The compounds according to the present invention can be used for preservation of platelets. For this purpose, the compound is added to platelet concentrate at the range of 0.01 ng-1 μg per 1 ml of the concentrate.

The compounds of the present invention are effective for the prevention of platelet aggregation and adhesion when an artificial heart and lung, an artificial kidney, an artificial liver, an artificial valve, an artificial blood vessel are employed. For this purpose, the compound is added in the dosage forms for oral administration or injection. Upon oral administration, the doses of 0.01 μg/Kg-10 mg/Kg of the compound will result in good effects. The application of the compound to an inlet of blood flowing circuit in an artificial organ by instillation may be useful. For this purpose, the compound is given at administration rates of 0.01 ng/Kg/min.-1 mg/Kg/min.

The compounds according to the present invention are useful in treatment and prophylaxis of duodenal ulcer, gastric ulcer, chronic gastritis, digestive system disease and the like caused by non-steroidal anti-inflammatory, analgesic agents and the like. For this purpose, the compound may be orally or intravenuously administered at a dose in the range of from 0.01 μg/Kg to 10 mg/Kg per day. Adequate schedule is one to four times a day.

The compounds according to the present invention are also effective for the treatment of asthma, bronchitis and respiratory disorders in pneumonia. For this purpose, the compound may be given at doses of 0.01 μg/Kg/-1 mg/Kg in the forms for oral administration or inhalation.

The compounds according to the present invention are also effective for the induction of labor and the relaxation and softening of uterine cervix. For this purpose, the compound may be preferably administered orally, pervaginally, or intravenously by instillation. Upon oral or pervaginal administration, the compound may be given at doses of 0.01 μg/Kg-5 mg/Kg. Upon intravenous instillation, the pharmaceutical composition containing the compound may be administered at rates of 0.01 ng/Kg/min.-1 μg/Kg/min.

The compounds of the present invention are useful in synchronizing a menstrual cycle among mammal animals (horse, bovine, hog and sheep). For this purpose, the compound may be usually given orally, pervaginally or intramascularly at doses of 0.01 μg/Kg-10 mg/Kg.

The compounds of the present invention are also useful in removing congestion of nasal mucosa. For this purpose, either a solution containing from 0.1 μg/ml to 10 mg/ml of the compound in the aerosol formulations, or topically an ointment, a lotion and a liniment containing from 0.01 μg/ml-1 mg/ml of the compound may be applied.

The compounds of the present invention are useful in treating hepatitis and nephritis conditions. For this purpose, the compound may be given orally or intravenously at doses of 0.01 μg/Kg-1 mg/Kg.

The compounds according to the present invention are also useful in preventing a transfer of tumor. For this purpose, the compound may be given orally or intravenously at doses of 0.01 μg/Kg per day-1 mg/Kg per day once to four times a day.

The compounds of the present invention may be administered intravenously by instillation. For this instillation, the compound may be given at rates of 0.01 ng/Kg/min.-100 μg/Kg/min.

The compounds according to the present invention are useful as an anti-inflammatory and analgesic agent. For this purpose, the compound may be given orally or intravenously at doses of 0.01 μg/Kg/day-1 mg/Kg/day.

The compounds according to the present invention may be administered in the forms of solid compositions containing vehicles such as starch, lactose, sucrose, glucose, fine crystalline cellulose, a certain bole; colorant; lubricant; binder; disintegrating agent; and coating.

The compounds according to the present invention can be given parenterally in the forms of a sterile solution which may contain solutes, for example, sodium chloride, glucose and the like in an amount sufficient to make it isotonic.

The compounds according to the present invention are stable inherently by their chemical structures, thereby are encountered with no difficulties in preparing pharmaceutical formulations, and find wide uses by a variety of routes of administration such as oral preparations (tablets, powders, granules), injections, suppositories, ointments, and lotions.

EXAMPLE

The present invention will be illustrated by the following examples. These examples should not be construed as limiting the scope of the invention which is defined solely by the claims appended to this application.

EXAMPLE 1 d-(E)-3-(2α-hydroxy-1β-hydroxymethyl-3aβH,8bβH-2,3,3a,8b-tetrahydro-5-1H-cyclopenta[b]benzofuran)-acrylic acid methyl ester (1)

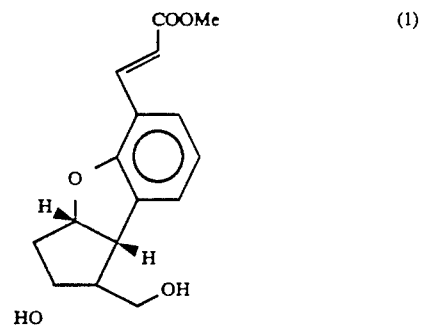

To a solution of d-2α-tetrahydropyranyloxy-1β-tetrahydropyranyloxymethyl-3aβH,8bβH-2,3,3a,8b-tetrahydro-5-1H-cyclopenta[b]benzofurancarboxylic acid methyl ester (22.4 g, 51.8 mmoles) in dry THF at −20° C. was added lithium aluminum hydride (1.97 g, 51.8 mmoles) and stirred under argon at −20° C. for 30 minutes. To the reaction mixture was added water (20 ml), followed by 3N hydrochloric acid (100 ml), and then extracted with ethyl acetate (500 ml, 250 ml×2). The organic layers were combined, washed with saturated aqueous sodium hydrogen carbonate (100 ml) and with brine (100 ml), dried over anhydrous magnesium sulfate, and concentrated. The resulting oily product was dissolved in dichloromethane (250 ml). To this solution then was added manganese dioxide (22.5 g, 259 mmoles), followed by the addition of 13.5 g (155 mmoles), 13.5 g (155 mmoles), and 9.0 g (104 mmoles) of manganese dioxide after 24 hours, 48 hours, and 60 hours respectively while stirring at room temperature, and stirred for further 6 hours. This reaction solution was filtered with celite by suction, and concentrated to yield 21.4 g of an oily product.

To a suspension of sodium hydride (60% mineral oil dispersion, 3.52 g, 88.1 mmoles) in dry THF (60 ml) was added dry DMSO (120 ml), and cooled to −10° C. To the suspension was added a solution of dimethyl carbomethoxymethylphosphonate (16.0 g, 88.1 mmoles) in dry THF (60 ml), and stirred at 0° C. for 30 minutes. To this solution then was added a solution of the above-obtained oily product in dry THF (80 ml), and stirred at 0° C. for 30 minutes. To this reaction mixture was added acetic acid (5.55 ml), and concentrated. To the residue was added water (50 ml), and then extracted with ethyl acetate (200 ml, 100 ml×2). The organic layers were combined, washed with water (50 ml×2) and with brine (50 ml), dried over anhydrous magnesium sulfate, and concentrated. The resulting oily product was dissolved in methanol (300 ml), to which concentrated hydrochloric acid (1.0 ml) was added, and stirred at 50° C. for 1 hours. To the reaction mixture cooled to 0° C. was added sodium hydrogen carbonate (1.2 g), stirred at room temperature for 30 minutes, and concentrated. To the residue was added 5% aqueous sodium chloride (100 ml), and then extracted with ethyl acetate (200 ml, 100 ml×2). The organic layers were combined, washed with brine (50 ml), dried over anhydrous magnesium sulfate, and concentrated. The residue was recrystallized to give 67.0% yield of d-(E)-3-(2α-hydroxy-1β-hydroxymethyl-3aβH,8bβH-2,3,3a,8b-tetrahydro-5-1H-cyclopenta[b]benzofuran)-acrylic acid methyl ester (10.1 g, 34.8 mmoles) as a white crystal. The mother liquid was concentrated and purified by column chromatography (silica gel: ethyl acetate/cyclohexane) to afford 3.70 g (12.8 mmoles) of d-(E)-3-(2α-hydroxy-1β-hydroxymethyl-3aβH,8bβH-2,3,3a,8b-tetrahydro-5-1H-cyclopenta[b]benzofuran)-acrylic acid methyl ester (overall yield 91.9%).

The structure was confirmed by the following data:
m.p. 155°–156° C.

[α]$_D^{25}$: +216.99 (c 0.400, MeOH).

IR (KBr): 3250, 2950, 2870, 1705, 1630, 1600, 1440, 1380, 1350, 1310, 1270, 1250, 1220, 1200, 1170, 1060, 1020, 980, 900, 860, 780, 750, 720, 600 cm$^{-1}$.

NMR (400 MHz, CDCl$_3$, δ): 1.75–1.85 (1H, m), 2.05–2.25 (3H, m), 2.65 (1H, dt, J=6.9, 13.5 Hz), 3.45 (1H, t, J=8.6 Hz), 3.80 (3H, s), 3.8–3.9 (1H, m), 3.95–4.0 (1H, m), 4.1–4.2 (1H, m), 5.26 (1H, ddd, J=5.1, 6.9, 8.6 Hz), 6.72 (1H, d, J=15.6 Hz), 6.87 (1H, t, J=7.6 Hz), 7.19 (1H, d, J=7.6 Hz), 7.24 (1H, d, J=7.6 Hz), 7.68 (1H, d, J=15.6 Hz).

MASS (EI, m/e): 290 (M+).

High resolution mass spectrum: Calcd. (C$_{16}$H$_{18}$O$_5$, M+): 290.1154. Found (M+): 290.1150.

Anal.: Calcd. for C$_{16}$H$_{18}$O$_5$: C: 66.19; H: 6.25. Found: C: 66.07; H: 6.24.

EXAMPLE 2 d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (2)

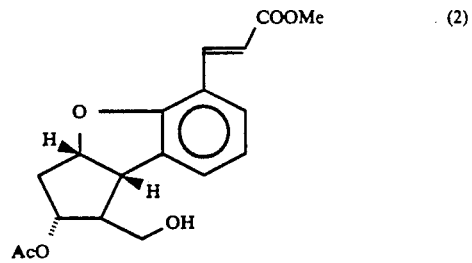

To a solution of d-(E)-3-(2α-hydroxy-1β-hydroxymethyl-3aβH,8bβH-2,3,3a,8b-tetrahydro-5-1H-cyclopenta[b]benzofuran)-acrylic acid methyl ester (11.3 g 38.9 mmoles) in dry THF were added anhydrous triethylamine (16.3 ml, 116.7 mmoles) and trityl chloride (16.3 g, 58.4 mmoles), and heated under reflux for 2 hours.

To the reaction mixture were added anhydrous pyridine (18.8 ml, 233.4 mmoles) and acetic anhydride (22.0 ml, 233.4 mmoles), which was stirred at 50° C. for 4 hours, followed by at room temperature for further 14 hours. To the reaction mixture cooled to 0° C. was added 3.76N methanolic hydrochloric acid (94 ml), and stirred at room temperature for 2 hours. To this reaction mixture was added water (50 ml), and then extracted with ethyl acetate (400 ml, 200 ml×2). The organic layers were combined, washed with saturated aqueous sodium hydrogen carbonate (30 ml) and with brine (30 ml), dried over anhydro us magnesium sulfate, and concentrated. The residue was purified by column chromatography (silica gel: ethyl acetate/cyclohexane=⅓~½) to afford d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (11.1 g, 33.4 mmoles, yield 86.0%).

The structure was confirmed by the following data:
m.p. 155°–156° C. (recrystallized from ethyl acetate/cyclohexane).

[α]$_D^{25}$: +264.61 (c 0.438, MeOH).

IR (KBr): 3450, 2950, 2900, 2860, 1710, 1630, 1600, 1590, 1470, 1440, 1370, 1310, 1260, 1200, 1160, 1100, 1060, 1040, 1020, 980, 950, 910, 900, 860, 840, 790, 770, 750, 720, 580, 560, 490 cm$^{-1}$.

NMR (400 MHz, CDCl$_3$, δ): 1.79 (3H, s), 2.05–2.15 (1H, m), 2.25–2.35 (2H, m), 2.58 (1H, dt, J=6.1, 14.6 Hz), 3.65–3.75 (3H, m), 3.80 (3H, s), 5.08 (1H, q, J=6.1 Hz), 5.33 (1H, ddd, J=5.4, 6.1, 8.3 Hz), 6.72 (1H, d, J=15.9 Hz), 6.86 (1H, t, J=7.3 Hz), 7.19 (1H, d, J=7.3 Hz), 7.23 (1H, d, J=7.3 Hz), 7.69 (1H, d, J=15.9 Hz).

MASS (EI, m/e): 332 (M+).

High resolution mass spectrum: Calcd. (C$_{18}$H$_{20}$O$_6$, M+): 332.1260. Found (M+): 332.1258.

Anal. Calcd. for C$_{18}$H$_{20}$O$_6$: C: 65.05; H: 6.07. Found: C: 64.66; H: 6.06.

EXAMPLE 3 d-(3E)-15-oxo-2,5,6,7-tetranor-3,4-didehydro-4,8-inter-m-phenylene PGI₂ methyl ester, 11-acetate (3)

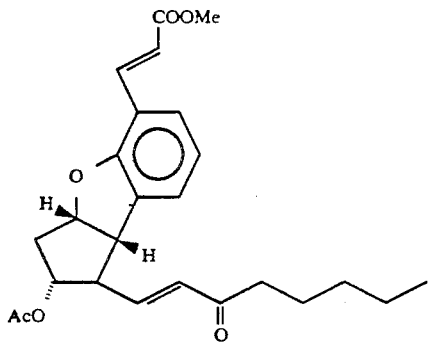

(3)

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (1.00 g 3.01 mmoles) in dry THF (15 ml) under argon atomosphere were added anhydrous pyridine (0.075 ml, 0.933 mmoles), dry DMSO (2.14 ml), trifluoroacetic acid (0.070 ml, 0.903 mmoles), and DCC (931 mg, 4.52 mmoles), and stirred at room temperature for 4 hours.

Then sodium hydride (60% mineral oil dispersion 199 mg, 4.97 mmoles) was suspended in dry THF (5 ml), to which a solution of dimethyl 2-oxoheptylphosphonate (1.14 g, 5.12 mmoles) in dry THF (5 ml) was added, and stirred under argon atomosphere at 0° C. for 15 minutes. To this solution then was added the above-prepared aldehyde solution by syringe while cooling with ice. The reaction mixture was stirred at 0° C. for 30 minutes, to which acetic acid (0.3 ml) was added, and concentrated. To the residue was added ethyl acetate (40 ml), filtered, and the filtrate was washed with water (30 ml). The aqueous layers were then re-extracted with ethyl acetate (30 ml). The organic layers were combined, washed with brine (30 ml), dried over anhydrous magnesium sulfate, and concentrated. The residue was passed through a short column of silica gel, and purified by Lobar Column (Merck, silica gel: ethyl acetate/cyclohexane=1/6) to afford 89.7% yield of d-(3E)-15-oxo-2,5,6,7-tetranor-3,4-didehydro-4,8-inter-m-phenylene PGI₂ methyl ester, 11-acetate (1.15 g, 2.70 mmoles).

The structure was confirmed by the following data:

$[\alpha]_D^{25}$: +202.25 (c 0.886, CHCl₃).

IR (liquid film): 2950, 2870, 1730, 1710, 1670, 1630, 1450, 1370, 1320, 1240, 1170, 1060, 980, 950, 860, 750 cm⁻¹.

NMR (90 MHz, CDCl₃, δ): 0.8–1.1 (3H, m), 1.2–2.0 (6H, m), 1.73 (3H, s), 2.1–3.2 (5H, m), 3.6–3.9 (1H, m), 3.80 (3H, s), 4.9–5.1 (1H, m), 5.3–5.6 (1H, m), 6.20 (1H, d, J=15.8 Hz), 6.6–7.3 (5H, m), 7.69 (1H, d, J=16.1 Hz).

Mass (EI, m/e): 426 (M⁺).

EXAMPLE 4 d-(3E)-16-methyl-15-oxo-2,5,6,7-tetranor-3,4-didehydro-4,8-inter-m-phenylene PGI₂ methyl ester, 11-acetate (4)

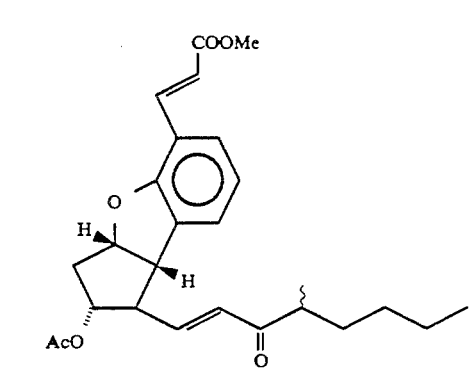

(4)

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (1.00 g, 3.01 mmoles) in dry THF (10 ml) under argon atomosphere were added anhydrous pyridine (0.075 ml, 0.933 mmoles), dry DMSO (2.41 ml), and trifluoroacetic acid (0.070 ml, 0.903 mmoles), to which a solution of DCC (931 mg, 4.52 mmoles) in dry THF (5 ml) was added and stirred at room temperature for 3 hours.

Then sodium hydride (60% mineral oil dispersion 199 mg, 5.12 mmoles) was suspended in dry THF (5 ml), to which a solution of dimethyl 3-methyl-2-oxoheptylphosphonate (1.21 g, 5.12 mmoles) in dry THF (5 ml) was added, and stirred under argon atomosphere at room temperature for 20 minutes. To this solution then was added the above-prepared aldehyde solution by syringe while cooling with ice. The reaction mixture was stirred at 0° C. for 30 minutes, to which acetic acid (0.3 ml) was added, and concentrated. To the residue was added ethyl acetate (30 ml), filtered, and the filtrate was washed with water (20 ml×2). The aqueous layers were then re-extracted with ethyl acetate (20 ml). The organic layers were combined, washed with brine (20 ml), dried over anhydrous magnesium sulfate, and concentrated. The residue was passed through a short column of silica gel, and purified by Lobar Column (Merck, silica gel: ethyl acetate/cyclohexane=1/5) to afford 95.0% yield of d-(3E)-16-methyl-15-oxo-2,5,6,7-tetranor-3,4-didehydro-4,8-inter-m-phenylene PGI₂ methyl ester, 11-acetate (1.26 g, 2.86 mmoles).

The structure was confirmed by the following data:

$[\alpha]_D^{25}$: +201.00 (c 0.996, CHCl₃).

IR (liquid film): 2940, 2870, 1740, 1720, 1670, 1630, 1450, 1380, 1320, 1240, 1180, 1060, 990, 870, 780, 750 cm⁻¹.

NMR (90 MHz, CDCl₃, δ): 0.8–1.8 (12H, m), 1.72 (3H, s), 2.0–3.2 (4H, m), 3.6–3.9 (1H, m), 3.80 (3H, s), 4.9–5.1 (1H, m), 5.2–5.6 (1H, m), 6.27 (1H, d, J=15.6 Hz), 6.6–7.4 (5H, m), 7.69 (1H, d, J=16.1 Hz).

MASS (EI, m/e): 440 (M⁺).

EXAMPLE 5 d-(3E, 17S)-17-methyl-15-oxo-20a-homo-2,5,6,7-tetranor-3,4-didehydro-4,8-inter-m-phenylene PGI₂ methyl ester, 11-acetate (5)

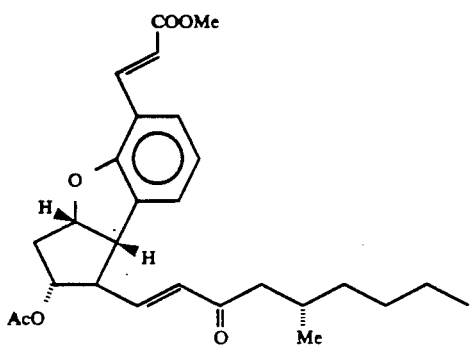

(5)

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (1.00 g, 3.01 mmoles) in dry THF (10 ml) under argon atomosphere were added anhydrous pyridine (0.073 ml, 0.964 mmoles), dry DMSO (1.1 ml), and trifluoroacetic acid (0.1 ml, 1.3 mmoles), to which a solution of DCC (744 mg, 3.61 mmoles) in dry THF (5 ml) was added and stirred at room temperature for 2.5 hours.

Then sodium hydride (60% mineral oil dispersion 190 mg, 4.75 mmoles) was suspended in dry THF (10 ml), to which a solution of dimethyl (S)-4-methyl-2-oxooctyl-phosphonate (1.20 g, 4.78 mmoles) in dry THF (5 ml) was added, and stirred under argon atomosphere at 0° C. for 30 minutes. To this solution then was added the above-prepared aldehyde solution by syringe while cooling with ice. The reaction mixture was stirred at 0° C. for 2 hours, to which acetic acid (0.5 ml) was added, and concentrated. To the residue was added ethyl acetate (40 ml), filtered, and the filtrate was washed with water (20 ml). The aqueous layers were then re-extracted with ethyl acetate (20 ml). The organic layers were combined, washed with brine (20 ml), dried over anhydrous magnesium sulfate, and concentrated. The residue was purified by Lobar Column (Merck, silica gel: ethyl acetate/cyclohexane=1/9) to afford 79.0% yield of d-(3E, 17S)-17-methyl-15-oxo-20a-homo-2,5,6,7-tetranor-3,4-didehydro-4,8-inter-m-phenylene PGI₂ methyl ester, 11-acetate (1.08 g, 2.38 mmoles).

The structure was confirmed by the following data:

IR (liquid film): 3024, 2960, 1740, 1717, 1632, 1450, 1241, 1174, 1058, 986, 864, 667 cm⁻¹.

NMR (90 MHz, CDCl₃, δ): 0.9–1.0 (6H, m), 1.2–1.7 (9H, m), 1.72 (3H, s), 2.1–3.1 (3H, m), 3.6–3.8 (1H, m), 3.80 (3H, s), 5.03 (1H, q, J=5.5 Hz), 5.39 (1H, m), 6.19 (1H, dd, J=0.9, 15.9 Hz), 6.6–7.3 (5H, m), 7.69 (1H, d, J=15.9 Hz).

MASS (EI, m/e): 454 (M⁺).

EXAMPLE 6 d-(3E)-16,16-dimethyl-15-oxo-2,5,6,7-tetranor-3,4-didehydro-4,8-inter-m-phenylene PGI₂ methyl ester 11-acetate (6)

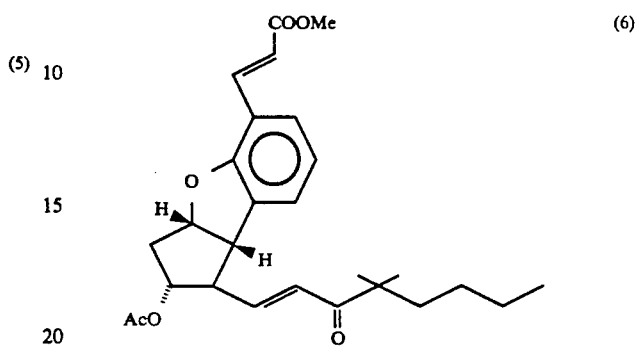

(6)

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (800 mg, 2.41 mmoles) in dry THF (8 ml) under argon atomosphere were added anhydrous pyridine (0.060 ml, 0.747 mmoles), dry DMSO (1.71 ml), and trifluoroacetic acid (0.056 ml, 0.723 mmoles), to which a solution of DCC (745 mg, 3.62 mmoles) in dry THF (3 ml) was added and stirred at room temperature for 4 hours.

Then sodium hydride (60% mineral oil dispersion 159 mg, 3.98 mmoles) was suspended in dry THF (5 ml), to which a solution of dimethyl 3,3-dimethyl-2-oxoheptyl-phosphonate (1.02 g, 4.08 mmoles) in dry THF (5 ml) was added, and stirred under argon atomosphere at room temperature for 30 minutes. To this solution then was added the above-prepared aldehyde solution by syringe while cooling with ice. The reaction mixture was stirred at 0° C. for 20 minutes, and raised to room temperature, to which acetic acid (0.25 ml) was added and concentrated. To the residue was added ethyl acetate (30 ml), filtered, and the filtrate was washed with water (20 ml×2). The aqueous layers were then re-extracted with ethyl acetate (20 ml). The organic layers were combined, washed with brine (20 ml), dried over anhydrous magnesium sulfate, and concentrated. The residue was purified by Lobar Column (Merck, silica gel: ethyl acetate/cyclohexane=1/5) to afford 81.4% yield of d-(3E)-16,16-dimethyl-15-oxo-2,5,6,7-tetranor-3,4-didehydro-4,8-inter-m-phenylene PGI₂ methyl ester, 11-acetate (891 mg, 1.96 mmoles).

The structure was confirmed by the following data:

$[\alpha]_D^{25}$: +215.52 (c 0.438, CHCl₃).

IR (liquid film): 3020, 2950, 2870, 1730, 1710, 1630, 1590, 1445, 1370, 1320, 1240, 1170, 1050, 980, 955, 865, 755, 665 cm⁻¹.

NMR (90 MHz, CDCl₃, δ): 0.95 (3H, t, J=5.7 Hz), 0.8–1.8 (6H, m), 1.13 (6H, s), 1.73 (3H, s), 2.0–3.1 (3H, m), 3.6–3.8 (1H, m), 3.80 (3H, s), 4.9–5.1 (1H, m), 5.2–5.5 (1H, m), 6.5–7.4 (6H, m), 7.69 (1H, d, J=16.1 Hz).

MASS (EI, m/e): 454 (M⁺).

EXAMPLE 7 d-(3E)-15-oxo-15-phenyl-2,5,6,7,16,17,18,19,20-nonanor-3,4-didehydro-4,8-inter-m-phenylene PGI₂ methyl ester, 11-acetate (7)

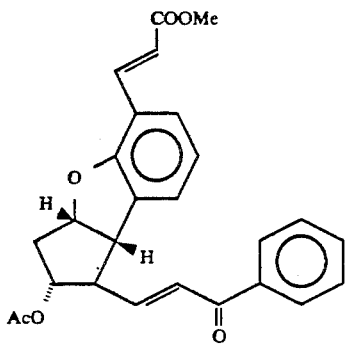

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (800 mg, 2.41 mmoles) in dry THF (8 ml) under argon atmosphere were added anhydrous pyridine (0.060 ml, 0.747 mmoles), dry DMSO (1.71 ml), and trifluoroacetic acid (0.056 ml, 0.723 mmoles), to which a solution of DCC (745 mg, 3.62 mmoles) in dry THF (3 ml) was added and stirred at room temperature for 4 hours.

Then sodium hydride (60% mineral oil dispersion 159 mg, 3.98 mmoles) was suspended in dry THF (5 ml), to which a solution of dimethyl 2-oxo-phenylethylphosphonate (935 mg, 4.10 mmoles) in dry THF (3 ml) was added, and stirred under argon atmosphere at room temperature for 20 minutes. To this solution then was added the above-prepared aldehyde solution by syringe while cooling with ice. The reaction mixture was stirred at 0° C. for 15 minutes and at room temperature for 15 minutes, to which acetic acid (0.25 ml) was added and concentrated. To the residue was added ethyl acetate (50 ml), filtered, and the filtrate was washed with water (20 ml). The aqueous layers were then re-extracted with ethyl acetate (20 ml). The organic layers were combined, washed with brine (20 ml), dried over anhydrous magnesium sulfate, and concentrated. The residue was passed through a short column of silica gel, and purified by Lobar Column (Merck, silica gel: ethyl acetate/cyclohexane=1/5) to afford 70.5% yield of d-(3E)-15-oxo-15-phenyl-2,5,6,7,16,17,18,19,20-nonanor-3,4-didehydro-4,8-inter-m-phenylene PGI₂ methyl ester, 11-acetate (734 mg, 1.70 mmoles).

The structure was confirmed by the following data:
[α]$_D^{25}$: +266.58 (c 0.416, CHCl₃).

IR (liquid film): 3020, 2950, 1730, 1710, 1665, 1620, 1445, 1370, 1320, 1240, 1170, 1010, 980, 945, 865, 750, 700 cm$^{-1}$.

NMR (90 MHz, CDCl₃, δ): 1.74 (3H, s), 2.0–3.3 (3H, m), 3.7–3.9 (1H, m), 3.80 (3H, s) 5.0–5.6 (2H, m), 6.6–8.1 (12H, m).

MASS (EI, m/e): 432 (M⁺).

EXAMPLE 8 d-(3E)-15-(p-chlorophenyl)-15-oxo-2,5,6,7,16,17,18,19,20-nonanor-3,4-didehydro-4,8-inter-m-phenylene PGI₂ methyl ester, 11-acetate (8)

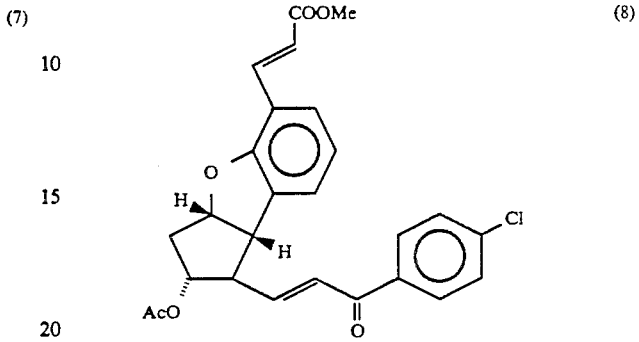

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (800 mg, 2.41 mmoles) in dry THF (8 ml) under argon atmosphere were added anhydrous pyridine (0.060 ml, 0.747 mmoles), dry DMSO (1.71 ml), and trifluoroacetic acid (0.056 ml, 0.723 mmoles), to which a solution of DCC (745 mg, 3.62 mmoles) in dry THF (3 ml) was added and stirred at room temperature for 4 hours.

Then sodium hydride (60% mineral oil dispersion 159 mg, 3.98 mmoles) was suspended in dry THF (5 ml), to which a solution of dimethyl 2-(4-chlorophenyl)-2-oxo-ethylphosphonate (1.08 g, 4.12 mmoles) in dry THF (5 ml) was added, and stirred under argon atmosphere at room temperature for 30 minutes. To this solution then was added the above-prepared aldehyde solution by syringe while cooling with ice. The reaction mixture was stirred at 0° C. for 15 minutes, and raised to room temperature, to which acetic acid (0.25 ml) was added and concentrated. To the residue was added ethyl acetate (40 ml), filtered, and the filtrate was washed with water (20 ml×2). The aqueous layers were then re-extracted with ethyl acetate (20 ml). The organic layers were combined, washed with brine (20 ml), dried over anhydrous magnesium sulfate, and concentrated. The residue was passed through a short column of silica gel, and purified by Lobar Column (Merck, silica gel: ethyl acetate/cyclohexane=1/10) to afford 71.4% yield of d-(3E)-15-(p-chlorophenyl)-15-oxo-2,5,6,7,16,17,18,19,20-nonanor-3,4-didehydro-4,8-inter-m-phenylene PGI₂ methyl ester, 11-acetate (801 mg, 1.72 mmoles).

The structure was confirmed by the following data:
[α]$_D^{25}$: +253.57 (c 0.532, CHCl₃).

IR (liquid film): 3010, 2950, 1730, 1700, 1670, 1620, 1590, 1450, 1400, 1370, 1320, 1240, 1170, 1090, 1010, 750 cm$^{-1}$.

NMR (90 MHz, CDCl₃, δ): 1.74 (3H, s), 2.1–3.2 (3H, m), 3.7–3.9 (1H, m), 3.81 (3H, s) 5.0–5.2 (1H, m), 5.3–5.5 (1H, m), 6.6–8.0 (11H, m).

MASS (EI, m/e): 466 (M⁺).

EXAMPLE 9 d-(3E)-15-(m-fluorophenyl)-15-oxo-2,5,6,7,16,17,18,19,20-nonanor-3,4-didehydro-4,8-inter-m-phenylene PGI₂ methyl ester, 11-acetate (9)

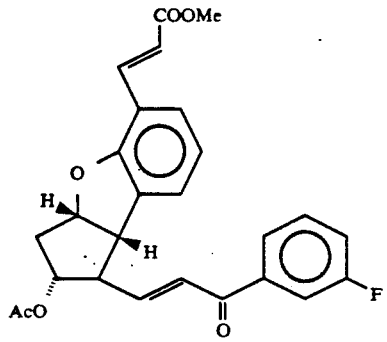

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (800 mg, 2.41 mmoles) in dry THF (8 ml) under argon atmosphere were added anhydrous pyridine (0.060 ml, 0.747 mmoles), dry DMSO (1.71 ml), and trifluoroacetic acid (0.056 ml, 0.723 mmoles), to which a solution of DCC (745 mg, 3.62 mmoles) in dry THF (3 ml) was added and stirred at room temperature for 4 hours.

Then sodium hydride (60% mineral oil dispersion 159 mg, 3.98 mmoles) was suspended in dry THF (5 ml), to which a solution of dimethyl 2-(m-fluorophenyl)-2-oxoethylphosphonate (1.01 g, 4.10 mmoles) in dry THF (3 ml) was added, and stirred under argon atmosphere at room temperature for 20 minutes. To this solution then was added the above-prepared aldehyde solution by syringe while cooling with ice. The reaction mixture was stirred at 0° C. for 15 minutes and at room temperature for 15 minutes, to which acetic acid (0.25 ml) was added and concentrated. To the residue was added ethyl acetate (40 ml), filtered, and the filtrate was washed with water (20 ml×2). The aqueous layers were then re-extracted with ethyl acetate (20 ml). The organic layers were combined, washed with brine (20 ml), dried over anhydrous magnesium sulfate, and concentrated. The residue was passed through a short column of silica gel, and purified by Lobar Column (Merck, silica gel: ethyl acetate/cyclohexane=1/10) to afford 73.0% yield of d-(3E)-15-(m-fluorophenyl)-15-oxo-2,5,6,7,16,17,18,19,20-nonanor-3,4-didehydro-4,8-inter-m-phenylene PGI₂ methyl ester, 11-acetate (792 mg, 1.76 mmoles).

The structure was confirmed by the following data:
$[\alpha]_D^{25}$: +257.46 (c 0.442, CHCl₃).

IR (liquid film): 3024, 2954, 1738, 1715, 1673, 1630, 1609, 1589, 1487, 1450, 1375, 1323, 1243, 1218, 1176, 1056, 986, 951, 897, 866, 756, 667 cm⁻¹.

NMR (90 MHz, CDCl₃, δ): 1.75 (3H, s), 2.1-3.2 (3H, m), 3.7-3.9 (1H, m), 3.81 (3H, s) 5.0-5.2 (1H, m), 5.25-5.5 (1H, m), 6.6-7.8 (11H, m).

MASS (EI, m/e): 450 (M⁺).

EXAMPLE 10 d-(3E)-15-(p-bromophenyl)-15-oxo-2,5,6,7,16,17,18,19,20-nonanor-3,4-didehydro-4,8-inter-m-phenylene PGI₂ methyl ester, 11-acetate (10)

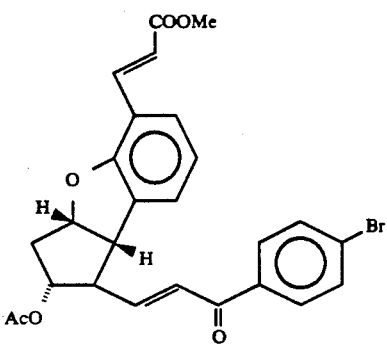

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (1.00 g, 3.01 mmoles) in dry THF (10 ml) under argon atmosphere were added anhydrous pyridine (0.073 ml, 0.903 mmoles), dry DMSO (1.1 ml), and trifluoroacetic acid (0.07 ml, 0.903 mmoles), to which a solution of DCC (744 mg, 3.61 mmoles) in dry THF (5 ml) was added and stirred at room temperature for 2.5 hours.

Then sodium hydride (60% mineral oil dispersion 175 mg, 4.38 mmoles) was suspended in dry THF (10 ml), to which a solution of dimethyl 2-(p-bromophenyl)-2-oxoethylphosphonate (1.38 g, 4.50 mmoles) in dry THF (10 ml) was added, and stirred under argon atmosphere at room temperature for 30 minutes. To this solution then was added the above-prepared aldehyde solution by syringe while cooling with ice. The reaction mixture was stirred at 0° C. for an hour, to which acetic acid (0.5 ml) was added and concentrated. To the residue was added ethyl acetate (40 ml), filtered, and the filtrate was washed with water (20 ml). The aqueous layers were then re-extracted with ethyl acetate (20 ml). The organic layers were combined, washed with brine (20 ml), dried over anhydrous magnesium sulfate, and concentrated. The residue was purified by Lobar Column (Merck, silica gel: ethyl acetate/cyclohexane=1/7) to afford 65.9% yield of d-(3E)-15-(p-bromophenyl)-15-oxo-2,5,6,7,16,17,18,19,20-nonanor-3,4-didehydro-4,8-inter-m-phenylene PGI₂ methyl ester, 11-acetate (1.04 g, 2.04 mmoles).

The structure was confirmed by the following data:
$[\alpha]_D$: +259.82 (c 0.468, Me OH).

IR (liquid film): 3028, 3018, 1734, 1673, 1624, 1589, 1450, 1437, 1400, 1377, 1323, 1245, 1205, 1178, 1071, 988, 779, 766 cm⁻¹.

NMR (90 MHz, CDCl₃, δ): 1.76 (3H, s), 2.1-3.2 (3H, m), 3.81 (3H, s), 3.7-3.9 (1H, m), 5.10 (1H, q, J=8 Hz), 5.41 (1H, m), 6.8-7.9 (11H, m).

MASS (EI, m/e): 510 (M⁺).

EXAMPLE 11 d-(3E)-15-(2,6-difluorophenyl)-15-oxo-2,5,6,7,16,17,18,19,20-nonanor-3,4-didehydro-4,8-inter-m-phenylene PGI$_2$ methyl ester, 11-acetate (11)

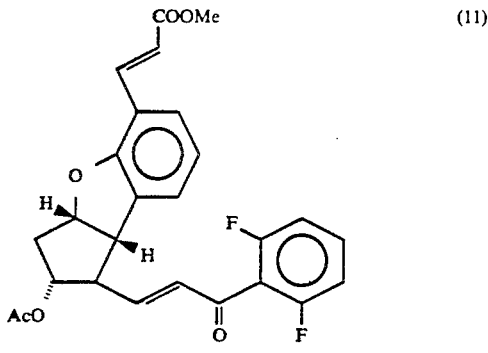
(11)

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (800 mg, 2.41 mmoles) in dry THF (8 ml) under argon atmosphere were added anhydrous pyridine (0.060 ml, 0.747 mmoles), dry DMSO (1.71 ml), and trifluoroacetic acid (0.056 ml, 0.723 mmoles), to which a solution of DCC (745 mg, 3.62 mmoles) in dry THF (3 ml) was added and stirred at room temperature for 4 hours.

Then sodium hydride (60% mineral oil dispersion 159 mg, 3.98 mmoles) was suspended in dry THF (5 ml), to which a solution of dimethyl 2-(2,6-difluorophenyl)-2-oxoethylphosphonate (1.08 g, 4.10 mmoles) in dry THF (5 ml) was added, and stirred under argon atmosphere at room temperature for 30 minutes. To this solution was then added the above-prepared aldehyde solution by syringe while cooling with ice. The reaction mixture was stirred at 10° C. for an hour and then at room temperature for 2 hours, to which acetic acid (0.25 ml) was added and concentrated. To the residue was added ethyl acetate (40 ml), filtered, and the filtrate was washed with water (20 ml×2). The aqueous layers were then re-extracted with ethyl acetate (20 ml). The organic layers were combined, washed with brine (20 ml), dried over anhydrous magnesium sulfate, and concentrated. The residue was passed through a short column of silica gel, and purified by Lobar Column (Merck, silica gel: ethyl acetate/cyclohexane=1/5) to afford 62.2% yield of d-(3E)-15-(2,6-difluorophenyl)-15-oxo-2,5,6,7,16,17,18,19,20-nonanor-3,4-didehydro-4,8-inter-m-phenylene PGI$_2$ methyl ester, 11-acetate (701 mg, 1.50 mmoles).

The structure was confirmed by the following data:
$[\alpha]_D^{25}$: +241.15 (c 0.452, CHCl$_3$).

IR (liquid film): 3026, 2954, 1740, 1717, 1667, 1626, 1593, 1466, 1452, 1375, 1323, 1282, 1238, 1176, 1035, 1007, 948, 868, 793, 756 cm$^{-1}$.

NMR (90 MHz, CDCl$_3$, δ): 1.75 (3H, s), 2.1–3.2 (3H, m), 3.6–3.9 (1H, m), 3.80 (3H, s), 4.9–5.2 (1H, m), 5.25–5.5 (1H, m), 6.4–7.6 (9H, m), 7.69 (1H, d, J=16.1 Hz).

MASS (EI, m/e): 468 (M+).

EXAMPLE 12 d-(3E)-16-methyl-15-oxo-16-phenyl-2,5,6,7,18,19,20,-heptanor-3,4-didehydro-4,8-inter-m-phenylene PGI$_2$ methyl ester, 11-acetate (12)

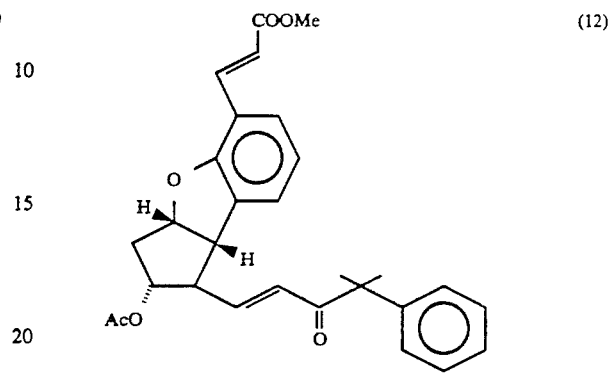
(12)

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (1.00 g, 3.01 mmoles) in dry THF (10 ml) under argon atomosphere were added anhydrous pyridine (0.12 ml, 1.48 mmoles), dry DMSO (1.1 ml), and trifluoroacetic acid (0.115 ml, 1.49 mmoles), to which a solution of DCC (744 mg, 3.61 mmoles) in dry THF (5 ml) was added and stirred at room temperature for an hour.

Then sodium hydride (60% mineral oil dispersion 180 mg, 4.50 mmoles) was suspended in dry THF (10 ml), to which a solution of dimethyl 3-methyl-2-oxo-3-phenyl-butylphosphonate (1.22 g, 4.52 mmoles) in dry THF (10 ml) was added, and stirred under argon atmosphere at room temperature for 30 minutes. To this solution was then added the above-prepared aldehyde solution by syringe while cooling with ice. The reaction mixture was stirred at 0° C. for an hour and then for 1.5 hours after the mixture was raised to room temperature, to which acetic acid (0.5 ml) was added and concentrated. To the residue was added ethyl acetate (40 ml), filtered, and the filtrate was washed with water (20 ml). The aqueous layers were then re-extracted with ethyl acetate (20 ml). The organic layers were combined, washed with brine (20 ml), dried over anhydrous magnesium sulfate, and concentrated. The residue was purified by Lobar Column (Merck, silica gel: ethyl acetate/cyclohexane=1/9) to afford 72.2% yield of d-(3E)-16-methyl-15-oxo-16-phenyl-2,5,6,7,18,19,20-heptanor-3,4-didehydro-4,8-inter-m-phenylene PGI$_2$ methyl ester, 11-acetate (1.03 g, 2.17 mmoles).

The structure was confirmed by the following data:

IR (liquid film): 2974, 2952, 1744, 1696, 1634, 1448, 1323, 1236, 1212, 1195, 1178, 1054, 1000, 953, 781, 706 cm$^{-1}$.

NMR (90 MHz, CDCl$_3$, δ): 1.53 (6H, s), 1.70 (3H, s), 2.1–2.9 (3H, m), 3.53 (1H, m), 3.80 (3H, s), 4.91 (1H, q, J=8 Hz), 5.22 (1H, m), 6.02 (1H, d, J=15 Hz), 6.8–7.4 (10H, m), 7.61 (1H, d, J=15 Hz).

MASS (EI, m/e): 474 (M+).

EXAMPLE 13 d-(3E)-15-oxo-17-phenyl-2,5,6,7,18,19,20-heptanor-3,4-didehydro-4,8-inter-m-phenylene PGI$_2$ methyl ester, 11-acetate (13)

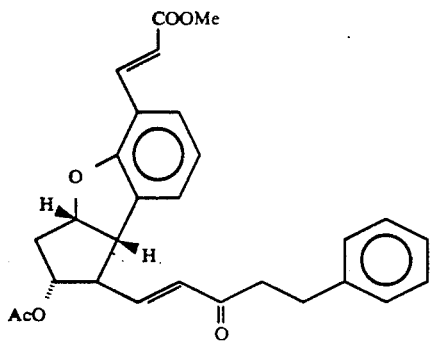

(13)

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (1.00 g, 3.01 mmoles) in dry THF (15 ml) under argon atomosphere were added anhydrous pyridine (0.081 ml, 0.100 mmoles), dry DMSO (1.50 ml), and trifluoroacetic acid (0.080 ml, 0.103 mmoles), to which a solution of DCC (850 mg, 4.13 mmoles) in dry THF (5 ml) was added and stirred at room temperature for 4 hours.

Then sodium hydride (60% mineral oil dispersion 220 mg, 5.50 mmoles) was suspended in dry THF (15 ml), to which a solution of dimethyl 2-oxo-4-phenylbutylphosphonate (1.44 g, 5.63 mmoles) in dry THF (5 ml) was added, and stirred under argon atomosphere at room temperature for 30 minutes. To this solution was then added the above-prepared aldehyde solution by syringe while cooling with ice. The reaction mixture was stirred at 0° C. for an hour, to which acetic acid (0.3 ml) was added and concentrated. To the residue was added ethyl acetate (40 ml), filtered, and the filtrate was washed with water (20 ml). The aqueous layers were then re-extracted with ethyl acetate (20 ml). The organic layers were combined, washed with brine (20 ml), dried over anhydrous magnesium sulfate, and concentrated. The residue was purified by Lobar Column (Merck, silica gel: ethyl acetate/cyclohexane=1/6) to afford 88.8% yield of d-(3E)-15-oxo-17-phenyl-2,5,6,7,18,19,20-heptanor-3,4-didehydro-4,8-inter-m-phenylene PGI$_2$ methyl ester, 11-acetate (1.03 mg, 2.17 mmoles).

The structure was confirmed by the following data:

IR (liquid film): 3030, 2986, 2954, 1740, 1700, 1632, 1607, 1593, 1497, 1375, 1321, 1048, 988, 948, 866, 785, 750, 702 cm$^{-1}$.

NMR (90 MHz, CDCl$_3$, δ): 1.71 (3H, s), 2.1–3.1 (7H, m), 3.6–3,8 (1H, m), 3.90 (3H, m), 5.00 (1H, q, J=11 Hz), 5.25–5.5 (1H, m), 6.18 (1H, d, J=16 Hz), 6.6–7.3 (10H, m), 7.50 (1H, d, J=16 Hz).

MASS (EI, m/e): 460 (M+).

EXAMPLE 14 d-(3E)-15-cyclopentyl-15-oxo-2,5,6,7,16,17,18,19,20-nonanor-3,4-didehydro-4,8-inter-m-phenylene PGI$_2$ methyl ester, 11-acetate (14)

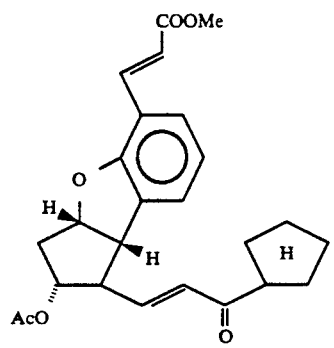

(14)

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (800 mg, 2.41 mmoles) in dry THF (8 ml) under argon atomosphere were added anhydrous pyridine (0.060 ml, 0.747 mmoles), dry DMSO (1.71 ml), and trifluoroacetic acid (0.056 ml, 0.723 mmoles), to which a solution of DCC (745 mg, 3.62 mmoles) in dry THF (3 ml) was added and stirred at room temperature for 5 hours.

Then sodium hydride (60% mineral oil dispersion 159 mg, 3.98 mmoles) was suspended in dry THF (5 ml), to which a solution of dimethyl 2-cyclopentyl-2-oxoethylphosphonate (901 mg, 4.10 mmoles) in dry THF (5 ml) was added, and stirred under argon atomosphere at room temperature for 30 minutes. To this solution was then added the above-prepared aldehyde solution by syringe while cooling with ice. The reaction mixture was stirred at 0° C. for an hour, to which acetic acid (0.3 ml) was added and concentrated. To the residue was added ethyl acetate (40 ml), filtered, and the filtrate was washed with water (20 ml×2). The aqueous layers were then re-extracted with ethylacetate (20 ml). The organic layers were combined, washed with brine (20 ml), dried over anhydrous magnesium sulfate, and concentrated. The residue was passed through a short column of silica gel, and purified by Lobar Column (Merck, silica gel: ethyl acetate/cyclohexane=1/6) to afford 92.5% yield of d-(3E)-15-cyclopentyl-15-oxo-2,5,6,7,16,17,18,19,20-nonanor-3,4-didehydro-4,8-inter-m-phenylene PGI$_2$ methyl ester, 11-acetate (947 mg, 2.23 mmoles).

The structure was confirmed by the following data:

$[\alpha]_D^{25}$: +206.43 (c 0.482, CHCl$_3$).

IR (liquid film): 2950, 2880, 1740, 1720, 1670, 1630, 1550, 1450, 1380, 1320, 1240, 1180, 1060, 1030, 990, 950, 870, 840, 760 cm$^{-1}$.

NMR (90 MHz, CDCl$_3$, δ): 1.5–3.3 (12H, m), 1.72 (3H, s), 3.6–3.9 (1H, m), 3.80 (3H, s), 4.9–5.1 (1H, m), 5.2–5.5 (1H, m), 6.23 (1H, d, J=15.8 Hz), 6.6–7.4 (5H, m), 7.69 (1H, d, J=16.3 Hz).

MASS (EI, m/e): 424 (M+).

EXAMPLE 15 d-(3E)-15-cyclohexyl-15-oxo-2,5,6,7,16,17,18,19,20-nonanor-3,4-didehydro-4,8-inter-m-phenylene PGI₂ methyl ester, 11-acetate (15)

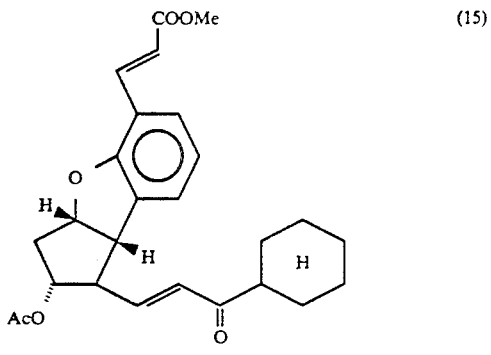

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (800 mg, 2.41 mmoles) in dry THF (8 ml) under argon atomosphere were added anhydrous pyridine (0.060 ml, 0.747 mmoles), dry DMSO (1.71 ml), and trifluoroacetic acid (0.056 ml, 0.723 mmoles), to which a solution of DCC (745 mg, 3.62 mmoles) in dry THF (3 ml) was added and stirred at room temperature for 4 hours.

Then sodium hydride (60% mineral oil dispersion 159 mg, 3.98 mmoles) was suspended in dry THF (5 ml), to which a solution of dimethyl 2-cyclohexyl-2-oxoethylphosphonate (959 mg, 4.10 mmoles) in dry THF (5 ml) was added, and stirred under argon atomosphere at room temperature for 20 minutes. To this solution was then added the above-prepared aldehyde solution by syringe while cooling with ice. The reaction mixture was stirred at 0° C. for 15 minutes and then at room temperature for 15 minutes, to which acetic acid (0.25 ml) was added and concentrated. To the residue was added ethyl acetate (40 ml), filtered, and the filtrate was washed with water (20 ml). The aqueous layers were then re-extracted with ethyl acetate (20 ml). The organic layers were combined, washed with brine (20 ml), dried over anhydrous magnesium sulfate, and concentrated. The residue was passed through a short column of silica gel, and purified by Lobar Column (Merck, silica gel: ethyl acetate/cyclohexane=1/6) to afford 88.4% yield of d-(3E)-15-cyclohexyl-15-oxo-2,5,6,7,16,17,18,19,20-nonanor-3,4-didehydro-4,8-inter-m-phenylene PGI₂ methyl ester, 11-acetate (932 mg, 2.13 mmoles).

The structure was confirmed by the following data:
$[\alpha]_D^{25}$: +206.74 (c 0.534, CHCl₃).

IR (liquid film): 3020, 2930, 2850, 1740, 1720, 1660, 1630, 1590, 1540, 1450, 1370, 1320, 1240, 1170, 1060, 980, 950, 860, 750, 670 cm⁻¹.

NMR (90 MHz, CDCl₃, δ): 1.0–3.1 (14H, m), 1.71 (3H, s), 3.6–3.9 (1H, m), 3.81 (3H, s), 4.9–5.1 (1H, m), 5.3–5.5 (1H, m), 6.27 (1H, d, J=15.6 Hz), 6.6–7.4 (5H, m), 7.69 (1H, d, J=16.1 Hz).

MASS (EI, m/e): 438 (M⁺).

EXAMPLE 16 d-(3E, 16S)-16-methyl-15-oxo-2,5,6,7-tetranor-3,4,18,18,19,19-hexadehydro-4,8-inter-m-phenylene PGI₂ methyl ester, 11-acetate (16)

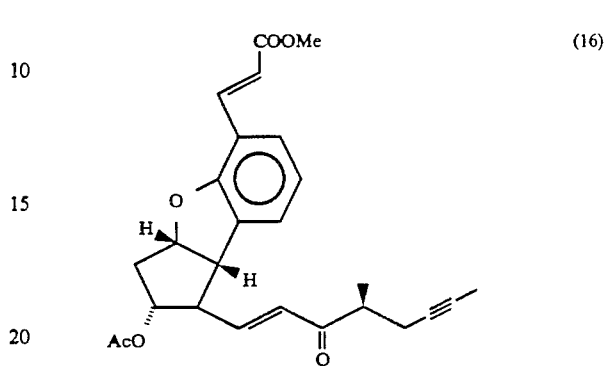

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (800 mg, 2.41 mmoles) in dry THF (8 ml) under argon atomosphere were added anhydrous pyridine (0.060 ml, 0.747 mmoles), dry DMSO (1.71 ml), and trifluoroacetic acid (0.056 ml, 0.723 mmoles), to which a solution of DCC (745 mg, 3.62 mmoles) in dry THF (3 ml) was added and stirred at room temperature for 4 hours.

Then sodium hydride (60% mineral oil dispersion 159 mg, 3.98 mmoles) was suspended in dry THF (5 ml), to which a solution of dimethyl (S)-3-methyl-2-oxo-5-heptynylphosphonate (950 mg, 4.09 mmoles) in dry THF (5 ml) was added, and stirred under argon atomosphere at room temperature for 20 minutes. To this solution was then added the above-prepared aldehyde solution by syringe while cooling with ice. The reaction mixture was stirred at 0° C. for 15 minutes and then at room temperature for 15 minutes, to which acetic acid (0.25 ml) was added and concentrated. To the residue was added ethyl acetate (30 ml), filtered, and the filtrate was washed with water (30 ml). The aqueous layers were then re-extracted with ethyl acetate (20 ml). The organic layers were combined, washed with brine (30 ml), dried over anhydrous magnesium sulfate, and concentrated. The residue was passed through a short column of silica gel, and purified by Lobar Column (Merck, silica gel: ethyl acetate/cyclohexane=1/5) to afford 90.0% yield of d-(3E, 16S)-16-methyl-15-oxo-2,5,6,7-tetranor-3,4,18,18,19,19-hexadehydro-4,8-inter-m-phenylene PGI₂ methyl ester, 11-acetate (945 mg, 2.17 mmoles).

The structure was confirmed by the following data:
$[\alpha]_D^{25}$: +217.56 (c 0.410, CHCl₃).

IR (liquid film): 2928, 1710, 1696, 1669, 1634, 1593, 1557, 1450, 1375, 1321, 1048, 988, 752 cm⁻¹.

NMR (90 MHz, CDCl₃, δ): 1.21 (3H, d, J=7.0 Hz), 1.72 (3H, s), 1.77 (3H, t, J=2.4 Hz), 2.1–3.2 (6H, m), 3.6–3.9 (1H, m), 3.80 (3H, s), 4.9–5.2 (1H, m), 5.3–5.6 (1H, m), 6.29 (1H, d, J=15.8 Hz), 6.6–7.4 (5H, m), 7.69 (1H, d, J=16.1 Hz).

MASS (EI, m/e): 436 (M⁺).

EXAMPLE 17 d-(3E)-16,16-dimethyl-15-oxo-2,5,6,7-tetranor-3,4,18,18,19,19-hexadehydro-4,8-inter-m-phenylene PGI₂ methyl ester, 11-acetate (17)

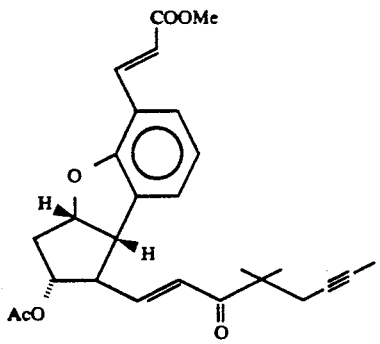

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (800 mg, 2.41 mmoles) in dry THF (5.3 ml) under argon atmosphere were added anhydrous pyridine (0.059 ml, 0.745 mmoles), dry DMSO (1.70 ml), and trifluoroacetic acid (0.055 ml, 0.703 mmoles), to which a solution of DCC (737 mg, 3.61 mmoles) in dry THF (1.3 ml) was added and stirred at room temperature for 4 hours.

Then sodium hydride (60% mineral oil dispersion 159 mg, 3.98 mmoles) was suspended in dry THF (5.3 ml), to which a solution of dimethyl 3,3-dimethyl-2-oxo-5-heptynylphosphonate (0.889 g, 3.61 mmoles) in dry THF (4 ml) was added, and stirred under argon atmosphere at room temperature for 30 minutes. To this solution was then added the above-prepared aldehyde solution by syringe while cooling with ice. The reaction mixture was stirred at 0° C. for 2 hours, to which acetic acid (0.27 ml) was added and concentrated. To the residue was added ethyl acetate (40 ml), filtered, and the filtrate was washed with water (20 ml). The aqueous layers were then re-extracted with ethyl acetate (20 ml). The organic layers were combined, washed with brine (20 ml), dried over anhydrous magnesium sulfate, and concentrated. The residue was purified by Lobar Column (Merck, silica gel: ethyl acetate/cyclohexane=1/5) to afford 79.8% yield of d-(3E)-16,16-dimethyl-15-oxo-2,5,6,7-tetranor-3,4,18,18,19,19-hexadehydro-4,8-inter-m-phenylene PGI₂ methyl ester, 11-acetate (865.5 mg 1.92 mmoles).

The structure was confirmed by the following data:

IR (liquid film): 2972, 1742, 1717, 1630, 1593, 1450, 1373, 1321, 1241, 1174, 1056, 988, 948, 878, 785, 748, 719, 605 cm⁻¹.

NMR (90 MHz, CDCl₃, δ): 1.23 (6H, s), 1.73 (3H, s), 1.77 (3H, t, J=2.6 Hz), 2.37 (2H, q, J=2.6 Hz), 2.0-3.1 (3H, m), 3.6-3.8 (1H, m), 3.80 (3H, s), 5.02 (1H, q, J=5.5 Hz), 5.3-5.5 (1H, m), 6.5-7.0 (4H, m), 7.1-7.3 (2H, m), 7.69 (1H, d, J=16.1 Hz).

MASS (EI, m/e): 450 (M⁺).

EXAMPLE 18 d-(3E)-15-oxo-2,5,6,7-tetranor-17-oxa-3,4-didehydro-4,8-inter-m-phenylene PGI₂ methyl ester, 11-acetate (18)

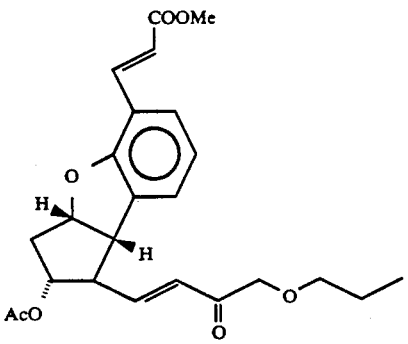

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (800 mg, 2.41 mmoles) in dry THF (8 ml) under argon atmosphere were added anhydrous pyridine (0.060 ml, 0.747 mmoles), dry DMSO (1.71 ml), and trifluoroacetic acid (0.056 ml, 0.723 mmoles), to which a solution of DCC (745 mg, 3.62 mmoles) in dry THF (3 ml) was added and stirred at room temperature for 4 hours.

Then sodium hydride (60% mineral oil dispersion 159 mg, 3.98 mmoles) was suspended in dry THF (5 ml), to which a solution of dimethyl 2-oxo-4-oxaheptylphosphonate (918 mg, 4.10 mmoles) in dry THF (5 ml) was added, and stirred under argon atmosphere at room temperature for 20 minutes. To this solution was then added the above-prepared aldehyde solution by syringe while cooling with ice. The reaction mixture was stirred at 0° C. for 20 minutes, and raised to room temperature, to which acetic acid (0.25 ml) was added and concentrated. To the residue was added ethyl acetate (30 ml), filtered, and the filtrate was washed with water (20 ml×2). The aqueous layers were then re-extracted with ethyl acetate (20 ml). The organic layers were combined, washed with brine (20 ml), dried over anhydrous magnesium sulfate, and concentrated. The residue was purified by Lobar Column (Merck, silica gel: ethyl acetate/cyclohexane=1/6) to afford 78.4% yield of d-(3E)-15-oxo-2,5,6,7-tetranor-17-oxa-3,4-didehydro-4,8-inter-m-phenylene PGI₂ methyl ester, 11-acetate (808 mg, 1.89 mmoles).

The structure was confirmed by the following data:
$[\alpha]_D^{25}$: +216.90 (c 0.568, CHCl₃).

IR (liquid film): 3000, 2930, 2870, 1730, 1700, 1620, 1440, 1360, 1310, 1230, 1160, 1100, 1050, 980, 940, 860, 750, 660 cm⁻¹.

NMR (90 MHz, CDCl₃, δ): 0.96 (3H, t, J=7.3 Hz), 1.5-1.9 (2H, m), 1.72 (3H, s), 2.1-3.1 (3H, m), 3.48 (2H, t, J=6.5 Hz), 3.6-3.9 (1H, m), 3.80 (3H, s), 4.19 (2H, s), 5.2-5.5 (1H, m), 6.4-7.4 (6H, m), 7.69 (1H, d, J=16.1 Hz).

MASS (EI, m/e): 428 (M⁺).

EXAMPLE 19 d-(3E)-16,16-dimethyl-15-oxo-2,5,6,7-tetranor-18-oxa-3,4-didehydro-4,8-inter-m-phenylene PGI₂ methyl ester, 11-acetate (19)

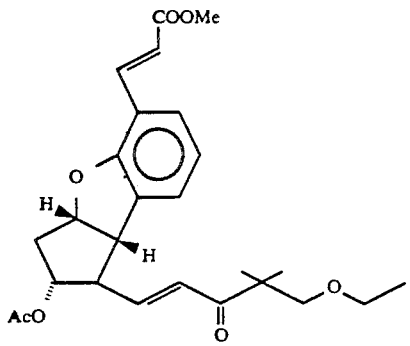

(19)

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (800 mg, 2.41 mmoles) in dry THF (8 ml) under argon atmosphere were added anhydrous pyridine (0.060 ml, 0.747 mmoles), dry DMSO (1.71 ml), and trifluoroacetic acid (0.056 ml, 0.723 mmoles), to which a solution of DCC (745 mg, 3.62 mmoles) in dry THF (3 ml) was added and stirred at room temperature for 4 hours.

Then sodium hydride (60% mineral oil dispersion 159 mg, 3.98 mmoles) was suspended in dry THF (5 ml), to which a solution of dimethyl 3,3-dimethyl-2-oxo-5-oxaheptylphosphonate (1.03 g, 4.09 mmoles) in dry THF (5 ml) was added, and stirred under argon atmosphere at room temperature for 30 minutes. To this solution was then added the above-prepared aldehyde solution by syringe while cooling with ice. The reaction mixture was stirred at 0° C. for an hour, to which acetic acid (0.25 ml) was added and concentrated. To the residue was added ethyl acetate (40 ml), filtered, and the filtrate was washed with water (20 ml). The aqueous layers were then re-extracted with ethyl acetate (20 ml). The organic layers were combined, washed with brine (20 ml), dried overanhydrous magnesium sulfate, and concentrated. The residue was purified by Lobar Column (Merck, silica gel: ethyl acetate/cyclohexane=1/5) to afford 87.2% yield of d-(3E)-16,16-dimethyl-15-oxo-2,5,6,7-tetranor-18-oxa-3,4-didehydro-4,8-inter-m-phenylene PGI₂ methyl ester, 11-acetate (958 mg, 2.10 mmoles).

The structure was confirmed by the following data:
$[\alpha]_D^{25}$: +196.43 (c 0.870, CHCl₃).

IR (liquid film): 2960, 2860, 1730, 1710, 1630, 1450, 1370, 1320, 1240, 1170, 1110, 1060, 980, 950, 860, 780, 750 cm⁻¹.

NMR (90 MHz, CDCl₃, δ): 1.0–1.4 (9H, m), 1.71 (3H, s), 2.1–3.1 (3H, m), 3.3–3.9 (5H, m), 3.80 (3H, s), 4.9–5.1 (1H, m), 5.2–5.6 (1H, m), 6.5–7.3 (6H, m), 7.69 (1H, d, J=16.3 Hz).

MASS (EI, m/e): 456 (M⁺).

EXAMPLE 20 d-(3E)-15-oxo-16-phenoxy-2,5,6,7,17,18,19,20-octanor-3,4-didehydro-4,8-inter-m-phenylene PGI₂ methyl ester, 11-acetate (20)

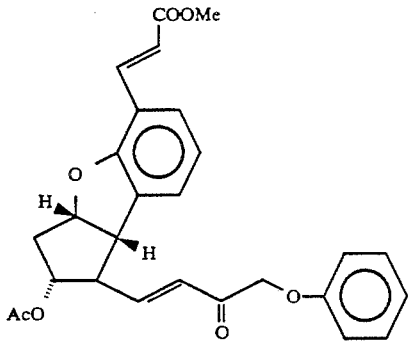

(20)

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (800 mg, 2.41 mmoles) in dry THF (8 ml) under argon atmosphere were added anhydrous pyridine (0.060 ml, 0.747 mmoles), dry DMSO (1.71 ml), and trifluoroacetic acid (0.056 ml, 0.723 mmoles), to which a solution of DCC (745 mg, 3.62 mmoles) in dry THF (3 ml) was added and stirred at room temperature for 3 hours.

Then sodium hydride (60% mineral oil dispersion 159 mg, 3.98 mmoles) was suspended in dry THF (5 ml), to which a solution of dimethyl 2-oxo-3-phenoxypropylphosphonate (1.06 g, 4.10 mmoles) in dry THF (5 ml) was added, and stirred under argon atmosphere at room temperature for 30 minutes. To this solution was then added the above-prepared aldehyde solution by syringe while cooling with ice. The reaction mixture was stirred at room temperature for 30 minutes, to which acetic acid (0.25 ml) was added and concentrated. To the residue was added ethyl acetate (50 ml), filtered, and the filtrate was washed with water (20 ml). The aqueous layers were then re-extracted with ethyl acetate (20 ml). The organic layers were combined, washed with brine (20 ml), dried over anhydrous magnesium sulfate, and concentrated. The residue was purified by Lobar Column (Merck, silica gel: ethyl acetate/cyclohexane=1/5) to afford 69.1% yield of d-(3E)-15-oxo-16-phenoxy-2,5,6,7,17,18,19,20-octanor-3,4-didehydro-4,8-inter-m-phenylene PGI₂ methyl ester, 11-acetate (769 mg, 1.66 mmoles).

The structure was confirmed by the following data:
$[\alpha]_D^{25}$: +220.02 (c 0.734, CHCl₃).

IR (liquid film): 3010, 2930, 2850, 1700, 1630, 1600, 1500, 1450, 1370, 1320, 1240, 1170, 1050, 980, 950, 910, 860, 760, 690, 670 cm⁻¹.

NMR (90 MHz, CDCl₃, δ): 1.72 (3H, s), 2.0–3.1 (3H, m), 3.5–3.9 (1H, m), 3.80 (3H, s), 4.9–5.1 (1H, m), 5.2–5.5 (1H, m), 6.5–7.5 (11H, m), 7.68 (1H, d, J=16.0 Hz).

MASS (EI, m/e): 462 (M⁺).

EXAMPLE 21 d-(3E,16R)-15-oxo-16-phenoxy-2,5,6,7,18,19,20-heptanor-3,4-didehydro-4,8-inter-m-phenylene PGI₂ methyl ester, 11-acetate (21)

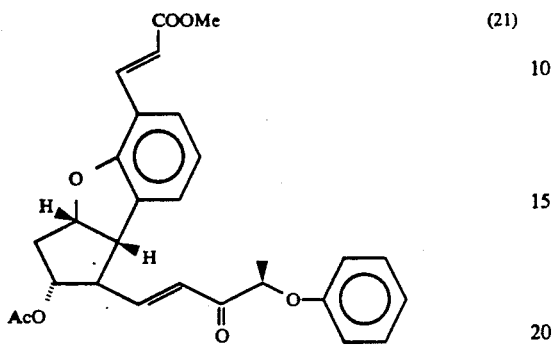

To a solution of d-(E)-3-(2α-acetoxy-1β-hydroxymethyl-3aβH,8bβH-2,3,3a,8b-tetrahydro-5-1H-cyclopenta[b]benzofuran)-acrylic acid methyl ester (800 mg, 2.41 mmoles) in dry THF (8 ml) under argon atmosphere were added anhydrous pyridine (0.060 ml, 0.747 mmoles), dry DMSO (1.71 ml), and trifluoroacetic acid (0.056 ml, 0.723 mmoles), to which a solution of DCC (745 mg, 3.62 mmoles) in dry THF (3 ml) was added and stirred at room temperature for 4 hours.

Then sodium hydride (60% mineral oil dispersion 159 mg, 3.98 mmoles) was suspended in dry THF (5 ml), to which a solution of dimethyl (R)-2-oxo-3-phenoxybutylphosphonate (1.11 g, 4.10 mmoles) in dry THF (5 ml) was added, and stirred under argon atmosphere at room temperature for 30 minutes. To this solution was then added the above-prepared aldehyde solution by syringe while cooling with ice. The reaction mixture was stirred at 0° C. for 15 minutes and then at room temperature for an hour, to which acetic acid (0.25 ml) was added and concentrated. To the residue was added ethyl acetate (40 ml), filtered, and the filtrate was washed with water (20 ml). The aqueous layers were then re-extracted with ethyl acetate (20 ml). The organic layers were combined, washed with brine (20 ml), dried over anhydrous magnesium sulfate, and concentrated. The residue was purified by Lobar Column (Merck, silica gel: ethyl acetate/cyclohexane=1/5) to afford 73.7% yield of d-(3E,16R)-15-oxo-16-phenoxy-2,5,6,7,18,19,20-heptanor-3,4-didehydro-4,8-inter-m-phenylene PGI₂ methyl ester, 11-acetate (846 mg, 1.78 mmoles).

The structure was confirmed by the following data:

$[\alpha]_D^{25}$: +240.81 (c 1.012, CHCl₃).

IR (liquid film): 2980, 2950, 1730, 1700, 1630, 1600, 1580, 1490, 1440, 1370, 1320, 1230, 1170, 1120, 1060, 980, 950, 870, 800, 780, 750, 690 cm⁻¹.

NMR (90 MHz, CDCl₃, δ): 1.55 (3H, d, J=7.0 Hz), 1.72 (3H, s), 2.0–3.0 (3H, m), 3.5–3.7 (1H, m), 3.79 (3H, s), 4.6–5.1 (2H, m), 5.2–5.4 (1H, m), 6.4–7.4 (11H, m), 7.66 (1H, d, J=16.3 Hz).

MASS (EI, m/e): 476 (M⁺).

EXAMPLE 22 d-(3E)-2,5,6,7-tetranor-3,4-didehydro-4,8-inter-m-phenylene PGI₂ methyl ester (22) and 15-epimer thereof (23)

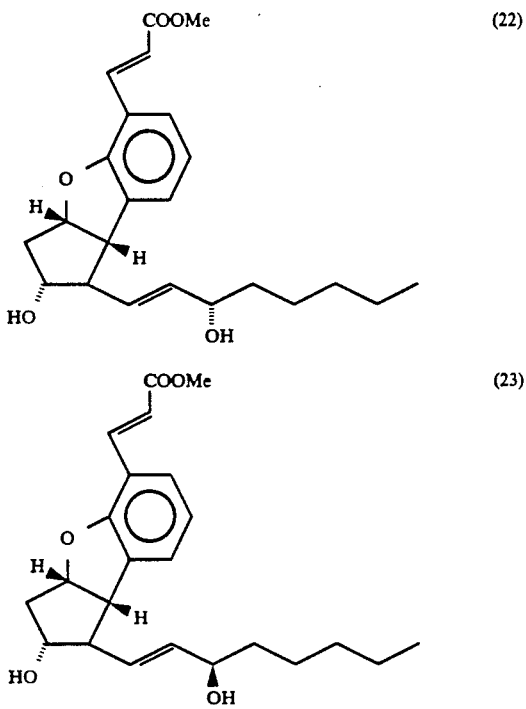

To a solution of d-(3E)-15-oxo-2,5,6,7-tetranor-3,4-didehydro-4,8-inter-m-phenylene PGI₂ methyl ester, 11-acetate (1.12 g, 2.63 mmoles) in methanol (40 ml) was added cerous trichloride heptahydrate (1.96 g, 5.26 mmoles), to which sodium borohydride (99.5 mg, 2.63 mmoles) was added after cooling to 0° C. The solution stirred at 0° C. for 30 minutes, to which saturated aqueous sodium hydrogen carbonate (5 ml) was added and concentrated. To the residue was added ethyl acetate (40 ml), filtered, and the precipitate was washed with ethyl acetate (10 ml×2).

The filtrates were combined, washed with water (30 ml) and brine (20 ml), dried over anhydrous magnesium sulfate, and concentrated. Then, the resultant oily product was dissolved in dry methanol (25 ml) under argon atomosphere, to which a solution of sodium methoxide in methanol (5.22N, 0.15 ml, 0.79 mmoles) was added and stirred at room temperature for 3 hours. This reaction mixture was then neutralized with acetic acid and concentrated. To the residue was added water (20 ml) and extracted with ethyl acetate (50 ml, 20 ml). The organic layers were combined, washed with brine (20 ml), dried over anhydrous magnesium sulfate, and concentrated.

The resultant residue was purified by Lobar Column (Merck, silica gel: ethyl acetate/cyclohexane=2/1) to afford 45.4% yield of d-(3E)-15-epi-2,5,6,7-tetranor-3,4-didehydro-4,8-inter-m-phenylene PGI₂ methyl ester (461 mg, 1.194 mmoles) as a low polar eluate, followed by 44.4% yield of d-(3E)-2,5,6,7-tetranor-3,4-didehydro-4,8-inter-m-phenylene PGI₂ methyl ester (451 mg, 1.168 mmoles) as a high polar eluate.

The structure was confirmed by the following data:

d-(3E)-2,5,6,7-tetranor-3,4-didehydro-4,8-inter-m-phenylene PGI₂ methyl ester m.p. 99°–100° C. (recrystallized from ethyl acetate/n-hexane).

$[\alpha]_D^{25}$: +282.19 (c 0.910, MeOH).

IR (KBr): 3450, 2950, 1720, 1700, 1630, 1610, 1450, 1320, 1290, 1280, 1250, 1200, 1160, 1090, 980, 970, 940, 920, 870, 780, 750, 620 cm⁻¹.

NMR (400 MHz, CDCl₃, δ): 0.91 (3H, t, J=6.6 HZ), 1.3–1.7 (8H, m), 2.02 (1H, ddd, J=5.5, 9.2, 13.5 Hz), 2.41 (1H, q, J=8.3 Hz), 2.71 (1H, dt, J=6.8, 13.5 Hz), 3.43 (1H, t, J=8.3 Hz), 3.80 (3H, s), 3.9–4.0 (1H, m), 4.13 (1H, q, J=6.3 Hz), 5.15–5.3 (1H, m), 5.55–5.6 (2H, m), 6.71 (1H, d, J=16.0 Hz), 6.84 (1H, t, J=7.4 Hz), 7.08 (1H, d, J=7.4 Hz), 7.28 (1H, d, J=7.4 Hz), 7.68 (1H, J=16.0 Hz).

MASS (EI, m/e): 368 (M+).

High resolution mass spectrum: Calcd. (C₂₃H₃₀O₅, M+): 386.2093. Found (M+): 386.2079.

d-(3E)-15-epi-2,5,6,7-tetranor-3,4-didehydro-4,8-inter-m-phenylene PGI₂ methyl ester $[\alpha]_D$: +243.01 (c 0.930, MeOH).

IR (liquid film): 3380, 2920, 2850, 1700, 1620, 1600, 1440, 1370, 1320, 1260, 1240, 1200, 1170, 1070, 1030, 980, 860, 750, 660 cm⁻¹.

NMR (400 MHz, CDCl₃, δ): 0.91 (3H, t, J=6.7 HZ), 1.2–1.8 (8H, m), 2.06 (1H, ddd, J=4.9, 8.2, 13.9 Hz), 2.45–2.55 (1H, m), 2.68 (1H, dt, J=7.1, 13.9 Hz), 3.50 (1H, t, J=8.7 Hz), 3.80 (3H, s), 3.95–4.05 (1H, m), 4.13–4.25 (1H, m), 5.26 (1H, ddd, J=4.9, 7.1, 8.7 Hz), 5.65–5.75 (2H, m), 6.71 (1H, d, J=16.2 Hz), 6.85 (1H, t, J=7.5 Hz), 7.14 (1H, d, J=7.5 Hz), 7.24 (1H, d, J=7.5 Hz), 7.68 (1H, d, J=16.2 Hz).

MASS (EI, m/e): 368 (M+).

High resolution mass spectrum: Calcd. (C₂₃H₃₀O₅, M+): 386.2093. Found (M+): 386.2108.

EXAMPLE 23 d-(3E)-2,5,6,7-tetranor-3,4-didehydro-4,8-inter-m-phenylene PGI₂ (24)

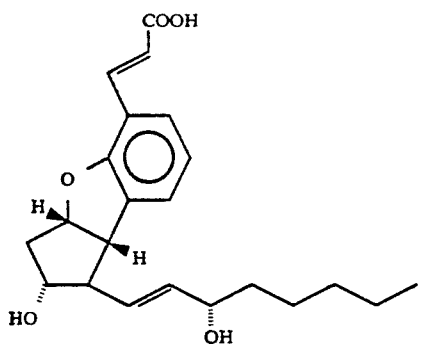

To a solution of d-(3E)-2,5,6,7-tetranor-3,4-didehydro-4,8-inter-m-phenylene PGI₂ methyl ester (231 mg, 0.598 mmoles) in methanol (20 ml) was added 1.015N aqueous sodium hydroxide solution (2.95 ml, 2.99 mmoles) and stirred at room temperature for 40 hours. The reaction mixture was concentrated. To the residue was added water (20 ml), then neutralized with 1.0N hydrochloric acid (2.99 ml), and extracted with ethyl acetate (50 ml, 20 ml). The organic layers were combined, washed with water (20 ml) and with brine (20 ml), dried over anhydrous magnesium sulfate, and concentrated to give 263 mg of crude crystalline product. The crude crystalline product was recrystallized from ethyl acetate/n-hexane to afford 84.4% yield of d-(3E)-2,5,6,7-tetranor-3,4-didehydro-4,8-inter-m-phenylene PGI₂ (188 mg, 0.505 mmoles) as a white crystal. The structure was confirmed by the following data:

m.p. 179°–180° C.

$[\alpha]_D^{25}$: +285.74 (c 0.400, MeOH).

IR (KBr): 3300, 2920, 2850, 1690, 1630, 1600, 1590, 1440, 1280, 1240, 1190, 1080, 1030, 980, 860, 740, 610 cm⁻¹.

NMR (400 MHz, CDCl₃+DMSO-d₆, δ): 0.85–0.95 (3H, m), 1.25–1.7 (8H, m), 1.95–2.05 (1H, m), 2.3–2.45 (1H, m), 2.70 (1H, dt, J=6.8, 13.7 Hz), 3.41 (1H, t, J=8.6 Hz), 3.85–3.95 (1H, m), 4.05–4.15 (1H, m), 5.15–5.25 (1H, m), 5.55–5.7 (2H, m), 6.70 (1H, d, J=16.1 Hz), 6.82 (1H, t, J=7.2 Hz), 7.04 (1H, d, J=7.2 Hz), 7.23 (1H, d, J=7.2 Hz), 7.68 (1H, d, J=16.1 Hz).

MASS (EI, m/e): 372 (M+)

High resolution mass spectrum: Calcd. (C₂₂H₂₈O₅, M+): 372.1937. Found (M+): 372.1961.

Anal.: Calcd. for C₂₂H₂₈O₅: C: 70.94; H: 7.58. Found: C: 70.77; H: 7.55.

EXAMPLE 24 d-(3E)-15-epi-2,5,6,7-tetranor-3,4-didehydro-4,8-inter-m-phenylene PGI₂ (25)

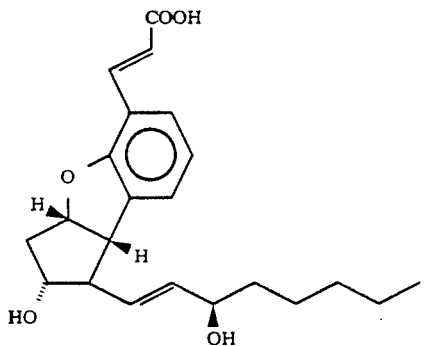

To a solution of d-(3E)-15-epi-2,5,6,7-tetranor-3,4-didehydro-4,8-inter-m-phenylene PGI₂ methyl ester (374 mg, 0.669 mmoles) in methanol (20 ml) was added 1.015N aqueous sodium hydroxide solution (6.69 ml 6.79 mmoles) and stirred at room temperature for 24 hours. The reaction mixture was concentrated. To the residue was added water (15 ml), then neutralized with 1.0N hydrochloric acid (6.79 ml), and extracted with ethyl acetate (50 ml, 30 ml). The organic layers were combined, washed with water (20 ml) and with brine (20 ml), dried over anhydrous magnesium sulfate, and concentrated to give 284 mg of crude crystalline product. The crude crystalline product was recrystallized from ethyl acetate/n-hexane to afford 57.7% yield of d-(3E)-15-epi-2,5,6,7-tetranor-3,4-didehydro-4,8-inter-m-phenylene PGI₂ (208 mg, 0.559 mmoles) as a white crystal. The structure was confirmed by the following data:

m.p. 128°–129° C.

$[\alpha]_D^{25}$: +259.45 (c 0.402, MeOH).

IR (KBr): 3350, 2930, 2850, 1700, 1630, 1440, 1280, 1250, 1210, 1180, 1020, 990, 960, 880, 860, 780, 740 cm⁻¹.

NMR (400 MHz, CDCl₃+DMSO-d₆, δ): 0.91 (3H, t, J=6.8 Hz), 1.25–1.65 (8H, m), 2.04 (1H, ddd, J=5.4, 8.8, 13.7 Hz), 2.4–2.5 (1H, m), 2.67 (1H, dt, J=6.8, 13.7 Hz), 3.48 (1H, t, J=8.5 Hz), 3.9–4.0 (1H, m), 4.1–4.2 (1H, m), 5.2–5.3 (1H, m), 5.65–5.75 (2H, m), 6.70 (1H, d, J=16.1 Hz), 6.84 (1H, t, J=7.3 Hz), 7.14 (1H, d, J=7.3 Hz), 7.23 (1H, d, J=7.3 Hz), 7.69 (1H, d, J=16.1 Hz).

MASS (EI, m/e): 372 (M+).

High resolution mass spectrum: Calcd. ($C_{22}H_{28}O_5$, M+): 372.1937. Found (M+): 372.1935.

Anal.: Calcd. for $C_{22}H_{28}O_5$: C: 70.94; H: 7.58. Found: C: 71.15; H: 7.67.

EXAMPLE 25 d-(3E)-16-methyl-2,5,6,7-tetranor-3,4-didehydro-4,8-inter-m-phenylene PGI$_2$ methyl ester (26) and 15-epimer thereof (27)

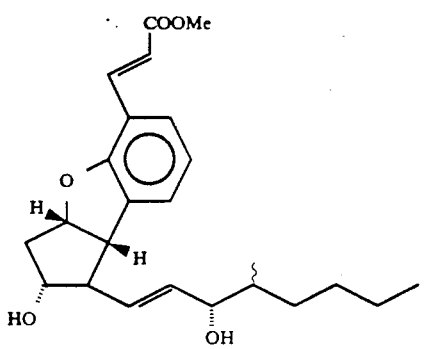

(26)

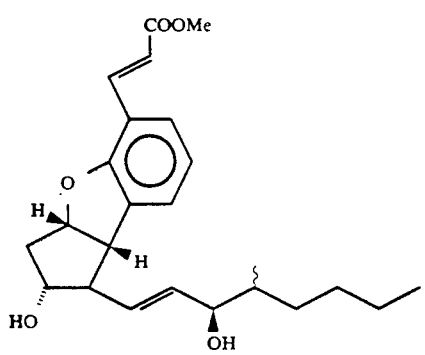

(27)

To a solution of d-(3E)-16-methyl-15-oxo-2,5,6,7-tetranor-3,4-didehydro-4,8-inter-m-phenylene PGI$_2$ methyl ester, 11-acetate (1.20 g, 2.73 mmoles) in methanol (40 ml) was added cerous trichloride heptahydrate (2.03 g, 5.46 mmoles), to which sodium borohydride (103 mg, 2.73 mmoles) was added after cooling to 0° C. The solution stirred at 0° C. for 20 minutes, to which saturated aqueous sodium hydrogen carbonate (5 ml) was added and concentrated. To the residue was added ethyl acetate (50 ml), filtered, and the precipitate was washed with ethyl acetate (20 ml×2).

The filtrates were combined, washed with water (30 ml) and with brine (30 ml), dried over anhydrous magnesium sulfate, and concentrated. Then, the resultant oily product was dissolved in dry methanol (25 ml) under an argon atomosphere, to which a solution of sodium methoxide in methanol (5.22N, 0.17 ml, 0.89 mmoles) was added and stirred at room temperature for 2 hours. This reaction mixture was then neutralized with acetic acid and concentrated. To the residue was added water (20 ml) and extracted with ethyl acetate (60 ml, 20 ml). The organic layers were combined, washed with brine (20 ml), dried over anhydrous magnesium sulfate, and concentrated.

The resultant residue was purified by Lobar Column (Merck, silica gel: ethyl acetate/cyclohexane=2/1) to afford 45.1% yield of d-(3E)-16-methyl-15-epi-2,5,6,7-tetranor-3,4-didehydro-4,8-inter-m-phenylene PGI$_2$ methyl ester (492 mg, 1.23 mmoles) as a less polar eluate, followed by 40.1% yield of d-(3E)-16-methyl-2,5,6,7-tetranor-3,4-didehydro-4,8-inter-m-phenylene PGI$_2$ methyl ester (438 mg, 1.095 mmoles) as a more polar eluate.

The structure was confirmed by the following data: d-(3E)-16-methyl-2,5,6,7-tetranor-3,4-didehydro-4,8-inter-m-phenylene PGI$_2$ methyl ester:

$[\alpha]_D^{25}$: +249.87 (c 0.792, MeOH).

IR (liquid film): 3370, 3010, 2950, 2920, 2860, 1700, 1630, 1600, 1590, 1440, 1370, 1320, 1270, 1250, 1210, 1170, 1030, 980, 970, 890, 860, 750, 660 cm$^{-1}$.

NMR (400 MHz, CDCl$_3$, δ): 0.85–1.0 (6H, m), 1.0–1.7 (7H, m), 2.03 (1H, ddd, J=5.3, 8.9, 13.8 Hz), 2.4–2.5 (1H, m), 2.71 (1H, dt, J=6.8, 13.8 Hz), 3.44 (1H, t, J=8.7 Hz), 3.80 (3H, s), 3.9–4.0 (2H, m), 5.2–5.3 (1H, m), 5.6–5.7 (2H, m), 6.71 (1H, d, J=16.0 Hz), 6.8–6.9 (1H, m), 7.05–7.15 (1H, m), 7.24 (1H, d, J=7.3 Hz), 7.68 (1H, d, J=16.0 Hz).

MASS (EI, m/e): 400 (M+)

High resolution mass spectrum: Calcd. ($C_{24}H_{32}O_5$, M+): 400.2250. Found (M+): 400.2276.

d-(3E)-16-methyl-15-epi-2,5,6,7-tetranor-3,4-didehydro-4,8-inter-m-phenylene PGI$_2$ methyl ester $[\alpha]_D^{25}$: +210.44 (c 0.852, MeOH).

IR (liquid film): 3400, 3030, 2970, 2940, 2880, 1700, 1630, 1600, 1590, 1450, 1320, 1220, 1180, 980, 870, 760, 670 cm$^{-1}$.

NMR (400 MHz, CDCl$_3$, δ): 0.85–1.0 (6H, m), 1.05–1.7 (7H, m), 2.06 (1H, ddd, J=4.9, 8.2, 13.9 Hz), 2.45–2.55 (1H, m), 2.69 (1H, dt, J=6.8, 13.9 Hz), 3.45–3.55 (1H, m), 3.80 (3H, s), 3.95–4.1 (2H, m), 5.2–5.3 (1H, m), 5.65–5.75 (2H, m), 6.72 (1H, d, J=16.0 Hz), 6.85 (1H, t, J=7.6 Hz), 7.1–7.15 (1H, m), 7.23 (1H, d, J=7.6 Hz), 7.68 (1H, d, J=16.0 Hz).

MASS (EI, m/e): 400 (M+).

High resolution mass spectrum: Calcd. ($C_{24}H_{32}O_5$, M+): 400.2250. Found (M+): 400.2258.

EXAMPLE 26 d-(3E)-16-methyl-2,5,6,7-tetranor-3,4-didehydro-4,8-inter-m-phenylene PGI$_2$ (28)

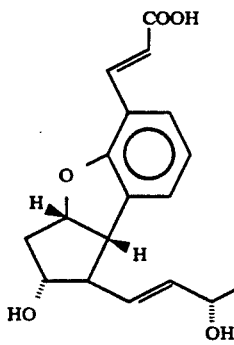

(28)

To a solution of d-(3E)-16-methyl-2,5,6,7-tetranor-3,4-didehydro-4,8-inter-m-phenylene PGI$_2$ methyl ester (350 mg, 0.875 mmoles) in methanol (15 ml) was added 1.0N aqueous sodium hydroxide solution (7.0 ml, 7.0 mmoles) and stirred at room temperature for 16 hours.

The reaction mixture was concentrated. To the residue was added water (10 ml), then neutralized with 1.0N hydrochloric acid (7.0 ml), and extracted with ethyl acetate (50 ml, 20 ml). The organic layers were combined, washed with water (20 ml) and with brine (20 ml), dried over anhydrous magnesium sulfate, and concentrated. The resultant residue was purified by Lobar Column (Merck, R P-8, MeOH/H$_2$O 1/1~3/1) to afford 60.7% yield of d-(3E)-16-methyl-2,5,6,7-tetranor-3,4-didehydro-4,8-inter-m-phenylene PGI$_2$ (205 mg, 0.531 mmoles). The structure was confirmed by the following data:

$[\alpha]_D^{25}$: +232.43 (c 0.632, MeOH).

IR (liquid film): 3350, 2940, 1690, 1630, 1600, 1450, 1250, 1200, 1030, 890, 860, 780, 740 cm$^{-1}$.

NMR (400 MHz, CDCl$_3$, δ): 0.85–1.0 (6H, m), 1.05–1.7 (7H, m), 2.0–2.1 (1H, m), 2.4–2.5 (1H, m), 2.65–2.75 (1H, m), 3.44 (1H, t, J=8.5 Hz), 3.9–4.0 (2H, m), 5.2–5.3 (1H, m), 5.55–5.7 (2H, m), 6.71 (1H, d, J=15.9 Hz), 6.8–6.9 (1H, m), 7.1–7.15 (1H, m), 7.2–7.3 (1H, m), 7.75 (1H, d, J=15.9 Hz).

MASS (EI, m/e): 386 (M$^+$).

High resolution mass spectrum: Calcd. (C$_{23}$H$_{30}$O$_5$, M$^+$): 386.2093. Found (M$^+$): 386.2110.

EXAMPLE 27 d-(3E, 17S)-17-methyl-20a-homo-2,5,6,7-tetranor-3,4-didehydro-4,8-inter-m-phenylene PGI$_2$ methyl ester (29) and 15-epimer thereof (30)

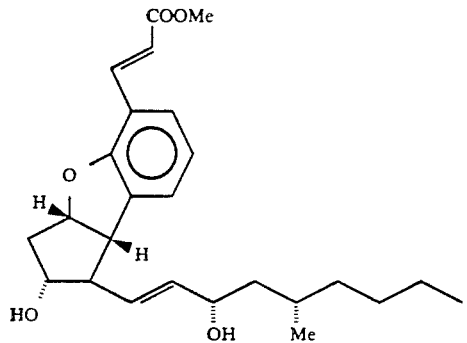
(29)

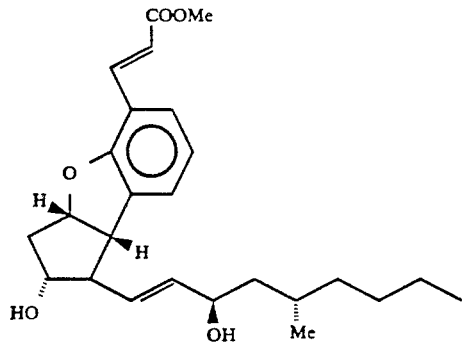
(30)

To a solution of d-(3E, 17S)-17-methyl-20a-homo-15-oxo-2,5,6,7-tetranor-3,4-didehydro-4,8-inter-m-phenylene PGI$_2$ methyl ester, 11-acetate (1.02 g, 2.25 mmoles) in methanol (10 ml) was added cerous trichloride heptahydrate (930 mg, 2.49 mmoles), to which sodium borohydride (108 mg, 2.84 mmoles) was added after cooling to 0° C. The solution stirred at 0° C. for 10 minutes, to which saturated aqueous sodium hydrogen carbonate (5 ml) was added and concentrated. To the residue was added ethyl acetate (50 ml), filtered, and the precipitate was washed with ethyl acetate (10 ml×2). The filtrates were combined, washed with water (20 ml) and with brine (20 ml), dried over anhydrous magnesium sulfate, and concentrated. Then, the resultant oily product was dissolved in dry methanol (25 ml) under argon atmosphere, to which a solution of sodium methoxide in methanol (5.22N, 0.1 ml, 0.52 mmoles) was added and stirred at room temperature for an hour. This reaction mixture was then neutralized with acetic acid and concentrated. To the residue was added water (20 ml) and extracted with ethyl acetate (50 ml, 20 ml). The organic layers were combined, washed with brine (20 ml), dried over anhydrous magnesium sulfate, and concentrated.

The resultant residue was purified by Lobar Column (Merck, silica gel: ethyl acetate/cyclohexane=2/1) to afford 32.6% yield of d-(3E, 17S)-17-methyl-15-epi-20a-homo-2,5,6,7-tetranor-3,4-didehydro-4,8-inter-m-phenylene PGI$_2$ methyl ester (304 mg, 0.734 mmoles) as a less polar eluate, followed by 27.7% yield of d-(3E, 17S)-17-methyl-20a-homo-2,5,6,7-tetranor-3,4-didehydro-4,8-inter-m-phenylene PGI$_2$ methyl ester (258 mg, 0.623 mmoles) as a more polar eluate.

The structure was confirmed by the following data:

d-(3E, 17S)-17-methyl-20a-homo-2,5,6,7-tetranor-3,4-didehydro-4,8-inter-m-phenylene PGI$_2$ methyl ester IR (liquid film): 3382, 2958, 2930, 1717, 1632, 1445, 1321, 1251, 1205, 1174, 1077, 1038, 971, 868, 748 cm$^{-1}$.

NMR (400 MHz, CDCl$_3$, δ): 0.91 (3H, t, J=6.7 Hz), 0.92 (3H, d, J=6.1 Hz), 1.14–1.50 (9H, m), 1.99 (1H, ddd, J=5.5, 9.8, 14.0 Hz), 2.36 (1H, q, J=8.6 Hz), 2.71 (1H, dt, J=6.7, 14.0 Hz), 3.39 (1H, t, J=9.1 Hz), 3.80 (3H, s), 3.90 (1H, dt, J=6.1, 9.2 Hz), 4.19 (1H, q, J=7.3 Hz), 5.19 (1H, m), 5.52 (1H, dd, J=7.3, 15.3 Hz), 5.60 (1H, dd, J=8.5, 15.3 Hz), 6.71 (1H, d, J=15.9 Hz), 6.82 (1H, t, J=7.3 Hz), 7.04 (1H, d, J=7.3 Hz), 7.22 (1H, d, J=7.3 Hz), 7.67 (1H, d, J=15.9 Hz).

MASS (EI, m/e): 414 (M$^+$).

High resolution mass spectrum: Calcd. (C$_{25}$H$_{34}$O$_5$, M$^+$): 414.2407. Found (M$^+$): 414.2379.

d-(3E, 17S)-17-methyl-15-epi-20a-homo-2,5,6,7-tetranor-3,4-didehydro-4,8-inter-m-phenylene PGI$_2$ methyl ester IR (liquid film): 3392, 2958, 2930, 2874, 1700, 1632, 1450, 1323, 1278, 1251, 1207, 1178, 1042, 988, 911, 868, 733, 646 cm$^{-1}$.

NMR (400 MHz, CDCl$_3$, δ): 0.89 (3H, t, J=6.7 Hz), 0.92 (1H, d, J=6.7 Hz), 1.1–1.35 (8H, m), 1.56 (1H, m), 2.01 (1H, ddd, J=5.4, 6.5, 14.8 Hz), 2.41 (1H, m), 2.66 (1H, m), 3.43 (1H, t, J=8.5 Hz), 3.78 (3H, s), 3.92 (1H, m), 4.22 (1H, m), 5.20 (1H, m), 5.67–5.68 (2H, m), 6.69 (1H, d, J=15.9 Hz), 6.82 (1H, t, J=7.3 Hz), 7.11 (1H, d, J=6.7 Hz), 7.21 (1H, d, J=8.0 Hz), 7.67 (1H, d, J=16.5 Hz).

MASS (EI, m/e): 414 (M$^+$).

High resolution mass spectrum: Calcd. (C$_{25}$H$_{34}$O$_5$, M$^+$): 414.2407. Found (M$^+$): 414.2418.

EXAMPLE 28 d-(3E, 17S)-17-methyl-20a-homo-2,5,6,7-tetranor-3,4-didehydro-4,8-inter-m-phenylene PGI$_2$ (31)

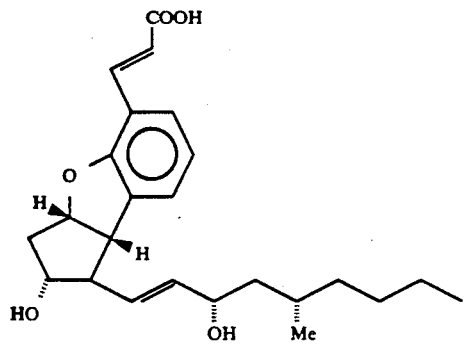

(31)

To a solution of d-(3E, 17S)-17-methyl-20a-homo-2,5,6,7-tetranor-3,4-didehydro-4,8-inter-m-phenylene PGI$_2$ methyl ester (218 mg, 0.527 mmoles) in methanol (15 ml) was added 2.0N aqueous sodium hydroxide solution (2.5 ml, 5.0 mmoles) and stirred at room temperature for 17 hours. The reaction mixture was concentrated. To the residue was added water (20 ml), then neutralized with 1.0N hydrochloric acid (6.0 ml), and extracted with ethyl acetate (50 ml, 20 ml). The organic layers were combined, washed with water (20 ml) and with brine (20 ml), dried over anhydrous magnesium sulfate, and concentrated.

The resulting crude crystalline product was recrystallized from water-methanol to afford 52.6% yield of d-(3E, 17S)-17-methyl-20a-homo-2,5,6,7-tetranor-3,4-didehydro-4,8-inter-m-phenylene PGI$_2$ (112 mg, 0.28 mmoles) as a white crystal. The structure was confirmed by the following data:

m.p. 79°–80° C.

$[\alpha]_D^{25}$: +264.99 (c 0.100, MeOH).

IR (KBr): 3400, 2928, 1630, 1692, 1448, 1197, 870, 743 cm$^{-1}$.

NMR (400 MHz, CDCl$_3$, δ): 0.91 (3H, t, J=7.3 Hz), 0.94 (3H, d, J=6.7 Hz), 1.16–1.52 (9H, m), 2.06 (1H, ddd, J=4.9, 8.4, 13.4 Hz), 2.71 (1H, m) 3.47 (1H, t, J=8.1 Hz), 3.98 (1H, dt, J=6.1, 7.9 Hz), 4.24 (1H, q, J=6.7 Hz), 5.25 (1H, m), 5.60 (1H, dd, J=6.7, 15.3 Hz), 5.67 (1H, dd, J=8.5, 15.3 Hz), 6.72 (1H, d, J=15.8 Hz), 6.85 (1H, t, J=7.9 Hz), 7.11 (1H, d, J=7.3 Hz), 7.25–7.3 (3H, m), 7.75 (1H, d, J=15.8 Hz).

MASS (EI, m/e): 400 (M+).

High resolution mass spectrum: Calcd. (C$_{24}$H$_{32}$O$_5$, M+): 400.2250. Found (M+): 400.2274.

EXAMPLE 29 d-(3E)-16,16-dimethyl-2,5,6,7-tetranor-3,4-didehydro-4,8-inter-m-phenylene PGI$_2$ methyl ester (32) and 15-epimer thereof (33)

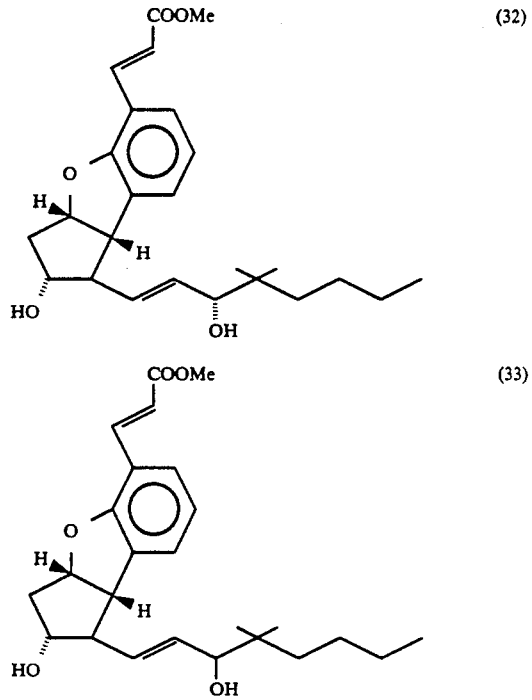

To a solution of d-(3E)-16,16-dimethyl-15-oxo-2,5,6,7-tetranor-3,4-didehydro-4,8-inter-m-phenylene PGI$_2$ methyl ester, 11-acetate (847 mg, 1.87 mmoles) in methanol (20 ml) was added cerous trichloride heptahydrate (1.39 g, 3.73 mmoles), to which sodium borohydride (70.7 mg, 1.87 mmoles) was added after cooling to 0° C. The solution stirred at 0° C. for 20 minutes, to which saturated aqueous sodium hydrogen carbonate (3 ml) was added and concentrated. To the residue was added ethyl acetate (30 ml), filtered, and the precipitate was washed with ethyl acetate (10 ml×2).

The filtrates were combined, washed with water (20 ml) and with brine (20 ml), dried over anhydrous magnesium sulfate, and concentrated.

Then, the resultant oily product was dissolved in dry methanol (20 ml) under argon atmosphere, to which a solution of sodium methoxide in methanol (5.22N, 0.11 ml, 0.57 mmoles) was added and stirred at room temperature for 2 hours.

This reaction mixture was then neutralized with acetic acid and concentrated. To the residue was added water (20 ml) and extracted with ethyl acetate (40 ml, 20 ml). The organic layers were combined, washed with brine (20 ml), dried over anhydrous magnesium sulfate, and concentrated.

The resultant residue was purified by Lobar Column (Merck, silica gel: ethyl acetate/cyclohexane=2/1) to afford 44.2% yield of d-(3E)-16,16-dimethyl-15-epi-2,5,6,7-tetranor-3,4-didehydro-4,8-inter-m-phenylene PGI$_2$ methyl ester (342 mg, 0.926 mmoles) as a less polar eluate, followed by 47.3% yield of d-(3E)-16,16-dimethyl-2,5,6,7-tetranor-3,4-didehydro-4,8-inter-m-phenylene PGI$_2$ methyl ester (366 mg, 0.884 mmoles) as a more polar eluate.

The structure was confirmed by the following data:

d-(3E)-16,16-dimethyl-2,5,6,7-tetranor-3,4-didehydro-4,8-inter-m-phenylene PGI$_2$ methyl ester $[\alpha]_D^{25}$: +265.76 (c 0.444, MeOH).

IR (liquid film): 3380, 2945, 2850, 1700, 1625, 1600, 1580, 1440, 1315, 1270, 1240, 1200, 1170, 1065, 1030, 980, 860, 750 cm$^{-1}$.

NMR (400 MHz, CDCl$_3$, δ): 0.87 (3H, s), 0.91 (3H, s), 0.92 (3H, t, J=6.8 Hz), 1.2-1.4 (6H, m), 1.8-1.85 (1H, m), 2.03 (1H, ddd, J=5.2, 8.8, 13.6 Hz), 2.3-2.4 (1H, m), 2.45 (1H, q, J=8.6 Hz), 2.71 (1H, ddd, J=6.1, 7.4, 13.6 Hz), 3.46 (1H, t, J=8.6 Hz), 3.80 (3H, s), 3.86 (1H, d, J=6.4 Hz), 3.9-4.0 (1H, m), 5.23 (1H, ddd, J=5.2, 7.4, 8.6 Hz), 5.6-5.75 (2H, m), 6.72 (1H, d, J=16.1 Hz), 6.84 (1H, t, J=7.6 Hz), 7.09 (1H, d, J=7.6 Hz), 7.24 (1H, d, J=7.6 Hz), 7.68 (1H, d, J=16.1 Hz).

MASS (EI, m/e): 414 (M$^+$).

High resolution mass spectrum: Calcd. (C$_{25}$H$_{34}$O$_5$, M$^+$): 414.2406. Found (M$^+$): 414.2406.

d-(3E)-16,16-dimethyl-15-epi-2,5,6,7-tetranor-3,4-didehydro-4,8-inter-m-phenylene PGI$_2$ methyl ester m.p. 87°-88° C. (recrystallized from ethyl acetate/n-hexane).

$[\alpha]_D^{25}$: +238.50 (c 0.496, MeOH).

IR (KBr): 3530, 3460, 2950, 2860, 1695, 1630, 1600, 1585, 1445, 1330, 1320, 1265, 1220, 1200, 1180, 1100, 990, 980, 960, 950, 865, 800, 780, 765, 720 cm$^{-1}$.

NMR (400 MHz, CDCl$_3$, δ): 0.88 (3H, s), 0.91 (3H, s), 0.85-0.95 (3H, m), 1.2-1.4 (6H, m), 1.51 (1H, d, J=4.4 Hz), 1.66 (1H, d, J=4.9 Hz), 2.06 (1H, ddd, J=5.1, 8.5, 13.8 Hz), 2.52 (1H, q, J=8.3 Hz), 2.69 (1H, ddd, J=5.9, 7.1, 13.8 Hz), 3.51 (1H, t, J=8.3 Hz), 3.80 (3H, s), 3.85-3.95 (1H, m), 3.95-4.15 (1H, m), 5.26 (1H, ddd, J=5.1, 7.1, 8.3 Hz), 5.65-5.8 (2H, m), 6.72 (1H, d, J=16.1 Hz), 6.85 (1H, t, J=7.6 Hz), 7.1-7.15 (1H, m), 7.2-7.3 (1H, m), 7.68 (1H, d, J=16.1 Hz).

MASS (EI, m/e): 414 (M$^+$).

High resolution mass spectrum: Calcd. (C$_{25}$H$_{34}$O$_5$, M$^+$): 414.2406. Found (M$^+$): 414.2386.

EXAMPLE 30 d-(3E)-16,16-dimethyl-2,5,6,7-tetranor-3,4-didehydro-4,8-inter-m-phenylene PGI$_2$ (34)

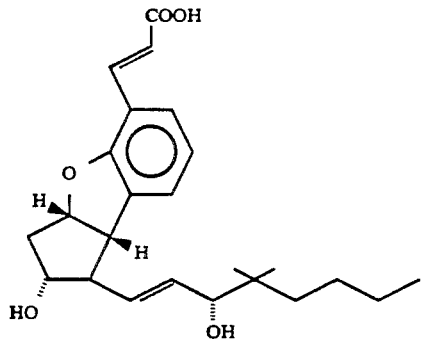

(34)

To a solution of d-(3E)-16,16-dimethyl-2,5,6,7-tetranor-3,4-didehydro-4,8-inter-m-phenylene PGI$_2$ methyl ester (261 mg, 0.61 mmoles) in methanol (25 ml) was added 1.0N aqueous sodium hydroxide solution (6.0 ml, 6.0 mmoles) and stirred at room temperature for 24 hours. The reaction mixture was concentrated. To the residue was added water (15 ml), then neutralized with 1.0N hydrochloric acid (6.0 ml), and extracted with ethyl acetate (50 ml, 20 ml). The organic layers were combined, washed with water (20 ml) and with brine (20 ml), dried over anhydrous magnesium sulfate, and concentrated. The resultant residue was purified by Lobar Column (Merck, R P-8, MeOH/H$_2$O=3/1) to afford 66.3% yield of d-(3E)-16,16-dimethyl-2,5,6,7-tetranor-3,4-didehydro-4,8-inter-m-phenylene PGI$_2$ (167 mg, 0.418 mmoles). The structure was confirmed by the following data:

m.p. 84°-85° C. (recrystallized from EtOH/H$_2$O).

$[\alpha]_D^{25}$: +270.23 (c 0.252, MeOH).

IR (KBr): 3370, 2950, 2925, 1685, 1625, 1600, 1445, 1420, 1250, 1200, 990, 950, 860, 740 cm$^{-1}$.

NMR (400 MHz, CDCl$_3$+DMSO-d$_6$, δ): 0.87 (3H, s), 0.91 (3H, s), 0.92 (3H, t, J=6.8 Hz), 1.2-1.4 (6H, m), 2.00 (1H, ddd, J=5.8, 9.5, 13.8 Hz), 2.39 (1H, q, J=8.5 Hz), 2.70 (1H, dt, J=7.1, 13.8 Hz), 3.42 (1H, t, J=8.5 Hz), 3.82 (1H, d, J=7.3 Hz), 3.85-3.95 (1H, m), 5.21 (1H, ddd, J=5.8, 7.1, 8.5 Hz), 5.61 (1H, dd, J=8.5, 15.1 Hz), 5.69 (1H, dd, J=7.3, 15.1 Hz), 6.70 (1H, d, J=15.9 Hz), 6.83 (1H, t, J=7.4 Hz), 7.07 (1H, d, J=7.4 Hz), 7.23 (1H, d, J=7.4 Hz), 7.68 (1H, d, J=15.9 Hz).

MASS (EI, m/e): 400 (M$^+$).

High resolution mass spectrum: Calcd. (C$_{24}$H$_{32}$O$_5$, M$^+$): 400.2250. Found (M$^+$): 400.2258.

EXAMPLE 31 d-(3E)-15-phenyl-2,5,6,7,16,17,18,19,20-nonanor-3,4-didehydro-4,8-inter-m-phenylene PGI$_2$ methyl ester (35) and 15-epimer thereof (36)

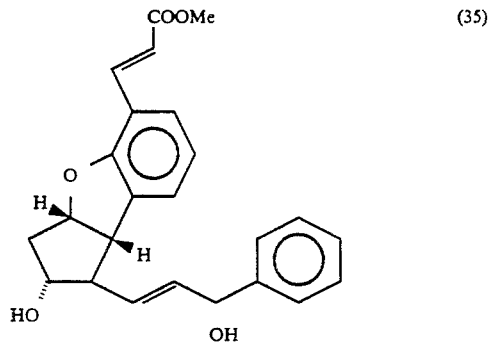

(35)

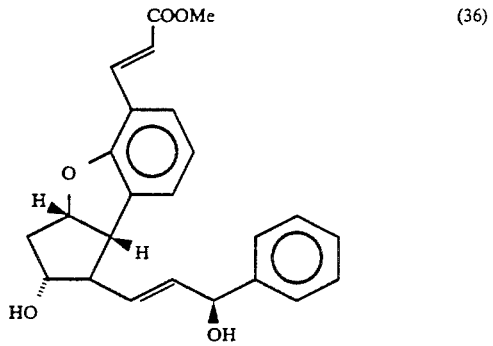

(36)

To a solution of d-(3E)-15-oxo-15-phenyl-2,5,6,7,16,17,18,19,20-nonanor-3,4-didehydro-4,8-inter-m-phenylene PGI$_2$ methyl ester, 11-acetate (698 mg, 1.62 mmoles) in methanol (20 ml) was added cerous trichloride heptahydrate (1.21 g, 3.24 mmoles), to which sodium borohydride (61.3 mg, 1.62 mmoles) was added after cooling to 0° C. The solution stirred at 0° C. for 15 minutes, to which saturated aqueous sodium hydrogen carbonate (3 ml) was added and concentrated. To the residue was added ethyl acetate (40 ml), filtered, and the precipitate was washed with ethyl acetate (10 ml×2). The filtrates were combined, washed with water (20 ml) and with brine (20 ml), dried over anhydrous magnesium sulfate, and concentrated. Then, the resultant oily product was dissolved in dry methanol (20 ml) under argon atmosphere, to which a solution of sodium methoxide in methanol (5.22N, 0.093 ml, 0.486 mmoles) was added and stirred at room temperature for 4 hours. This reaction mixture was then neutralized with acetic acid and concentrated. To the residue was added water (20 ml) and extracted with ethyl acetate (50 ml, 20 ml). The organic layers were combined, washed with brine (20 ml), dried over anhydrous magnesium sulfate, and concentrated.

The resultant residue was purified by Lobar Column (Merck, silica gel: ethyl acetate/cyclohexane=2/1) to afford 47.4% yield of d-(3E)-15-phenyl-15-epi-2,5,6,7,16,17,18,19,20-nonanor-3,4-didehydro-4,8-inter-m-phenylene $PGI_2$ methyl ester (301 mg, 0.768 mmoles) as a less polar eluate, followed by 43.4% yield of d-(3E)-15-phenyl-2,5,6,7,16,17,18,19,20-nonanor-3,4-didehydro-4,8-inter-m-phenylene $PGI_2$ methyl ester (275 mg, 0.702 mmoles) as a more polar eluate.

The structure was confirmed by the following data:

d-(3E)-15-phenyl-2,5,6,7,16,17,18,19,20-nonanor-3,4-didehydro-4,8-inter-m-phenylene $PGI_2$ methyl ester m.p. 130°-131° C. (recrystallized from ethyl acetate/n-hexane).

$[\alpha]_D^{25}$: +310.26 (c 0.604, MeOH).

IR (KBr): 3400, 3025, 2945, 2880, 1700, 1630, 1445, 1340, 1275, 1250, 1200, 1180, 1100, 1060, 1030, 990, 950, 860, 775, 740, 700 cm$^{-1}$.

NMR (400 MHz, $CDCl_3$, δ): 2.0–2.1 (2H, m), 2.24 (1H, d, J=3.4 Hz), 2.49 (1H, q, J=8.3 Hz), 2.68 (1H, ddd, J=6.1, 7.1, 13.7 Hz), 3.48 (1H, t, J=8.3 Hz), 3.79 (3H, s), 3.95–4.05 (1H, m), 5.2–5.3 (2H, m), 5.75–5.9 (2H, m), 6.70 (1H, d, J=16.1 Hz), 6.79 (1H, t, J=7.3 Hz), 7.00 (1H, d, J=7.3 Hz), 7.21 (1H, d, J=7.3 Hz), 7.3–7.45 (5H, m), 7.66 (1H, d, J=16.1 Hz).

MASS (EI, m/e): 392 (M+).

High resolution mass spectrum: Calcd. ($C_{24}H_{24}O_5$, M+): 392.1624. Found (M+): 392.1670.

Anal.: Calcd. for $C_{24}H_{24}O_5$: C: 73.45; H: 6.16. Found: C: 73.16; H: 6.38.

d-(3E)-15-phenyl-15-epi-2,5,6,7,16,17,18,19,20-nonanor-3,4-didehydro-4,8-inter-m-phenylene $PGI_2$ methyl ester m.p. 156°-157° C. (recrystallized from ethyl acetate/n-hexane).

$[\alpha]_D^{25}$: +287.20 (c 0.430, MeOH).

IR (KBr): 3250, 2945, 1700, 1620, 1490, 1440, 1445, 1270, 1250, 1230, 1210, 1190, 1165, 1080, 1040, 1030, 990, 980, 950, 930, 875, 850, 790, 760, 700 cm$^{-1}$.

NMR (400 MHz, $CDCl_3$, δ): 1.95–2.1 (1H, m), 2.48 (1H, q, J=8.1 Hz), 2.66 (1H, ddd, J=6.4, 7.3, 13.7 Hz), 2.84 (1H, d, J=4.9 Hz), 3.24 (1H, d, J=4.4 Hz), 3.48 (1H, t, J=8.1 Hz), 3.79 (3H, s), 3.9–4.05 (1H, m), 5.15–5.3 (2H, m), 5.78 (1H, ddd, J=1.0, 8.1, 15.5 Hz), 5.88 (1H, dd, J=5.6, 15.5 Hz), 6.69 (1H, d, J=16.1 Hz), 6.81 (1H, t, J=7.4 Hz), 7.09 (1H, d, J=7.4 Hz), 7.21 (1H, d, J=7.4 Hz), 7.25–7.45 (5H, m), 7.67 (1H, d, J=16.1 Hz).

MASS (EI, m/e): 392 (M+).

High resolution mass spectrum: Calcd. ($C_{24}H_{24}O_5$, M+): 392.1624. Found (M+): 392.1607.

EXAMPLE 32 d-(3E)-15-phenyl-2,5,6,7,16,17,18,19,20-nonanor-3,4-didehydro-4,8-inter-m-phenylene $PGI_2$ (37)

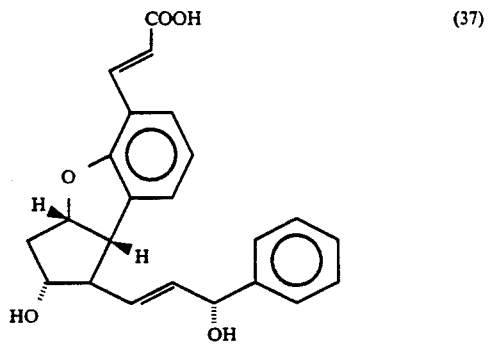

To a solution of d-(3E)-15-phenyl-2,5,6,7,16,17,18,19,20-nonanor-3,4-didehydro-4,8-inter-m-phenylene $PGI_2$ methyl ester (178 mg, 0.454 mmoles) in methanol (15 ml) was added 1.0N aqueous sodium hydroxide solution (4.0 ml, 4.0 mmoles) and stirred at room temperature for 48 hours. The reaction mixture was concentrated. To the residue was added water (10 ml), then neutralized with 1.0N hydrochloric acid (4.0 ml), and extracted with ethyl acetate (50 ml, 20 ml). The organic layers were combined, washed with water (20 ml) and with brine (20 ml), dried over anhydrous magnesium sulfate, and concentrated to give 165 mg of crude crystalline product. The crude crystalline product was recrystallized from ethyl acetate/n-hexane to afford 73.4% yield of d-(3E)-15-phenyl-2,5,6,7,16,17,18,19,20-nonanor-3,4-didehydro-4,8-inter-m-phenylene $PGI_2$ (126 mg, 0.333 mmoles) as a white crystal. The structure was confirmed by the following data:

m.p. 177°-178.5° C.

$[\alpha]_D^{25}$: +317.41 (c 0.356, MeOH).

IR (KBr): 3350, 3030, 2970, 2930, 1680, 1625, 1600, 1490, 1440, 1320, 1300, 1275, 1245, 1200, 1080, 1070, 1030, 980, 870, 740, 700 cm$^{-1}$.

NMR (400 MHz, $CDCl_3$+DMSO-$d_6$, δ): 1.98 (1H, ddd, J=5.6, 9.8, 13.4 Hz), 2.35–2.45 (1H, m), 2.65–2.75 (1H, m), 3.44 (1H, t, J=9.0 Hz), 3.9–4.0 (1H, m), 5.65–5.75 (2H, m), 5.75–5.85 (2H, m), 6.67 (1H, d, J=15.9 Hz), 6.77 (1H, t, J=7.4 Hz), 7.00 (1H, d, J=7.4 Hz), 7.19 (1H, d, J=7.4 Hz), 7.25–7.45 (5H, m), 7.64 (1H, d, J=15.9 Hz).

MASS (EI, m/e): 378 (M+).

High resolution mass spectrum: Calcd. ($C_{23}H_{22}O_5$, M+): 378.1467. Found (M+): 378.1494.

EXAMPLE 33 d-(3E)-15-(p-chlorophenyl)-2,5,6,7,16,17,18,19,20-nonanor-3,4-didehydro-4,8-inter-m-phenylene PGI₂ methyl ester (38) and 15-epimer thereof (39)

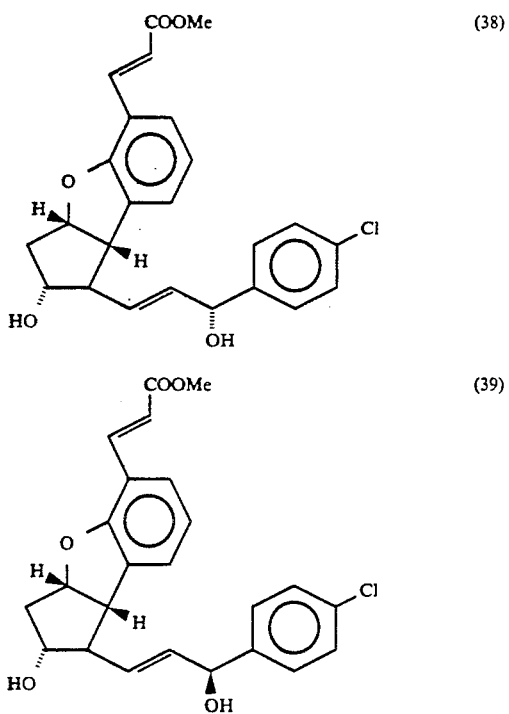

To a solution of d-(3E)-15-(p-chlorophenyl)-15-oxo-15-phenyl-2,5,6,7,16,17,18,19,20-nonanor-3,4-didehydro-4,8-inter-m-phenylene PGI₂ methyl ester, 11-acetate (784 mg, 1.68 mmoles) in methanol (20 ml) was added cerous trichloride heptahydrate (1.25 g, 3.36 mmoles), to which sodium borohydride (63.6 mg, 1.68 mmoles) was added after cooling to 0° C. The solution stirred at 0° C. for 15 minutes, to which saturated aqueous sodium hydrogen carbonate (3 ml) was added and concentrated. To the residue was added ethyl acetate (30 ml), filtered, and the precipitate was washed with ethyl acetate (15 ml×2).

The filtrates were combined, washed with water (20 ml) and with brine (20 ml), dried over anhydrous magnesium sulfate, and concentrated. Then, the resultant oily product was dissolved in dry methanol (20 ml) under an argon atmosphere, to which a solution of sodium met hoxide in methanol (5.22N, 0.13 ml, 0.67 mmoles) was added and stirred at room temperature for 3 hours. This reaction mixture was then neutralized with acetic acid and concentrated. To the residue was added water (20 ml) and extracted with ethyl acetate (60 ml, 20 ml). The organic layers were combined, washed with brine (20 ml), dried over anhydrous magnesium sulfate, and concentrated.

The resultant residue was purified by Lobar Column (Merck, silica gel: ethyl acetate/cyclohexane=2/1) to afford 45.9% yield of d-(3E)-15-(p-chlorophenyl)-15-epi-2,5,6,7,16,17,18,19,20-nonanor-3,4-didehydro-4,8-inter-m-phenylene PGI₂ methyl ester (329 mg, 0.771 mmoles) as a less polar eluate, followed by 46.1% yield of d-(3E)-15-(p-chlorophenyl)-2,5,6,7,16,17,18,19,20-nonanor-3,4-didehydro-4,8-inter-m-phenylene PGI₂ methyl ester (331 mg, 0.775 mmoles) as a more polar eluate.

The structure was confirmed by the following data:

d-(3E)-15-(p-chlorophenyl)-2,5,6,7,16,17,18,19,20-nonanor-3,4-didehydro-4,8-inter-m-phenylene PGI₂ methyl ester m.p. 137°-138° C. (recrystallized from ethyl acetate/n-hexane).

$[\alpha]_D^{25}$: +301.28 (c 0.312, MeOH).

IR (KBr): 3462, 3430, 3292, 2958, 2872, 1705, 1690, 1632, 1491, 1448, 1334, 1286, 1243, 1207, 1183, 1089, 1064, 1035, 1015, 973, 862, 816, 779, 746, 719, 557 cm⁻¹.

NMR (500 MHz, CDCl₃, δ): 2.0-2.1 (2H, m), 2.29 (1H, d, J=3.3 Hz), 2.45-2.55 (1H, m), 2.68 (1H, ddd, J=6.2, 7.0, 13.6 Hz), 3.47 (1H, t, J=8.4 Hz), 3.79 (3H, s), 3.95-4.05 (1H, m), 5.2-5.3 (2H, m), 5.75-5.85 (2H, m), 6.70 (1H, d, J=16.0 Hz), 6.80 (1H, t, J=7.5 Hz), 6.99 (1H, d, J=7.5 Hz), 7.22 (1H, d, J=7.5 Hz), 7.4-7.5 (4H, m), 7.66 (1H, d, J=16.0 Hz).

MASS (EI, m/e): 426 (M⁺).

High resolution mass spectrum: Calcd. (C₂₄H₂₃ClO₅, M⁺): 426.1234. Found (M⁺): 426.1234.

Anal.: Calcd. for C₂₄H₂₃ClO₅: C: 67.53; H: 5.43. Found: C: 67.71; H: 5.52.

d-(3E)-15-(p-chlorophenyl)-15-epi-2,5,6,7,16,17,18,19,20-nonanor-3,4-didehydro-4,8-inter-m-phenylene PGI₂ methyl ester m.p. 136°-137° C. (recrystallized from ethyl acetate/n-hexane).

$[\alpha]_D^{25}$: +276.26 (c 0.476, MeOH).

IR (KBr): 3510, 3442, 3302, 2954, 1711, 1632, 1605, 1491, 1448, 1402, 1344, 1317, 1292, 1276, 1249, 1203, 1168, 1093, 1013, 973, 861, 806, 781, 748, 719 cm⁻¹.

NMR (500 MHz, CDCl₃, δ): 1.71 (1H, d, J=5.1 Hz), 2.0-2.1 (2H, m), 2.55-2.65 (1H, m), 2.67 (1H, ddd, J=6.2, 6.9, 13.9 Hz), 3.51 (1H, t, J=8.3 Hz), 3.79 (3H, s), 3.95-4.05 (1H, m), 5.2-5.3 (2H, m), 5.85-5.95 (2H, m), 6.70 (1H, d, J=16.0 Hz), 6.83 (1H, t, J=7.3 Hz), 7.07 (1H, d, J=7.3 Hz), 7.23 (1H, d, J=7.3 Hz), 7.3-7.4 (4H, m), 7.67 (1H, d, J=16.0 Hz).

MASS (EI, m/e): 426 (M⁺).

High resolution mass spectrum: Calcd. (C₂₄H₂₃ClO₅, M⁺): 426.1234. Found (M⁺): 426.1264.

EXAMPLE 34 d-(3E)-15-(p-chlorophenyl)-2,5,6,7,16,17,18,19,20-nonanor-3,4-didehydro-4,8-inter-m-phenylene PGI₂ (40)

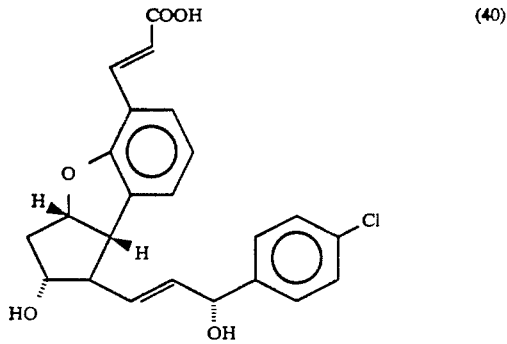

To a solution of d-(3E)-15-(p-chlorophenyl)-2,5,6,7,16,17,18,19,20-nonanor-3,4-didehydro-4,8-interm-phenylene PGI$_2$ methyl ester (173 mg, 0.405 mmoles) in methanol (20 ml) was added 1.0N aqueous sodium hydroxide solution (5.0 ml, 5.0 mmoles) and stirred at room temperature for 20 hours. The reaction mixture was concentrated. To the residue was added water (10 ml), then neutralized with 1.0N hydrochloric acid (5.0 ml), and extracted with ethyl acetate (50 ml, 20 ml). The organic layers were combined, washed with water (20 ml) and with brine (20 ml), dried over anhydrous magnesium sulfate, and concentrated. The resultant residue was purified by Lobar Column (Merck, RP-8, MeOH/H$_2$O=3/1) to afford 71.9% yield of d-(3E)-15-(p-chlorophenyl)-2,5,6,7,16,17,18,19,20-nonanor-3,4-didehydro-4,8-inter-m-phenylene PGI$_2$ (120 mg, 0.291 mmoles). The structure was confirmed by the following data:

m.p. 134°-135° C. (recrystallized from ethyl acetate/methylene chloride).

$[\alpha]_D^{25}$: +284.25 (c 0.254, MeOH).

IR (KBr): 3350, 2936, 1688, 1630, 1605, 1491, 1448, 1412, 1377, 1278, 1251, 1197, 1091, 1035, 1013, 988, 866, 830, 746 cm$^{-1}$.

NMR (500 MHz, CDCl$_3$+DMSO-d$_6$, δ): 2.00 (1H, ddd, J=5.1, 9.5, 13.6 Hz), 2.35-2.45 (1H, m), 2.70 (1H, dt, J=6.6, 13.6 Hz), 3.43 (1H, t, J=8.8 Hz), 3.93 (1H, ddd, J=6.6, 8.6, 9.5 Hz), 5.15-5.25 (2H, m), 5.7-5.8 (2H, m), 6.69 (1H, d, J=16.1 Hz), 6.78 (1H, t, J=7.3 Hz), 6.99 (1H, d, J=7.3 Hz), 7.21 (1H, d, J=7.3 Hz), 7.3-7.4 (4H, m), 7.68 (1H, d, J=16.1 Hz).

MASS (EI, m/e): 412 (M+).

High resolution mass spectrum: Calcd. (C$_{23}$H$_{21}$ClO$_5$, M+): 412.1078. Found (M+): 426.1084.

Anal. Calcd. for C$_{23}$H$_{21}$ClO$_5$: C: 66.91; H: 5.13. Found: C: 66.81; H: 5.50.

EXAMPLE 35 d-(3E)-15-(m-fluorophenyl)-2,5,6,7,16,17,18,19,20-nonanor-3,4-didehydro-4,8-inter-m-phenylene PGI$_2$ methyl ester (41) and 15-epimer thereof (42)

To a solution of d-(3E)-15-(m-fluorophenyl)-15-oxo-2,5,6,7,16,17,18,19,20-nonanor-3,4-didehydro-4,8-inter-m-phenylene PGI$_2$ methyl ester, 11-acetate (760 mg, 1.69 mmoles) in methanol (20 ml) was added cerous trichloride heptahydrate (1.26 g, 3.38 mmoles), to which sodium borohydride (63.9 mg, 1.69 mmoles) was added after cooling to 0° C. The solution stirred at 0° C. for 10 minutes, to which saturated aqueous sodium hydrogen carbonate (3 ml) was added and concentrated. To the residue was added ethyl acetate (40 ml), filtered, and the precipitate was washed with ethyl acetate (15 ml×2).

The filtrates were combined, washed with water (20 ml) and with brine (20 ml), dried over anhydrous magnesium sulfate, and concentrated. Then, the resultant oily product was dissolved in dry methanol (20 ml) under argon atmosphere, to which a solution of sodium methoxide in methanol (5.22N, 0.13 ml, 0.68 mmoles) was added and stirred at room temperature for 3 hours. This reaction mixture was then neutralized with acetic acid and concentrated. To the residue was added water (20 ml) and extracted with ethyl acetate (60 ml, 20 ml). The organic layers were combined, washed with brine (20 ml), dried over anhydrous magnesium sulfate, and concentrated.

The resultant residue was purified by Lobar Column (Merck, silica gel: ethyl acetate/cyclohexane=2/1) to afford 43.8% yield of d-(3E)-15-(m-fluorophenyl)-15-epi-2,5,6,7,16,17,18,19,20-nonanor-3,4-didehydro-4,8-inter-m-phenylene PGI$_2$ methyl ester (304 mg, 0.741 mmoles) as a less polar eluate, followed by 41.3% yield of d-(3E)-15-(m-fluorophenyl)-2,5,6,7,16,17,18,19,20-nonanor-3,4-didehydro-4,8-inter-m-phenylene PGI$_2$ methyl ester (286 mg, 0.698 mmoles) as a more polar eluate.

The structure was confirmed by the following data:

d-(3E)-15-(m-fluorophenyl)-2,5,6,7,16,17,18,19,20-nonanor-3,4-didehydro-4,8-inter-m-phenylene PGI$_2$ methyl ester m.p. 169°-170° C. (recrystallized from ethyl acetate/n-hexane).

$[\alpha]_D^{25}$: +289.36 (c 0.282, MeOH).

IR (KBr): 3406, 2890, 1702, 1634, 1613, 1591, 1489, 1477, 1448, 1348, 1321, 1294, 1280, 1251, 1207, 1183, 1168, 1120, 1100, 1069, 1035, 1015, 994, 975, 955, 948, 864, 777, 745, 719, 694, 522 cm$^{-1}$.

NMR (400 MHz, CDCl$_3$, δ): 2.05 (1H, ddd, J=5.1, 8.8, 13.8 Hz), 2.12 (1H, d, J=5.4 Hz), 2.38 (1H, d, J=3.4 Hz), 2.45-2.55 (1H, m), 2.69 (1H, ddd, J=6.4, 7.3, 13.8 Hz), 3.47 (1H, t, J=8.5 Hz), 3.79 (3H, s), 3.95-4.05 (1H, m), 5.2-5.3 (2H, m), 5.75-5.85 (2H, m), 6.70 (1H, d, J=15.9 Hz), 6.80 (1H, t, J=7.6 Hz), 6.95-7.05 (2H, m), 7.10-7.25 (3H, m), 7.35 (1H, dt, J=5.9, 7.8 Hz), 7.66 (1H, d, J=15.9 Hz).

MASS (EI, m/e): 410 (M+).

High resolution mass spectrum: Calcd. (C$_{24}$H$_{23}$FO$_5$, M+): 410.1530. Found (M+): 410.1501.

Anal. Calcd. for C$_{24}$H$_{23}$FO$_5$: C: 70.23; H: 5.65. Found: C: 70.61; H: 5.75.

d-(3E)-15-(m-fluorophenyl)-15-epi-2,5,6,7,16,17,18,19,20-nonanor-3,4-didehydro-4,8-inter-m-phenylene PGI$_2$ methyl ester m.p. 161°-162° C. (recrystallized from ethyl acetate/n-hexane).

$[\alpha]_D^{25}$: +278.15 (c 0.586, MeOH).

IR (KBr): 3440, 2956, 2886, 1700, 1632, 1593, 1485, 1448, 1346, 1317, 1280, 1251, 1207, 1181, 1166, 1127, 1096, 1071, 1038, 1013, 994, 980, 961, 948, 866, 783, 748, 696, 520 cm$^{-1}$.

NMR (400 MHz, CDCl$_3$, δ): 1.72 (1H, d, J=4.9 Hz), 2.07 (1H, ddd, J=4.9, 8.3, 13.7 Hz), 2.12 (1H, d, J=3.9 Hz), 2.45-2.55 (1H, m), 2.68 (1H, ddd, J=6.4, 7.3, 13.7 Hz), 3.52 (1H, t, J=8.3 Hz), 3.79 (3H, s), 3.95-4.05 (1H, m), 5.2-5.3 (2H, m), 5.75-5.85 (2H, m), 6.71 (1H, d, J=16.1 Hz), 6.83 (1H, t, J=7.6 Hz), 6.95-7.03 (1H, m), 7.05-7.17 (3H, m), 7.2-7.25 (1H, m), 7.35 (1H, dt, 5.9, 7.8 Hz), 7.67 (1H, d, J=16.1 Hz).

MASS (EI, m/e): 410 (M+).

High resolved mass spectrum: Calcd. (C$_{24}$H$_{23}$FO$_5$, M+): 410.1530. Found (M+): 410.1548.

Anal. Calcd. for C$_{24}$H$_{23}$FO$_5$: C: 70.23; H: 5.65. Found: C: 69.88; H: 5.56.

EXAMPLE 36 d-(3E)-15-(m-fluorophenyl)-2,5,6,7,16,17,18,19,20-nonanor-3,4-didehydro-4,8-inter-m-phenylene PGI$_2$ (43)

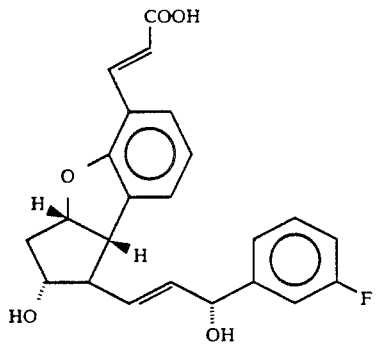

(43)

To a solution of d-(3E)-15-(m-fluorophenyl)-2,5,6,7,16,17,18,19,20-nonanor-3,4-didehydro-4,8-inter-m-phenylene PGI$_2$ methyl ester (176 mg, 0.429 mmoles) in methanol (20 ml) was added 1.0N aqueous sodium hydroxide solution (5.0 ml, 5.0 mmoles) and stirred at room temperature for 40 hours. The reaction mixture was concentrated. To the residue was added water (10 ml), then neutralized with 1.0N hydrochloric acid (5.0 ml), and extracted with ethyl acetate (50 ml, 20 ml).

The organic layers were combined, washed with water (20 ml) and with brine (20 ml), dried over anhydrous magnesium sulfate, and concentrated to give 170 mg of crude crystalline product. The crude crystalline product was recrystallized from ethyl acetate/n-hexane to afford 79.5% yield of d-(3E)-15-(m-fluorophenyl)-2,5,6,7,16,17,18,19,20-nonanor-3,4-didehydro-4,8-inter-m-phenylene PGI$_2$ (135 mg, 0.341 mmoles) as a white crystal. The structure was confirmed by the following data:

m.p. 189°-190° C.

[α]$_D^{25}$: +291.36 (c 0.336, MeOH).

IR (KBr): 3364, 2976, 1688, 1634, 1593, 1450, 1305, 1278, 1249, 1205, 1073, 990, 870, 746 cm$^{-1}$.

NMR (400 MHz, CDCl$_3$+DMSO-d$_6$, δ): 2.00 (1H, ddd, J=5.9, 9.8, 13.5 Hz), 2.35-2.45 (1H, m), 2.70 (1H, dt, J=6.7, 13.5 Hz), 3.44 (1H, t, J=8.8 Hz), 3.85-4.0 (1H, m), 5.15-5.25 (2H, m), 5.7-5.85 (2H, m), 6.69 (1H, d, J=15.9 Hz), 6.79 (1H, t, J=7.6 Hz), 6.9-7.05 (2H, m), 7.15-7.25 (3H, m), 7.3-7.4 (1H, m), 7.66 (1H, d, J=15.9 Hz).

MASS (EI, m/e): 396 (M+).

High resolution mass spectrum: Calcd. (C$_{23}$H$_{21}$FO$_5$, M+): 396.1373. Found (M+): 396.1358.

Anal. Calcd. for C$_{23}$H$_{21}$FO$_5$: C: 69.69; H: 5.34. Found: C: 69.63; H: 5.40.

EXAMPLE 37 d-(3E)-15-(p-bromophenyl)-2,5,6,7,16,17,18,19,20-nonanor-3,4-didehydro-4,8-inter-m-phenylene PGI$_2$ methyl ester (44) and 15-epimer thereof (45)

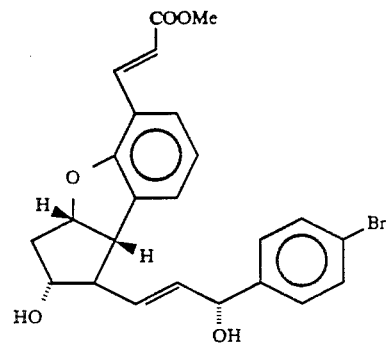

(44)

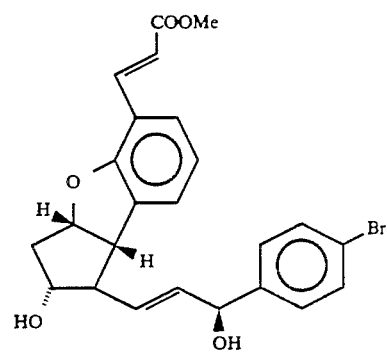

(45)

To a solution of d-(3E)-15-(p-bromophenyl)-15-oxo-2,5,6,7,16,17,18,19,20-nonanor-3,4-didehydro-4,8-inter-m-phenylene PGI$_2$ methyl ester, 11-acetate (1.0 g, 1.91 mmoles) in methanol (20 ml) was added cerous trichloride heptahydrate (1.42 g, 3.81 mmoles), to which sodium borohydride (63 mg, 2.32 mmoles) was added after cooling to 0° C. The solution stirred at 0° C. for 10 minutes, to which saturated aqueous sodium hydrogen carbonate (5 ml) was added and concentrated. To the residue was added ethyl acetate (50 ml), filtered, and the precipitate was washed with ethyl acetate (10 ml×2).

The filtrates were combined, washed with water (20 ml) and with brine (20 ml), dried over anhydrous magnesium sulfate, and concentrated. Then, the resultant oily product was dissolved in dry methanol (20 ml) under argon atmosphere, to which a solution of sodium methoxide in methanol (5.22N, 0.1 ml, 0.52 mmoles) was added and stirred at room temperature for an hour. This reaction mixture was then neutralized with acetic acid and concentrated. To the residue was added water (20 ml) and extracted with ethyl acetate (50 ml, 20 ml). The organic layers were combined, washed with brine (20 ml), dried over anhydrous magnesium sulfate, and concentrated.

The resultant residue was purified by Lobar Column (Merck, silica gel: ethyl acetate/cyclohexane=1/2) to afford 33% yield of d-(3E)-15-(p-bromophenyl)-15-epi-2,5,6,7,16,17,18,19,20-nonanor-3,4-didehydro-4,8-inter-m-phenylene PGI$_2$ methyl ester (306 mg, 0.60 mmoles)

as a less polar eluate, followed by 31% yield of d-(3E)-15-(p-bromophenyl)-2,5,6,7,16,17,18,19,20-nonanor-3,4-didehydro-4,8-inter-m-phenylene PGI₂ methyl ester (293 mg 0.57 mmoles) as a more polar eluate.

The structure was confirmed by the following data:

d-(3E)-15-(p-bromophenyl)-2,5,6,7,16,17,18,19,20-nonanor-3,4-didehydro-4,8-inter-m-phenylene PGI₂ methyl ester $[\alpha]_D^{25}$: +253.30 (c 0.490, MeOH).

IR (liquid film): 3390, 2936, 2870, 1744, 1719, 1620, 1491, 1466, 1437, 1292, 1249, 1195, 1168, 1118, 1031, 967, 861, 760 cm⁻¹.

NMR (400 MHz, CDCl₃, δ): 1.96 (1H, m), 2.0-2.2 (1H, m), 2.25 (1H, m), 2.48 (1H, m), 2.68 (1H, m), 3.47 (1H, t, J=8.4 Hz), 3.79 (3H, s), 4.00 (1H, m), 5.23-5.26 (2H, m), 5.78-5.79 (2H, m), 6.70 (1H, d, J=16.1 Hz), 6.81 (1H, t, J=7.3 Hz), 6.99 (1H, d, J=7.4 Hz), 7.22 (1H, d, J=6.9 Hz), 7.25 (2H, d, J=8.3 Hz), 7.51 (2H, d, J=8.3 Hz), 7.66 (1H, d, J=15.6 Hz).

MASS (EI, m/e): 470 (M⁺).

High resolution mass spectrum: Calcd. ($C_{24}H_{23}O_5Br$, M⁺): 470.0729. Found (M⁺): 470.0703.

d-(3E)-15-(p-bromophenyl)-15-epi-2,5,6,7,16,17,18,19,20-nonanor-3,4-didehydro-4,8-inter-m-phenylene; PGI₂ methyl ester $[\alpha]_D^{25}$: +249.19 (c 0.500, MeOH).

IR (KBr): 3508, 3434, 2980, 1711, 1632, 1489, 1448, 1344, 1319, 1276, 1249, 1205, 1011, 973, 862, 748 cm⁻¹.

NMR (90 MHz, CDCl₃, δ): 1.84-2.80 (5H, m), 3.49 (1H, t, J=8.6 Hz), 3.79 (3H, s), 3.95 (1H, m), 5.12-5.25 (2H, m), 5.76-5.83 (2H, m), 6.69 (1H, d, J=16.1 Hz), 6.73-7.56 (7H, m), 7.67 (1H, d, J=16.1 Hz).

MASS (EI, m/e): 470 (M⁺).

High resolution mass spectrum: Calcd. ($C_{24}H_{23}O_5Br$, M⁺): 470.0729. Found (M⁺): 470.0736.

EXAMPLE 38 d-(3E)-15-(2,6-difluorophenyl)-2,5,6,7,16,17,18,19,20-nonanor-3,4-didehydro-4,8-inter-m-phenylene PGI₂ methyl ester (46) and 15-epimer thereof (47)

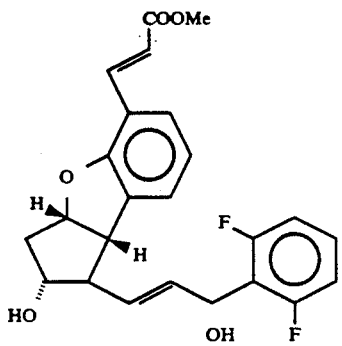
(46)

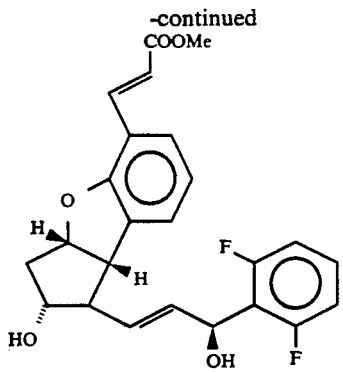
(47)

To a solution of d-(3E)-15-(2,6-difluorophenyl)-15-oxo-2,5,6,7,16,17,18,19,20-nonanor-3,4-didehydro-4,8-inter-m-phenylene PGI₂ methyl ester, 11-acetate (661 mg, 1.41 mmoles) in methanol (20 ml) was added cerous trichloride heptahydrate (1.05 g, 2.82 mmoles), to which sodium borohydride (53.3 mg, 1.41 mmoles) was added after cooling to 0° C. The solution stirred at 0° C. for 15 minutes, to which saturated aqueous sodium hydrogen carbonate (3 ml) was added and concentrated. To the residue was added ethyl acetate (40 ml), filtered, and the precipitate was washed with ethyl acetate (20 ml×2). The filtrates were combined, washed with water (20 ml) and with brine (20 ml), dried over anhydrous magnesium sulfate, and concentrated.

Then, the resultant oily product was dissolved in dry methanol (20 ml) under argon atmosphere, to which a solution of sodium methoxide in methanol (5.22N, 0.11 ml, 0.67 mmoles) was added and stirred at room temperature for 3 hours. This reaction mixture was then neutralized with acetic acid and concentrated.

To the residue was added water (20 ml) and extracted with ethyl acetate (50 ml, 30 ml). The organic layers were combined, washed with brine (20 ml), dried over anhydrous magnesium sulfate, and concentrated.

The resultant residue was purified by Lobar Column (Merck, silica gel: ethyl acetate/cyclohexane=2/1) to afford 48.2% yield of d-(3E)-15-(2,6-difluorophenyl)-15-epi-2,5,6,7,16,17,18,19,20-nonanor-3,4-didehydro-4,8-inter-m-phenylene PGI₂ methyl ester (291 mg, 0.680 mmoles) as a less polar eluate, followed by 44.9% yield of d-(3E)-15-(2,6-difluorophenyl)-2,5,6,7,16,17,18,19,20-nonanor-3,4-didehydro-4,8-inter-m-phenylene PGI₂ methyl ester (271 mg, 0.633 mmoles) as a more polar eluate.

The structure was confirmed by the following data:

d-(3E)-15-(2,6-difluorophenyl)-2,5,6,7,16,17,18,19,20-nonanor-3,4-didehydro-4,8-inter-m-phenylene PGI₂ methyl ester $[\alpha]_D^{25}$: +274.20 (c 0.314, MeOH).

IR (liquid film): 3400, 3020, 2954, 1696, 1634, 1595, 1473, 1437, 1375, 1038, 994, 866, 789, 748, 667 cm⁻¹.

NMR (400 MHz, CDCl₃, δ): 1.9-1.95 (1H, m), 2.05 (1H, ddd, J=4.9, 8.8, 13.7 Hz), 2.45-2.55 (2H, m), 2.68 (1H, ddd, J=6.3, 7.3, 13.7 Hz), 3.46 (1H, t, J=8.7 Hz), 3.79 (3H, s), 3.95-4.05 (1H, m), 5.23 (1H, ddd, J=J=4.9, 7.3, 8.7 Hz), 5.6-5.65 (1H, m), 5.76 (1H, dd, J=8.6, 15.2 Hz), 6.02 (1H, dd, J=5.6, 15.2 Hz), 6.70 (1H, d, J=15.9 Hz), 6.81 (1H, t, J=7.5 Hz), 6.85-6.95 (2H, m), 7.01 (1H, d, J=7.5 Hz), 7.2-7.5 (2H, m), 7.67 (1H, d, J=15.9 Hz).

MASS (EI, m/e): 428 (M⁺).

High resolution mass spectrum: Calcd. ($C_{24}H_{22}F_2O_5$, M+): 428.1435. Found: (M+): 428.1432.

d-(3E)-15-(2,6-difluorophenyl)-15-epi-2,5,6,7,16,17,18,19,20-nonanor-3,4-didehydro-4,8-inter-m-phenylene $PGI_2$ methyl ester m.p. 137°–140° C. (recrystallized from ethyl acetate/n-hexane).

$[\alpha]_D^{25}$: +238.40 (c 0.526, MeOH).

IR (KBr): 3356, 2952, 1688, 1628, 1603, 1473, 1450, 1325, 1261, 1199, 1180, 1075, 1004, 868, 795, 746, 567 cm$^{-1}$.

NMR (400 MHz, CDCl$_3$, δ): 1.65–1.75 (1H, m), 2.06 (1H, ddd, J=4.9, 8.5, 13.7 Hz), 2.4–2.55 (2H, m), 2.67 (1H, ddd, J=6.4, 7.3, 13.7 Hz), 3.51 (1H, t, J=8.6 Hz), 3.79 (3H, s), 3.95–4.05 (1H, m), 5.24 (1H, ddd, J=4.9, 7.3, 8.6 Hz), 5.6–5.7 (1H, m), 5.80 (1H, dd, J=8.3, 15.3 Hz), 6.01 (1H, dd, J=6.1, 15.3 Hz), 6.70 (1H, d, J=16.1 Hz), 6.84 (1H, t, J=7.5 Hz), 6.9–7.0 (2H, m), 7.13 (1H, d, J=7.5 Hz), 7.2–7.35 (2H, m), 7.67 (1H, d, J=16.1 Hz).

MASS (EI, m/e): 428 (M+).

High resolution mass spectrum: Calcd. ($C_{24}H_{22}F_2O_5$, M+): 428.1435. Found (M+): 428.1453.

Anal. Calcd. for $C_{24}H_{22}F_2O_5$: C: 67.28; H: 5.18. Found: C: 67.47; H: 5.22.

EXAMPLE 39 d-(3E)-15-(2,6-difluorophenyl)-2,5,6,7,16,17,18,19,20-nonanor-3,4-didehydro-4,8-inter-m-phenylene $PGI_2$ (48)

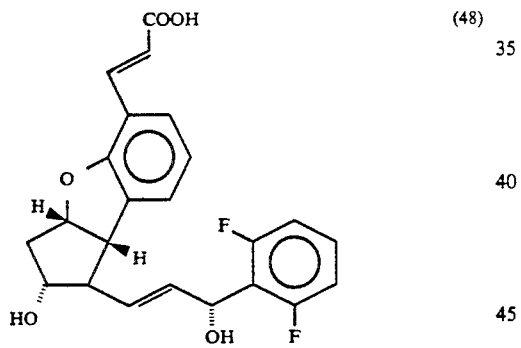

(48)

To a solution of d-(3E)-15-(2,6-difluorophenyl)-2,5,6,7,16,17,18,19,20-nonanor-3,4-didehydro-4,8-inter-m-phenylene $PGI_2$ methyl ester (184 mg 0.430 mmoles) in methanol (20 ml) was added 1.0N aqueous sodium hydroxide solution (5.0 ml, 5.0 mmoles) and stirred at room temperature for 40 hours. The reaction mixture was concentrated. To the residue was added water (15 ml), then neutralized with 1.0N hydrochloric acid (5.0 ml), and extracted with ethyl acetate (50 ml, 20 ml).

The organic layers were combined, washed with water (20 ml) and with brine (20 ml), dried over anhydrous magnesium sulfate, and concentrated to give 212 mg of crude crystalline product. The crude crystalline product was recrystallized from ethyl acetate/n-hexane to afford 69.8% yield of d-(3E)-15-(2,6-difluorophenyl)-2,5,6,7,16,17,18,19,20-nonanor-3,4-didehydro-4,8-inter-m-phenylene $PGI_2$ (124 mg, 0.300 mmoles) as a white crystal. The structure was confirmed by the following data:

M.P. 152°–153° C.

$[\alpha]_D^{25}$: +268.66 (c 0.434, MeOH).

IR (KBr): 3450, 2936, 1690, 1626, 1593, 1473, 1448, 1251, 1234, 1197, 1075, 994, 868, 787, 746 cm$^{-1}$.

NMR (400 MHz, CDCl$_3$+DMSO-d$_6$δ): 1.95–2.05 (1H, m), 2.35–2.5 (1H, m), 2.68 (1H, dt, J=6.8, 13.7 Hz), 3.43 (1H, t, J=8.8 Hz), 3.85–4.0 (1H, m), 5.15–5.25 (1H, m), 5.61 (1H, d, J=7.2 Hz), 5.78 (1H, dd, J=8.8, 15.1 Hz), 6.09 (1H, dd, J=7.2, 15.1 Hz), 6.68 (1H, d, J=16.1 Hz), 6.77 (1H, t, J=7.5 Hz), 6.85–6.95 (2H, m), 6.99 (1H, d, J=7.5 Hz), 7.15–7.3 (2H, m), 7.66 (1H, d, J=16.1 Hz).

MASS (EI, m/e): 414 (M+).

High resolution mass spectrum: Calcd. ($C_{23}H_{20}F_2O_5$, M+): 414.1279. Found (M+): 414.1290.

Anal. Calcd. for $C_{23}H_{20}F_2O_5$: C: 66.66; H: 4.86. Found: C: 66.56; H: 4.89.

EXAMPLE 40 d-(3E)-16-methyl-16-phenyl-2,5,6,7,18,19,20-heptanor-3,4-didehydro-4,8-inter-m-phenylene $PGI_2$ methyl ester (49) and 15-epimer thereof (50)

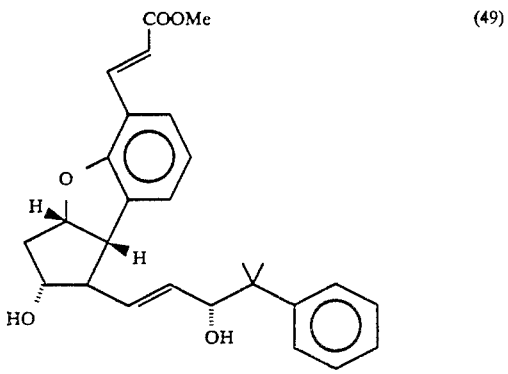

(49)

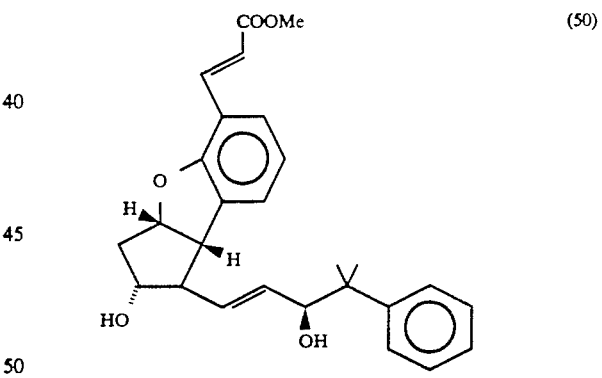

(50)

To a solution of d-(3E)-16-methyl-15-oxo-16-phenyl-2,5,6,7,18,19,20-heptanor-3,4-didehydro-4,8-inter-m-phenylene $PGI_2$ methyl ester, 11-acetate (1.03 g, 2.17 mmoles) in methanol (40 ml) was added cerous trichloride heptahydrate (890 mg, 2.39 mmoles), to which sodium borohydride (175 mg, 4.61 mmoles) was added after cooling to 0° C. The solution stirred at 0° C. for 10 minutes, to which saturated aqueous sodium hydrogen carbonate (5 ml) was added and concentrated. To the residue was added ethyl acetate (50 ml), filtered, and the precipitate was washed with ethyl acetate (10 ml×2). The filtrates were combined, washed with water (20 ml) and with brine (20 ml), dried over anhydrous magnesium sulfate, and concentrated. Then, the resultant oily product was dissolved in dry methanol (20 ml) under argon atmosphere, to which a solution of sodium methoxide in methanol (5.22N, 0.10 ml, 0.52 mmoles) was added and stirred at room temperature for 1.5 hours. This reaction mixture was then neutralized with acetic acid and concentrated. To the residue was added water (20 ml) and extracted with ethyl acetate (50 ml, 20 ml). The organic layers were combined, washed with brine (20 ml), dried over anhydrous magnesium sulfate, and concentrated.

The resultant residue was purified by Lobar Column (Merck, silica gel: ethyl acetate/cyclohexane=1/2) to afford 49.8% yield of d-(3E)-15-epi-16-methyl-16-phenyl-2,5,6,7,18,19,20-heptanor-3,4-didehydro-4,8-inter-m-phenylene $PGI_2$ methyl ester (469 mg, 0.99 mmoles, recrystallization solvent: hexane/ethyl acetate) as a less polar eluate, followed by 38.2% yield of d-(3E)-16-methyl-16-phenyl-2,5,6,7,18,19,20-heptanor-3,4-didehydro-4,8-inter-m-phenylene $PGI_2$ methyl ester (360 mg, 0.76 mmoles) as a more polar eluate.

The structure was confirmed by the following data:

d-(3E)-16-methyl-16-phenyl-2,5,6,7,18,19,20-heptanor-3,4-didehydro-4,8-inter-m-phenylene $PGI_2$ methyl ester $[\alpha]_D^{25}$: +239.91 (c 0.496, MeOH).

IR (liquid film): 3364, 2972, 1702, 1632, 1605, 1448, 1251, 1205, 1176, 1035, 990, 866, 766, 700 $cm^{-1}$.

NMR (400 MHz, $CDCl_3$, δ): 1.30, 1.31 (each 3H, s), 1.92 (1H, ddd, J=4.9, 8.8, 13.7 Hz), 2.31 (1H, q, J=7.8 Hz), 2.57 (1H, dt, J=6.8, 13.7 Hz), 3.31 (1H, t, J=8.8 Hz), 3.73 (3H, s), 4.13 (1H, m), 5.12 (1H, m), 5.49 (2H, t, J=5.9 Hz), 6.63 (1H, d, J=16.1 Hz), 6.76 (1H, t, J=7.3 Hz), 6.88 (1H, d, J=7.3 Hz), 7.14–7.34 (6H, m), 7.60 (1H, d, J=16.1 Hz).

MASS (EI, m/e): 434 (M+).

High resolution mass spectrum: Calcd. ($C_{27}H_{30}O_5$, M+): 434.2093. Found (M+): 434.2119.

d-(3E)-16-methyl-16-phenyl-15-epi-2,5,6,7,18,19,20-heptanor-3,4-didehydro-4,8-inter-m-phenylene $PGI_2$ methyl ester m.p. 146°–147° C.

$[\alpha]_D^{25}$: +214.51 (c 0.248, MeOH).

IR (KBr): 3418, 3290, 2972, 1719, 1634, 1448, 1207, 1176, 1096, 982, 866, 702 $cm^{-1}$.

NMR (400 MHz, $CDCl_3$, δ): 1.29, 1.34 (each 3H, s), 1.91 (1H, ddd, J=4.9, 8.8, 13.7 Hz), 2.30 (1H, m), 2.55 (1H, m), 3.33 (1H, t, J=8.8 Hz), 3.73 (3H, s), 4.16 (1H, m), 5.12 (1H, m), 5.41–5.50 (2H, m), 6.63 (1H, d, J=16.1 Hz), 6.77 (1H, t, J=7.3 Hz), 6.98 (1H, d, J=7.3 Hz), 7.15–7.34 (6H, m), 7.58 (1H, d, J=16.1 Hz).

MASS (EI, m/e): 434 (M+).

High resolution mass spectrum: Calcd. ($C_{27}H_{30}O_5$, M+): 434.2093. Found (M+): 434.2116.

EXAMPLE 41 d-(3E)-16-methyl-16-phenyl-2,5,6,7,18,19,20-heptanor-3,4-didehydro-4,8-inter-m-phenylene $PGI_2$ (51)

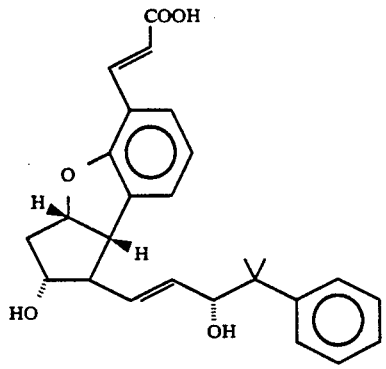

To a solution of d-(3E)-16-methyl-16-phenyl-2,5,6,7,18,19,20-heptanor-3,4-didehydro-4,8-inter-m-phenylene $PGI_2$ methyl ester (249 mg 0.57 mmoles) in methanol (15 ml) was added 2.0N aqueous sodium hydroxide solution (2.5 ml, 5.0 mmoles) and stirred at room temperature for 18.5 hours.

The reaction mixture was concentrated. To the residue was added water (20 ml), then neutralized with 1.0N hydrochloric acid (10 ml), and extracted with ethyl acetate (50 ml, 20 ml).

The organic layers were combined, washed with water (20 ml) and with brine (20 ml), dried over anhydrous magnesium sulfate, and concentrated.

The resultant crude crystalline product was recrystallized from ethyl acetate/cyclohexane to afford 64.7% yield of d-(3E)-16-methyl-16-phenyl-2,5,6,7,18,19,20-heptanor-3,4-didehydro-4,8-inter-m-phenylene $PGI_2$ (155 mg, 0.369 mmoles) as a white crystal. The structure was confirmed by the following data:

m.p. 184°–185° C.

$[\alpha]_D^{25}$: +272.83 (c 0.162, MeOH).

IR (KBr): 3400, 2974, 1682, 1630, 1605, 1450, 1330, 1299, 1251, 1212, 988, 702 $cm^{-1}$.

NMR (400 MHz, $CDCl_3$+DMSO-$d_6$, δ): 1.36, 1.38, (each 3H, s), 1.93 (1H, ddd, J=5.5, 9.8, 15.3 Hz), 2.26 (1H, q, J=8.6 Hz), 2.64 (1H, dt, J=7.0–15.3 Hz), 3.29 (1H, t, J=8.6 Hz), 3.80 (1H, dt, J=5.5, 6.1 Hz), 4.18 (1H, d, J=6.1 Hz), 5.14 (1H, ddd, J=5.5, 7.3, 8.5 Hz), 5.50 (1H, m), 6.68 (1H, d, J=15.9 Hz), 6.78–6.82 (2H, m), 7.22 (2H, m), 7.33 (2H, t, J=7.9 Hz), 7.40 (2H, d, J=7.3 Hz), 7.66 (1H, d, J=15.9 Hz).

MASS (EI, m/e): 420 (M+).

High resolution mass spectrum: Calcd. ($C_{26}H_{28}O_5$, M+): 420.1937. Found (M+): 420.1934.

EXAMPLE 42 d-(3E)-17-phenyl-2,5,6,7,18,19,20-heptanor-3,4-didehydro-4,8-inter-m-phenylene PGI₂ methyl ester (52) and 15-epimer thereof (53)

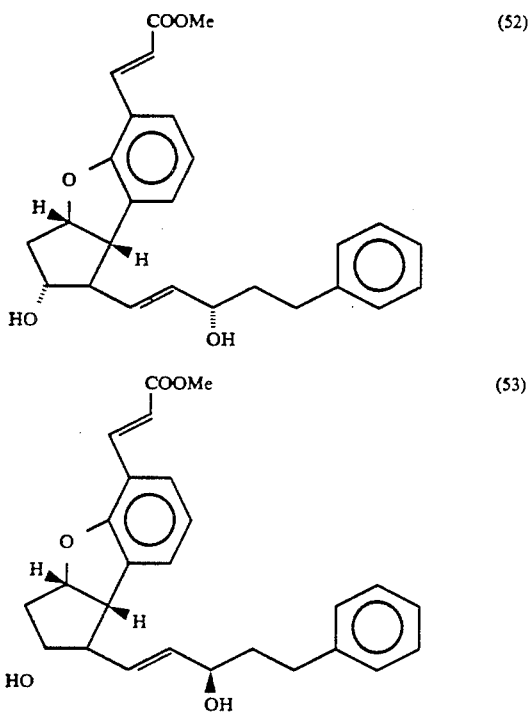

To a solution of d-(3E)-15-oxo-17-phenyl-2,5,6,7,18,19,20-heptanor-3,4-didehydro-4,8-inter-m-phenylene PGI₂ methyl ester, 11-acetate (1.08 g, 2.35 mmoles) in methanol (30 ml) was added cerous trichloride heptahydrate (1.88 g, 5.04 mmoles), to which sodium borohydride (120 mg, 3.16 mmoles) was added after cooling to 0° C. The solution stirred at 0° C. for 10 minutes, to which saturated aqueous sodium hydrogen carbonate (5 ml) was added and concentrated. To the residue was added ethyl acetate (50 ml), filtered, and the precipitate was washed with ethyl acetate (10 ml×2).

The filtrates were combined, washed with water (20 ml) and with brine (20 ml), dried over anhydrous magnesium sulfate, and concentrated.

Then, the resultant oily product was dissolved in dry methanol (20 ml) under argon atomosphere, to which a solution of sodium methoxide in methanol (5.22N, 0.10 ml, 0.52 mmoles) was added and stirred at room temperature for 2 hours. This reaction mixture was then neutralized with acetic acid and concentrated.

To the residue was added water (20 ml) and extracted with ethyl acetate (50 ml, 20 ml). The organic layers were combined, washed with brine (20 ml), dried over anhydrous magnesium sulfate, and concentrated.

The resultant residue was purified by Lobar Column (Merck, silica gel: ethyl acetate/cyclohexane=1/2) to afford 44.2% yield of d-(3E)-17-phenyl-15-epi-2,5,6,7,18,19,20-heptanor-3,4-didehydro-4,8-inter-m-phenylene PGI₂ methyl ester (436 mg, 1.04 mmoles, recrystallization solvent: hexane/ethyl acetate) as a less polar eluate, followed by 38.3% yield of d-(3E)-17-phenyl-2,5,6,7,18,19,20-heptanor-3,4-didehydro-4,8-inter-m-phenylene PGI₂ methyl ester (378 mg, 0.90 mmoles, recrystallization solvent: hexane/ethyl acetate) as a more polar eluate.

The structure was confirmed by the following data:

d-(3E)-17-phenyl-2,5,6,7,18,19,20-heptanor-3,4-didehydro-4,8-inter-m-phenylene PGI₂ methyl ester m.p. 98°-99° C.

$[\alpha]_D^{25}$: +253.77 (c 0.106, MeOH).

IR (KBr): 3400, 2938, 1715, 1634, 1448, 1319, 1207, 1172, 1064, 986, 866, 746 cm⁻¹.

NMR (400 MHz, CDCl₃, δ): 1.43-2.00 (3H, m), 2.34 (1H, m), 2.65-2.72 (3H, m), 2.91 (1H, m), 3.30 (1H, d, J=4.4 Hz), 3.36 (1H, t, J=8.8 Hz), 3.78 (3H, s), 3.85 (1H, m), 4.10 (1H, brm), 5.17 (1H, q, J=7.3 Hz), 5.58 (2H, m), 6.70 (1H, d, J=16.1 Hz), 6.81 (1H, t, J=7.3 Hz), 7.06 (1H, d, J=6.8 Hz), 7.17-7.31 (6H, m), 7.66 (1H, d, J=16 Hz).

MASS (EI, m/e): 420 (M+).

High resolution mass spectrum: Calcd. (C₂₆H₂₈O₅, M+): 420.1937. Found (M+): 420.1946.

d-(3E)-17-phenyl-15-epi-2,5,6,7,18,19,20-heptanor-3,4-didehydro-4,8-inter-m-phenylene PGI₂ methyl ester m.p. 138° C.

$[\alpha]_D^{25}$: +242.65 (c 0.558, MeOH).

IR (KBr): 3408, 2950, 1727, 1638, 1448, 1319, 1270, 1210, 1172, 1075, 986, 868, 750, 700 cm⁻¹.

NMR (400 MHz, CDCl₃, δ): 1.89 (2H, m), 1.99-2.24 (2H, m), 2.44 (1H, m), 2.63-2.81 (3H, m), 3.44 (1H, t, J=8.5 Hz), 3.78 (3H, s), 3.96 (1H, brq, J=7.3 Hz), 4.17 (1H, brm), 5.21 (1H, dt, J=5.5, 7.3 Hz), 5.66 (2H, m), 6.70 (1H, d, J=16 Hz), 6.83 (1H, t, J=7.4 Hz), 7.11 (1H, d, J=7.3 Hz), 7.18-7.31 (6H, m), 7.67 (1H, d, J=16 Hz).

MASS (EI, m/e): 420 (M+).

High resolution mass spectrum: Calcd. (C₂₆H₂₈O₅, M+): 420.1937. Found (M+): 420.1916.

EXAMPLE 43 d-(3E)-17-phenyl-2,5,6,7,18,19,20-heptanor-3,4-didehydro-4,8-inter-m-phenylene PGI₂ (54)

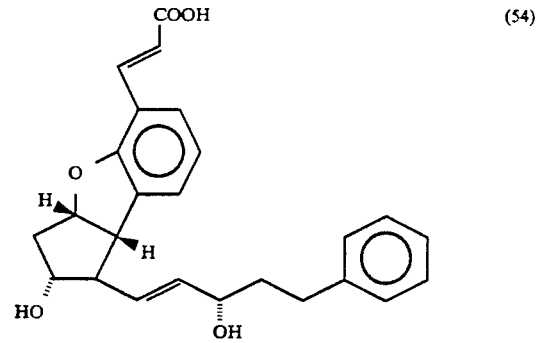

To a solution of d-(3E)-17-phenyl-2,5,6,7,18,19,20-heptanor-3,4-didehydro-4,8-inter-m-phenylene PGI₂ methyl ester (310 mg 0.738 mmoles) in methanol (20 ml) was added 1.0N aqueous sodium hydroxide solution (6.0 ml, 6.0 mmoles) and stirred at room temperature for 24 hours. The reaction mixture was concentrated. To the residue was added water (20 ml), then neutralized with 1.0N hydrochloric acid (10 ml), and extracted with ethyl acetate (50 ml, 20 ml). The organic layers were combined, washed with water (20 ml) and with brine (20 ml), dried over anhydrous magnesium sulfate, and concentrated.

The resultant crude crystalline product was recrystallized from methanol/ether to afford 44.0% yield of d-(3E)-17-phenyl-2,5,6,7,18,19,20-heptanor-3,4-didehydro-4,8-inter-m-phenylene PGI$_2$ (133 mg, 0.328 mmoles) as a white crystal. The structure was confirmed by the following data:

m.p. 163°-164° C.

$[\alpha]_D^{25}$: +277.86 (c 0.176, MeOH).

IR (KBr): 3400, 2950, 1688, 1632, 1450, 1197, 965, 866, 746 cm$^{-1}$.

NMR (400 MHz, CDCl$_3$+DMSO-d$_6$, δ): 1.90 (1H, m), 2.07 (1H, ddd, J=5.3, 8.3, 13.7 Hz), 2.48-2.79 (4H, m), 3.48 (1H, t, J=8.3 Hz), 3.99 (1H, dt, J=6.4, 7.8 Hz), 4.20 (1H, m), 5.26 (1H, m), 5.69 (2H, m), 6.72 (1H, d, J=16.1 Hz), 6.86 (1H, t, J=7.3 Hz), 7.13 (1H, d, J=6.8 Hz), 7.22-7.52 (6H, m), 7.75 (1H, d, J=16.1 Hz).

MASS (EI, m/e): 406 (M+).

High resolution mass spectrum: Calcd. (C$_{25}$H$_{26}$O$_5$, M+): 406.1718. Found (M+): 406.1718.

EXAMPLE 44 d-(3E)-15-cyclopentyl-2,5,6,7,16,17,18,19,20-nonanor-3,4-didehydro-4,8-inter-m-phenylene PGI$_2$ methyl ester (55) and 15-epimer thereof (56)

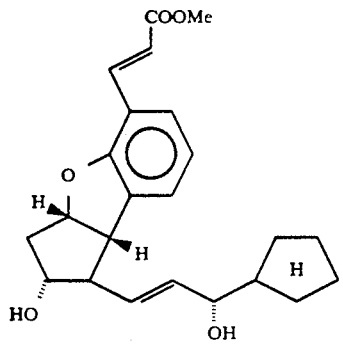

(55)

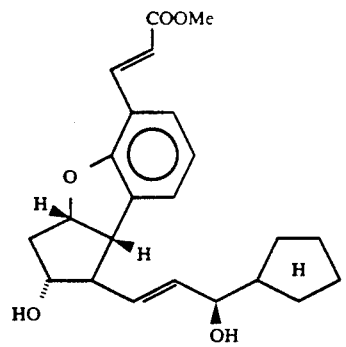

(55)

To a solution of d-(3E)-15-cyclopentyl-15-oxo-2,5,6,7,16,17,18,19,20-nonanor-3,4-didehydro-4,8-inter-m-phenylene PGI$_2$ methyl ester, 11-acetate (907 mg, 2.14 mmoles) in methanol (20 ml) was added cerous trichloride heptahydrate (1.59 g, 4.28 mmoles), to which sodium borohydride (81.0 mg, 2.14 mmoles) was added after cooling to 0° C. The solution stirred at 0° C. for 15 minutes, to which saturated aqueous sodium hydrogen carbonate (3 ml) was added and concentrated.

To the residue was added ethyl acetate (30 ml), filtered, and the precipitate was washed with ethyl acetate (20 ml×2).

The filtrates were combined, washed with water (20 ml) and with brine (20 ml), dried over anhydrous magnesium sulfate, and concentrated. Then, the resultant oily product was dissolved in dry methanol (20 ml) under argon atomosphere, to which a solution of sodium methoxide in methanol (5.22N, 0.16 ml, 0.84 mmoles) was added and stirred at room temperature for 2 hours. This reaction mixture was then neutralized with acetic acid and concentrated. To the residue was added water (20 ml) and extracted with ethyl acetate (50 ml, 20 ml). The organic layers were combined, washed with saturated aqueous sodium chloride (20 ml), dried over anhydrous magnesium sulfate, and concentrated.

The resultant residue was purified by Rober Column, Merck (silica gel: ethyl acetate/cyclohexane 2/1) to afford 44.2% yield of d-(3E)-15-cyclopentyl-15-epi-2,5,6,7,16,17,18,19,20-nonanor-3,4-didehydro-4,8-inter-m-phenylene PGI$_2$ methyl ester (363 mg, 0.945 mmoles) as a less polar eluate, followed by 37.2% yield of d-(3E)-15-cyclopentyl-2,5,6,7,16,17,18,19,20-nonanor-3,4-didehydro-4,8-inter-m-phenylene PGI$_2$ methyl ester (306 mg 0.797 mmoles) as a more polar eluate.

The structure was confirmed by the following data:

d-(3E)-15-cyclopentyl-2,5,6,7,16,17,18,19,20-nonanor-3,4-didehydro-4,8-inter-m-phenylene PGI$_2$ methyl ester m.p. 141°-142° C. (recrystallized from ethyl acetate/n-hexane).

$[\alpha]_D^{25}$: +291.35 (c 0.266, MeOH).

IR (KBr): 3320, 2950, 2914, 2870, 1717, 1630, 1605, 1591, 1475, 1448, 1346, 1319, 1270, 1255, 1205, 1170, 1083, 1062, 1029, 988, 971, 868, 777, 746, 719 cm$^{-1}$.

NMR (400 MHz, CDCl$_3$, δ): 1.2-2.1 (11H, m), 2.3-2.5 (2H, m), 2.71 (1H, ddd, J=6.4, 7.3, 13.7 Hz), 3.45 (1H, t, J=8.7 Hz), 3.80 (3H, s), 3.9-4.0 (2H, m), 5.23 (1H, ddd, J=5.4, 7.3, 8.7 Hz), 5.55-5.7 (2H, m), 6.72 (1H, d, J=16.1 Hz), 6.85 (1H, t, J=7.1 Hz), 7.09 (1H, d, J=7.1 Hz), 7.23 (1H, d, J=7.1 Hz), 7.68 (1H, d, J=16.1 Hz).

MASS (EI, m/e): 384 (M+).

High resolution mass spectrum: Calcd. (C$_{23}$H$_{28}$O$_5$, M+): 384.1937. Found (M+): 384.1965.

Anal. Calcd. for C$_{23}$H$_{28}$O$_5$: C: 71.85; H: 7.34. Found: C: 71.68; H: 7.40.

d-(3E)-15-cyclopentyl-15-epi-2,5,6,7,16,17,18,19,20-nonanor-3,4-didehydro-4,8-inter-m-phenylene PGI$_2$ methyl ester m.p. 133.5°-134° C. (recrystallized from ethyl acetate/n-hexane).

$[\alpha]_D^{25}$: +264.36 (c 0.564, MeOH).

IR (KBr): 3532, 3492, 3304, 2954, 2904, 2868, 1705, 1634, 1448, 1342, 1313, 1276, 1249, 1205, 1187, 1166, 1091, 1027, 975, 866, 743 cm$^{-1}$.

NMR (400 MHz, CDCl$_3$, δ): 1.2-1.85 (10H, m), 1.95-2.1 (2H, m), 2.45-2.55 (1H, m), 2.68 (1H, ddd, J=5.9, 7.3, 14.2 Hz), 3.50 (1H, t, J=8.6 Hz), 3.80 (3H, s), 3.9-4.05 (2H, m), 5.26 (1H, ddd, J=4.9, 7.3, 8.6 Hz) 5.65-5.75 (2H, m), 6.72 (1H, d, J=16.1 Hz), 6.86 (1H, t, J=7.6 Hz), 7.14 (1H, t, J=7.6 Hz), 7.24 (1H, d, J=7.6 Hz), 7.68 (1H, d, J=16.1 Hz).

MASS (EI, m/e): 384 (M+).

High resolution mass spectrum: Calcd. (C$_{23}$H$_{28}$O$_5$, M+): 384.1937. Found (M+): 384.1963.

EXAMPLE 45 d-(3E)-15-cyclopentyl-2,5,6,7,16,17,18,19,20-nonanor-3,4-didehydro-4,8-inter-m-phenylene PGI$_2$ (57)

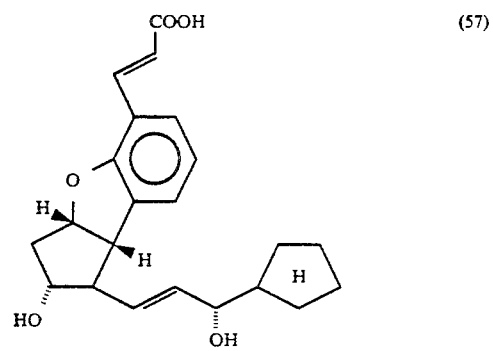

To a solution of d-(3E)-15-cyclopentyl-2,5,6,7,16,17,18,19,20-nonanor-3,4-didehydro-4,8-inter-m-phenylene PGI$_2$ methyl ester (195 mg 0.501 mmoles) in methanol (20 ml) was added 1.0N aqueous sodium hydroxide solution (5.0 ml, 5.0 mmoles) and stirred at room temperature for 45 hours. The reaction mixture was concentrated. To the residue was added water (15 ml), then neutralized with 1.0N hydrochloric acid (5.0 ml), and extracted with ethyl acetate (50 ml, 20 ml). The organic layers were combined, washed with water (20 ml) and with brine (20 ml), dried over anhydrous magnesium sulfate, and concentrated to give 187 mg of crude crystalline product. The crude crystalline product was recrystallized from MeOH/n-hexane to afford 69.8% yield of d-(3E)-15-cyclopentyl-2,5,6,7,16,17,18,19,20-nonanor-3,4-didehydro-4,8-inter-m-phenylene PGI$_2$ (79 mg, 0.278 mmoles) as a white crystal. The structure was confirmed by the following data:

m.p. 178.5°–179.5° C.

$[\alpha]_D^{25}$: +295.28 (c 0.276, MeOH).

IR (KBr): 3310, 2958, 2870, 1692, 1630, 1607, 1450, 1415, 1344, 1311, 1278, 1251, 1210, 1102, 1077, 1035, 973, 866, 746 cm$^{-1}$.

NMR (500 MHz, CDCl$_3$+DMSO-d$_6$, δ): 1.25–2.05 (10H, m), 2.3–2.4 (1H, m), 2.65–2.75 (1H, m), 3.41 (1H, t, J=9.0 Hz), 3.85–3.95 (2H, m), 5.15–5.25 (1H, m), 5.55–5.65 (2H, m), 6.79 (1H, d, J=16.1 Hz), 6.83 (1H, t, J=7.5 Hz), 7.07 (1H, d, J=7.5 Hz), 7.23 (1H, d, J=7.5 Hz), 7.67 (1H, d, J=16.1 Hz).

MASS (EI, m/e): 370 (M+).

High resolution mass spectrum: Calcd. (C$_{22}$H$_{26}$O$_5$, M+): 370.1780. Found (M+): 370.1758.

EXAMPLE 46 d-(3E)-15-cyclohexyl-2,5,6,7,16,17,18,19,20-nonanor-3,4-didehydro-4,8-inter-m-phenylene PGI$_2$ methyl ester (58) and 15-epimer thereof (59)

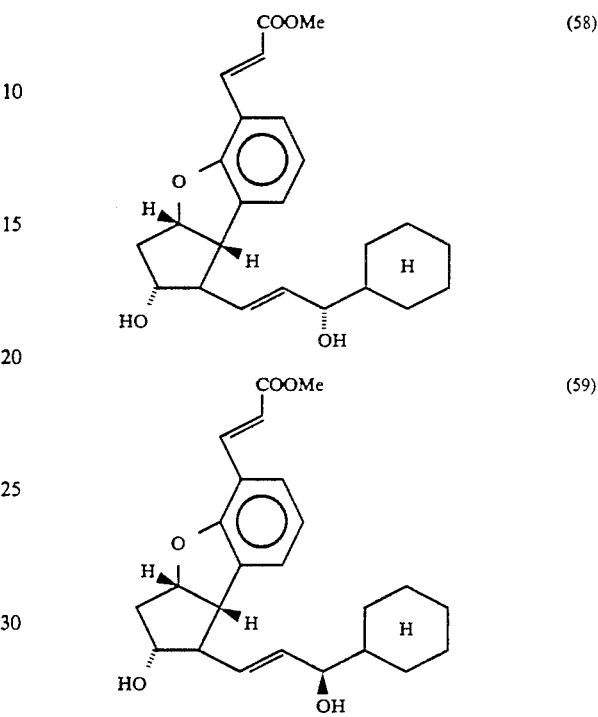

To a solution of d-(3E)-15-cyclohexyl-15-oxo-2,5,6,7,16,17,18,19,20-nonanor-3,4-didehydro-4,8-inter-m-phenylene PGI$_2$ methyl ester, 11-acetate (870 mg, 1.99 mmoles) in methanol (20 ml) was added cerous trichloride heptahydrate (1.48 g, 3.98 mmoles), to which sodium borohydride (75.3 mg, 1.99 mmoles) was added after cooling to 0° C. The solution stirred at 0° C. for 20 minutes, to which saturated aqueous sodium hydrogen carbonate (3 ml) was added and concentrated.

To the residue was added ethyl acetate (30 ml), filtered, and the precipitate was washed with ethyl acetate (20 ml×2).

The filtrates were combined, washed with water (30 ml) and with brine (30 ml), dried over anhydrous magnesium sulfate, and concentrated.

Then, the resultant oily product was dissolved in dry methanol (20 ml) under argon atmosphere, to which a solution of sodium methoxide in methanol (5.22N, 0.15 ml, 0.80 mmoles) was added and stirred at room temperature for 2 hours. This reaction mixture was then neutralized with acetic acid and concentrated. To the residue was added water (20 ml) and extracted with ethyl acetate (50 ml, 30 ml). The organic layers were combined, washed with brine (20 ml), dried over anhydrous magnesium sulfate, and concentrated.

The resultant residue was purified by Lobar Column (Merck, silica gel: ethyl acetate/cyclohexane=2/1) to afford 46.8% yield of d-(3E)-15-cyclohexyl-15-epi-2,5,6,7,16,17,18,19,20-nonanor-3,4-didehydro-4,8-inter-m-phenylene PGI$_2$ methyl ester (371 mg, 0.932 mmoles) as a less polar eluate, followed by 37.4% yield of d-(3E)-15-cyclohexyl-2,5,6,7,16,17,18,19,20-nonanor-3,4- didehydro-4,8-inter-m-phenylene PGI$_2$ methyl ester (296 mg 0.744 mmoles) as a more polar eluate.

The structure was confirmed by the following data:

d-(3E)-15-cyclohexyl-2,5,6,7,16,17,18,19,20-nonanor-3,4-didehydro-4,8-inter-m-phenylene PGI$_2$ methyl ester m.p. 146°-146.5° C. (recrystallized from ethyl acetate/n-hexane).

$[\alpha]_D^{25}$: +295.59 (c 0.318, MeOH).

IR (KBr): 3400, 2930, 2860, 1710, 1695, 1630, 1600, 1590, 1440, 1320, 1280, 1250, 1220, 1200, 1180, 1090, 1030, 990, 970, 950, 890, 860, 780, 750 cm$^{-1}$.

NMR (400 MHz, CDCl$_3$, δ): 0.9-1.5 (6H, m), 1.65-1.95 (6H, m), 2.03 (1H, ddd, J=4.9, 9.0, 13.9 Hz), 2.25-2.5 (2H, m), 2.70 (1H, dt, J=6.8, 13.9 Hz), 3.46 (1H, t, J=8.5 Hz), 3.80 (3H, s), 3.85-4.0 (2H, m), 5.2-5.3 (1H, m), 5.55-5.7 (2H, m), 6.72 (1H, d, J=16.1 Hz), 6.85 (1H, t, J=7.3 Hz), 7.10 (1H, d, J=7.3 Hz), 7.24 (1H, d, J=7.3 Hz), 7.68 (1H, d, J=16.1 Hz).

MASS (EI, m/e): 398 (M+).

High resolution mass spectrum: Calcd. (C$_{24}$H$_{30}$O$_5$, M+): 398.2093. Found (M+): 398.2136.

Anal. Calcd. for C$_{24}$H$_{30}$O$_5$: C: 72.34; H: 7.59. Found: C: 72.12; H: 7.57.

d-(3E)-15-cyclohexyl-15-epi-2,5,6,7,16,17,18,19,20-nonanor-3,4-didehydro-4,8-inter-m-phenylene PGI$_2$ methyl ester M.P. 134°-135° C. (recrystallized from ethyl acetate/n-hexane).

$[\alpha]_D^{25}$: +253.57 (c 0.504, MeOH).

IR (KBr): 3400, 2925, 2850, 1720, 1680, 1630, 1600, 1440, 1320, 1220, 1160, 1080, 1000, 890, 860, 750 cm$^{-1}$.

NMR (400 MHz, CDCl$_3$, δ): 0.9-1.5 (6H, m), 1.55-1.9 (7H, m), 2.07 (1H, ddd, J=5.2, 8.3, 13.8 Hz), 2.45-2.55 (1H, m), 2.68 (1H, ddd, J=5.9, 7.2, 13.8 Hz), 3.51 (1H, t, J=8.6 Hz), 3.80 (3H, s), 3.85-4.05 (2H, m), 5.26 (1H, ddd, J=5.2, 7.2, 8.6 Hz), 5.6-5.75 (2H, m), 6.72 (1H, d, J=16.1 Hz), 6.86 (1H, t, J=7.6 Hz), 7.14 (1H, d, J=7.6 Hz), 7.24 (1H, d, J=7.6 Hz), 7.68 (1H, d, J=16.1 Hz).

MASS (EI, m/e): 398 (M+).

High resolution mass spectrum: Calcd. (C$_{24}$H$_{30}$O$_5$, M+): 398.2093. Found (M+): 398.2065.

Anal. Calcd. for C$_{24}$H$_{30}$O$_5$: C: 72.34; H: 7.59. Found: C: 72.02; H: 7.54.

EXAMPLE 47 d-(3E)-15-cyclohexyl-2,5,6,7,16,17,18,19,20-nonanor-3,4-didehydro-4,8-inter-m-phenylene PGI$_2$ (60)

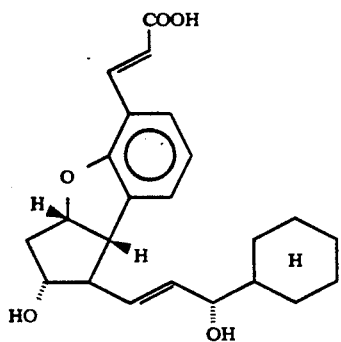
(60)

To a solution of d-(3E)-15-cyclohexyl-2,5,6,7,16,17,18,19,20-nonanor-3,4-didehydro-4,8-inter-m-phenylene PGI$_2$ methyl ester (183 mg, 0.460 mmoles) in methanol (20 ml) was added 1.0N aqueous sodium hydroxide solution (5.0 ml, 5.0 mmoles) and stirred at room temperature for 24 hours. The reaction mixture was concentrated. To the residue was added water (15 ml), then neutralized with 1.0N hydrochloric acid (5.0 ml), and extracted with ethyl acetate (50 ml, 20 ml). The organic layers were combined, washed with water (20 ml) and with brine (20 ml), dried over anhydrous magnesium sulfate, and concentrated to give 198 mg of crude crystalline product.

The crude crystalline product was recrystallized from ethyl acetate/MeOH to afford 70.1% yield of d-(3E)-15-cyclohexyl-2,5,6,7,16,17,18,19,20-nonanor-3,4-didehydro-4,8-inter-m-phenylene PGI$_2$ (125 mg, 0.326 mmoles) as a white crystal. The structure was confirmed by the following data:

m.p. 213°-214° C.

$[\alpha]_D^{25}$: +275.75 (c 0.438, MeOH).

IR (KBr): 3400, 2920, 2850, 1680, 1630, 1450, 1300, 1280, 1250, 1200, 1080, 1100, 1030, 980, 970, 950, 900, 860, 780, 750 cm$^{-1}$.

NMR (400 MHz, CDCl$_3$+DMSO-d$_6$, δ): 0.9-1.5 (6H, m), 1.65-1.8 (4H, m), 1.9-2.05 (2H, m), 2.3-2.4 (1H, m), 2.65-2.75 (1H, m), 3.35-3.45 (1H, m), 3.75-3.95 (2H, m), 5.15-5.25 (1H, m), 5.55-5.65 (2H, m), 6.68 (1H, d, J=16.1 Hz), 6.83 (1H, t, J=7.3 Hz), 7.08 (1H, d, J=7.3 Hz), 7.23 (1H, d, J=7.3 Hz), 7.66 (1H, d, J=16.1 Hz).

MASS (EI, m/e): 384 (M+).

High recrystallized mass spectrum: Calcd. (C$_{23}$H$_{28}$O$_5$, M+): 384.1937. Found (M+): 384.1955.

Anal. Calcd. for C$_{23}$H$_{28}$O$_5$: C: 71.85; H: 7.34. Found: C: 71.69; H: 7.28.

EXAMPLE 48 d-(3E, 16S)-16-methyl-2,5,6,7-tetranor-3,4,18,18,19,19-hexadehydro-4,8-inter-m-phenylene PGI$_2$ methyl ester (61) and 15-epimer thereof (62)

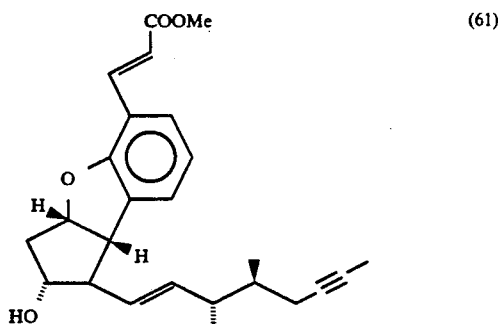
(61)

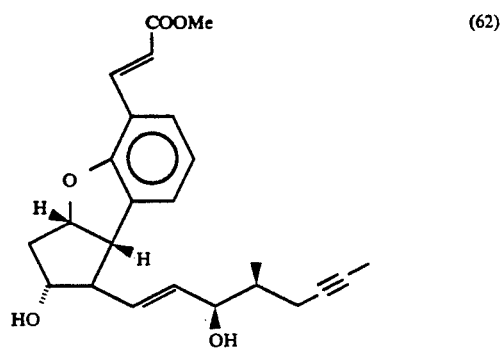
(62)

To a solution of d-(3E, 16S)-16-methyl-15-oxo-2,5,6,7-tetranor-3,4,18,18,19,19-hexadehydro-4,8-inter-m-phenylene PGI₂ methyl ester, 11-acetate (910 mg, 2.09 mmoles) in methanol (30 ml) was added cerous trichloride heptahydrate (1.56 g, 4.18 mmoles), to which sodium borohydride (79.0 mg, 2.09 mmoles) was added after cooling to 0° C. The solution stirred at 0° C. for 15 minutes, to which saturated aqueous sodium hydrogen carbonate (3 ml) was added and concentrated.

To the residue was added ethyl acetate (40 ml), filtered, and the precipitate was washed with ethyl acetate (20 ml×2).

The filtrates were combined, washed with water (20 ml) and with brine (30 ml), dried over anhydrous magnesium sulfate, and concentrated. Then, the resultant oily product was dissolved in dry methanol (25 ml) under argon atomosphere, to which a solution of sodium methoxide in methanol (5.22N, 0.16 ml, 0.84 mmoles) was added and stirred at room temperature for 2 hours. This reaction mixture was then neutralized with acetic acid and concentrated. To the residue was added water (20 ml) and extracted with ethyl acetate (50 ml, 30 ml).

The organic layers were combined, washed with brine (20 ml), dried over anhydrous magnesium sulfate, and concentrated.

The resultant residue was purified by Lobar Column (Merck, silica gel: ethyl acetate/cyclohexane=2/1) to afford 45.4% yield of d-(3E, 16S)-16-methyl-15-epi-2,5,6,7-tetranor-3,4,18,18,19,19-hexadehydro-4,8-inter-m-phenylene PGI₂ methyl ester (376 mg, 0.949 mmoles) as a less polar eluate, followed by 40.6% yield of d-(3E, 16S)-16-methyl-2,5,6,7-tetranor-3,4,18,18,19,19-hexadehydro-4,8-inter-m-phenylene PGI₂ methyl ester (336 mg, 0.848 mmoles) as a more polar eluate.

The structure was confirmed by the following data:

d-(3E, 16S)-16-methyl-2,5,6,7-tetranor-3,4,18,18,19,19-hexadehydro-4,8-inter-m-phenylene PGI₂ methyl ester $[\alpha]_D^{25}$: +292.70 (c 0.466, MeOH).

IR (liquid film): 3384, 2956, 2922, 1705, 1632, 1448, 1323, 1278, 1249, 1207, 1176, 1075, 1036, 990, 866, 756 cm⁻¹.

NMR (400 MHz, CDCl₃, δ): 1.00 (3H, d, J=6.8 Hz), 1.7-1.85 (1H, m), 1.80 (3H, t, J=2.7 Hz), 2.02 (1H, ddd, J=5.2, 8.8, 13.7 Hz), 2.15-2.3 (2H, m), 2.35-2.5 (2H, m), 2.55-2.6 (1H, m), 2.71 (1H, ddd, J=6.4, 7.3, 8.8 Hz), 3.45 (1H, t, J=8.8 Hz), 3.80 (3H, s), 3.9-4.0 (1H, m), 4.05-4.1 (1H, m), 5.23 (1H, ddd, J=5.2, 7.3, 8.8 Hz), 5.60 (1H, dd, J=7.1, 15.4 Hz), 5.69 (1H, dd, J=8.1, 15.4 Hz), 6.71 (1H, d, J=15.9 Hz), 6.84 (1H, t, J=7.4 Hz), 7.08 (1H, d, J=7.4 Hz), 7.28 (1H, d, J=7.4 Hz), 7.68 (1H, d, J=15.9 Hz).

MASS (EI, m/e): 396 (M+).

High resolution mass spectrum: Calcd. (C₂₄H₂₈O₅, M+): 396.1937. Found (M+): 396.1952.

d-(3E, 16S)-16-methyl-15-epi-2,5,6,7-tetranor-3,4,18,18,19,19-hexadehydro-4,8-inter-m-phenylene PGI₂ methyl ester m.p. 134°-135° C. (recrystallized from ethyl acetate/n-hexane).

$[\alpha]_D^{25}$: +233.72 (c 0.430, MeOH).

IR (KBr): 3532, 3322, 3244, 2970, 2902, 1711, 1634, 1448, 1346, 1315, 1278, 1253, 1203, 1185, 1168, 1096, 1035, 1017, 978, 949, 864, 748 cm⁻¹.

NMR (400 MHz, CDCl₃, δ): 1.01 (3H, d, J=6.8 Hz), 1.75 (1H, d, J=4.9 Hz), 1.80 (3H, t, J=2.4 Hz), 1.77-1.85 (1H, m), 1.95 (1H, d, J=4.9 Hz), 2.06 (1H, ddd, J=4.9, 8.8, 13.7 Hz), 2.1-2.3 (2H, m), 2.50 (1H, q, J=8.3 Hz), 2.70 (1H, ddd, J=6.4, 7.3, 13.7 Hz), 3.50 (1H, t, J=8.3 Hz), 3.80 (3H, s), 3.95-4.05 (1H, m), 4.25-4.35 (1H, m), 5.25 (1H, ddd, J=4.9, 7.3, 8.3 Hz), 5.67 (1H, dd, J=5.1, 16.1 Hz), 5.74 (1H, dd, J=8.3, 16.1 Hz), 6.72 (1H, d, J=16.1 Hz), 6.85 (1H, t, J=7.6 Hz), 7.14 (1H, d, J=7.6 Hz), 7.24 (1H, d, J=7.6 Hz), 7.68 (1H, d, J=16.1 Hz).

MASS (EI, m/e): 396 (M+).

High resolution mass spectrum: Calcd. (C₂₄H₂₈O₅, M+): 396.1937. Found (M+): 396.1959.

Anal. Calcd. for C₂₄H₂₈O₅: C: 72.71; H: 7.12. Found: C: 72.59; H: 7.22.

EXAMPLE 49 d-(3E, 16S)-16-methyl-2,5,6,7-tetranor-3,4,18,18,19,19-hexadehydro-4,8-inter-m-phenylene PGI₂ (63)

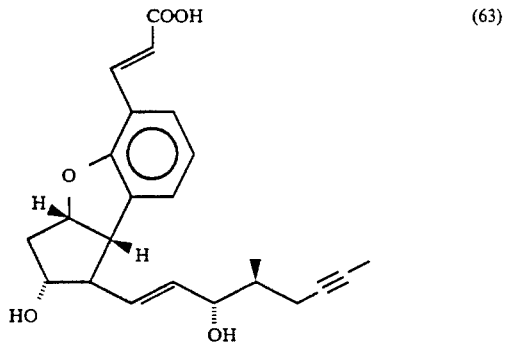

(63)

To a solution of d-(3E, 16S)-16-methyl-2,5,6,7-tetranor-3,4,18,18,19,19-hexadehydro-4,8-inter-m-phenylene PGI₂ methyl ester (221 mg, 0.558 mmoles) in methanol (20 ml) was added 1.0N aqueous sodium hydroxide solution (5.0 ml 5.0 mmoles) and stirred at room temperature for 40 hours. The reaction mixture was concentrated. To the residue was added water (10 ml), then neutralized with 1.0N hydrochloric acid (5.0 ml), and extracted with ethyl acetate (50 ml, 20 ml). The organic layers were combined, washed with water (20 ml) and with brine (20 ml), dried over anhydrous magnesium sulfate, and concentrated. The resultant residue was purified by Lobar Column (Merck, R P-8, MeOH/H₂O) to afford 47.8% yield of d-(3E, 16S)-16-methyl-2,5,6,7-tetranor-3,4,18,18,19,19-hexadehydro-4,8-inter-m-phenylene PGI₂ (102 mg, 0.267 mmoles). The structure was confirmed by the following data:

$[\alpha]_D^{25}$: +276.79 (c 0.556, MeOH).

IR (liquid film): 3384, 2956, 2922, 1705, 1632, 1448, 1323, 1278, 1249, 1207, 1176, 1075, 1036, 990, 866, 756 cm⁻¹.

NMR (500 MHz, CDCl₃, δ): 0.98 (3H, d, J=6.7 Hz), 1.7-1.85 (4H, m), 1.95-2.05 (1H, m), 2.2-2.3 (2H, m), 2.35-2.45 (1H, m), 2.65-2.8 (1H, m), 3.35-3.45 (1H, m), 3.85-4.05 (2H, m), 5.15-5.25 (1H, m), 5.55-5.7 (2H, m), 6.70 (1H, d, J=15.9 Hz), 6.8-6.9 (1H, m), 7.05-7.15 (1H, m), 7.2-7.25 (1H, m), 7.73 (1H, d, J=15.9 Hz).

MASS (EI, m/e): 382 (M+).

High resolution mass spectrum: Calcd. (C₂₃H₂₆O₅, M+): 382.1780. Found (M+): 382.1800.

EXAMPLE 50 d-(3E)-16,16-dimethyl-2,5,6,7-tetranor-3,4,18,18,19,19-hexadehydro-4,8-inter-m-phenylene PGI$_2$ methyl ester (64) and 15-epimer thereof (65)

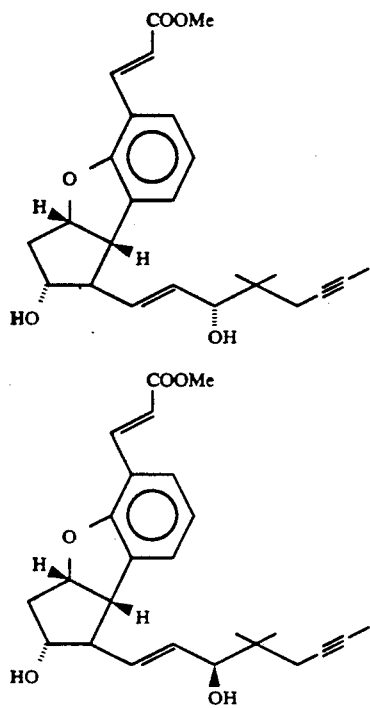

To a solution of d-(3E)-16,16-dimethyl-15-oxo-2,5,6,7-tetranor-3,4,18,18,19,19-hexadehydro-4,8-inter-m-phenylene PGI$_2$ methyl ester, 11-acetate (770 mg, 1.71 mmoles) in methanol (35 ml) was added cerous trichloride heptahydrate (1.28 g, 3.42 mmoles), to which sodium borohydride (65.0 mg, 1.71 mmoles) was added after cooling to 0° C. The solution stirred at 0° C. for 20 minutes, to which saturated aqueous sodium hydrogen carbonate (5 ml) was added and concentrated. To the residue was added ethyl acetate (50 ml), filtered, and the precipitate was washed with ethyl acetate (10 ml×2).

The filtrates were combined, washed with water (20 ml) and with brine (20 ml), dried over anhydrous magnesium sulfate, and concentrated. Then, the resultant oily product was dissolved in dry methanol (20 ml) under argon atomosphere, to which a solution of sodium methoxide in methanol (5.22N, 0.085 ml, 0.44 mmoles) was added and stirred at room temperature for 8 hours. This reaction mixture was then neutralized with acetic acid and concentrated. To the residue was added water (20 ml) and extracted with ethyl acetate (50 ml, 20 ml). The organic layers were combined, washed with brine (20 ml), dried over anhydrous magnesium sulfate, and concentrated.

The resultant residue was purified by Lobar Column (Merck, silica gel: ethyl acetate/cyclohexane=1/1) to afford 43.7% yield of d-(3E)-16,16-dimethyl-15-epi-2,5,6,7-tetranor-3,4,18,18,19,19-hexadehydro-4,8-inter-m-phenylene PGI$_2$ methyl ester (306 mg, 0.746 mmoles) as a less polar eluate, followed by 45.1% yield of d-(3E)-16,16-dimethyl-2,5,6,7-tetranor-3,4,18,18,19,19-hexadehydro-4,8-inter-m-phenylene PGI$_2$ methyl ester (316 mg, 0.771 mmoles) as a more polar eluate.

The structure was confirmed by the following data:

d-(3E)-16,16-dimethyl-2,5,6,7-tetranor-3,4,18,18,19,19-hexadehydro-4,8-inter-m-phenylene PGI$_2$ methyl ester m.p. 65.0°–68° C. (recrystallized from ethyl acetate/n-hexane).

$[\alpha]_D^{25}$: +284.98 (c 0.666, MeOH).

IR (KBr): 3378, 2964, 2922, 2370, 2334, 1715, 1632, 1605, 1593, 1448, 1323, 1276, 1251, 1207, 1176, 1073, 1036, 990, 866, 801, 779, 748, 717, 605, 563 cm$^{-1}$.

NMR (400 MHz, CDCl$_3$, δ): 0.97 (3H, s), 0.98 (3H, s), 1.81 (3H, t, J=2.9 Hz), 2.00–2.05 (1H, m), 2.08 (1H, dq, J=2.9, 16.1 Hz), 2.22 (1H, dq, J=2.9, 16.1 Hz), 2.40–2.50 (1H, m), 2.71 (1H, ddd, J=6.4, 7.3, 13.7 Hz), 3.47 (1H, t, J=8.3 Hz), 3.80 (3H, s), 3.90–4.00 (1H, m), 4.00–4.05 (1H, m), 5.23 (1H, ddd, J=5.4, 7.3, 8.8 Hz), 5.65–5.75 (2H, m), 6.71 (1H, d, J=16.1 Hz), 6.85 (1H, t, J=7.3 Hz), 7.10 (1H, d, J=7.3 Hz), 7.24 (1H, d, J=7.3 Hz), 7.68 (1H, d, J=16.1 Hz).

MASS (EI, m/e): 410 (M+).

d-(3E)-16,16-dimethyl-15-epi-2,5,6,7-tetranor-3,4,18,18,19,19-hexadehydro-4,8-inter-m-phenylene PGI$_2$ methyl ester IR (liquid film): 3422, 2932, 1694, 1632, 1607, 1593, 1448, 1377, 1323, 1249, 1178, 1044, 986, 866, 783, 748, 719 cm$^{-1}$.

NMR (400 MHz, CDCl$_3$, δ): 0.98 (6H, s), 1.80 (3H, t, J=3.0 Hz), 2.05–2.10 (1H, m), 2.23 (1H, dq, J=2.5, 16.5 Hz), 2.45–2.55 (1H, m), 2.69 (1H, dt, J=7.3, 14.0 Hz), 3.51 (1H, t, J=8.5 Hz), 3.80 (3H, s), 3.99 (1H, dt, J=5.5, 8.5 Hz), 4.06 (1H, d, J=3.0 Hz), 5.26 (1H, ddd, J=4.9, 7.3, 9.2 Hz), 5.70–5.80 (2H, m), 6.71 (1H, d, J=15.9 Hz), 6.86 (1H, t, J=7.9 Hz), 7.14 (1H, d, J=7.3 Hz), 7.24 (1H, d, J=7.9 Hz), 7.68 (1H, d, J=15.9 Hz).

MASS (EI, m/e): 410 (M+).

EXAMPLE 51 d-(3E)-16,16-dimethyl-2,5,6,7-tetranor-3,4,18,18,19,19-hexadehydro-4,8-inter-m-phenylene PGI$_2$ (66)

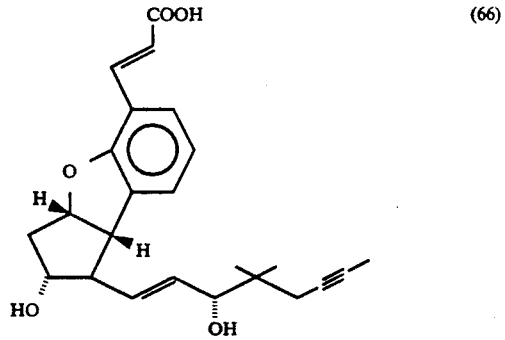

To a solution of d-(3E)-16,16-dimethyl-2,5,6,7-tetranor-3,4,18,18,19,19-hexadehydro-4,8-inter-m-phenylene PGI$_2$ methyl ester (200 mg, 0.488 mmoles) in methanol (20 ml) was added 1.0N aqueous sodium hydroxide solution (3.9 ml, 3.9 mmoles) and stirred at room temperature for 18 hours. The reaction mixture was concentrated. To the residue was added water (15 ml), then neutralized with 1.0N hydrochloric acid and extracted with ethyl acetate (50 ml, 20 ml). The organic layers were combined, washed with water (20 ml) and with brine (20 ml), dried over anhydrous magnesium sulfate, and concentrated to give 95.7% yield of d-(3E)-16,16- dimethyl-2,5,6,7-tetranor-3,4,18,18,19,19-hexadehydro-4,8-inter-m-phenylene PGI$_2$ (185 mg, 0.467 mmoles) as a crude crystal. The structure was confirmed by the following data:

[α]$_D^{25}$: +228.57 (c 0.728, MeOH).

IR (KBr): 3700–2500, 2970, 2366, 1688, 1630, 1450, 1251, 1210, 1075, 1036, 990, 866, 781, 748, 669, 609, 542, 443 cm$^{-1}$.

NMR (400 MHz, DMSO-d$_6$, δ): 0.88 (3H, s), 0.89 (3H, s), 1.75–1.8 (1H, m), 1.76 (3H, t, J=2.4 Hz), 2.05 (1H, dq, J=2.4, 16.5 Hz), 2.12 (1H, dq, J=2.4, 16.5 Hz), 2.25 (1H, q, J=7.9 Hz), 2.50–2.60 (1H, m), 3.50 (1H, t, J=8.6 Hz), 3.75–3.80 (2H, m), 5.20–5.30 (1H, m), 5.54 (1H, dd, J=7.3, 15.9 Hz), 5.66 (1H, dd, J=7.3, 15.3 Hz), 6.58 (1H, d, J=16.5 Hz), 6.86 (1H, t, J=7.3 Hz), 7.13 (1H, d, J=7.3 Hz), 7.38 (1H, d, J=7.3 Hz), 7.55 (1H, d, J=16.5 Hz).

MASS (EI, m/e): 396 (M+).

High resolution mass spectrum: Calcd. (C$_{24}$H$_{28}$O$_5$, M+): 396.1937. Found (M+): 396.1948.

EXAMPLE 52 d-(3E)-2,5,6,7-tetranor-17-oxa-3,4-didehydro-4,8-inter-m-phenylene PGI$_2$ methyl ester (67) and 15-epimer thereof (68)

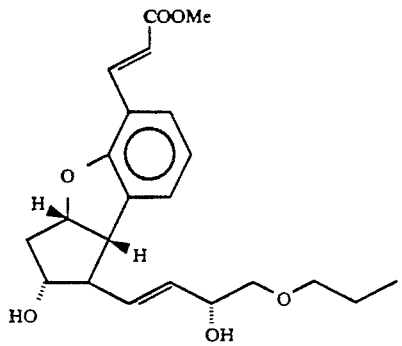
(67)

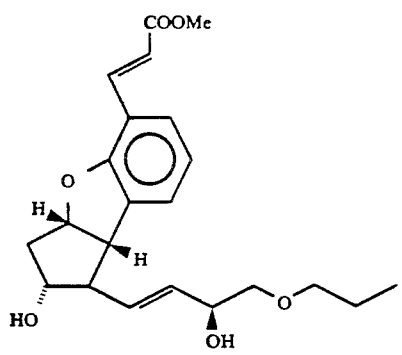
(68)

To a solution of d-(3E)-15-oxo-2,5,6,7-tetranor-17-oxa-3,4-didehydro-4,8-inter-m-phenylene PGI$_2$ methyl ester, 11-acetate (756 mg, 1.77 mmoles) in methanol (20 ml) was added cerous trichloride heptahydrate (1.32 g, 3.54 mmoles), to which sodium borohydride (67.0 mg, 1.77 mmoles) was added aftercooling to 0° C. The solution stirred at 0° C. for 20 minutes, to which saturated aqueous sodium hydrogen carbonate (3 ml) was added and concentrated.

To the residue was added ethyl acetate (30 ml), filtered, and the precipitate was washed with ethyl acetate (10 ml×2).

The filtrates were combined, washed with water (20 ml) and with brine (20 ml), dried over anhydrous magnesium sulfate, and concentrated. Then, the resultant oily product was dissolved in dry methanol (20 ml) under argon atmosphere, to which a solution of sodium methoxide in methanol (5.22N, 0.10 ml, 0.53 mmoles) was added and stirred at room temperature for 3 hours. This reaction mixture was then neutralized with acetic acid and concentrated. To the residue was added water (20 ml) and extracted with ethyl acetate (40 ml, 20 ml). The organic layers were combined, washed with brine (20 ml), dried over anhydrous magnesium sulfate, and concentrated.

The resultant residue was purified by Lobar Column (Merck, silica gel: ethyl acetate/cyclohexane=2/1) to afford 45.3% yield of d-(3E)-15-epi-2,5,6,7-tetranor-17-oxa-3,4-didehydro-4,8-inter-m-phenylene PGI$_2$ methyl ester (311 mg, 0.802 mmoles) as a less polar eluate, followed by 39.9% yield of d-(3E)-2,5,6,7-tetranor-17-oxa-3,4-didehydro-4,8-inter-m-phenylene PGI$_2$ methyl ester (274 mg 0.706 mmoles) as a more polar eluate.

The structure was confirmed by the following data:

d-(3E)-2,5,6,7-tetranor-17-oxa-3,4-didehydro-4,8-inter-m-phenylene PGI$_2$ methyl ester

[α]$_D^{25}$: +248.62 (c 0.582, MeOH).

IR (liquid film): 3400, 2950, 2870, 1710, 1630, 1600, 1590, 1440, 1370, 1320, 1240, 1200, 1170, 1100, 1070, 1040, 980, 890, 860, 800, 780, 750, 720 cm$^{-1}$.

NMR (400 MHz, CDCl$_3$, δ): 0.94 (3H, t, J=7.6 Hz), 1.55–1.7 (2H, m), 2.04 (1H, ddd, J=5.1, 8.8, 13.9 Hz), 2.15–2.3 (1H, m), 2.46 (1H, q, J=8.1 Hz), 2.65–2.8 (2H, m), 3.34 (1H, dd, J=8.1, 9.3 Hz), 3.4–3.55 (4H, m), 3.80 (3H, s), 3.9–4.05 (1H, m), 4.3–4.4 (1H, m), 5.2–5.3 (1H, m), 5.60 (1H, dd, J=6.1, 15.4 Hz), 5.81 (1H, dd, J=8.1, 15.4 Hz), 6.71 (1H, d, J=16.1 Hz), 6.84 (1H, t, J=7.3 Hz), 7.11 (1H, d, J=7.3 Hz), 7.23 (1H, d, J=7.3 Hz), 7.68 (1H, d, J=16.1 Hz).

MASS (EI, m/e): 388 (M+).

High resolution mass spectrum: Calcd. (C$_{22}$H$_{28}$O$_6$, M+): 388.1886. Found (M+): 388.1884.

d-(3E)-15-epi-2,5,6,7-tetranor-17-oxa-3,4-didehydro-4,8-inter-m-phenylene PGI$_2$ methyl ester

[α]$_D^{25}$: +242.61 (c 0.528, MeOH).

IR (liquid film): 3420, 2950, 2870, 1700, 1630, 1600, 1590, 1440, 1370, 1320, 1240, 1200, 1170, 1100, 1040, 980, 860, 800, 780, 750, 720 cm$^{-1}$.

NMR (400 MHz, CDCl$_3$, δ): 0.95 (3H, t, J=7.3 Hz), 1.55–1.7 (2H, m), 1.8–1.9 (1H, m), 2.06 (1H, ddd, J=4.9, 8.8, 13.7 Hz), 2.49 (1H, q, J=8.1 Hz), 2.55–2.65 (1H, m), 2.68 (1H, ddd, J=6.4, 7.3, 13.7 Hz), 3.33 (1H, dd, J=8.1, 9.5 Hz), 3.4–3.55 (4H, m), 3.80 (3H, s), 3.95–4.05 (1H, m), 4.3–4.4 (1H, m) 5.2–5.3 (1H, m), 5.63 (1H, dd, J=5.6, 15.5 Hz), 5.82 (1H, dd, J=8.1, 15.5 Hz), 6.71 (1H, d, J=16.1 Hz), 6.84 (1H, t, J=7.3 Hz), 7.14 (1H, d, J=7.3 Hz), 7.23 (1H, d, J=7.3 Hz), 7.68 (1H, d, J=16.1 Hz).

MASS (EI, m/e): 388 (M+).

High resolution mass spectrum; Calcd. (C$_{22}$H$_{28}$O$_6$, M+): 388.1886. Found (M+): 388.1882.

EXAMPLE 53 d-(3E)-2,5,6,7-tetranor-17-oxa-3,4-didehydro-4,8-inter-m-phenylene PGI₂ (69)

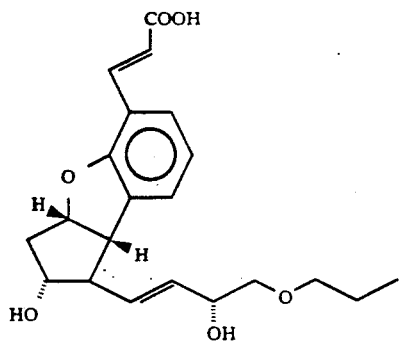

To a solution of d-(3E)-2,5,6,7-tetranor-17-oxa-3,4-didehydro-4,8-inter-m-phenylene PGI₂ methyl ester (225 mg, 0.580 mmoles) in methanol (15 ml) was added 1.0N aqueous sodium hydroxide solution (6.0 ml, 6.0 mmoles) and stirred at room temperature for 20 hours. The reaction mixture was concentrated. To the residue was added water (10 ml), then neutralized with 1.0N hydrochloric acid (6.0 ml), and extracted with ethyl acetate (50 ml, 20 ml).

The organic layers were combined, washed with water (20 ml) and with brine (20 ml), dried over anhydrous magnesium sulfate, and concentrated to give 201 mg of crude crystalline product. The resulting crude crystalline product was recrystallized from ethyl acetate/n-hexane to afford 63.1% yield of d-(3E)-2,5,6,7-tetranor-17-oxa-3,4-didehydro-4,8-inter-m-phenylene PGI₂ (137 mg, 0.366 mmoles) as a white crystal. The structure was confirmed by the following data:

m.p. 154°-155° C.

$[\alpha]_D^{25}$: +271.14 (c 0.402, MeOH).

IR (KBr): 3350, 2960, 2930, 2870, 1700, 1630, 1600, 1590, 1450, 1360, 1290, 1210, 1200, 1110, 1070, 980, 860, 780, 740, 620, 560 cm$^{-1}$.

NMR (400 MHz, CDCl₃+DMSO-D₆, δ): 0.94 (3H, t, J=7.2 Hz), 1.6–1.7 (2H, m), 2.02 (1H, ddd, J=5.1, 9.0, 13.9 Hz), 2.43 (1H, q, J=8.3 Hz), 2.67 (1H, dt, J=6.8, 13.9 Hz), 3.35–3.55 (5H, m), 3.9–4.0 (1H, m), 4.3–4.4 (1H, m), 5.2–5.3 (1H, m), 5.62 (1H, dd, J=6.4, 15.6 Hz), 5.79 (1H, dd, J=8.3, 15.6 Hz), 6.69 (1H, d, J=15.9 Hz), 6.82 (1H, t, J=7.3 Hz), 7.11 (1H, d, J=7.3 Hz), 7.22 (1H, d, J=7.3 Hz), 7.68 (1H, d, J=15.9 Hz).

MASS (EI, m/e): 374 (M⁺).

High resolution mass spectrum: Calcd. (C₂₁H₂₆O₆, M⁺): 374.1729. Found (M⁺): 374.1709.

Anal. Calcd. for C₂₁H₂₆O₆: C: 67.36; H: 7.00. Found: C: 67.24; H: 7.11.

EXAMPLE 54 d-(3E)-16,16-dimethyl-2,5,6,7-tetranor-18-oxa-3,4-didehydro-4,8-inter-m-phenylene PGI₂ methyl ester (70) and 15-epimer thereof (71)

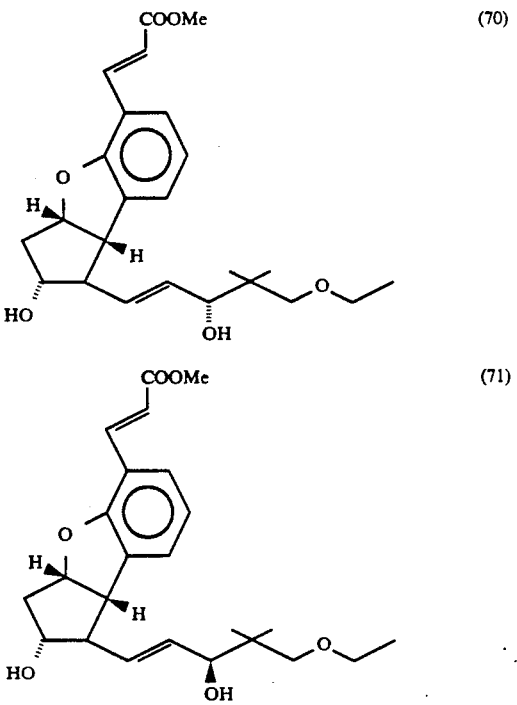

To a solution of d-(3E)-16,16-dimethyl-15-oxo-2,5,6,7-tetranor-18-oxa-3,4-didehydro-4,8-inter-m-phenylene PGI₂ methyl ester, 11-acetate (945 mg, 2.07 mmoles) in methanol (25 ml) was added cerous trichloride heptahydrate (1.54 g, 4.14 mmoles), to which sodium borohydride (78.3 mg, 2.07 mmoles) was added after cooling to 0° C. The solution stirred at 0° C. for 20 minutes, to which saturated aqueous sodium hydrogen carbonate (5 ml) was added and concentrated. To the residue was added ethyl acetate (50 ml), filtered, and the precipitate was washed with ethyl acetate (10 ml×2).

The filtrates were combined, washed with water (20 ml) and with brine (20 ml), dried over anhydrous magnesium sulfate, and concentrated. Then, the resultant oily product was dissolved in dry methanol (20 ml) under argon atomosphere, to which a solution of sodium methoxide in methanol (5.22N, 0.16 ml, 0.83 mmoles) was added and stirred at room temperature for 2 hours. This reaction mixture was then neutralized with acetic acid and concentrated. To the residue was added water (20 ml) and extracted with ethyl acetate (50 ml, 20 ml). The organic layers were combined, washed with brine (20 ml), dried over anhydrous magnesium sulfate, and concentrated.

The resultant residue was purified by Lobar Column (Merck, silica gel: ethyl acetate/cyclohexane=2/1) to afford 42.0% yield of d-(3E)-16,16-dimethyl-15-epi-2,5,6,7-tetranor-18-oxa-3,4-didehydro-4,8-inter-m-phenylene PGI₂ methyl ester (362 mg, 0.870 mmoles) as a less polar eluate, followed by 41.6% yield of d-(3E)-16,16-dimethyl-2,5,6,7-tetranor-18-oxa-3,4-didehydro-4,8-inter-m-phenylene PGI₂ methyl ester (358 mg 0.861 mmoles) as a more polar eluate.

The structure was confirmed by the following data:

d-(3E)-16,16-dimethyl-2,5,6,7-tetranor-18-oxa-3,4-didehydro-4,8-inter-m-phenylene PGI₂ methyl ester $[\alpha]_D^{25}$: +263.88 (c 0.760, MeOH).

IR (liquid film): 3380, 2950, 2860, 1700, 1630, 1600, 1440, 1320, 1270, 1240, 1200, 1160, 1100, 1030, 980, 860, 780, 740, 720 cm⁻¹.

NMR (400 MHz, CDCl₃, δ): 0.92 (3H, s), 1.20 (3H, t, J=7.1 Hz), 2.0–2.1 (1H, m), 2.4–2.5 (1H, m), 2.70 (1H, dt, J=6.8, 13.7 Hz), 3.29 (1H, d, J=9.0 Hz), 3.37 (1H, d, J=9.0 Hz), 3.4–3.55 (3H, m), 3.80 (3H, s), 3.9–4.0 (2H, m), 5.2–5.3 (1H, m), 5.6–5.7 (2H, m), 6.72 (1H, d, J=15.9 Hz), 6.84 (1H, t, J=7.6 Hz), 7.08 (1H, d, J=7.6 Hz), 7.23 (1H, d, J=7.6 Hz), 7.68 (1H, d, J=15.9 Hz).

MASS (EI, m/e): 416 (M⁺).

High resolution mass spectrum: Calcd. (C₂₄H₃₂O₆, M⁺): 416.2199. Found (M⁺): 416.2197.

d-(3E)-16,16-dimethyl-15-epi-2,5,6,7-tetranor-18-oxa-3,4-didehydro-4,8-inter-m-phenylene PGI₂ methyl ester $[\alpha]_D^{25}$: +220.00 (c 1.090, MeOH).

IR (liquid film): 3400, 2950, 2860, 1700, 1630, 1600, 1440, 1320, 1260, 1240, 1200, 1160, 1100, 1030, 980, 860, 780, 740, 710 cm⁻¹.

NMR (400 MHz, CDCl₃, δ): 0.92 (3H, s), 0.94 (3H, s), 1.22 (3H, t, J=6.8 Hz), 2.0–2.1 (1H, m), 2.45–2.55 (1H, m), 2.68 (1H, dt, J=6.8, 14.0 Hz), 3.31 (1H, d, J=9.0 Hz), 3.37 (1H, d, J=9.0 Hz), 3.45–3.55 (3H, m), 3.80 (3H, s), 3.9–4.05 (2H, m), 5.2–5.3 (1H, m), 5.65–5.75 (2H, m), 6.72 (1H, d, J=16.1 Hz), 6.85 (1H, t, J=7.6 Hz), 7.16 (1H, d, J=7.6 Hz), 7.24 (1H, d, J=7.6 Hz), 7.68 (1H, d, J=16.1 Hz).

MASS (EI, m/e): 416 (M⁺).

High resolution mass spectrum: Calcd. (C₂₄H₃₂O₆, M⁺): 416.2199. Found (M⁺): 416.2198.

EXAMPLE 55 d-(3E)-16,16-dimethyl-2,5,6,7-tetranor-18-oxa-3,4-didehydro-4,8-inter-m-phenylene PGI₂ (72)

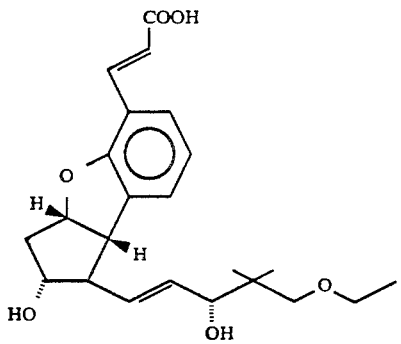
(72)

To a solution of d-(3E)-16,16-dimethyl-2,5,6,7-tetranor-18-oxa-3,4-didehydro-4,8-inter-m-phenylene PGI₂ methyl ester (340 mg, 0.817 mmoles) in methanol (25 ml) was added 1.0N aqueous sodium hydroxide solution (7.0 ml, 7.0 mmoles) and stirred at room temperature for 20 hours. The reaction mixture was concentrated. To the residue was added water (15 ml), then neutralized with 1.0N hydrochloric acid (7.0 ml), and extracted with ethyl acetate (50 ml, 20 ml). The organic layers were combined, washed with water (20 ml) and with brine (20 ml), dried over anhydrous magnesium sulfate, and concentrated to give 322 mg of crude crystalline product. The resulting crude crystalline product was recrystallized from ethyl acetate/n-hexane to afford 65.7% yield of d-(3E)-16,16-dimethyl-2,5,6,7-tetranor-18-oxa-3,4-didehydro-4,8-inter-m-phenylene PGI₂ (215 mg, 0.537 mmoles) as a white crystal. The structure was confirmed by the following data:

m.p. 130°–131° C.

$[\alpha]_D^{25}$: +273.02 (c 0.482, MeOH).

IR (KBr): 3400, 2970, 2870, 1690, 1630, 1600, 1590, 1440, 1420, 1360, 1320, 1280, 1240, 1220, 1200, 1100, 1040, 980, 870, 800, 780, 740, 620, 560 cm⁻¹.

NMR (400 MHz, CDCl₃, δ): 0.92 (3H, s), 0.95 (3H, s), 1.21 (3H, t, J=6.8 Hz), 2.06 (1H, ddd, J=5.4, 8.8, 13.9 Hz), 2.45–2.55 (1H, m), 2.69 (1H, dt, J=6.8, 13.9 Hz), 3.30 (1H, d, J=9.0 Hz), 3.37 (1H, d, J=9.0 Hz), 3.45–3.55 (3H, m), 3.9–4.0 (2H, m), 5.2–5.3 (1H, m), 5.65–5.75 (2H, m), 6.72 (1H, d, J=16.1 Hz), 6.85 (1H, t, J=7.2 Hz), 7.12 (1H, d, J=7.2 Hz), 7.25 (1H, d, J=7.2 Hz), 7.76 (1H, d, J=16.1 Hz).

MASS (EI, m/e): 402 (M⁺).

High resolution mass spectrum: Calcd. (C₂₃H₃₀O₆, M⁺): 402.2042. Found (M⁺): 402.2014.

Anal. Calcd. for C₂₃H₃₀O₆: C: 68.64; H: 7.51. Found: C: 68.41; H: 7.61.

EXAMPLE 56 d-(3E)-16-phenoxy-2,5,6,7,17,18,19,20-octanor-3,4-didehydro-4,8-inter-m-phenylene PGI₂ methyl ester (73) and 15-epimer thereof (74)

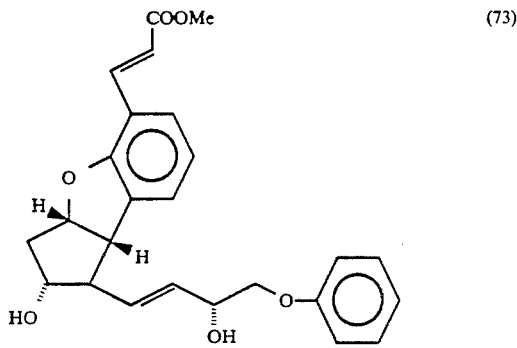
(73)

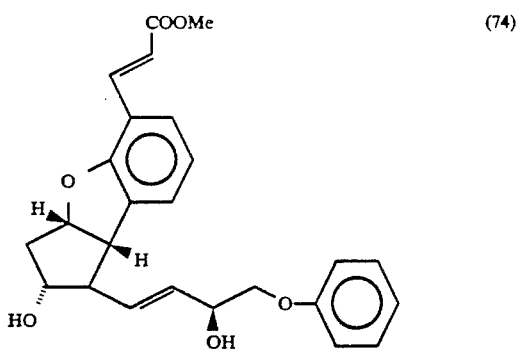
(74)

To a solution of d-(3E)-15-oxo-16-phenoxy-2,5,6,7,17,18,19,20-octanor-3,4-didehydro-4,8-inter-m-phenylene PGI₂ methyl ester, 11-acetate (739 mg, 1.60 mmoles) in methanol (25 ml) was added cerous trichloride heptahydrate (1.19 g, 3.20 mmoles), to which sodium borohydride (60.5 mg, 1.60 mmoles) was added after cooling to 0° C. The solution stirred at 0° C. for 20 minutes, to which saturated aqueous sodium hydrogen carbonate (5 ml) was added and concentrated. To the residue was added ethyl acetate (50 ml), filtered, and the precipitate was washed with ethyl acetate (10 ml×2).

The filtrates were combined, washed with water (20 ml) and with brine (20 ml), dried over anhydrous magnesium sulfate, and concentrated. Then, the resultant oily product was dissolved in dry methanol (20 ml) under argon atomosphere, to which a solution of sodium methoxide in methanol (5.22N, 0.12 ml, 0.64 mmoles) was added and stirred at room temperature for 3 hours. This reaction mixture was then neutralized with acetic acid and concentrated. To the residue was added water (20 ml) and extracted with ethyl acetate (50 ml, 20 ml). The organic layers were combined, washed with brine (20 ml), dried over anhydrous magnesium sulfate, and concentrated.

The resultant residue was purified by Lobar Column (Merck, silica gel: ethyl acetate/cyclohexane=2/1) to afford 48.8% yield of d-(3E)-16-phenoxy-15-epi-2,5,6,7,17,18,19,20-octanor-3,4-didehydro-4,8-inter-m-phenylene PGI$_2$ methyl ester (329 mg, 0.780 mmoles) as a less polar eluate, followed by 40.1% yield of d-(3E)-16-phenoxy-2,5,6,7,17,18,19,20-octanor-3,4-didehydro-4,8-inter-m-phenylene PGI$_2$ methyl ester (271 mg 0.642 mmoles) as a more polar eluate.

The structure was confirmed by the following data:

d-(3E)-16-phenoxy-2,5,6,7,17,18,19,20-octanor-3,4-didehydro-4,8-inter-m-phenylene PGI$_2$ methyl ester m.p. 105°-106° C. (recrystallized from MeOH)
[α]$_D^{25}$: +276.27 (c 0.704, MeOH).
IR (KBr): 3430, 2950, 2930, 2900, 1720, 1630, 1590, 1500, 1440, 1370, 1260, 1240, 1230, 1190, 1090, 1040, 990, 960, 950, 900, 870, 820, 800, 780, 750, 720, 700, 620 cm$^{-1}$.
NMR (400 MHz, CDCl$_3$, δ): 2.06 (1H, ddd, J=5.2, 8.9, 13.7 Hz), 2.15-2.2 (1H, m), 2.50 (1H, q, J=8.5 Hz), 2.65-2.75 (2H, m), 3.49 (1H, t, J=8.5 Hz), 3.91 (3H, s), 3.93 (1H, dd, J=7.6, 9.4 Hz), 3.95-4.05 (1H, m), 4.04 (1H, dd, J=3.8, 9.4 Hz), 4.55-4.65 (1H, m), 5.24 (1H, ddd, J=5.2, 7.3, 8.5 Hz), 5.72 (1H, dd, J=6.1, 15.6 Hz), 5.89 (1H, ddd, J=1.1, 8.5, 15.6 Hz), 6.71 (1H, d, J=15.9 Hz), 6.83 (1H, t, J=7.3 Hz), 6.9-7.05 (3H, m), 7.11 (1H, d, J=7.3 Hz), 7.23 (1H, d, J=7.3 Hz), 7.25-7.35 (2H, m), 7.68 (1H, d, J=15.9 Hz).
MASS (EI, m/e): 422 (M+).
High resolution mass spectrum: Calcd. (C$_{25}$H$_{26}$O$_6$, M+): 422.1729. Found (M+): 422.1728.
Anal. Calcd. for C$_{25}$H$_{26}$O$_6$: C: 71.07; H: 6.20. Found: C: 71.36; H: 6.24.

d-(3E)-16-phenoxy-15-epi-2,5,6,7,17,18,19,20-octanor-3,4-didehydro-4,8-inter-m-phenylene PGI$_2$ methyl ester m.p. 111°-112° C. (recrystallized from ethyl acetate/cyclohexane).
[α]$_D^{25}$: +263.19 (c 0.614, MeOH).
IR (KBr): 3500, 2930, 2900, 1690, 1630, 1600, 1590, 1500, 1440, 1380, 1350, 1320, 1290, 1250, 1210, 1200, 1170, 1150, 1130, 1090, 1080, 1050, 1040, 1010, 990, 940, 880, 860, 840, 820, 800, 780, 750, 740, 700, 620, 560, 520 cm$^{-1}$.
NMR (400 MHz, CDCl$_3$, δ): 1.75-1.85 (1H, m), 2.07 (1H, ddd, J=5.1, 8.2, 13.9 Hz), 2.5-2.6 (2H, m), 2.69 (1H, ddd, J=6.1, 7.2, 13.9 Hz), 3.52 (1H, t, J=8.6 Hz), 3.80 (3H, s), 3.92 (1H, dd, J=7.3, 9.5 Hz), 3.95-4.05 (1H, m), 4.06 (1H, dd, J=3.7, 9.5 Hz), 4.55-4.65 (1H, m), 5.26 (1H, ddd, J=5.1, 7.2, 8.6 Hz), 5.74 (1H, dd, J=5.5, 15.5 Hz), 5.91 (1H, ddd, J=1.2, 8.2, 15.5 Hz), 6.71 (1H, d, J=16.2 Hz), 6.83 (1H, t, J=7.4 Hz), 6.9-7.05 (3H, m), 7.15 (1H, d, J=7.4 Hz), 7.23 (1H, d, J=7.4 Hz), 7.3-7.4 (2H, m), 7.68 (1H, d, J=16.2 Hz).
MASS (EI, m/e): 422 (M+).
High resolution mass spectrum: Calcd. (C$_{25}$H$_{26}$O$_6$, M+): 422.1729. Found (M+): 422.1707.
Anal. Calcd. for C$_{25}$H$_{26}$O$_6$: C: 71.07; H: 6.20. Found: C: 71.16; H: 6.22.

EXAMPLE 57 d-(3E)-16-phenoxy-2,5,6,7,17,18,19,20-octanor-3,4-didehydro-4,8-inter-m-phenylene PGI$_2$ (75)

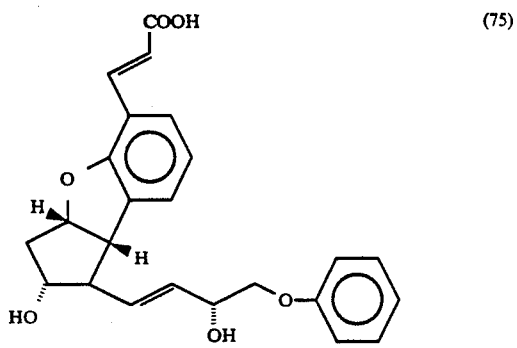

(75)

To a solution of d-(3E)-16-phenoxy-2,5,6,7,17,18,19,20-octanor-3,4-didehydro-4,8-inter-m-phenylene PGI$_2$ methyl ester (180 mg, 0.427 mmoles) in methanol (15 ml) was added 1.0N aqueous sodium hydroxide solution (3.41 ml, 3.41 mmoles) and stirred at room temperature for 30 hours. The reaction mixture was concentrated. To the residue was added water (10 ml), then neutralized with 1.0N hydrochloric acid (3.41 ml), and extracted with ethyl acetate (60 ml, 20 ml).

The organic layers were combined, washed with water (20 ml) and with brine (20 ml), dried over anhydrous magnesium sulfate, and concentrated to give 203 mg of crude crystalline product.

The crude crystalline product was recrystallized from ethyl acetate to afford 67.7% yield of d-(3E)-16-phenoxy-2,5,6,7,17,18,19,20-octanor-3,4-didehydro-4,8-inter-m-phenylene PGI$_2$ methyl ester (118 mg, 0.289 mmoles) as a white crystal. The structure was confirmed by the following data:

m.p. 191°-192° C.
[α]$_D^{25}$: +273.37 (c 0.462, MeOH).
IR (KBr): 3320, 3430, 3030, 2950, 1690, 1630, 1600, 1590, 1500, 1440, 1410, 1380, 1340, 1280, 1240, 1220, 1130, 1080, 1040, 1020, 990, 970, 940, 900, 860, 810, 780, 750, 740, 700, 620, 600, 570, 520 cm$^{-1}$.
NMR (400 MHz, CDCl$_3$+DMSO-d$_6$, δ): 1.99 (1H, ddd, J=5.5, 9.5, 13.6 Hz), 2.41 (1H, q, J=8.6 Hz), 2.69 (1H, dt, J=6.7, 13.6 Hz), 3.44 (1H, t, J=8.6 Hz), 3.9-4.05 (3H, m), 4.5-4.6 (1H, m), 5.15-5.25 (1H, m), 5.73 (1H, dd, J=6.7, 15.6 Hz), 5.86 (1H, dd, J=8.6, 15.6 Hz), 6.67 (1H, d, J=16.0 Hz), 6.79 (1H, t, J=7.3 Hz), 6.9-7.0 (3H, m), 7.10 (1H, d, J=7.3 Hz), 7.21 (1H, d, J=7.3 Hz), 7.25-7.35 (2H, m), 7.65 (1H, d, J=16.0 Hz).
MASS (EI, m/e): 408 (M+).
High resolution mass spectrum: Calcd. (C$_{24}$H$_{24}$O$_6$, M+): 408.1573. Found (M+): 408.1573.
Anal. Calcd. for C$_{24}$H$_{24}$O$_6$: C: 70.58; H: 5.92. Found: C: 70.29; H: 6.02.

EXAMPLE 58 d-(3E,16R)-16-phenoxy-2,5,6,7,18,19,20-heptanor-3,4-didehydro-4,8-inter-m-phenylene PGI₂ methyl ester (76)

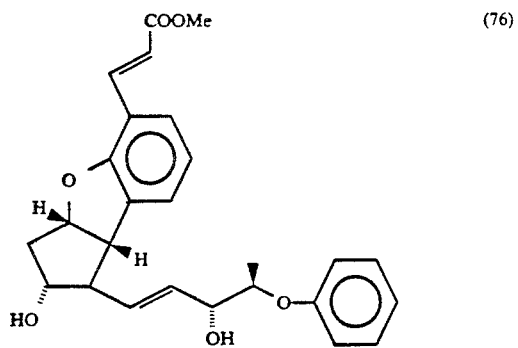

To a solution of d-(3E,16R)-15-oxo-16-phenoxy-2,5,6,7,18,19,20-heptanor-3,4-didehydro-4,8-inter-m-phenylene PGI₂ methyl ester, 11-acetate (770 mg, 1.62 mmoles) in methanol (20 ml) was added cerous trichloride heptahydrate (1.21 g, 3.24 mmoles), to which sodium borohydride (61.3 mg, 1.62 mmoles) was added after cooling to 0° C. The solution stirred at 0° C. for 10 minutes, to which saturated aqueous sodium hydrogen carbonate (5 ml) was added and concentrated. To the residue was added ethyl acetate (30 ml), filtered, and the precipitate was washed with ethyl acetate (20 ml×2).

The filtrates were combined, washed with water (20 ml) and with brine (20 ml), dried over anhydrous magnesium sulfate, and concentrated. Then, the resultant oily product was dissolved in dry methanol (20 ml) under argon atmosphere, to which a solution of sodium methoxide in methanol (5.22N, 0.12 ml, 0.65 mmoles) was added and stirred at room temperature for 2 hours.

This reaction mixture was then neutralized with acetic acid and concentrated. To the residue was added water (20 ml) and extracted with ethyl acetate (50 ml, 20 ml). The organic layers were combined, washed with brine (20 ml), dried over anhydrous magnesium sulfate, and concentrated.

The resultant residue was purified by Lobar Column (Merck, silica gel: ethyl acetate/cyclohexane=2/1) to afford 79.0% yield of d-(3E,16R)-16-phenoxy-2,5,6,7,18,19,20-heptanor-3,4-didehydro-4,8-inter-m-phenylene PGI₂ methyl ester (556 mg, 1.28 mmoles).

The structure was confirmed by the following data:

$[\alpha]_D^{25}$: +265.13 (c 0.436, MeOH).

IR (KBr): 3340, 2960, 1710, 1630, 1600, 1590, 1490, 1450, 1320, 1270, 1240, 1200, 1170, 1100, 1080, 1060, 990, 970, 950, 920, 860, 800, 780, 750, 720, 700 cm⁻¹.

NMR (400 MHz, CDCl₃, δ): 1.30 (3H, d, J=6.4 Hz), 2.04 (1H, ddd, J=5.1, 8.8, 14.0 Hz), 2.46 (1H, q, J=8.4 Hz), 2.70 (1H, dt, J=6.8, 14.0 Hz), 3.47 (1H, t, J=8.4 Hz), 3.80 (3H, s), 3.9–4.0 (1H, m), 4.21 (1H, t, J=6.4 Hz), 4.25–4.35 (1H, m), 5.2–5.3 (1H, m), 5.67 (1H, dd, J=6.4, 15.1 Hz), 5.84 (1H, dd, J=8.4, 15.1 Hz), 6.71 (1H, d, J=16.1 Hz), 6.81 (1H, t, J=7.3 Hz), 6.9–7.0 (3H, m), 7.06 (1H, d, J=7.3 Hz), 7.23 (1H, d, J=7.3 Hz), 7.25–7.35 (2H, m), 7.67 (1H, d, J=16.1 Hz).

MASS (EI, m/e): 436 (M⁺).

High resolution mass spectrum: Calcd. ($C_{26}H_{28}O_6$, M⁺): 436.1886. Found (M⁺): 436.1862.

Anal. Calcd. for $C_{26}H_{28}O_6$: C: 71.54; H: 6.47. Found: C: 71.54; H: 6.62.

EXAMPLE 59 d-(3E,16R)-16-phenoxy-2,5,6,7,18,19,20-heptanor-3,4-didehydro-4,8-inter-m-phenylene PGI₂ (77)

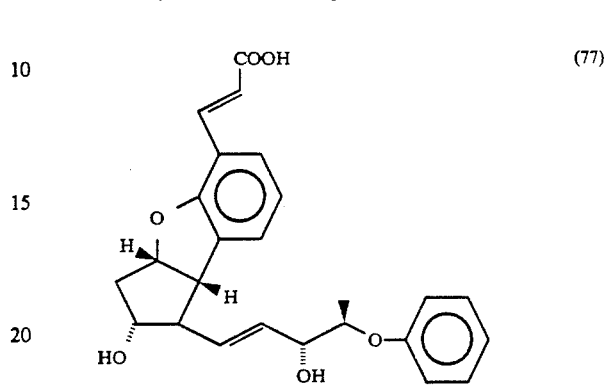

To a solution of d-(3E,16R)-16-phenoxy-2,5,6,7,18,19,20-heptanor-3,4-didehydro-4,8-inter-m-phenylene PGI₂ methyl ester (270 mg, 0.619 mmoles) in methanol (20 ml) was added 1.0N aqueous sodium hydroxide solution (5.0 ml, 5.0 mmoles) and stirred at room temperature for 24 hours. The reaction mixture was concentrated. To the residue was added water (15 ml), then neutralized with 1.0N hydrochloric acid (5.0 ml), and extracted with ethyl acetate (50 ml, 20 ml). The organic layers were combined, washed with water (20 ml) and with brine (20 ml), dried over anhydrous magnesium sulfate, and concentrated to give 267 mg of crude crystalline product.

The crude crystalline product was recrystallized from ethyl acetate to afford 71.9% yield of d-(3E,16R)-16-phenoxy-2,5,6,7,18,19,20-heptanor-3,4-didehydro-4,8-inter-m-phenylene PGI₂ (188 mg, 0.445 mmoles) as a white crystal. The structure was confirmed by the following data:

m.p. 150.5°–151.5° C.

$[\alpha]_D^{25}$: +254.22 (c 0.402, MeOH).

IR (KBr): 3400, 2970, 1680, 1630, 1600, 1490, 1450, 1420, 1370, 1290, 1240, 1100, 1060, 1040, 980, 970, 940, 860, 800, 780, 750 cm⁻¹.

NMR (500 MHz, CDCl₃+DMSO-d₆, δ): 1.31 (3H, d, J=6.3 Hz), 1.95–2.05 (1H, m), 2.43 (1H, q, J=8.5 Hz), 2.68 (1H, dt, J=6.8, 13.7 Hz), 3.44 (1H, t, J=8.5 Hz), 3.85–3.95 (1H, m), 4.25 (1H, t, J=6.3 Hz), 4.3–4.4 (1H, m), 5.15–5.25 (1H, m), 5.70 (1H, dd, J=6.3, 15.4 Hz), 5.82 (1H, dd, J=8.5, 15.4 Hz), 6.69 (1H, d, J=16.1 Hz), 6.79 (1H, t, J=7.3 Hz), 6.9–7.0 (3H, m), 7.08 (1H, d, J=7.3 Hz), 7.22 (1H, d, J=7.3 Hz), 7.25–7.35 (2H, m), 7.66 (1H, d, J=16.1 Hz).

MASS (EI, m/e): 422 (M⁺).

High resolution mass spectrum: Calcd. ($C_{25}H_{26}O_6$, M⁺): 422.1729. Found (M⁺): 422.1729.

Anal. Calcd. for $C_{25}H_{26}O_6$: C: 71.07; H: 60.20. Found: C: 70.82; H: 6.28.

EXAMPLE 60 d-(3E)-16-methyl-16-phenoxy-2,5,6,7,18,19,20-heptanor-3,4-didehydro-4,8-inter-m-phenylene PGI$_2$ methyl ester (78)

(78)

To a solution of diisopropylamine (1.25 ml, 8.89 mmoles) in dry THF under argon at −78° C. was added 1.67N n-butyl lithium/n-hexane solution (5.00 ml, 8.35 mmoles), which was stirred for 20 minutes. To the solution was added d-16-methyl-16-phenoxy-2,5,6,7,18,19,20-heptanor-4,8-inter-m-phenylene PGI$_2$ methyl ester (1.1 g, 2.43 mmoles), which was stirred at −78° C. for 40 minutes. To the reaction mixture were added diphenyl diselenide (1.14 g, 3.65 mmoles) and hexamethylphosphoric triamide (HMPA) (0.85 ml), which was stirred at −78° C. for an hours.

After the addition of 1N hydrochloric acid (5 ml) and water (10 ml), the reaction mixture was raised to room temperature. The reaction mixture was extracted with ethyl acetate (30 ml×3) after THF was distilled off. The organic layers were combined, washed with brine (100 ml), dried over anhydrous sodium sulfate, and concentrated.

The residue was purified by column chromatography (Art 9385, Merck, ethyl acetate:cyclohexane=1:1, then 3:2) to afford 1.17 g of white crystalline product.

Then, 1.17 g of the white crystalline product was dissolved in 100 ml of diethyl ether, to which 3.5 ml of 35% aqueous hydrogen peroxide was added under cooling with ice and stirred for 20 minutes. To the reaction mixture was added 30 ml of saturated aqueous sodium bisulfite, stirred for 20 minutes, and partitioned. The aqueous layers were extracted twice with 50 ml of ethyl acetate. The organic layers were combined, washed with brine, dried over anhydrous sodium sulfate, and concentrated.

The residue was purified by column chromatography (Art 7734, Merck, ethyl acetate/cyclohexane=1/1) to afford 0.69 g of d-(3E)-16-methyl-16-phenoxy-2,5,6,7,18,19,20-heptanor-3,4-didehydro-4,8-inter-m-phenylene PGI$_2$ methyl ester (0.69 g, 1.53 mmoles, yield 63.0%). The structure was confirmed by the following data:

m.p. 133°–134° C. (recrystallized from ethyl acetate/cyclohexane).

$[\alpha]_D^{25}$: +252.54 (c 0.118, MeOH).

IR (KBr): 3400, 2980, 1700, 1630, 1590, 1495, 1440, 1378, 1365, 1320, 1280, 1240, 1225, 1200, 1170, 1150, 1130, 1095, 1090, 1065, 1030, 980, 975, 880, 870, 790, 740, 700 cm$^{-1}$.

NMR (400 MHz, CDCl$_3$, δ): 1.24 (3H, s), 1.26 (3H, s), 2.01–2.09 (1H, m), 2.45–2.51 (1H, m), 2.65–2.80 (2H, m), 3.2 (1H, br. s), 3.45–3.50 (1H, m), 3.79 (3H, s), 3.95–4.05 (1H, m), 4.17–4.23 (1H, m), 5.20–5.25 (1H, m), 5.70–5.81 (2H, m), 6.70–7.30 (9H, m), 7.65–7.72 (1H, m).

MASS (EI, m/e): 450 (M+).

EXAMPLE 61 d-(3E)-16-methyl-16-phenoxy-2,5,6,7,18,19,20-heptanor-3,4-didehydro-4,8-inter-m-phenylene PGI$_2$ (79)

(79)

To a solution of d-(3E)-16-methyl-16-phenoxy-2,5,6,7,18,19,20-heptanor-3,4-didehydro-4,8-inter-m-phenylene PGI$_2$ methyl ester (690 mg, 1.53 mmoles) in methanol (40 ml) was added 1.0N aqueous sodium hydroxide solution (15 ml, 15 mmoles) and allowed to stand at room temperature for 2 days. The reaction mixture was concentrated. To the residue was added water, then neutralized with 1.0N hydrochloric acid, and extracted with ethyl acetate (50 ml×2).

The organic layers were combined, washed with water and with brine, dried over sodium sulfate, and concentrated to give 660 mg of crude crystalline product. The crude crystalline product was recrystallized from ethyl acetate/cyclohexane to afford 72.5% yield of d-(3E)-16-methyl-16-phenoxy-2,5,6,7,18,19,20-heptanor-3,4-didehydro-4,8-inter-m-phenylene PGI$_2$ (482 mg, 1.11 mmoles) as a white crystal. The structure was confirmed by the following data:

m.p. 99.1°–100° C.

$[\alpha]_D^{25}$: +245.95 (c 0.420, MeOH), IR (KBr): 3500, 2970, 1680, 1630, 1590, 1485, 1440, 1220, 1130, 980, 955, 860, 780, 745, 700 cm$^{-1}$.

NMR (400 MHz, CDCl$_3$, δ): 1.25 (3H, s), 1.27 (3H, s), 2.06–2.12 (1H, m), 2.49–2.57 (1H, m), 2.68–2.75 (1H, m), 3.52 (1H, t, J=8.3 Hz), 3.98–4.08 (1H, m), 4.22 (1H, d, J=6.8 Hz), 5.24–5.30 (1H, m), 5.74 (1H, dd, J=6.8, 15.6 Hz), 5.85 (1H, dd, J=8.6, 15.6 Hz), 6.73 (1H, d, J=15.9 Hz), 6.85 (1H, t, J=7.8 Hz), 7.00 (2H, d, J=7.8 Hz), 7.11–7.15 (2H, m), 7.25–7.30 (3H, m), 7.76 (1H, d, J=15.9 Hz).

MASS (EI, m/e): 436 (M+).

High resolution mass spectrum: Calcd. (C$_{26}$H$_{28}$O$_6$, M+): 436.1886. Found (M+): 436.1840.

EXAMPLE 62

Gastric Cytoprotection

Gastric cytoprotection was measured according to the method of A. Robert, et al. (Gastroenterlogy 77 (3), 443 (1979).

Thirty minutes later after the test compound was administered, the animals were given orally 0.2N NaOH and killed one hour later by chloroform anesthesia.

The stomach was taken out, fixed with 5% formalin solution, and opened along greater curvature.

The length of the lesion brought about in the stomach is measured and expressed in terms of the ulcer index. Gastric cytoprotection activity is expressed in Table 1 below as an $ED_{50}$ value (dose in μg/Kg which reduces an ulcer index by 50% of that in a control animal (ulcer index: 100%)).

The observed values are shown in Table 1 below.

TABLE 1

| Gastric Cytoprotection Activity | |
|---|---|
| Compound No. | $ED_{50}$ (μg/Kg) |
| 24 | 21.4 |
| 28 | 0.26 |
| 34 | 1.6 |
| 37 | 0.83 |
| 40 | 0.46 |
| 43 | 0.39 |
| 57 | 5.07 |
| 60 | 0.88 |
| 69 | 6.5 |
| 72 | 2.7 |
| 75 | 0.89 |
| 77 | 0.4 |
| 79 | 0.50 |

EXAMPLE 63

Gastric Acid Secretion Inhibition

Male SD rats were operated by means of ventrotomy under urethane anesthesia. A double cannula was inserted into the fundus of the rat. The stomach lumen was continuously perfused with a physiological saline solution. The perfusate was drawn into the pH meter to continuously measure its pH (M. Ghosh, H. Schild, Br. J. Pharmacol. 13, 54 (1958)).

Pentagastrin was infused continuously at a rate of 0.05 μg/Kg/min. to stimulate gastric acid secretion.

The test compounds were injected intravenuously into the femoral vein when the pH reached a steady state at about 4.0.

Gastric acid secretion inhibition activity is calculated from the area made by pH augmentation against time.

The potency of the compounds is compared and expressed in terms of $PGE_2$ ratio where $PGE_2$ is set as 1.

The observed values are shown in Table 2 below.

TABLE 2

| Gastric Antisecretory Activity | |
|---|---|
| Compound No. | Relative Potency Ratio [$PGE_2$ = 1.0] |
| $PGE_2$ | 1 |
| 24 | 23 |
| 28 | 55 |
| 34 | 36 |
| 37 | 83 |
| 60 | 14 |
| 69 | 10 |
| 72 | 9 |
| 75 | 73 |
| 77 | 83 |
| 79 | 112 |

EXAMPLE 64

Inhibiting Effect of Platelet Aggregation

Blood collected from human intermediate cubital vein was centrifuged at 800 rpm for 10 minutes. The supernatant was taken out as platelet rich plasma (PRP). Aliquots of PRP were dispensed into test tubes to which adenosine 2-phosphate (ADP) was added (final concentration: 10 μM) to induce platelet aggregation. The extent of platelet aggregation is determined by an aggregometer (Rika Denki, Tokyo) as a change of turbidity. The test compound is added in one minute prior to the addition pf ADP. $IC_{50}$ values are calculated as a concentration of test compound which inhibits platelet aggregation by 50%. The observed results are shown in Table 3 below.

TABLE 3

| Inhibiting Effect of Platelet Aggregation | |
|---|---|
| Compound No. | $ED_{50}$ (ng/ml) |
| 24 | 0.4 |
| 28 | 1.6 |
| 31 | 0.14 |
| 34 | 45 |
| 37 | 0.56 |
| 51 | 1800 |
| 60 | 0.35 |
| 69 | 0.58 |
| 72 | 100 |
| 75 | 29 |
| 77 | 14 |
| 79 | (—) |

What is claimed is:
1. A 2,5,6,7-tetranor-4,8-inter-m-phenylene $PGI_2$ derivative having the following formula:

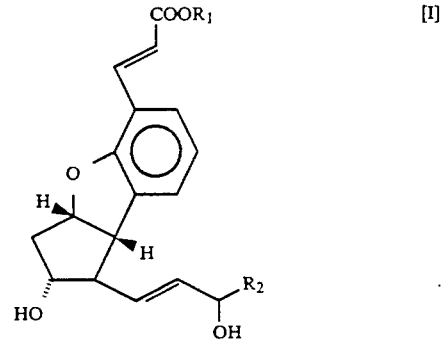

wherein $R_1$ is hydrogen, a pharmacologically acceptable cation, or an ester residue;

$R_2$ is (i) normal alkyl group having 1 to 12 carbon atoms or branched alkyl group having 3 to 14 carbon atoms;

(ii) —Z—Ar wherein Z is a valence bond or normal or branched alkylene group having the formula: $C_tH_{2t}$, t is an integer of 1 to 6, and Ar is phenyl group unsubstituted or substituted by 1 to 4 substituents selected from alkyl, methoxy, chloro, bromo, fluoro, iodo, trifluoromethyl, nitro, cyano, phenyl and phenoxy;

(iii) —Z—$R_3$ wherein Z is as defined above, $R_3$ is cycloalkyl group having 3 to 12 carbon atoms or cycloalkyl group having 3 to 12 carbon atoms substituted by 1 to 4 normal alkyl substituents containing 1 to 4 carbon atoms;

(iv) —$C_tH_{2t}$—C≡C—$R_4$ wherein $C_tH_{2t}$ is as defined above, $R_4$ is normal alkyl group having 1 to 6 carbon atoms;

(v) —$C_tH_{2t}$—O—$R_5$ wherein $C_tH_{2t}$ is as defined above, $R_5$ is (1) normal alkyl group having 1 to 6 carbon atoms or branched alkyl group having 3 to 6 carbon atoms, (2) cyclopentyl or cyclohexyl group unsubstituted or substituted by 1 to 4 normal alkyl substituents containing 1 to 4 carbon atoms, or (3) Ar wherein Ar is as defined above.

2. A PGI$_2$ derivative according to claim 1 wherein R$_1$ is selected from the group consisting of hydrogen, a pharmacologically acceptable cation, and methyl.

3. A PGI$_2$ derivative according to claim 1 or 2 wherein R$_2$ is selected from the group consisting of normal alkyl group having 4 to 8 carbon atoms and branched alkyl group having 3 to 8 carbon atoms.

4. A PGI$_2$ derivative according to claim 1 or 2 wherein R$_2$ is —Z—Ar wherein Z is a valence bond or normal or branched alkylene group having the formula: C$_t$H$_{2t}$, t is an integer of 1 to 4, and Ar is phenyl group unsubstituted or substituted by 1 or 2 substituents selected from alkyl, methoxy, chloro, bromo, fluoro, iodo, trifluoromethyl, nitro, cyano, phenyl and phenoxy.

5. A PGI$_2$ derivative according to claim 1 or 2 wherein R$_2$ is —Z—R$_3$ wherein Z is a valence bond or normal or branched alkylene having the formula: C$_t$H$_{2t}$, t is an integer of 1 to 4, and R$_3$ is cyclopentyl or cyclohexyl.

6. A PGI$_2$ derivative according to claim 1 or 2 wherein R$_2$ is —C$_t$H$_{2t}$—C≡C—R$_4$ wherein t is an integer of 1 to 4, and R$_4$ is methyl, ethyl, propyl, or butyl.

7. A PGI$_2$ derivative according to claim 1 or 2 wherein R$_2$ is —C$_t$H$_{2t}$—O—R$_5$ wherein t is an integer of 1 to 4, and R$_5$ is (1) methyl, ethyl, propyl, or butyl, (2) cyclopentyl or cyclohexyl or (3) Ar wherein Ar is phenyl group unsubstituted or substituted by 1 or 2 substituents selected from alkyl, methoxy, chloro, bromo, fluoro, iodo, trifluoromethyl, nitro, cyano, phenyl and phenoxy.

8. d-(3E)-16,16-dimethyl-2,5,6,7-tetranor-3,4-didehydro-4,8-inter-m-phenylene PGI$_2$.

9. d-(3E)-15-phenyl-2,5,6,7,16,17,18,19,20-nonanor-3,4-didehydro-4,8-inter-m-phenylene PGI$_2$.

10. d-(3E)-15-(p-chlorophenyl)-2,5,6,7,16,17,18,19,20-nonanor-3,4-didehydro-4,8-inter-m-phenylene PGI$_2$.

11. d-(3E)-15-cyclohexyl-2,5,6,7,16,17,18,19,20-nonanor-3,4-didehydro-4,8-inter-m-phenylene PGI$_2$.

12. d-(3E, 16S)-16-methyl-2,5,6,7-tetranor-3,4,18,18,19,19-hexadehydro-4,8-inter-m-phenylene PGI$_2$.

13. d-(3E)-16,16-dimethyl-2,5,6,7-tetranor-18-oxa-3,4-didehydro-4,8-inter-m-phenylene PGI$_2$.

14. d-(3E, 16R)-16-phenoxy-2,5,6,7,18,19,20-heptanor-3,4-didehydro-4,8-inter-m-phenylene PGI$_2$.

15. d-(3E)-16-methyl-16-phenoxy-2,5,6,7,18,19,20-heptanor-3,4-didehydro-4,8-inter-m-phenylene PGI$_2$.

16. A pharmaceutical composition for the induction of labor or the treatment of various diseases selected from the group consisting of ulcer, thrombosis, arteriosclerosis, cerebral infarction, peripheral circulatory disturbance, hepatitis and diabetic neuropathy which comprises a pharmaceutically effective amount of the PGI$_2$ derivative according to claim 1 and a pharmaceutical carrier therefor.

17. A method for the treatment of ulcers in an animal comprising administering to said animal in need of such treatment an anti-ulcer effective amount of the PGI$_2$ derivative according to claim 1.

18. A method for the treatment of thrombosis in an animal which comprises administering to said animal in need of such treatment an anti-thrombotic effective amount of the PGI$_2$ derivative according to claim 1.

19. A method for the treatment of arteriosclerosis in an animal which comprises administering to said animal in need of such treatment an anti-arteriosclerotic effective amount of the PGI$_2$ derivative according to claim 1.

20. A method for the treatment of cerebral infarction in an animal which comprises administering to said animal in need of such treatment an effective amount of the PGI$_2$ derivative according to claim 1.

21. A method for the treatment of peripheral circulatory disturbance in an animal which comprises administering to said animal in need of such treatment an effective amount of the PGI$_2$ derivative according to claim 1.

22. A method for the treatment of hepatitis in an animal which comprises administering to said animal in need of such treatment an effective amount of the PGI$_2$ derivative according to claim 1.

23. A method for the treatment of diabetic neuropathy in an animal which comprises administering to said animal in need of such treatment an effective amount of the PGI$_2$ derivative according to claim 1.

24. A method for the induction of labor in mammals which comprises administering to said mammal in need of such induction an effective amount of the PGI$_2$ derivative according to claim 1.

* * * * *

UNITED STATES PATENT AND TRADEMARK OFFICE
CERTIFICATE OF CORRECTION

PATENT NO. : 5,086,071
DATED : February 4, 1992
INVENTOR(S) : Kiyotaka Ohno, et al.

It is certified that error appears in the above-identified patent and that said Letters Patent is hereby corrected as shown below:

Column 11, line 48: "8inter" should read as --8-inter--

Column 21, line 4: "8inter" should read as --8-inter--

Column 55, line 41: "10°C" should read as --0°C--

Column 85, line 33: delete ";"

Column 94, line 34: "971, 868," should read as --971, 951, 868,--

Column 107, line 8: after "(3H, s)," insert --0. 94 (3H, s),--

Column 114, line 42: "1°-" should read as --1~--..

Signed and Sealed this

First Day of February, 1994

Attest:

BRUCE LEHMAN

Attesting Officer

Commissioner of Patents and Trademarks